(12) United States Patent  
Nakao et al.

(10) Patent No.: US 8,183,272 B2
(45) Date of Patent: May 22, 2012

(54) INDANYL COMPOUNDS

(75) Inventors: Akira Nakao, Tokyo (JP); Kentoku Gotanda, Chiba (JP); Kazumasa Aoki, Tokyo (JP); Shimpei Hirano, Chiba (JP); Yoshiharu Hiruma, Saitama (JP); Takeshi Shiiki, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/167,196

(22) Filed: Jun. 23, 2011

(65) Prior Publication Data

US 2011/0319359 A1 Dec. 29, 2011

Related U.S. Application Data

(63) Continuation of application No. PCT/JP2009/071339, filed on Dec. 22, 2009.

(30) Foreign Application Priority Data

Dec. 24, 2008 (JP) ................. 2008-327477

(51) Int. Cl.
- A61K 31/41 (2006.01)
- A61K 31/18 (2006.01)
- A61K 31/192 (2006.01)
- C07C 53/134 (2006.01)
- C07C 311/25 (2006.01)
- C07D 257/04 (2006.01)

(52) U.S. Cl. ........ 514/381; 514/603; 514/559; 548/252; 562/510; 564/79; 564/86

(58) Field of Classification Search .......... None
See application file for complete search history.

(56) References Cited

U.S. PATENT DOCUMENTS

2008/0234370 A1  9/2008  Marquis

FOREIGN PATENT DOCUMENTS

| EP | 1 308 436 A1 | 5/2003 |
|---|---|---|
| JP | 2002-510671 A | 4/2002 |
| JP | 2003-12616 A | 1/2003 |
| JP | 2006-507348 A | 3/2006 |
| JP | 2007-523076 A | 8/2007 |
| WO | 99/51569 A1 | 10/1999 |
| WO | 2004/047751 A2 | 6/2004 |
| WO | 2004/106280 A1 | 12/2004 |

OTHER PUBLICATIONS

Balan, et al., Bioorg. & Med. Chem. Lett., 19:3328 (2009).*
International Search Report and Written Opinion, mailed Feb. 23, 2010, issued in corresponding International Application No. PCT/JP2009/071339, filed Dec. 22, 2009, 11 pages.
International Preliminary Report on Patentability and Written Opinion, mailed Aug. 9, 2011, issued in corresponding International Application No. PCT/JP2009/071339, filed Dec. 22, 2009, 8 pages.

* cited by examiner

*Primary Examiner* — Kamal Saeed
*Assistant Examiner* — Michael Barker
(74) *Attorney, Agent, or Firm* — Christensen O'Connor Johnson Kindness PLLC

(57) ABSTRACT

Compounds exhibiting calcium receptor antagonist activity that are safe and orally administrable having Formula (I) or pharmaceutically acceptable salts thereof:

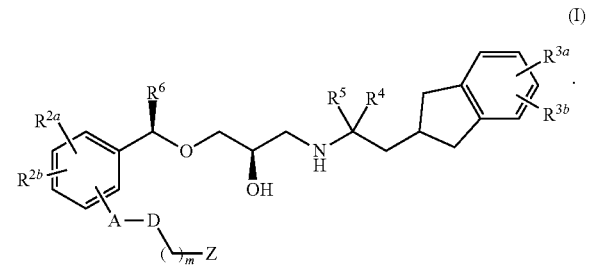

32 Claims, No Drawings

INDANYL COMPOUNDS

TECHNICAL FIELD

The present invention relates to a compound having calcium-sensing receptor (CaSR, hereinafter simply referred to as calcium receptor) antagonistic activity.

BACKGROUND ART

Bone is known as a dynamic organ which achieves bone reconstruction by constantly repeating formation and resorption for morphological change of the bone itself or for maintaining calcium concentration in the blood. In normal bone, osteogenesis by osteoblasts and bone resorption by osteoclasts have an equilibrium relationship, maintaining the bone mass in a constant state. However, when the equilibrium relationship between osteogenesis and bone resorption is disrupted, metabolic bone disorders such as osteoporosis are caused (Non-Patent Documents 1 and 2).

As bone metabolism-regulating factors, many kinds of systemic hormones or local cytokines have been reported and osteogenesis and bone maintenance are managed by interaction between these factors (Non-Patent Documents 1 and 3). The occurrence of osteoporosis is widely known as an age-related change in bone tissue. However, since the onset mechanism of osteoporosis involves many aspects including reduced secretion of sexual hormones or abnormality in the receptors therefor, changes in cytokine expression in local bone, expression of an aging genes, and differentiation or impaired function of osteoclasts or osteoblasts, etc., it is difficult to understand it as a simple physiological phenomenon which occurs with aging. Primary osteoporosis is mainly divided into post-menopausal osteoporosis due to reduced secretion of estrogen, and senile osteoporosis due to aging. For the elucidation of the onset mechanism and development of a therapeutic agent therefor, progress in basic research on regulatory mechanisms in bone resorption and osteogenesis is essential.

Osteoclasts are a multinuclear cells originating from hematopoietic stem cells, and by releasing chloride ions and hydrogen ions on their side adhered to bone they acidify the cleft between the cell and the adhesive side of the bone and simultaneously secretes cathepsin K, which is an acidic protease (Non-Patent Document 4). As a result, degradation of bone matrix protein and calcium phosphate is caused, yielding calcium recruitment into the blood.

The serum calcium concentration of healthy mammals is strictly maintained at about 9-10 mg/dl (about 2.5 mM) (i.e., calcium homeostasis). Parathyroid hormone (PTH) is a hormone which plays a key role in maintaining calcium homeostasis, and when the $Ca^{2+}$ concentration in the blood decreases, PTH secretion from the parathyroid is immediately promoted. In bone, the PTH secreted accordingly recruits $Ca^{2+}$ into the blood by promoting bone resorption, and in the kidney it promotes re-uptake of $Ca^{2+}$ in the distal tubules, thus functioning of increase the $Ca^{2+}$ concentration in the blood.

Because it is known that PTH can increase bone mass when it is intermittently administered to a human or an animal, it has already clinically been applied as a therapeutic agent for osteoporosis. Also, according to animal tests it has been reported that both osteogenesis and bone resorption of femoral cancellous bone are promoted by continuous administration of bovine PTH (1-84) to a rat from which the thyroid/parathyroid glands had been removed, consequently leading to an actual decrease in bone mass. However, subcutaneous intermittent administration thereof did not result in promotion of bone resorption but in promotion of osteogenesis alone, leading to an increase in the bone mass (Non-Patent Document 5). Furthermore, when human PTH (1-34) was intermittently administered to a rat for 15 weeks from 4 weeks post-ovariectomy, promotion of osteogenesis and inhibition of bone resorption were observed during the period from week 5 to week 10 after the start of the administration, showing an increased bone mass of about twice the bone mass of a sham operation group (Non-Patent Document 6). This report suggests that PTH not only prevents a decrease in bone mass in an osteoporosis model, but also has a bone mass recovery effect even in animals already suffering from a marked decrease in bone mass.

Although PTH preparations are therapeutic agents for osteoporosis which show a verified significant effect of lowering bone fracture rates according to clinical tests with patients suffering from post-menopausal osteoporosis, being biological preparations, they also have disadvantages. Specifically, injection has to be employed as the administration means, and therefore there is the problem that the patient may suffer pain associated with this. Thus, the development of a pharmaceutical preparation that can intermittently raise the PTH concentration in the blood and can be orally administered has been awaited.

The calcium receptor is a G protein coupled receptor which is mainly expressed in parathyroid cells, and it regulates PTH secretion by sensing $Ca^{2+}$ concentration in the blood (Non-Patent Document 7). The human calcium receptor consists of 1,078 amino acids, and it is reported that the human calcium receptor is expressed in the kidneys, thyroid C cells, the brain, bone marrow cells, etc., as well as in the parathyroid gland. By binding $Ca^{2+}$ as a ligand, the calcium receptor activates phospholipase C via coupling to G protein, causes the production of inositol triphosphate and an increase in the intracellular Ca2+ concentration and, as a result, suppresses the secretion of PTH (Non-Patent Document 8). Thus, it is expected that a pharmaceutical agent that inhibits activation of the calcium receptor, i.e., a pharmaceutical agent that antagonizes the calcium receptor, will promote PTH secretion from parathyroid gland cells and increase the PTH concentration in the blood of a living organism. In this regard, if the increase in blood PTH concentration is transient rather than continuous, it is expected to obtain the same bone mass-increasing effect as that provided by intermittent administration of PTH.

Meanwhile, as compounds containing an indanyl group, the compounds disclosed in Patent Document 1 are known. However, although they are similar to the compounds of the invention in that they include an indanyl group, the structure of the other end, etc. is different.

CITATION LIST

Non-Patent Documents

Non-Patent Document 1: Endocrinological Review, (1992) 13, p 66-80
Non-Patent Document 2: Principles of Bone Biology, Academic Press, New York, (1996) p 87-102
Non-Patent Document 3: Endocrinological Review, (1996) 17, p 308-332
Non-Patent Document 4: American Journal of Physiology, (1991) 260, C1315-C1324
Non-Patent Document 5: Endocrinology, 1982, 110, 506-512
Non-Patent Document 6: Endocrinology, 1993, 132, 823-831

Non-Patent Document 7: Brown, E. M., "Homeostatic mechanisms regulating extracellular and intracellular calcium metabolism in the parathyroids", (US), Raven press, 1994, 19

Non-Patent Document 8: Nature, 1993, 366, 575-580

Patent Documents

Patent Document 1: WO2004/047751 (US 2006058391)

DISCLOSURE OF THE INVENTION

Problems to be Solved by the Invention

An object of the invention is to provide novel low-molecular compounds which exhibit antagonistic activity against the calcium receptor, and which are highly safe and orally administrable.

Means for Solving the Problems

A pharmaceutical preparation which inhibits activation of the calcium receptor, i.e., a pharmaceutical preparation which antagonizes the calcium receptor, is expected to promote PTH secretion from parathyroid gland cells, thus yielding an increase in blood PTH concentration in a living organism. In this regard, if the increase in blood PTH concentration is transient rather than continuous, it is expected to obtain the same bone mass-increasing effect as that provided by intermittent administration of PTH.

The indanyl compounds of the invention are compounds having a calcium receptor antagonist activity. The expression "having a calcium receptor antagonist activity" means that one or more calcium receptor activities that are induced by extracellular $Ca^{2+}$ are inhibited.

Specifically, the invention relates to the following.

(1)

A compound represented by the following Formula (I) or a pharmaceutically acceptable salt thereof.

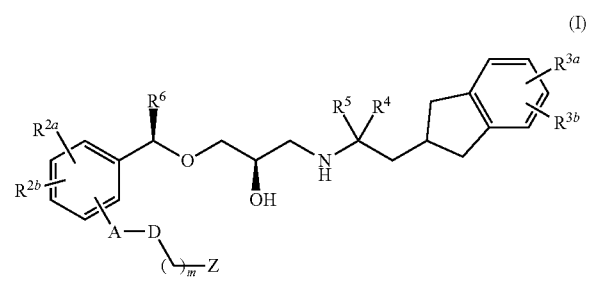

(I)

[in the formula, each substituent group is defined as follows.

A: a single bond, a C1-C6 alkylene group, or a phenylene group which may be substituted by $R^1$ $R^1$: a halogen atom, a cyano group, a C1-C6 alkyl group, a C1-C6 alkoxy group, a halogeno C1-C6 alkyl group, or a halogeno C1-C6 alkoxy group D: a single bond, an oxygen atom, or a sulfur atom $R^{2a}$ and $R^{2b}$: the same or different from each other, a hydrogen atom, a halogen atom, a cyano group, a C1-C6 alkyl group, a C1-C6 alkoxy group, a halogeno C1-C6 alkyl group, or a halogeno C1-C6 alkoxy group $R^{3a}$ and $R^{3b}$: the same or different from each other, a hydrogen atom, a halogen atom, a cyano group, a C1-C6 alkyl group, a C1-C6 alkoxy group, a halogeno C1-C6 alkyl group, or a halogeno C1-C6 alkoxy group $R^4$ and $R^5$: the same or different from each other, a hydrogen atom, a halogen atom, or a C1-C6 alkyl group, or $R^4$ and $R^5$ are bonded to each other to form a C2-C6 alkylene group $R^6$: a halogen atom, a cyano group, a C1-C6 alkyl group, a C1-C6 alkoxy group, a halogeno C1-C6 alkyl group, or a halogeno C1-C6 alkoxy group m: an integer of 0 to 6

Z: a carboxy group or a group equivalent to a carboxy group ($-SO_2NHR^Z$, a tetrazolyl group, or the like)

$R^Z$: a hydrogen atom or a C1-C6 alkyl group]

Preferred embodiments of the invention include the following.

(2)

The compound described in (1) above or a pharmaceutically acceptable salt thereof wherein $R^1$ represents a hydrogen atom or a methyl group.

(3)

The compound described in (1) or (2) above or a pharmaceutically acceptable salt thereof wherein $R^{2a}$ and $R^{2b}$, which are identical or different from each other, represent a hydrogen atom, a fluorine atom, a chlorine atom, a cyano group, a methyl group, a methoxy group, an ethoxy group, a trifluoromethyl group, or a trifluoromethoxy group.

(4)

The compound described in any one selected from (1) to (3) above or a pharmaceutically acceptable salt thereof wherein $R^{3a}$ and $R^{3b}$, the same or different from each other, represent a hydrogen atom, a fluorine atom, a chlorine atom, a cyano group, a methyl group, a methoxy group, an ethoxy group, a trifluoromethyl group, or a trifluoromethoxy group.

(5)

The compound described in any one selected from (1) to (4) above or a pharmaceutically acceptable salt thereof wherein $R^4$ and $R^5$ represent methyl groups.

(6)

The compound described in any one selected from (1) to (4) above or a pharmaceutically acceptable salt thereof wherein $R^4$ and $R^5$ represent an ethylene group.

(7)

The compound described in any one selected from (1) to (6) above or a pharmaceutically acceptable salt thereof wherein m is 0 or 1.

(8)

The compound described in any one selected from (1) to (6) above or a pharmaceutically acceptable salt thereof wherein m is 2 to 4.

(9)

The compound described in any one selected from (1) to (8) above or a pharmaceutically acceptable salt thereof wherein A is a single bond.

(10)

The compound described in any one selected from (1) to (9) above or a pharmaceutically acceptable salt thereof wherein D is a single bond.

(11)

The compound described in any one selected from (1) to (10) above or a pharmaceutically acceptable salt thereof wherein Z is a carboxy group.

(12)

The compound described in any one selected from (1) to (11) above or a pharmaceutically acceptable salt thereof wherein $R^6$ represents a methyl group or an ethyl group.

(13)
A compound selected from the following group of compounds, or a pharmaceutically acceptable salt thereof:
3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}propanoic acid,
4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}butanoic acid,
2'-[(1R)-1-{[(2R)-3-{[1-(2,3-dihydro-1H-inden-2-yl)-2-methylpropan-2-yl]amino}-2-hydroxypropyl]oxy}ethyl]-3-methylbiphenyl-4-carboxylic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}propanoic acid,
2'-[(1R)-1-{[(2R)-3-{[1-(2,3-dihydro-1H-inden-2-ylmethyl)cyclopropyl]amino}-2-hydroxypropyl]oxy}ethyl]-3-methylbiphenyl-4-carboxylic acid,
5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pentanoic acid,
3-{2-[(1R)-1-{[(2R)-3-{[1-(2,3-dihydro-1H-inden-2-ylmethyl)cyclopropyl]amino}-2-hydroxypropyl]oxy}ethyl]phenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoic acid,
3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoic acid,
3-{2-chloro-6-[(1R)-1-{[(2R)-3-{[1-(2,3-dihydro-1H-inden-2-yl)-2-methylpropan-2-yl]amino}-2-hydroxypropyl]oxy}ethyl]phenyl}propanoic acid,
3-{2-[(1R)-1-{[(2R)-3-{[2-(2,3-dihydro-1H-inden-2-yl)-1,1-dimethylethyl]amino}-2-hydroxypropyl]oxy}propyl]-6-methoxyphenyl}propanoic acid,
3-{2-[(1R)-1-{[(2R)-3-{[2-(2,3-dihydro-1H-inden-2-yl)-1,1-dimethylethyl]amino}-2-hydroxypropyl]oxy}ethyl]-6-ethoxyphenyl}propanoic acid,
3-{2-[(1R)-1-{[(2R)-3-{[2-(2,3-dihydro-1H-inden-2-yl)-1,1-dimethylethyl]amino}-2-hydroxypropyl]oxy}ethyl]-4-fluoro-6-methoxyphenyl}propanoic acid.

(14)
The compound described in any one selected from (1) to (13) or a pharmaceutically acceptable salt thereof for use as a calcium receptor antagonist.

(15)
A pharmaceutical composition which comprises the compound described in any one selected from (1) to (13) above or a pharmaceutically acceptable salt thereof as an effective component.

(16)
The pharmaceutical composition described in (15) above for use as a calcium receptor antagonist.

(17)
The pharmaceutical composition described in (15) above for use for treatment or prevention of a disorder associated with abnormal bone or mineral homeostasis.

(18)
The pharmaceutical composition described in (17) above, wherein the disorder associated with abnormal bone or mineral homeostasis is hypoparathyroidism; osteosarcoma; periodontitis; bone fracture healing; deformative arthritis; rheumatoid arthritis; Paget's disease; humoral hypercalcemia syndrome associated with malignant tumor and bone fracture healing; or osteoporosis.

(19)
The pharmaceutical composition described in (17) above, wherein the disorder associated with abnormal bone or mineral homeostasis is osteoporosis.

(20)
A method of improving bone metabolism which is characterized in that an effective amount of the pharmaceutical composition described in (15) above is administered to a mammal.

(21)
A method of preventing or treating osteoporosis which is characterized in that an effective amount of the pharmaceutical composition described in (15) above is administered to a mammal.

Effects of the Invention

The compounds of the invention or pharmaceutically acceptable salts thereof are useful for treatment or prophylaxis of a disorder associated with abnormal bone or mineral homeostasis, for example, hypoparathyroidism, osteosarcoma, periodontitis, bone fracture healing, deformative arthritis, rheumatoid arthritis, Paget's disease, humoral hypercalcemia syndrome associated with malignant tumor and bone fracture healing, and osteoporosis.

BEST MODE FOR CARRYING OUT THE INVENTION

The invention will be explained hereinbelow.
Preferred examples of the compounds having the Formula (I) include those having the combination of substituent groups as follows.
A and D are a single bond,
$R^{2a}$ and $R^{2b}$, the same or different from each other, represent a hydrogen atom, a fluorine atom, a chlorine atom, a cyano group, a methyl group, a methoxy group, a trifluoromethyl group, or a trifluoromethoxy group,
$R^{3a}$ and $R^{3b}$, the same or different from each other, represent a hydrogen atom, a fluorine atom, a chlorine atom, a cyano group, a methyl group, a methoxy group, an ethoxy group, a trifluoromethyl group, or a trifluoromethoxy group,
$R^4$ and $R^5$ represent methyl groups or an ethylene group, $R^6$ represents a methyl group or an ethyl group, Z is a carboxy group, and m is 2 to 4.

More preferred examples of compounds having the Formula (I) include those described in the Examples.

A "halogen atom" refers to a fluorine atom, a chlorine atom, a bromine atom, or an iodine atom, for example, and it is preferably a fluorine atom or a chlorine atom.

A "C1-C6 alkyl group" refers to a linear or branched alkyl group having 1 to 6 carbon atoms, and it is preferably a methyl group, an ethyl group, a propyl group, an isopropyl group, or a t-butyl group, more preferably a methyl group.

A "C1-C6 alkoxy group" refers to a group in which an oxygen atom is bonded to the above-mentioned "C1-C6 alkyl group", and it is preferably a methoxy group, an ethoxy group, a propoxy group, an isopropoxy group, or a t-butoxy group, more preferably a methoxy group.

A "C1-C6 halogenated alkyl group" refers to a group in which a halogen atom is substituted on the above-mentioned "C1-C6 alkyl group". Examples thereof include a fluoromethyl group, a difluoromethyl group, a trifluoromethyl group, a fluoroethyl group, a difluoroethyl group, and a trifluoroethyl group, and preferably a trifluoromethyl group.

A "C1-C6 halogenated alkoxy group" refers to a group in which a halogen atom is substituted on the above-mentioned "C1-C6 alkoxy group". Examples thereof include a fluoromethoxy group, a difluoromethoxy group, a trifluoromethoxy group, a fluoroethoxy group, a difluoroethoxy group, and a trifluoroethoxy group, and preferably a trifluoromethoxy group.

A "C2-C6 alkylene group" refers to a linear or branched alkylene group having 2 to 6 carbon atoms, and it is preferably an ethylene group or a propylene group, and more preferably an ethylene group.

The "treatment" means treating or improving a disorder or a symptom, or inhibiting a symptom.

A "pharmaceutically acceptable salt thereof" refers to a salt which can be used as a pharmaceutical agent. The compound of the invention can be converted to a base salt or an acid salt by reacting it with a base or an acid when the compound has an acidic group or a basic group, and these salts are therefore referred to.

Examples of a pharmaceutically acceptable "base salt" of the compound of the invention preferably include salts of an alkali metal salt such as sodium salt, potassium salt, and lithium salt; salts of an alkaline earth metal such as magnesium salt and calcium salt; salts of an organic base such as N-methylmorpholine salt, triethylamine salt, tributylamine salt, diisopropyl ethylamine salt, dicyclohexylamine salt, N-methylpiperidine salt, pyridine salt, 4-pyrrolidinopyridine salt, and a picoline salt, or salts of an amino acid such as glycine salt, lysine salt, arginine salt, ornithine salt, glutamic acid salt, and asparaginic acid salt. Preferably, it is a salt of an alkali metal.

Preferred examples of the pharmaceutically acceptable "acid salt" of the compound of the invention include salts of a hydrogen halide acid such as hydrogen fluoride salt, hydrogen chloride salt, hydrogen bromide salt, and hydrogen iodide salt, salts of an inorganic acid such as nitrate salt, perchlorate salt, sulfate salt, or phosphate salt; lower alkane sulfonate salts such as methanesulfonate salt, trifluoromethanesulfonate salt, or ethanesulfonate salt, arylsulfonate salts such as benzene sulfonate salt or p-toluenesulfonate salt; salts of an organic acid such as acetate salt, malate salt, fumarate salt, succinate salt, citrate salt, ascorbate salt, tartarate salt, oxalate salt, or maleate salt; and, salts of an amino acid such as glycine salt, lysine salt, arginine salt, ornithine salt, glutamic acid salt, and asparaginic acid salt. Most preferably, it is a salt of hydrogen halide acid.

The compound or pharmaceutically acceptable salt thereof of the invention may be added with adsorption water or become a hydrate by incorporating water molecules by being left in the atmosphere or by recrystallization, and such hydrates as well as solvates and crystal polymorphs are also included in the invention. The compound, a salt thereof, or a solvate of the compound or salt of the invention may have various isomers such as a geometric isomer such as cis form, and trans form, or an optical isomer such as a tautomer, or a d form, and a 1 form, etc., depending on type and combination of the substituent groups. Unless specifically limited, the compounds of the invention include all isomers, stereoisomers, and mixtures of isomers and stereoisomers in any ratio. The mixtures of isomers can be resolved by resolution means that are well known in the art.

The compound of the invention includes labeled compounds, i.e., compounds in which one or more atoms of the compound of the invention is substituted with an isotope (for example, $^2H$, $^3H$, $^{13}C$, $^{14}C$, and $^{35}S$, etc.).

The invention includes pharmaceutically acceptable prodrugs of the compound of the invention. By pharmaceutically acceptable prodrug is meant a compound having a group which can be converted to an amino group, a hydroxy group, or a carboxy group, etc. of the compound of the invention by hydrolysis or under physiological conditions. Examples of groups which form such prodrugs include those described in Prog. Med., Vol. 5, pages 2157-2161, 1985 or "Development of Drugs", Molecular Design (Hirokawa Shoten, 1990), Vol. 7, pages 163-198. Specific examples of prodrugs include, when an amino group is present in the compound of the invention, a compound in which the amino group is acylated, alkylated, or phosphorylated (e.g., a compound in which the amino group is eicosanoylated, alanylated, or pentylaminocarbonylated, (5-methyl-2-oxo-1,3-dioxolen-4-yl)methoxycarbonylated, tetrahydrofuranylated, pyrrolidylmethylated, pyvaloyloxymethylated, or tert-butylated, etc.), etc. When a hydroxy group is present in the compound of the invention, examples include a compound in which the hydroxy group is acylated, alkylated, phosphorylated, or borated (e.g., a compound in which the hydroxy group is acetylated, palmitoylated, propanoylated, pivaloylated, succinylated, fumarylated, alanylated, or dimethylaminomethyl carbonylated, etc.), etc. Further, when a carboxy group is present in the compound of the invention, examples include a compound in which the carboxy group is esterified or amidated (e.g., a compound in which the carboxy group is ethyl esterified, phenyl esterified, carboxymethyl esterified, dimethylamino methyl esterified, pivaloyl oxymethyl esterified, ethoxycarbonyl oxyethyl esterified, amidated, or methyl amidated, etc.), etc.

Further, the invention includes compounds in which functional group of the compound of the invention is substituted with a so-called equivalent group. Examples of so-called equivalent groups include those described in The Practice of Medicinal Chemistry (Camille Georges Wermuth, Academic Press, 1996), for example. In particular, equivalent groups to a carboxy group are described at pages 215-217 of The Practice of Medicinal Chemistry.

(Production Process)

The compound of the invention can be produced by applying various well-known synthetic methods according to the characteristics that are based on the main skeleton or type of substituent groups of the compound. Examples of well-known methods include those described in "ORGANIC FUNCTIONAL GROUP PREPARATIONS", $2^{nd}$ edition, ACADEMIC PRESS, INC., 1989 or "Comprehensive Organic Transformations", VCH Publishers Inc., 1989.

In such case, depending on the type of functional group, it may be effective in terms of production techniques to protect the functional group with an appropriate protecting group during a raw material to intermediate step or to substitute the functional group with a group which can be easily converted.

Examples of functional groups include an amino group, a hydroxy group, and a carboxy group, etc., and protecting groups therefor include those described in "Protective groups in Organic Synthesis", written by T. W. Greene and P. G. Wuts, 3$^{rd}$ edition, (1999). Depending on the reaction conditions, they can be appropriately selected and used. According to these methods, the protecting group is introduced, the reaction is carried out, and if necessary, the protecting group is removed or converted to a desired group to obtain a desired compound.

Further, a prodrug of the compound of the invention can be produced by introducing a certain group during a raw material to intermediate step, in the same way as the protecting group described above, or by carrying out the reaction using the obtained compound of the invention. The reaction can be carried out by applying methods well known to a person skilled in the art based on typical esterification, amidation, dehydration, or hydrogenation, etc.

Hereinbelow, processes for production of the compounds of the invention will be explained. However, the production process is not limited to the following processes.

Process A

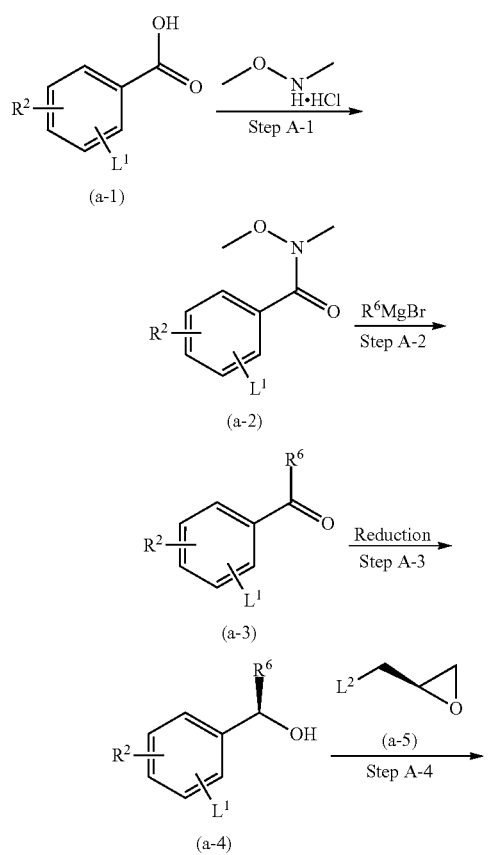

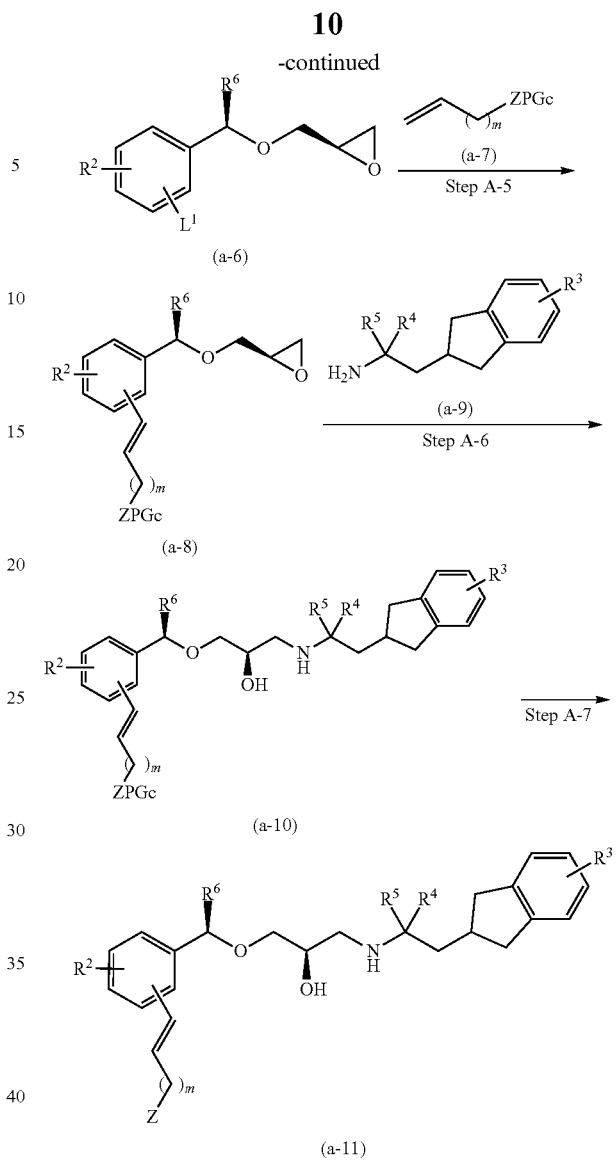

[in the formula, $R^2$ and $R^3$ each has the same meanings as $R^{2a}$ or $R^{2b}$ and $R^{3a}$ or $R^{3b}$, $R^4$, $R^5$, Z, and m have the same meanings as above, $R^6$ represents a C1-C6 alkyl group, $L^1$ and $L^2$ represent a leaving group for the substitution reaction, and PGc represents a protecting group for a carboxy group or a group equivalent to a carboxy group.]

Step A-1:

This step is a method of producing the compound (a-2) by using the compound (a-1), i.e., substituted benzoic acid, and N,O-dimethylhydroxylamine hydrochloride salt, and it can be produced according to the method described in Tetrahedron 1999, 55, 13159-13170 by Kunishima et. al.

Step A-2:

This step is a step of producing the compound (a-3), i.e., a ketone, by using the compound (a-2) and a Grignard reagent.

Step A-3:

This step is a step of converting the compound (a-3) into the compound (a-4) by reducing the ketone.

Step A-4:

This step is a step of producing the compound (a-6) by coupling the compound (a-4) to the compound (a-5).

Step A-2 to Step A-4 can be performed according to the method described at page 40 of International Publication Pamphlet No. WO 02/14259. More specifically, Step A-2 can be performed according to Step 2 of Example 23 that is described at page 49 of WO 02/14259. Step A-3 can be performed according to Step 1 of Example 21 that is described at page 66 of WO 02/14259. Step A-4 can be performed according to Step 2 of Example 1 that is described at page 50 of WO 02/14259.

Step A-5:

This step is a step of producing the compound (a-8) by a coupling reaction between the compound (a-6) and the compound (a-7).

Step A-6:

This step is a step of producing the compound (a-10) by a coupling reaction between the compound (a-8) and the compound (a-9).

Step A-7:

This step is a step of producing the compound (a-11) by deprotecting the protecting group of the compound (a-10).

Step A-5 to Step A-7 can be performed according to the reaction example that is described at page 61 of WO 04/106280. More specifically, Step A-5 can be performed based on Step 2 of Example 1 that is described at page 67 of WO 04/106280. Step A-6 can be performed according to Step 4 of Example 1 that is described at page 68 of WO 04/106280. Step A-7 can be performed according to Step 5 of Example 1 that is described at page 68 of WO 04/106280.

Process B

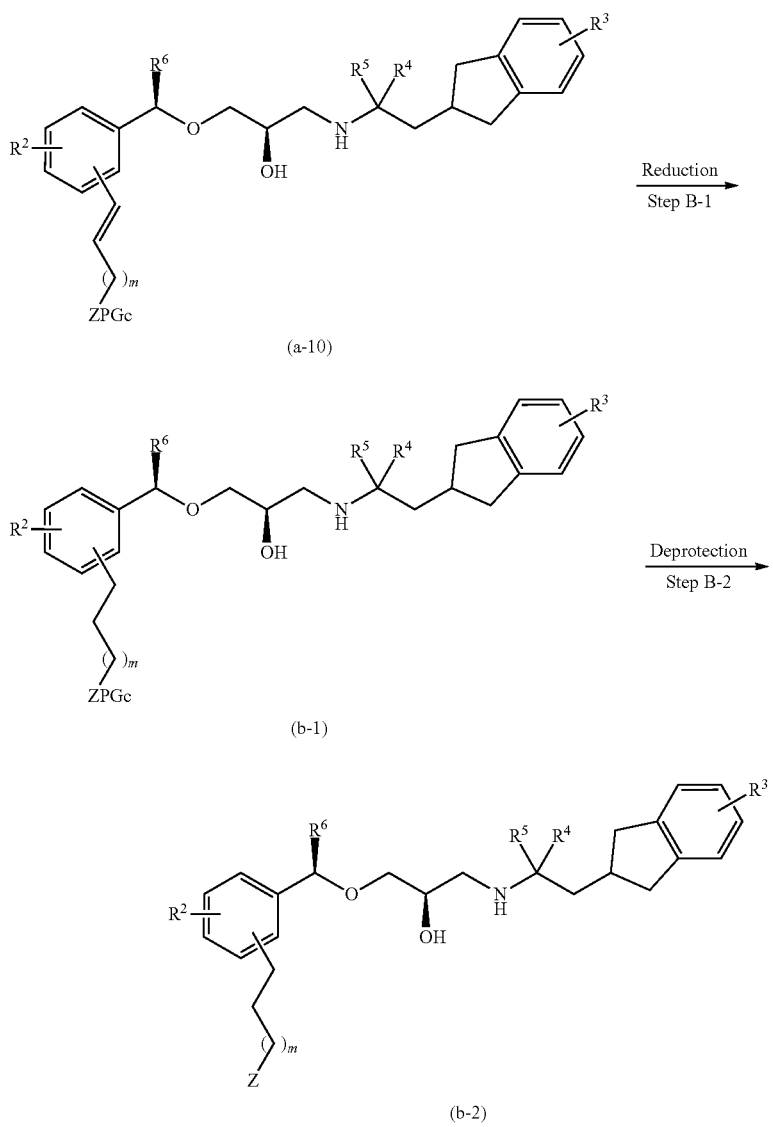

[in the formula,
$R^2$, $R^3$, $R^4$, $R^5$, $R^6$, Z, PGc, and m have the same meanings as above.]

Step B-1:

This step is a step of producing the compound (b-1) by reducing the compound (a-10).

Step B-2:

This step is a step of producing the compound (b-2) by deprotecting the protecting group of the compound (b-1).

Step B-1 can be performed according to the Example 2 shown at page 16 of WO 2005/077886. Step B-2 can be carried out in the same manner as the Step A-7 described above.

Process C

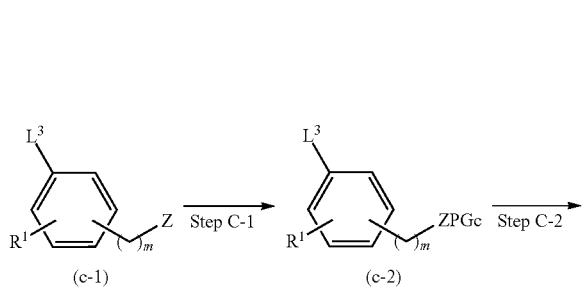

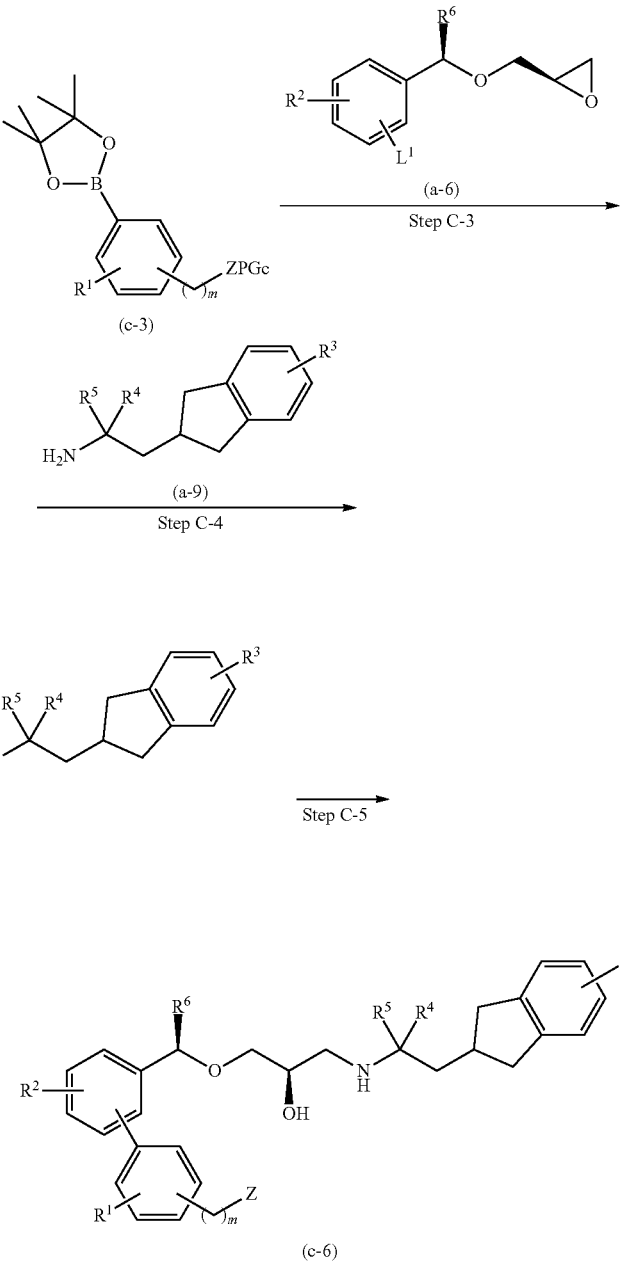

[in the formula,
$R^1$, $R^2$, $R^3$, $R^4$, $R^5$, $R^6$, Z, $L^1$, PGc, and m have the same meanings as above and $L^3$ represents a leaving group for the substitution reaction.]

Step C-1:
This step is a step of protecting the carboxylic acid of the compound (c-1) or an equivalent group thereof with a protecting group.

Step C-2:
This step is a step of producing the compound (c-3), i.e., boron ester, by a coupling reaction.

Step C-3:
This step is a step of producing the compound (c-4) by a coupling reaction between the compound (c-3) and the compound (a-6) using a catalyst.

Step C-4:
This step is a step of producing the compound (c-5) by a coupling reaction between the compound (c-4) and the compound (a-9) via a substitution reaction on the epoxide.

Step C-5:
This step is a step of producing the compound (c-6) by deprotecting the protecting group of the compound (c-5).

Step C-1 to Step C-5 can be performed according to the reaction example shown at page 77 of WO 2004/094362. More specifically, Step C-1 can be performed according to Step 2 of Example 1-1 that is described at page 99 of WO 2004/094362. Step C-2 and Step-C-3 can be performed according to Step 3 of Example 1-1 that is described at page 100 of WO 2004/094362. Step C-4 can be performed according to Step 8 of Example 1-1 that is described at page 103 of WO 2004/094362. Step C-5 can be performed according to Step 9 of Example 1-1 that is described at page 103 of WO 2004/094362.

The compound (a-9) can be performed according to the reaction example and Example 1 of WO 01/53254, which are described at page 15 and 23, respectively.

The compound (d-2) can be produced according to the following Process D.

Process D

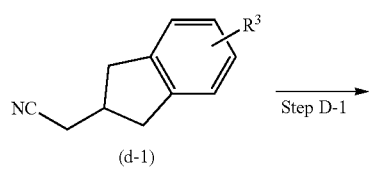

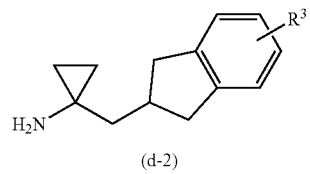

[in the formula,
R³ has the same meaning as above.]

Step D-1:

It can be performed according to the method described in J. Org. Chem. 2002, 67, 3965-3968 by using the compound (d-1) disclosed in WO 98/05651.

Process E

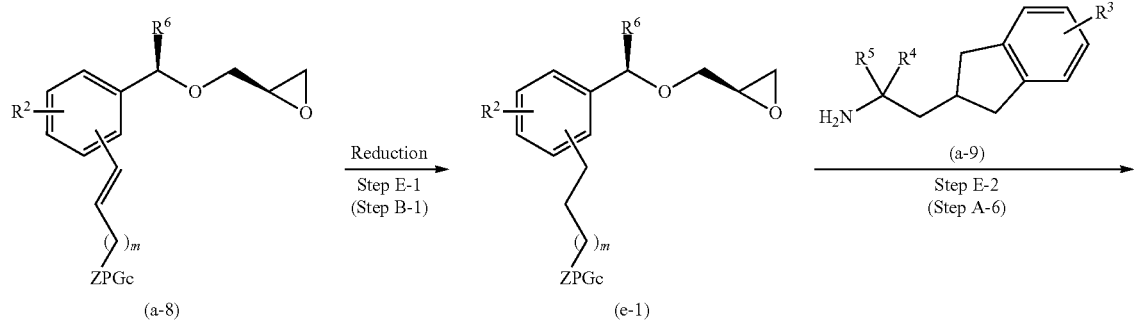

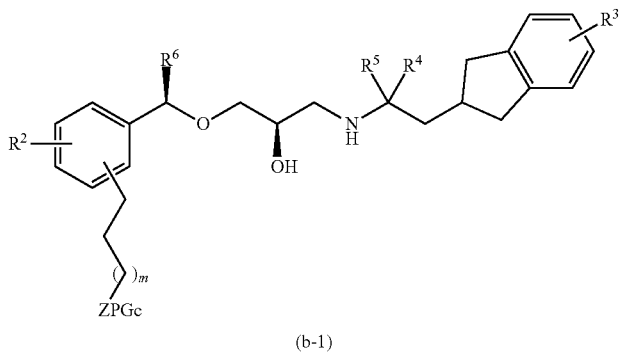

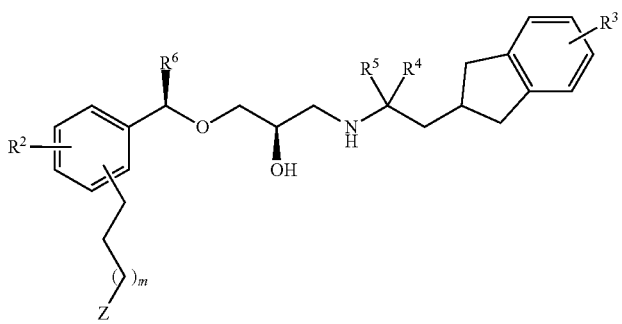

[in the formula,
$R^2, R^3, R^4, R^5, R^6, Z, L^1$, PGc, and m have the same meanings as above.]

Process E is a method of producing the compound (b-2) of the invention, similar to Process B.

Step E-1:

This step is a step of producing the compound (e-1) from the compound (a-8) by carrying out a reduction reaction in the same manner as Step B-1.

Step E-2:

This step is a step of producing the compound (b-1) by carrying out a coupling reaction in the same manner as Step A-6.

Step E-3:

This step is a step of producing the compound (b-2) by carrying out a deprotection reaction of a protecting group in the same manner as Step B-2.

Process F is a method to produce the compound (a-3)', which is a production intermediate of the compounds of the invention.

Process F

[Chemical structures: (f-1) → (f-2) → (a-3)']

[in the formula, $R^6$ and $L^1$ have the same meanings as above, $R^{2'}$ represents a C1-C6 alkyl group or a halogeno C1-C6 alkyl group, and PGh represents a protecting group for hydroxy group.]

Step F-1:

This step is a step of producing the compound (f-2) by deprotecting the protecting group for the hydroxy group of the compound (f-1).

Step F-2:

This step is a step of producing the compound (a-3)' by reacting the hydroxy group of the compound (f-2) with an alkylating reagent.

Process G is a method to produce the compound (a-1), which is a production intermediate of the compound of the invention.

Process G

[Chemical structures: (g-1) → (g-2) → (f-3) → (a-1)]

[in the formula, $R^2, L^1$, and PGc have the same meanings as above, and X represents a halogen group.]

Step G-1:

This step is a step of producing the compound (g-2) by carrying out a CO insertion reaction of the compound (g-1) in the presence of a palladium catalyst.

Step G-2:

This step is a step of producing the compound (g-3) by converting the amino group of the compound (g-2) to a leaving group.

Step G-3:

This step is a step of producing the compound (a-1) by deprotecting the protecting group for the carboxy group of the compound (g-3).

Process H is a method to produce the compound (a-3)", which is a production intermediate of the compound of the invention.

Process H

[Chemical structures: (h-1) → (h-2) → (a-3)"]

[in the formula, $R^2$ and $L^2$ have the same meanings as above.]

Step H-1:

This step is a step of producing the compound (h-2) by reacting the compound (h-1) with an organo tin compound in the presence of a palladium catalyst.

Step H-2:

This step is a step of producing the compound (c-3)" by carrying out the same reaction as Step G-2 above.

Process I is a method to produce the compound (c-3), which is a production intermediate of the compound of the invention.

Process I

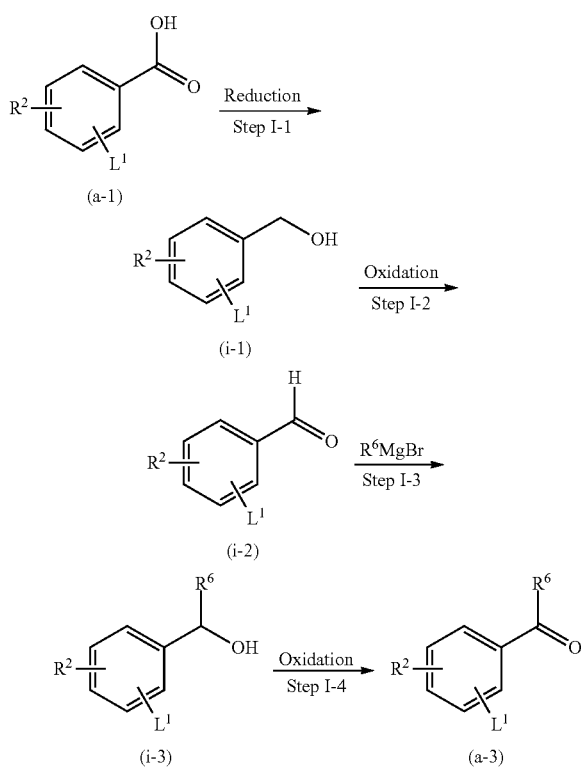

[in the formula, $R^2$, $R^6$, and $L^2$ have the same meanings as above.]

Step I-1:
This step is a step of producing the compound (i-1) by reducing the carboxy group of the compound (a-1).

Step I-2:
This step is a step of producing the compound (i-2) by oxidizing the hydroxy group of the compound (i-1) to an aldehyde.

Step I-3:
This step is a step of producing the compound (i-3) by reacting the compound (i-2) with a Grignard reagent.

Step I-4:
This step is a step of producing the compound (a-3) by oxidizing the hydroxy group of the compound (i-3) to a ketone.

Process J is a method to produce the compound (a-4)', which is a production intermediate of the compound of the invention.

Process J

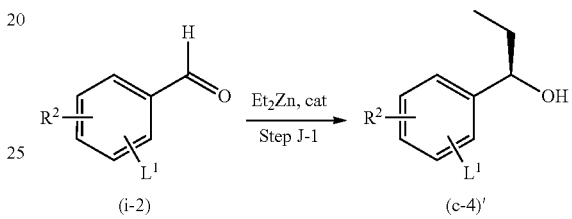

[in the formula, $R^2$ and $L^2$ have the same meanings as above.]

Step J-1:
This step is a step of producing the compound (a-4)' by reacting the aldehyde group of the compound (i-2) with an organo zinc reagent.

Process K

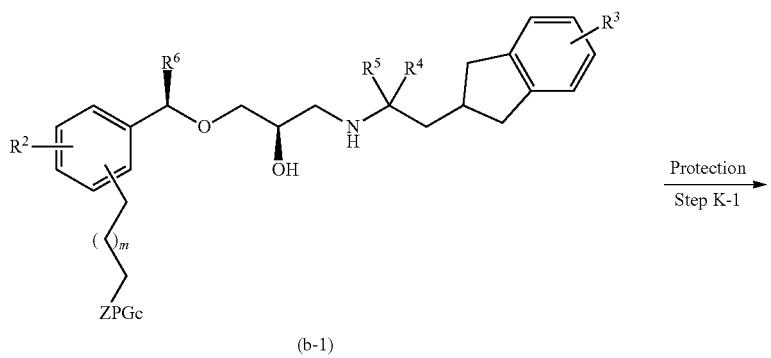

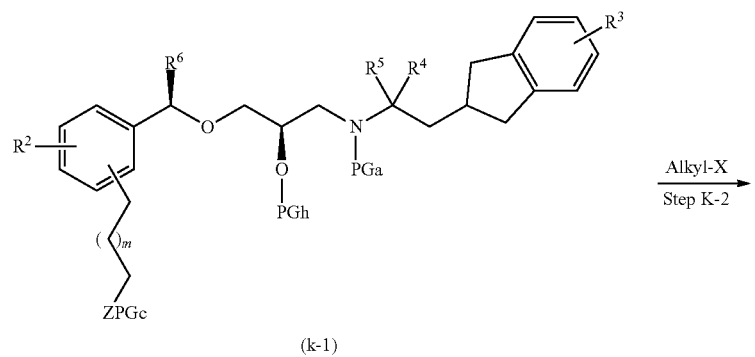

-continued

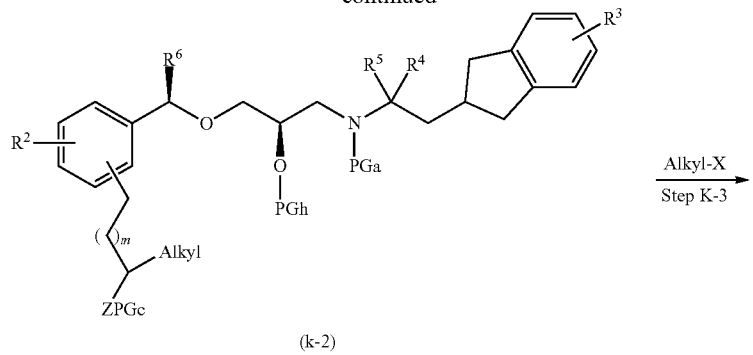

(k-2)

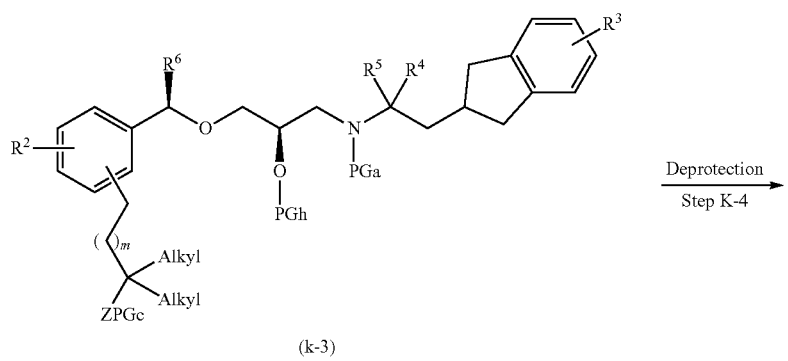

(k-3)

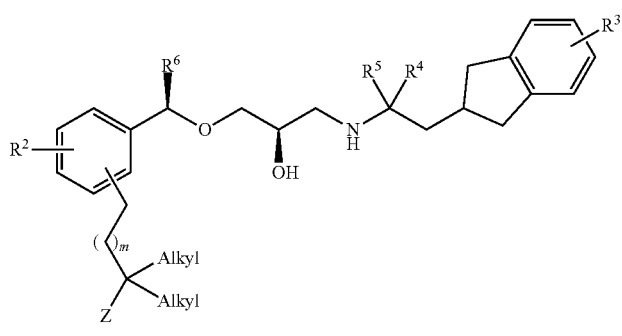

(k-4)

[in the formula, $R^2$, $R^3$, $R^4$, $R^5$, $R^6$, m, Z, PGc, PGh, PGa, and X have the same meanings as above, and Alkyl represents a C1-C6 alkyl group.]

Step K-1:
This step is a step of producing the compound (k-1) by protecting the secondary hydroxy group and amino group of the compound (b-1).

Step K-2 and Step K-3:
This step is a step of producing the compound (k-3) by stepwise alkylation of the compound (k-1).

Step K-4:
This step is a step of producing the compound (k-4) by deprotecting the protecting group of the compound (k-3).

Process L

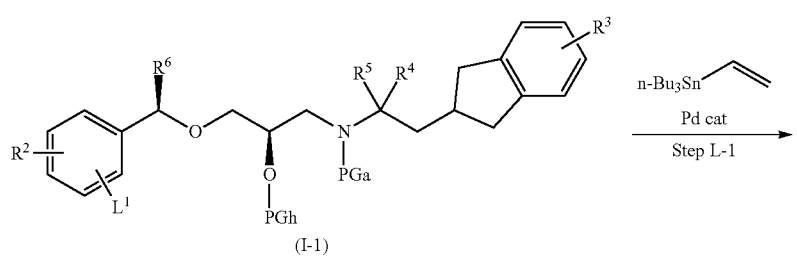

(I-1)

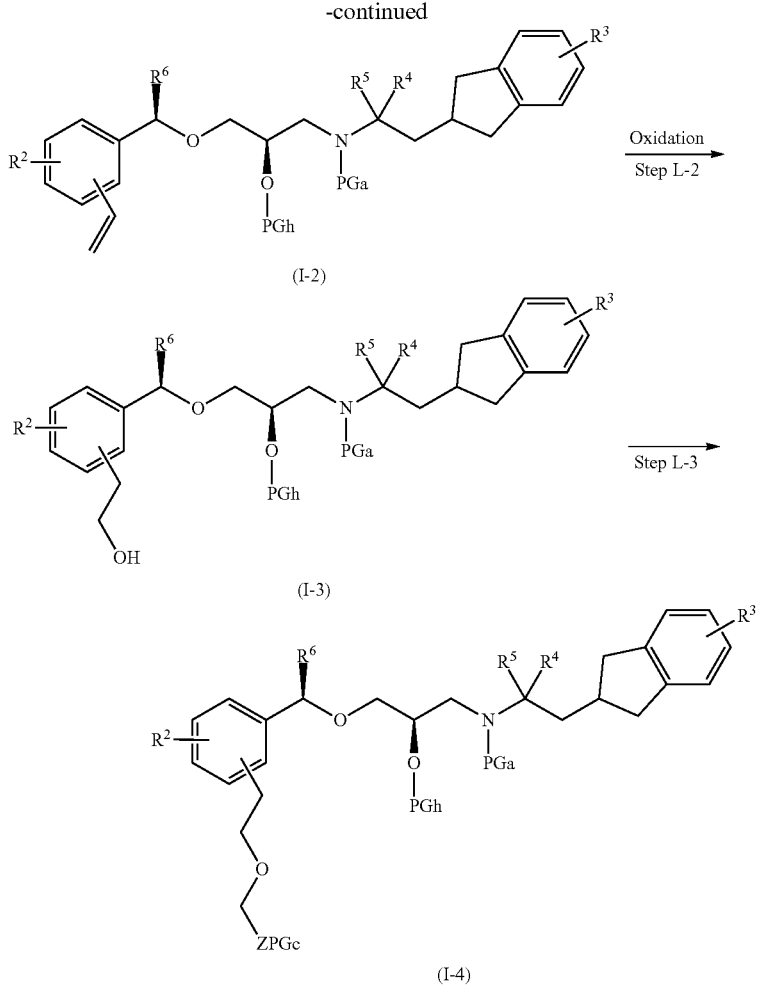

[in the formula, $R^2$, $R^3$, $R^4$, $R^5$, $R^6$, Z, PGc, PGh, and PGa have the same meanings as above.]

Step L-1:

This step is a step of producing the compound (l-2) by reacting the compound (l-1) with an organo tin compound in the presence of a palladium catalyst.

Step L-2:

This step is a step of producing the compound (l-3) via introduction of a primary hydroxy group by carrying out a hydroboration-oxidation reaction of the compound (l-2).

Step L-3:

This step is a step of producing the compound (l-4) via introduction of a carboxy group by carrying out an etherification reaction of the primary hydroxy group of the compound (l-3).

The compounds of the invention that are produced according to the methods described above can be isolated or purified according to well-known methods, for example, extraction, precipitation, distillation, chromatography, fractional recrystallization, and recrystallization, etc.

Further, when the compound having Formula (I) of the invention or an intermediate during the production process has a chiral carbon, optical isomers are present. The optical isomers can be isolated and purified into individual isomers according to general methods like fractional recrystallization (salt resolution) which involves recrystallization with an appropriate salt or column chromatography, etc. Examples of literature for referring to methods of resolving optical isomers from racemates include "Enantiomers, Racemates and Resolution, John Wiley And Sons, Inc." by J. Jacques, etc.

The compounds of the invention or pharmaceutically acceptable salts thereof are useful for treatment or prophylaxis of a disorder associated with abnormal bone or mineral homeostasis, for example, hypoparathyroidism, osteosarcoma, periodontitis, bone fracture healing, deformative arthritis, rheumatoid arthritis, Paget's disease, humoral hypercalcemia syndrome associated with malignant tumor and bone fracture healing, and osteoporosis.

When the compound or pharmaceutically acceptable salt thereof of the invention is administered to a mammal (in particular, a human), oral or parenteral administration can be used, either systemically or topically.

The pharmaceutical composition of the invention can be produced according to various methods for producing preparations that are generally used, after selecting the form which is suitable for the administration method.

Examples of forms of orally administered pharmaceutical composition include a tablet, a pill, a powder, a granule, a capsule, a liquid, a suspension, an emulsion, a syrup, and an elixir, etc. Preparation of the pharmaceuticals in such forms can be carried out according to typical methods, if necessary, using an additive that is appropriately selected from an excipient, a binding agent, a disintegrant, a lubricant, a swelling agent, a swelling aid, a coating agent, a plasticizer, a stabilizer, a preservative, an anti-oxidant, a coloring agent, a dissolving aid, a suspending agent, an emulsifying agent, a sweetening agent, a preserving agent, a buffering agent, a diluting agent, and a wetting agent, etc., which are normally used as additives.

Examples of parenteral pharmaceutical compositions include an injection solution, an ointment, a gel, a cream, a wet agent, a patch, a propellant agent, a spraying agent, an eye drop, a nasal drop, a suppository, and an inhaling agent, etc. Preparation of the pharmaceuticals in such forms can be carried out according to typical methods, if necessary, using an additive that is appropriately selected from a stabilizer, a preservative, a dissolving aid, a moisturizing agent, a preserving agent, an anti-oxidant, a flavoring agent, a gelling agent, a neutralizing agent, a dissolving aid, a buffering agent, an isotonicity agent, a surface active agent, a coloring agent, a buffering agent, a thickening agent, a wetting agent, a filler, an absorption promoter, a suspending agent, and a binding agent, etc which are normally used as additives.

The dose of the compound having Formula (I) or a pharmaceutically acceptable salt thereof varies depending on symptoms, age, body weight, and on the type and dosage of a pharmaceutical agent which is administered in combination, etc. However, in general, oral or parenteral administration can be used, either systemically or topically, once or several times per day within the range of 0.001 mg to 1000 mg per dose for an adult (with a body weight of about 60 kg) in terms of the compound having Formula (I), or continuous intravenous administration within the range of 1 hour to 24 hours per day is preferable.

Further, if necessary, the pharmaceutical composition of the invention can be used in combination with other effective components within a range which does not impair the effect of the invention.

The invention includes a method of preventing and/or treating the disorders described above which is characterized in that the compound of the invention or a pharmaceutically acceptable salt thereof is administered.

Still further, the invention includes the use of the compound of the invention or a pharmaceutically acceptable salt thereof for producing the pharmaceutical composition described above.

Formulation Example 1

Powders

A powder is obtained by mixing 5 g of the compound of the invention, 895 g of lactose, and 100 g of corn starch using a blender.

Formulation Example 2

Granules 5 g of the compound of the invention, 865 g of lactose, and 100 g of low-substituted hydroxypropyl cellulose are mixed, added with 300 g of 10% aqueous solution of hydroxypropyl cellulose, and kneaded. The mixture is granulated using an extrusion granulator and dried to obtain granules.

Formulation Example 3

Tablets 5 g of the compound of the invention, 90 g of lactose, 34 g of corn starch, 20 g of crystalline cellulose, and 1 g of magnesium stearate are mixed using a blender, and tabletted with a tabletting machine to obtain tablets.

Test Example 1

Evaluation of inhibitory activity on calcium-sensing receptor (CaSR) using intracellular calcium increase as an indicator By using CHO cells which have been transformed to stably express a human calcium-sensing receptor (CaSR) (CHO/hCaSR), CaSR antagonist activity was evaluated while the degree of inhibition of intracellular calcium increase by a test compound induced by increasing extracellular calcium concentration is taken as an indicator.

The preparation which is prepared by adding CHO/hCaSR to F12 medium (manufactured by Invitrogen) containing 10% fetal bovine serum to have $2 \times 10^5$ cells/mL was applied to a 384-well in an amount of 50 μL/well, and then incubated overnight in a $CO_2$ incubator. The culture supernatant was completely removed, the assay buffer (20 mM HEPES, HBSS (Ca and Mg free) containing 2.5 mM probenecid, pH 7.4) containing Calcium 3 (manufactured by Molecular Devices), i.e., a fluorescent intracellular calcium indicator, was added thereto in an amount of 25 μL/well, and the mixture was maintained for 1 hour in a $CO_2$ incubator. Meanwhile, Calcium 3 was prepared according to the protocol enclosed in FLIPR Calcium 3 Assay Kit (manufactured by Molecular Devices). After maintaining it for 1 hour, a solution in which the test compound is prepared to have 2.1 to 20,000 nM (final concentration of 1.05 to 10,000 nM) by an assay buffer was added thereto in an amount of 25 μL/well, and maintained for 15 minutes in a $CO_2$ incubator. Then, the $CaCl_2$ solution prepared to have 8.1 nM (final concentration of 2.7 nM) by using the assay buffer was added in an amount of 25 μL/well, and the resulting intracellular Ca increase (i.e., fluorescence intensity) was measured over time using a fluorescence imaging plate reader (FLIPR, manufactured by Molecular Devices). From the data obtained, the difference between the fluorescence intensity before the addition of $CaCl_2$ solution and the maximum fluorescence intensity after the addition of $CaCl_2$ solution was calculated, and the 50% inhibition concentration ($IC_{50}$) of the test compound was obtained.

According to the present test, the compounds shown in Examples 1, 2, 3, 4, 5, 6, 7, 8, 9, 10, 11, 12, 13, 14, 16, 17, 18, 21, 22, 23, 25, 26, 27, 29, 30, 31 low polarity, 32, 33, 34, 35, 36, 37, 38, 39, 40, 41, 42, 43, 44, 45, 46, 47, 48, 49, 50, 51, 52, 53, 54, 55, 56, 58, 60, 61, 62, 63, 64, 65, 66, 67, 68, 69, 70, 71, 72, 73, 74, 75, 76, 77, 78, 79, 80, 81, 82, 83, and 85 exhibited an inhibitory activity $IC_{50}$ of 1.1 μg/mL or less.

Test Example 2

Evaluation of PTH Secretion Promoting Activity in Rat

A 10 to 14-week old female F344 rat (Charles River Japan, Inc.) fasted overnight was anesthetized using ether, and blood serum before the administration was prepared by drawing blood from the jugular vein of the animal. Subsequently, the test compound was orally administered at a dose of 3 mg/5 mL/kg using a solvent (0.5% aqueous methyl cellulose solution containing 5% DMA). Blood was drawn from the jugular vein under ether anesthesia at 5, 15, 30, 60, 120, and 240 minutes after the administration of the test compound, and the blood serum was prepared. The blood serum PTH concentration was measured using rat Intact PTH ELISA kit (manufactured by Immutopics, Inc.).

According to the present test, the compounds shown in Examples 1, 2, 3, 4, 5, 7, 8, 9, 11, 13, 14, 17, 18, 21, 22, 23, 26, 27, 29, 33, 35, 37, 38, 39, 40, 41, 42, 43, 44, 45, 46, 47, 48, 52, 53, 60, 61, 62, 63, 66, 67, 69, 70, 71, 73, 75, 76, and 78 increased the blood serum PTH concentration from 100 pg/mL or less at 0 minute to 400 pg/mL or more at 15 minutes to 30 minutes, and after 240 minutes it reduced the concentration to 200 pg/mL or less.

Specific results are given in Table 1 and Table 2.

TABLE 1

| | Blood Serum PTH (1-84) Concentration (pg/mL) | | | |
|---|---|---|---|---|
| Test compound | 0 minute | After 5 minutes | After 15 minutes | After 30 minutes |
| Example 4 | 20.5 ± 6.6 | 68.2 ± 6.0 | 489.1 ± 106.0 | 538.6 ± 155.1 |
| Example 14 | 62.8 ± 11.4 | 211.6 ± 28.4 | 471.7 ± 112.8 | 146.1 ± 45.2 |

TABLE 2

| | Blood Serum PTH (1-84) Concentration (pg/mL) | | |
|---|---|---|---|
| Test compound | After 60 minutes | After 120 minutes | After 240 minutes |
| Example 4 | 117.0 ± 33.7 | 108.8 ± 27.4 | 91.9 ± 24.5 |
| Example 14 | 78.9 ± 5.0 | 81.8 ± 4.9 | 94.3 ± 15.7 |

Means ± S.D., n = 3

EXAMPLES

Example 1

3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}propanoic acid (1a) Methyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}prop-2-enoate A mixture of methyl (2E)-3-(2-{(1R)-1-[(2R)-oxiran-2-yl methoxy]ethyl}phenyl)prop-2-enoate (342 mg, 1.30 mmol) described in WO 2004/106280, 1-(2,3-dihydro-1H-inden-2-yl)-2-methylpropan-2-amine (234 mg, 1.24 mmol) described in WO 01/53254, and lithium perchlorate (79 mg, 0.74 mmol) in toluene (12 mL) was stirred at room temperature for 16 hours. Water (10 mL) was added to the reaction solution, which was then extracted with ethyl acetate (10 mL×3). After that, the organic layers were combined, washed with saturated brine, and washed with anhydrous magnesium sulfate. The solvent was distilled off under reduced pressure. The residue was purified by silica gel column chromatography (ethyl acetate) to give the title compound as a colorless oily substance (206 mg, yield 37%).

(1b) Methyl 3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}propanoate A solution of methyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}prop-2-enoate (206 mg, 0.46 mmol), which had been obtained in Example 1(1a), in ethanol (4.6 mL) was added with 10% palladium-carbon (wet, 50 wt %, 100 mg), and hydrogenated under atmospheric pressure for 3 hours. The reaction solution was filtered through Celite and washed with ethanol. The solvent was distilled off under reduced pressure to give the title compound as a colorless oily substance (209 mg, quantitative).

(1c) 3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}propanoic acid To a mixture solution of methyl 3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}propanoate (209 mg, 0.46 mmol), which had been obtained in Example 1(1b), in tetrahydrofuran (1.38 mL) and methanol (1.38 mL), 2 N aqueous sodium hydroxide solution (0.69 mL, 1.38 mmol) was added, and stirred at room temperature for 16 hours. The reaction solution was concentrated under reduced pressure. The residue was added with water (10 mL), and subsequently with 1 N aqueous hydrogen chloride solution (1.38 mL), and then extracted with ethyl acetate (10 mL×2). The organic layers were combined, washed with saturated brine and dried over anhydrous magnesium sulfate. The solvent was distilled off under reduced pressure to give the title compound as a white amorphous substance (178 mg, yield 88%).

Example 2

4-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}butanoic acid (2a) Methyl (3E)-4-(2-{(1R)-1-[(2R)-oxiran-2-yl methoxy]ethyl}phenyl)but-3-enoate Under an argon atmosphere, a mixture of (2R)-2-{[(1R)-1-(2-bromophenyl)ethoxy]methyl}oxirane (1.00 g, 3.89 mmol) described in WO 2004/094362, methyl but-3-enoate (497 μL, 4.67 mmol), palladium acetate (II) (44 mg, 0.19 mmol), tris(2-methylphenyl)phosphine (59 mg, 0.19 mmol), and triethylamine (0.65 mL, 4.67 mmol) in acetonitrile (10 mL) was stirred with heating under reflux for 3 hours. The reaction solution was cooled to room temperature, filtered through Celite, and washed with acetonitrile. The solvent was distilled off under reduced pressure. The residue was purified by silica gel column chromatography (n-hexane/ethyl acetate=4/1) to give the title compound as a yellow oily substance (246 mg, yield 23%).

(2b) Methyl (3E)-4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}but-3-enoate By using methyl (3E)-4-(2-{(1R)-1-[(2R)-oxiran-2-yl methoxy]ethyl}phenyl)but-3-enoate which had been obtained in Example 2(2a), the reaction was carried out in the same manner as the method described in Example 1(1a) to give the title compound as a pale yellow oily substance (yield 18%).

(2c) Methyl 4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}butanoate By using methyl (3E)-4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}but-3-enoate which had been obtained in Example 2(2b), the reaction was carried out in the same manner as the method described in Example 1(1b) to give the title compound as a colorless oily substance (yield 81%).

(2d) 4-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}butanoic acid By using methyl 4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}butanoate which had been obtained in Example 2(2c), the reaction was carried out in the same manner as the method described in Example 1(1c) to give the title compound as a pale brown amorphous substance (yield 59%).

Example 3

2'-[(1R)-1-{[(2R)-3-{[1-(2,3-Dihydro-1H-inden-2-yl)-2-methylpropan-2-yl]amino}-2-hydroxypropyl]oxy}ethyl]-3-methylbiphenyl-4-carboxylic acid (3a) Methyl 2'-[(1R)-1-{[(2R)-3-{[1-(2,3-dihydro-1H-inden-2-yl)-2-methylpropan-2-yl]amino}-2-hydroxypropyl]oxy}ethyl]-3-methylbiphenyl-4-carboxylate By using methyl 3-methyl-2'-{(1R)-1-[(2R)-oxiran-2-yl methoxy]ethyl}biphenyl-4-carboxylate described in WO 2004/094362, the reaction was carried out in the same manner as the method described in Example 1(1a) to give the title compound as a colorless oily substance (yield 37%).

(3b) 2'-[(1R)-1-{[(2R)-3-{[1-(2,3-Dihydro-1H-inden-2-yl)-2-methylpropan-2-yl]amino}-2-hydroxypropyl]oxy}ethyl]-3-methylbiphenyl-4-carboxylic acid By using methyl 2'-[(1R)-1-{[(2R)-3-{[1-(2,3-dihydro-1H-inden-2-yl)-2-methylpropan-2-yl]amino}-2-hydroxypropyl]oxy}ethyl]-3-methylbiphenyl-4-carboxylate which had been obtained in Example 3(3a), the reaction was carried out in the same manner as the method described in Example 1(1c) to give the title compound as a white amorphous substance (yield 54%).

Example 4

3-{2-[(1R)-1-{[(2R)-3-{[1-(2,3-Dihydro-1H-inden-2-yl)-2-methylpropan-2-yl]amino}-2-hydroxypropyl]oxy}ethyl]-6-methylphenyl}propanoic acid (4a) (1R)-1-(2-Bromo-3-methylphenyl)ethanol (+)-B-chlorodiisopinocampheylborane (8.46 g, 26.4 mmol) was dissolved in tetrahydrofuran (150 mL), cooled to −20° C., slowly added dropwise with a solution of 1-(2-bromo-3-methylphenyl)ethanone (4.30 g, 20.3 mmol) described in US 2007/167506 in tetrahydrofuran (50 mL), and stirred for 18 hours. The reaction solution was added with diethanolamine (6.38 g, 60.8 mmol), cooled to room temperature, and stirred at room temperature for 3 hours. The reaction solution was concentrated under reduced pressure and added with n-hexane (100 mL). The precipitated solids were filtered off and the solvent was distilled off under reduced pressure. The residue was purified by silica gel column chromatography (n-hexane/ethyl acetate=4/1) to give the title compound as a white solid (4.30 g, yield 99%, 95.6% ee).

(4b) (2R)-2-{[(1R)-1-(2-Bromo-3-methylphenyl)ethoxy]methyl}oxirane (1R)-1-(2-bromo-3-methylphenyl)ethanol (2.00 g, 9.30 mmol) obtained in Example 4(4a) and (R)-glycidyl 3-nitrobenzene sulfonic acid (3.13 g, 12.1 mmol) were dissolved in N,N-dimethyl formamide (45 mL), added with sodium hydride (608 mg, content 55%, 14.0 mmol), and stirred at room temperature for 2 hours. The reaction solution was added with water and extracted with ethyl acetate. After that, the organic layer was washed with saturated brine, and dried over anhydrous magnesium sulfate. The solvent was distilled off under reduced pressure. The residue was purified by silica gel column chromatography (n-hexane/ethyl acetate=4/1) to give the title compound as a colorless oily substance (1.51 g, yield 60%).

(4c) Ethyl (2E)-3-(2-methyl-6-{(1R)-1-[(2R)-oxiran-2-yl methoxy]ethyl}-6-methylphenyl)prop-2-enoate (2R)-2-{[(1R)-1-(2-Bromo-3-methylphenyl)ethoxy]methyl}oxirane (1505 mg, 5.57 mmol), which had been obtained in Example 4(4b), ethyl prop-2-enoate (910 μL, 8.36 mmol), palladium acetate (II) (126 mg, 0.56 mmol), tris(2-methylphenyl)phosphine (170 mg, 0.56 mmol), and potassium carbonate (1537 mg, 11.1 mmol) were suspended in a mixture solvent (27.5 mL) of propionitrile-water (2:1), and stirred with heating under reflux for 5 hours. The reaction solution was cooled to room temperature, filtered by using Millicup (registered trademark, manufactured by Millipore), and washed with ethyl acetate. The organic layer was washed with water and saturated brine, and then dried over anhydrous magnesium sulfate. After that, the solvent was distilled off under reduced pressure. The residue was purified by silica gel column chromatography (n-hexane/ethyl acetate=4/1) to give the title compound as a pale yellow oily substance (1025 mg, yield 63%).

(4d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}prop-2-enoate By using ethyl (2E)-3-(2-methyl-6-{(1R)-1-[(2R)-oxiran-2-yl methoxy]ethyl}phenyl)prop-2-enoate which had been obtained in Example 4(4c), the reaction was carried out in the same manner as the method described in Example 1(1a) to give the title compound as a colorless oily substance (yield 37%).

(4e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}prop-2-enoate which had been obtained in Example 4(4d), the reaction was carried out in the same manner as the method described in Example 1(1b) to give the title compound as a colorless oily substance (yield 95%).

(4f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-6-methylphenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoate which had been obtained in Example 4(4e), the reaction was carried out in the same manner as the method described in Example 1(1c) to give the title compound as a white amorphous substance (yield 87%).

Example 5

3-{2-[(1R)-1-{[(2R)-3-{[1-(2,3-Dihydro-1H-inden-2-yl)-2-methylpropan-2-yl]amino}-2-hydroxypropyl]oxy}ethyl]-5-methylphenyl}propanoic acid (5a) (1R)-1-(2-Bromo-4-methylphenyl)ethanol By using 1-(2-bromo-4-methylphenyl)ethanone described in WO 2001/049649, the reaction was carried out in the same manner as the method described in Example 4(4a) to give the title compound as a colorless oily substance (yield 99%, 95.3% ee).

(5b) (2R)-2-{[(1R)-1-(2-Bromo-4-methylphenyl)ethoxy]methyl}oxirane

By using (1R)-1-(2-bromo-4-methylphenyl)ethanol which had been obtained in Example 5(5a), the reaction was carried out in the same manner as the method described in Example 4(4b) to give the title compound as a colorless oily substance (yield 57%).

(5c) Ethyl (2E)-3-(3-methyl-6-{(1R)-1-[(2R)-oxiran-2-yl methoxy]ethyl}phenyl)prop-2-enoate By using (2R)-2-{[(1R)-1-(2-bromo-4-methylphenyl)ethoxy]methyl}oxirane which had been obtained in Example 5(5b), the reaction was carried out in the same manner as the method described in Example 4(4c) to give the title compound as a pale yellow oily substance (yield 51%).

(5d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}prop-2-enoate By using ethyl (2E)-3-(3-methyl-6-{(1R)-1-[(2R)-oxiran-2-yl methoxy]ethyl}phenyl)prop-2-enoate which had been obtained in Example 5(5c), the reaction was carried out in the same manner as the method described in Example 1(1a) to give the title compound (yield 99%) as a colorless oily substance.

(5e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}prop-2-enoate which had been obtained in Example 5(5d), the reaction was carried out in the same manner as the method described in Example 1(1b) to give the title compound as a colorless oily substance (yield 92%).

(5f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-5-methylphenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}propanoate which had been obtained in Example 5(5e), the reaction was carried out in the same manner as the method described in Example 1(1c) to give the title compound as a white amorphous substance (yield 84%).

Example 6

3-{2-[(1R)-1-{[(2R)-3-{[1-(2,3-Dihydro-1H-inden-2-yl)-2-methylpropan-2-yl]amino}-2-hydroxypropyl]oxy}ethyl]-4-methylphenyl}propanoic acid (6a) (1R)-1-(2-Bromo-5-methylphenyl)ethanol By using 1-(2-bromo-5-methylphenyl)ethanone described in J. Org. Chem. 1960, 25, 1016-1020, the reaction was carried out in the same manner as the method described in Example 4(4a) to give the title compound as a colorless oily substance (yield 96%, 95.4% ee).

(6b) (2R)-2-{[(1R)-1-(2-Bromo-5-methylphenyl)ethoxy]methyl}oxirane

By using (1R)-1-(2-bromo-5-methylphenyl)ethanol which had been obtained in Example 6(6a), the reaction was carried out in the same manner as the method described in Example 4(4b) to give the title compound as a colorless oily substance (yield 66%).

(6c) Ethyl (2E)-3-(4-methyl-2-{(1R)-1-[(2R)-oxiran-2-yl methoxy]ethyl}phenyl)prop-2-enoate By using (2R)-2-{[(1R)-1-(2-bromo-5-methylphenyl)ethoxy]methyl}oxirane which had been obtained in Example 6(6b), the reaction was carried out in the same manner as the method described in Example 4(4c) to give the title compound as a pale yellow oily substance (yield 78%).

(6d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}prop-2-enoate By using ethyl (2E)-3-(4-methyl-2-{(1R)-1-[(2R)-oxiran-2-yl methoxy]ethyl}phenyl)prop-2-enoate which had been obtained in Example 6(6c), the reaction was carried out in the same manner as the method described in Example 1(1a) to give the title compound as a colorless oily substance (yield 99%).

(6e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}prop-2-enoate which had been obtained in Example 6(6d), the reaction was carried out in the same manner as the method described in Example 1(1b) to give the title compound as a colorless oily substance (yield 84%).

(6f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-4-methylphenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}propanoate which had been obtained in Example 6(6e), the reaction was carried out in the same manner as the method described in Example 1(1c) to give the title compound as a white amorphous substance (yield 87%).

Example 7

3-{2-[(1R)-1-{[(2R)-3-{[1-(2,3-Dihydro-1H-inden-2-yl)-2-methylpropan-2-yl]amino}-2-hydroxypropyl]oxy}ethyl]-6-fluorophenyl}propanoic acid (7a) (1R)-1-(2-Bromo-3-fluorophenyl)ethanol By using 1-(2-bromo-3-fluorophenyl)ethanone described in Tetrahedron Lett. 1995, 36, 881-884, the reaction was carried out in the same manner as the method described in Example 4(4a) to give the title compound as a colorless oily substance (yield 99%, 96.3% ee).

(7b) (2R)-2-{[(1R)-1-(2-Bromo-3-fluorophenyl)ethoxy]methyl}oxirane

By using (1R)-1-(2-bromo-3-fluorophenyl)ethanol which had been obtained in Example 7(7a), the reaction was carried out in the same manner as the method described in Example 4(4b) to give the title compound as a colorless oily substance (yield 55%).

(7c) Ethyl (2E)-3-(2-fluoro-6-{(1R)-1-[(2R)-oxiran-2-yl methoxy]ethyl}phenyl)prop-2-enoate By using (2R)-2-{[(1R)-1-(2-bromo-3-fluorophenyl)ethoxy]methyl}oxirane which had been obtained in Example 7(7b), the reaction was carried out in the same manner as the method described in Example 4(4c) to give the title compound as a pale yellow oily substance (yield 85%).

(7d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}prop-2-enoate By using ethyl (2E)-3-(2-fluoro-6-{(1R)-1-[(2R)-oxiran-2-yl methoxy]ethyl}phenyl)prop-2-enoate which had been obtained in Example 7(7c), the reaction was carried out in the same manner as the method described in Example 1(1a) to give the title compound as a colorless oily substance (yield 75%).

(7e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}prop-2-enoate which had been obtained in Example 7(7d), the reaction was carried out in the same manner as the method described in Example 1(1b) to give the title compound as a colorless oily substance (yield 85%).

(7f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-6-fluorophenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoate which had been obtained in Example 7(7e), the reaction was carried out in the same manner as the method described in Example 1(1c) to give the title compound as a white amorphous substance (yield 99%).

Example 8

3-{2-[(1R)-1-{[(2R)-3-{[1-(2,3-Dihydro-1H-inden-2-yl)-2-methylpropan-2-yl]amino}-2-hydroxypropyl]oxy}ethyl]-5-fluorophenyl}propanoic acid (8a) (1R)-1-(2-Bromo-4-fluorophenyl)ethanol By using 1-(2-bromo-4-fluorophenyl)ethanone described in WO 2008/025509, the reaction was carried out in the same manner as the method described in Example 4(4a) to give the title compound as a colorless oily substance (yield 99%, 95.6% ee).

(8b) (2R)-2-{[(1R)-1-(2-Bromo-4-fluorophenyl)ethoxy]methyl}oxirane

By using (1R)-1-(2-bromo-4-fluorophenyl)ethanol which had been obtained in Example 8(8a), the reaction was carried out in the same manner as the method described in Example 4(4b) to give the title compound as a colorless oily substance (yield 58%).

(8c) Ethyl (2E)-3-(3-fluoro-6-{(1R)-1-[(2R)-oxiran-2-yl methoxy]ethyl}phenyl)prop-2-enoate By using (2R)-2-{[(1R)-1-(2-bromo-4-fluorophenyl)ethoxy]methyl}oxirane which had been obtained in Example 8(8b), the reaction was carried out in the same manner as the method described in Example 4(4c) to give the title compound as a pale yellow oily substance (yield 78%).

(8d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}prop-2-enoate By using ethyl (2E)-3-(3-fluoro-6-{(1R)-1-[(2R)-oxiran-2-yl methoxy]ethyl}phenyl)prop-2-enoate which had been obtained in Example 8(8c), the reaction was carried out in the same manner as the method described in Example 1(1a) to give the title compound as a colorless oily substance (yield 96%).

(8e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}prop-2-enoate which had been obtained in Example 8(8d), the reaction was carried out in the same manner as the method described in Example 1(1b) to give the title compound as a colorless oily substance (yield 86%).

(8f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-5-fluorophenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoate which had been obtained in Example 8(8e), the reaction was carried out in the same manner as the method described in Example 1(1c) to give the title compound as a white amorphous substance (yield 89%).

Example 9

3-{2-[(1R)-1-{[(2R)-3-{[1-(2,3-Dihydro-1H-inden-2-yl)-2-methylpropan-2-yl]amino}-2-hydroxypropyl]oxy}ethyl]-4-fluorophenyl}propanoic acid (9a) (1R)-1-(2-Bromo-5-fluorophenyl)ethanol By using 1-(2-bromo-5-fluorophenyl)ethanone, the reaction was carried out in the same manner as the method described in Example 4(4a) to give the title compound as a colorless oily substance (yield 96%, 95.7% ee).

(9b) (2R)-2-{[(1R)-1-(2-Bromo-5-fluorophenyl)ethoxy]methyl}oxirane

By using (1R)-1-(2-bromo-5-fluorophenyl)ethanol which had been obtained in Example 9(9a), the reaction was carried out in the same manner as the method described in Example 4(4b) to give the title compound as a colorless oily substance (yield 77%).

(9c) Ethyl (2E)-3-(4-fluoro-2-{(1R)-1-[(2R)-oxiran-2-yl methoxy]ethyl}phenyl)prop-2-enoate By using (2R)-2-{[(1R)-1-(2-bromo-5-fluorophenyl)ethoxy]methyl}oxirane which had been obtained in Example 9(9b), the reaction was carried out in the same manner as the method described in Example 4(4c) to give the title compound as a pale yellow oily substance (yield 54%).

(9d) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}prop-2-enoate By using ethyl (2E)-3-(4-fluoro-2-{(1R)-1-[(2R)-oxiran-2-yl methoxy]ethyl}phenyl)prop-2-enoate which had been obtained in Example 9(9c), the reaction was carried out in the same manner as the method described in Example 1(1a) to give the title compound as a colorless oily substance (yield 99%).

(9e) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}prop-2-enoate which had been obtained in Example 9(9d), the reaction was carried out in the same manner as the method described in Example 1(1b) to give the title compound as a colorless oily substance (yield 76%).

(9f) 3-{2-[(1R)-1-{[(2R)-3-{[1-(2,3-Dihydro-1H-inden-2-yl)-2-methylpropan-2-yl]amino}-2-hydroxypropyl]oxy}ethyl]-4-fluorophenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}propanoate which had been obtained in Example 9(9e), the reaction was carried out in the same manner as the method described in Example 1(1c) to give the title compound as a white solid (yield 79%).

Example 10

3-{2-[(1R)-1-{[(2R)-3-{[1-(2,3-Dihydro-1H-inden-2-yl)-2-methylpropan-2-yl]amino}-2-hydroxypropyl]oxy}ethyl]-6-(trifluoromethyl)phenyl}propanoic acid (10a) 1-[2-Bromo-3-(trifluoromethyl)phenyl]ethanone A mixture solution of 2-bromo-3-(trifluoromethyl)benzoic acid (2.50 g, 9.29 mmol), N, O-dimethylhydroxylamine hydrochloride (1.18 g, 12.1 mmol), N-methylmorpholine (2.1 mL, 18.6 mmol), and 4-(4,6-dimethoxy-1,3,5-triazin-2-yl)-4-methylmorpholinium chloride (3.78 g, 12.1 mmol) in acetonitrile (45 mL) was stirred at room temperature for 18 hours. The reaction solution was concentrated under reduced pressure. The resulting residue was added with 1 N aqueous hydrochloride solution and extracted with ethyl acetate. The organic layer was washed with saturated brine and dried over anhydrous magnesium sulfate. The solvent was distilled off under reduced pressure. The residue was dissolved in tetrahydrofuran (90 mL), added with a solution (0.93 M) of methyl magnesium bromide in tetrahydrofuran (13.0 mL, 12.1 mmol) at −20° C., and stirred at room temperature for 18 hours. The reaction solution was poured over 1 N aqueous hydrochloride solution and extracted with ethyl acetate. The organic layer was washed with saturated brine and dried over anhydrous magnesium sulfate. The solvent was distilled off under reduced pressure. The residue was purified by silica gel column chromatography (n-hexane/ethyl acetate=4/1) to give the title compound as a colorless oily substance (1.27 g, yield 44%).

(10b) (1R)-1-[2-Bromo-3-(trifluoromethyl)phenyl]ethanol

By using 1-[2-bromo-3-(trifluoromethyl)phenyl]ethanone which had been obtained in Example 10(10a), the reaction was carried out in the same manner as the method described in Example 4(4a) to give the title compound as a colorless oily substance (yield 99%, 97.5% ee).

(10c) (2R)-2-({(1R)-1-[2-Bromo-3-(trifluoromethyl)phenyl]ethoxy}methyl)oxirane

By using (1R)-1-[2-bromo-3-(trifluoromethyl)phenyl]ethanol which had been obtained in Example 10(10b), the reaction was carried out in the same manner as the method described in Example 4(4b) to give the title compound as a colorless oily substance (yield 55%).

(10d) Ethyl (2E)-3-[2-{(1R)-1-[(2R)-oxiran-2-yl methoxy]ethyl}-6-(trifluoromethyl)phenyl]prop-2-enoate By using (2R)-2-({(1R)-1-[2-bromo-3-(trifluoromethyl)phenyl]ethoxy}methyl)oxirane which had been obtained in Example 10(10c), the reaction was carried out in the same manner as the method described in Example 4(4c) to give the title compound as a pale yellow oily substance (yield 25%).

(10e) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}prop-2-enoate By using ethyl (2E)-3-[2-{(1R)-1-[(2R)-oxiran-2-yl methoxy]ethyl}-6-(trifluoromethyl)phenyl]prop-2-enoate which had been obtained in Example 10(10d), the reaction was carried out in the same manner as the method described in Example 1(1a) to give the title compound as a colorless oily substance (yield 82%).

(10f) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}prop-2-enoate which had been obtained in Example 10(10e), the reaction was carried out in the same manner as the method described in Example 1(1b) to give the title compound as a colorless oily substance (yield 87%).

(10g) 3-{2-[(1R)-1-{[(2R)-3-{[1-(2,3-Dihydro-1H-inden-2-yl)-2-methylpropan-2-yl]amino}-2-hydroxypropyl]oxy}ethyl]-6-(trifluoromethyl)phenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}propanoate which had been obtained in Example 10(10f), the reaction was carried out in the same manner as the method described in Example 1(1c) to give the title compound as a white solid (yield 96%).

Example 11

3-{2-[(1R)-1-{[(2R)-3-{[1-(2,3-Dihydro-1H-inden-2-yl)-2-methylpropan-2-yl]amino}-2-hydroxypropyl]oxy}ethyl]-5-(trifluoromethyl)phenyl}propanoic acid (11a) 1-[2-Bromo-4-(trifluoromethyl)phenyl]ethanone By using 2-bromo-4-(trifluoromethyl)benzoic acid, the reaction was carried out in the same manner as the method described in Example 10(10a) to give the title compound as a colorless oily substance (yield 84%).

(11b) (1R)-1-[2-Bromo-4-(trifluoromethyl)phenyl]ethanol

By using 1-[2-bromo-4-(trifluoromethyl)phenyl]ethanone which had been obtained in Example 11(11a), the reaction was carried out in the same manner as the method described in Example 4(4a) to give the title compound as a colorless oily substance (yield 99%, 94.7% ee).

(11c) (2R)-2-({(1R)-1-[2-Bromo-4-(trifluoromethyl)phenyl]ethoxy}methyl)oxirane

By using (1R)-1-[2-bromo-4-(trifluoromethyl)phenyl]ethanol which had been obtained in Example 11(11b), the reaction was carried out in the same manner as the method described in Example 4(4b) to give the title compound as a colorless oily substance (yield 70%).

(11d) Ethyl (2E)-3-[2-{(1R)-1-[(2R)-oxiran-2-yl methoxy]ethyl}-5-(trifluoromethyl)phenyl]prop-2-enoate By using (2R)-2-({(1R)-1-[2-bromo-4-(trifluoromethyl)phenyl]ethoxy}methyl)oxirane which had been obtained in Example 11(11c), the reaction was carried out in the same manner as the method described in Example 4(4c) to give the title compound as a colorless oily substance (yield 83%).

(11e) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}prop-2-enoate By using ethyl (2E)-3-[2-{(1R)-1-[(2R)-oxiran-2-yl methoxy]ethyl}-5-(trifluoromethyl)phenyl]prop-2-enoate which had been obtained in Example 11(11d), the reaction was carried out in the same manner as the method described in Example 1(1a) to give the title compound as a colorless oily substance (yield 98%).

(11f) Ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}propanoate By using ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}prop-2-enoate which had been obtained in Example 11(11e), the reaction was carried out in the same manner as the method described in Example 1(1b) to give the title compound as a colorless oily substance (yield 97%).

(11g) 3-{2-[(1R)-1-{[(2R)-3-{[1-(2,3-Dihydro-1H-inden-2-yl)-2-methylpropan-2-yl]amino}-2-hydroxypropyl]oxy}ethyl]-5-(trifluoromethyl)phenyl}propanoic acid By using ethyl 3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}propanoate which had been obtained in Example 11(11f), the reaction was carried out in the same manner as the method described in Example 1(1c) to give the title compound as a white amorphous substance (yield 97%).

Example 12

2'-[(1R)-1-{[(2R)-3-{[1-(2,3-Dihydro-1H-inden-2-ylmethyl)cyclopropyl]amino}-2-hydroxypropyl]oxy}ethyl]-3-methylbiphenyl-4-carboxylic acid (12a) 1-(2,3-Dihydro-1H-inden-2-ylmethyl)cyclopropanamine By using 2,3-dihydro-1H-inden-2-yl acetonitrile (157 mg, 1.00 mmol) described in WO 1998/005651, ethyl magnesium bromide (3 M diethyl ether solution, 0.67 mL, 2.00 mmol), tetraisopropoxy titanium (0.33 mL, 1.10 mmol), and trifluoroborane-diethyl ether complex (0.25 mL, 2.00 mmol), the reaction was carried out in the same manner as the method described in J. Org. Chem. 2002, 67, 3965 to give the title compound as a white solid (124 mg, yield 66%).

(12b) Methyl 2'-[(1R)-1-{[(2R)-3-{[1-(2,3-dihydro-1H-inden-2-ylmethyl)cyclopropyl]amino}-2-hydroxypropyl]oxy}ethyl-3-methylbiphenyl-4-carboxylate By using 1-(2,3-dihydro-1H-inden-2-ylmethyl)cyclopropanamine which had been obtained in Example 12(12a), the reaction was carried out in the same manner as the method described in Example 1(1a) to give the title compound as a colorless oily substance (yield 28%).

(12c) 2'-[(1R)-1-{[(2R)-3-{[1-(2,3-Dihydro-1H-inden-2-ylmethyl)cyclopropyl]amino}-2-hydroxypropyl]oxy}ethyl]-3-methylbiphenyl-4-carboxylic acid By using methyl 2'-[(1R)-1-{[(2R)-3-{[1-(2,3-dihydro-1H-inden-2-ylmethyl)cyclopropyl]amino}-2-hydroxypropyl]oxy}ethyl-3-methylbiphenyl-4-carboxylate which had been obtained in Example 12(12b), the reaction was carried out in the same manner as the method described in Example 1(1c) to give the title compound as a white solid (yield 93%).

Example 13

5-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}pentanoic acid (13a) Ethyl (4E)-5-(2-{(1R)-1-[(2R)-oxiran-2-yl methoxy]ethyl}phenyl)pent-4-enoate By using (2R)-2-{[(1R)-1-(2-bromo phenyl)ethoxy]methyl}oxirane described in WO 2004/094362 and ethyl pent-4-enoate, the reaction was carried out in the same manner as the method described in Example 4(4c) to give the title compound as a colorless oily substance (yield 82%).

(13b) Ethyl (4E)-5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pent-4-enoate By using ethyl (4E)-5-(2-{(1R)-1-[(2R)-oxiran-2-yl methoxy]ethyl}phenyl)pent-4-enoate which had been obtained in Example 13(13a), the reaction was carried out in the same manner as the method described in Example 1(1a) to give the title compound as a colorless oily substance (yield 100%).

(13c) Ethyl 5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pentanoate By using ethyl (4E)-5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pent-4-enoate which had been obtained in Example 13(13b), the reaction was carried out in the same manner as the method described in Example 1(1b) to give the title compound as a colorless oily substance (yield 90%).

(13d) 5-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}pentanoic acid By using ethyl 5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pentanoate which had been obtained in Example 13(13c), the reaction was carried out in the same manner as the method described in Example 1(1c) to give the title compound as a colorless amorphous substance (yield 96%).

Example 14

3-{2-[(1R)-1-{[(2R)-3-{[1-(2,3-Dihydro-1H-inden-2-ylmethyl)cyclopropyl]amino}-2-hydroxypropyl]oxy}ethyl]phenyl}propanoic acid (14a) Ethyl (2E)-3-(2-{(1R)-1-[(2R)-oxiran-2-yl methoxy]ethyl}phenyl)prop-2-enoate By using (2R)-2-{[(1R)-1-(2-bromo phenyl)ethoxy]methyl}oxirane described in WO 2004/094362, the reaction was carried out in the same manner as the method described in Example 4(4c) to give the title compound as a yellow oily substance (yield 95%).

(14b) Ethyl (2E)-3-{2-[(1R)-1-{[(2R)-3-{[1-(2,3-dihydro-1H-inden-2-ylmethyl)cyclopropyl]amino}-2-hydroxypropyl]oxy}ethyl]prop-2-enoate By using ethyl (2E)-3-(2-{(1R)-1-[(2R)-oxiran-2-yl methoxy]ethyl}phenyl)prop-2-enoate which had been obtained in Example 14(14a) and 1-(2,3-dihydro-1H-inden-2-ylmethyl)cyclopropanamine which had been obtained in Example 12(12a), the reaction was carried out in the same manner as the method described in Example 1(1a) to give the title compound as a colorless oily substance (yield 39%).

(14c) Ethyl 3-{2-[(1R)-1-{[(2R)-3-{[1-(2,3-dihydro-1H-inden-2-ylmethyl)cyclopropyl]amino}-2-hydroxypropyl]oxy}ethyl]phenyl}propanoate By using ethyl (2E)-3-{2-[(1R)-1-{[(2R)-3-{[1-(2,3-dihydro-1H-inden-2-ylmethyl)cyclopropyl]amino}-2-hydroxypropyl]oxy}ethyl]prop-2-enoate which had been obtained in Example 14(14b), the reaction was carried out in the same manner as the method described in Example 1(1b) to give the title compound as a colorless oily substance (yield 39%).

(14d) 3-{2-[(1R)-1-{[(2R)-3-{[1-(2,3-Dihydro-1H-inden-2-ylmethyl)cyclopropyl]amino}-2-hydroxypropyl]oxy}ethyl]phenyl}propanoic acid By using ethyl 3-{2-[(1R)-1-{[(2R)-3-{[1-(2,3-dihydro-1H-inden-2-ylmethyl)cyclopropyl]amino}-2-hydroxypropyl]oxy}ethyl]phenyl}propanoate which had been obtained in Example 14(14c), the reaction was carried out in the same manner as the method described in Example 1(1c) to give the title compound as a colorless amorphous substance (quantitative).

The structures and physicochemical data of the compounds that are described in Examples 1 to 14 are given below.

TABLE 3

| Example No. | Structure | Data |
|---|---|---|
| 1(1a) | 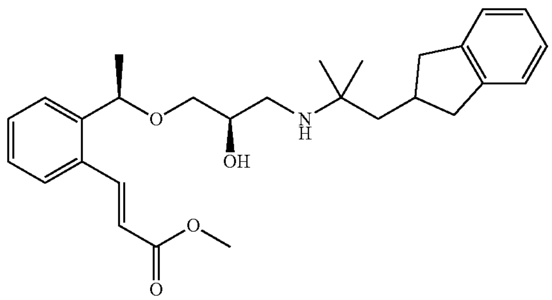 | $^1$H-NMR (CDCl$_3$) δ: 1.10 (6H, s), 1.45 (3H, d, J = 6.5 Hz), 1.67 (2H, d, J = 5.9 Hz), 2.50-2.63 (4H, m), 2.71 (1H, dd, J = 11.7, 4.2 Hz), 3.05 (2H, dd, J = 14.8, 7.0 Hz), 3.33-3.37 (2H, m), 3.73-3.78 (1H, m), 3.81 (3H, s), 4.82 (1H, q, J = 6.5 Hz), 6.33 (1H, d, J = 15.6 Hz), 7.06-7.17 (4H, m), 7.24-7.30 (1H, m), 7.39 (1H, td, J = 7.4, 1.2 Hz), 7.46-7.49 (1H, m), 7.53 (1H, d, J = 7.8 Hz), 8.11 (1H, d, J = 15.6 Hz). |
| 1(1b) | 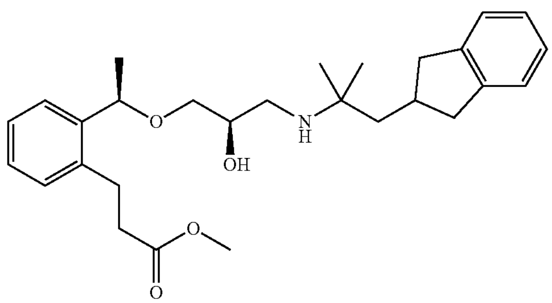 | $^1$H-NMR (CDCl$_3$) δ: 1.11 (6H, s), 1.45 (3H, d, J = 6.4 Hz), 1.68 (2H, d, J = 6.0 Hz), 2.53-2.62 (6H, m), 2.72 (1H, dd, J = 11.7, 3.9 Hz), 2.96-3.08 (4H, m), 3.28-3.36 (2H, m), 3.68 (3H, s), 3.77-3.79 (1H, m), 4.75 (1H, q, J = 6.4 Hz), 7.10-7.27 (7H, m), 7.42-7.44 (1H, m). |
| 1(1c) | 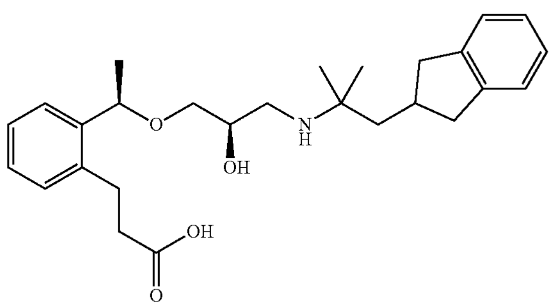 | $^1$H-NMR (CDCl$_3$) δ: 1.43-1.46 (9H, m), 2.00 (2H, d, J = 5.9 Hz), 2.53-2.66 (5H, m), 2.88-3.34 (6H, m), 3.48-3.58 (2H, m), 4.30-4.33 (1H, m), 4.99 (1H, q, J = 6.4 Hz), 7.10-7.18 (7H, m), 7.29-7.33 (1H, m). |
| 2(2a) | 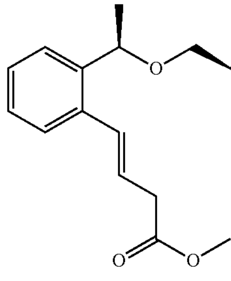 | $^1$H-NMR (CDCl$_3$) δ: 1.45 (3H, d, J = 6.4 Hz), 2.50 (1H, dd, J = 5.0, 3.2 Hz), 2.75 (1H, t, J = 4.6 Hz), 3.15-3.19 (1H, m), 3.21 (1H, dd, J = 11.5, 6.4 Hz), 3.28 (2H, dd, J = 7.3, 1.4 Hz), 3.58 (1H, dd, J = 11.5, 2.8 Hz), 3.72 (3H, s), 4.80 (1H, q, J = 6.4 Hz), 6.14 (1H, dt, J = 15.6, 7.1 Hz), 6.85 (1H, d, J = 15.6 Hz), 7.29-7.33 (2H, m), 7.42 (2H, ddd, J = 14.7, 7.3, 1.4 Hz). |

TABLE 3-continued

| Example No. | Structure | Data |
|---|---|---|
| 2(2b) | 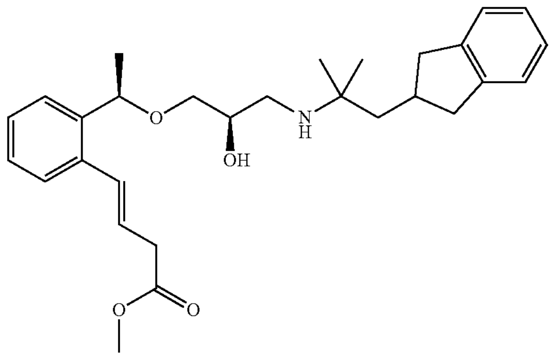 | $^1$H-NMR (CDCl$_3$) δ: 1.14 (6H, s), 1.43 (3H, d, J = 6.4 Hz), 1.71 (2H, d, J = 6.0 Hz), 2.50-2.59 (4H, m), 2.77 (1H, dd, J = 11.5, 3.4 Hz), 3.06 (2H, dd, J = 15.1, 7.3 Hz), 3.27-3.35 (4H, m), 3.72 (3H, s), 3.80-3.84 (1H, m), 4.74 (1H, q, J = 6.4 Hz), 6.13-6.15 (1H, m), 6.84 (1H, d, J = 15.1 Hz), 7.10-7.31 (6H, m), 7.38-7.43 (2H, m). |
| 2(2c) | 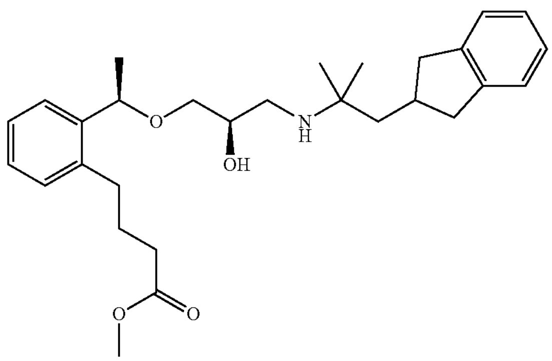 | $^1$H-NMR (CDCl$_3$) δ: 1.17 (6H, s), 1.44 (3H, d, J = 6.4 Hz), 1.73 (2H, d, J = 6.0 Hz), 1.89-1.91 (2H, m), 2.39 (2H, t, J = 6.9 Hz), 2.54-2.63 (6H, m), 2.81 (1H, dd, J = 11.7, 3.9 Hz), 3.06 (2H, dd, J = 14.7, 7.3 Hz), 3.30 (1H, dd, J = 9.6, 5.0 Hz), 3.37 (1H, dd, J = 9.6, 6.0 Hz), 3.67 (3H, s), 3.85-3.88 (1H, m), 4.76 (1H, q, J = 6.4 Hz), 7.14-7.23 (7H, m), 7.42-7.44 (1H, m). |

TABLE 4

| | | |
|---|---|---|
| 2(2d) | | $^1$H-NMR (CDCl$_3$) δ: 1.41 (3H, d, J = 6.3 Hz), 1.47 (6H, s), 1.87-1.96 (2H, m), 2.03 (2H, d, J = 6.0 Hz), 2.29-2.34 (2H, m), 2.51-2.74 (5H, m), 2.88 (1H, dd, J = 11.7, 9.4 Hz), 3.07-3.11 (2H, m), 3.26-3.29 (1H, m), 3.37 (1H, dd, J = 11.2, 7.1 Hz), 3.46 (1H, dd, J = 11.5, 5.0 Hz), 4.39-4.41 (1H, m), 4.92 (1H, q, J = 6.3 Hz), 7.11-7.21 (7H, m), 7.35-7.36 (1H, m). |
| 3(3a) | | $^1$H-NMR (CDCl$_3$) δ: 1.10 (6H, s), 1.36 (3H, d, J = 6.3 Hz), 1.67 (2H, d, J = 6.1 Hz), 2.50-2.71 (5H, m), 2.64 (3H, s), 3.05 (2H, dd, J = 14.8, 7.2 Hz), 3.16-3.23 (2H, m), 3.66-3.71 (1H, m), 3.92 (3H, s), 4.49 (1H, q, J = 6.3 Hz), 7.07-7.19 (7H, m), 7.30 (1H, td, J = 7.4, 1.2 Hz), 7.41 (1H, td, J = 7.6, 1.4 Hz), 7.57 (1H, dd, J = 8.1, 1.2 Hz), 7.95 (1H, d, J = 8.5 Hz). |

TABLE 4-continued

3(3b) 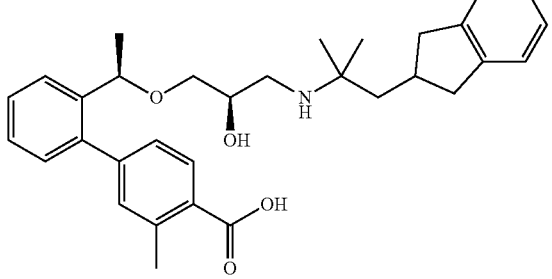

¹H-NMR (CDCl₃) δ: 1.30 (3H, d, J = 6.0 Hz), 1.47 (3H, s), 1.48 (3H, s), 2.01-2.06 (2H, m), 2.51 (3H, s), 2.53-2.68 (3H, m), 2.85 (1H, t, J = 10.5 Hz), 3.03-3.13 (2H, m), 3.18-3.37 (3H, m), 4.23-4.33 (1H, m), 4.57 (1H, q, J = 6.0 Hz), 7.03-7.16 (7H, m), 7.24-7.29 (1H, m), 7.38 (1H, t, J = 7.6 Hz), 7.52 (1H, d, J = 7.8 Hz), 7.82 (1H, d, J = 7.8 Hz).

4(4a) 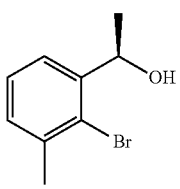

¹H-NMR (CDCl₃) δ: 1.49 (3H, d, J = 6.3 Hz), 1.97 (1H, br s), 2.42 (3H, s), 5.29-5.32 (1H, m), 7.16 (1H, d, J = 7.2 Hz), 7.24 (1H, t, J = 7.2 Hz), 7.42 (1H, d, J = 7.2 Hz).

4(4b) 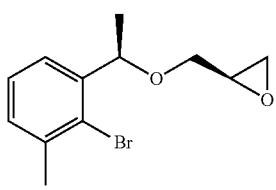

¹H-NMR (CDCl₃) δ: 1.43 (3H, d, J = 6.3 Hz), 2.42 (3H, s), 2.55 (1H, dd, J = 4.9, 2.7 Hz), 2.76 (1H, t, J = 4.9 Hz), 3.14-3.15 (1H, m), 3.30 (1H, dd, J = 11.3, 5.9 Hz), 3.59 (1H, dd, J = 11.3, 3.3 Hz), 4.97 (1H, q, J = 6.3 Hz), 7.16 (1H, d, J = 7.6 Hz), 7.24 (1H, t, J = 7.6 Hz), 7.34 (1H, d, J = 7.6 Hz).

4(4c) 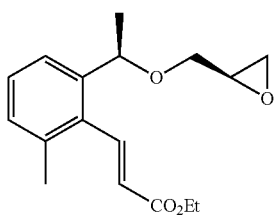

¹H-NMR (CDCl₃) δ: 1.35 (3H, t, J = 7.2 Hz), 1.42 (3H, d, J = 6.3 Hz), 2.32 (3H, s), 2.50 (1H, dd, J = 4.6, 2.7 Hz), 2.74 (1H, t, J = 4.6 Hz), 3.11-3.12 (1H, m), 3.21 (1H, dd, J = 11.2, 6.0 Hz), 3.50 (1H, dd, J = 11.2, 3.2 Hz), 4.29 (2H, q, J = 7.2 Hz), 4.74 (1H, q, J = 6.3 Hz), 5.96 (1H, d, J = 16.4 Hz), 7.14 (1H, d, J = 7.6 Hz), 7.27 (1H, m), 7.38 (1H, d, J = 7.6 Hz), 7.85 (1H, d, J = 16.4 Hz).

TABLE 5

4(4d) 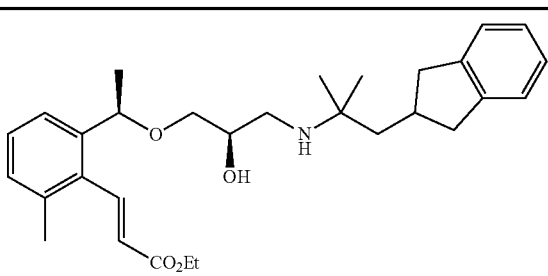

¹H-NMR (CDCl₃) δ: 1.10 (6H, s), 1.33-1.42 (6H, m), 1.66-1.67 (2H, m), 2.31 (3H, s), 2.51-2.70 (5H, m), 3.05 (2H, dd, J = 14.6, 6.8 Hz), 3.23-3.30 (2H, m), 3.69-3.75 (1H, m), 4.28 (2H, q, J = 7.2 Hz), 4.68 (1H, q, J = 6.5 Hz), 5.96 (1H, d, J = 16.4 Hz), 7.09-7.17 (5H, m), 7.24-7.26 (1H, m), 7.36 (1H, d, J = 7.6 Hz), 7.85 (1H, d, J = 16.4 Hz).

4(4e) 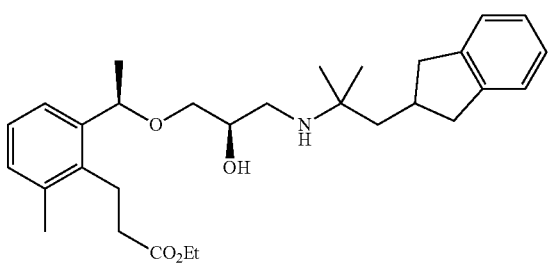

¹H-NMR (CDCl₃) δ: 1.11 (6H, s), 1.27 (3H, t, J = 7.4 Hz), 1.44 (3H, d, J = 6.3 Hz), 1.67-1.68 (2H, m), 2.33 (3H, s), 2.40-2.71 (7H, m), 2.89-3.08 (4H, m), 3.27-3.32 (2H, m), 3.72-3.78 (1H, m), 4.13-4.20 (2H, m), 4.74-4.75 (1H, m), 7.06-7.17 (6H, m), 7.30 (1H, d, J = 7.6 Hz).

US 8,183,272 B2

TABLE 5-continued

| 4(4f) | 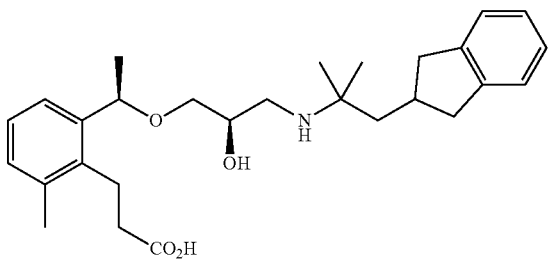 | ¹H-NMR (CDCl₃) δ: 1.43-1.46 (9H, m), 2.03-2.06 (2H, m), 2.33-2.68 (10H, m), 2.99-3.10 (7H, m), 3.58-3.63 (2H, m), 4.27-4.29 (1H, m), 5.06-5.09 (1H, m), 7.09-7.13 (5H, m). |
| --- | --- | --- |
| 5(5a) | 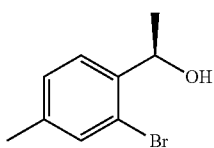 | ¹H-NMR (CDCl₃) δ: 1.47 (3H, d, J = 6.2 Hz), 1.93-1.96 (1H, m), 2.32 (3H, s), 5.20-5.22 (1H, m), 7.15 (1H, d, J = 7.3 Hz), 7.35 (1H, s), 7.46 (1H, d, J = 7.8 Hz). |
| 5(5b) | 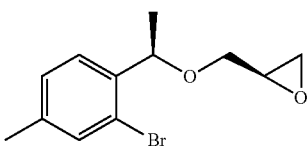 | ¹H-NMR (CDCl₃) δ: 1.42 (3H, d, J = 6.3 Hz), 2.31 (3H, s), 2.55 (1H, dd, J = 5.1, 2.7 Hz), 2.75-2.77 (1H, m), 3.12-3.14 (1H, m), 3.31 (1H, dd, J = 11.2, 5.9 Hz), 3.56 (1H, dd, J = 11.2, 3.3 Hz), 4.86 (1H, q, J = 6.3 Hz), 7.15 (1H, d, J = 8.1 Hz), 7.35-7.37 (2H, m). |
| 5(5c) | 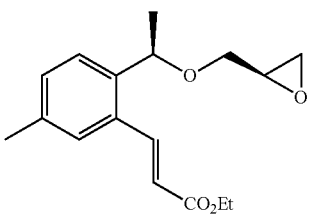 | ¹H-NMR (CDCl₃) δ: 1.34 (3H, t, J = 7.2 Hz), 1.44 (3H, d, J = 6.6 Hz), 2.35 (3H, s), 2.52 (1H, dd, J = 5.0, 2.6 Hz), 2.75-2.76 (1H, m), 3.13-3.14 (1H, m), 3.27 (1H, dd, J = 11.2, 5.9 Hz), 3.56 (1H, dd, J = 11.2, 3.2 Hz), 4.27 (2H, q, J = 7.2 Hz), 4.85 (1H, d, J = 6.6 Hz), 6.32 (1H, d, J = 15.6 Hz), 7.20-7.23 (1H, m), 7.36-7.37 (2H, m), 8.07 (1H, d, J = 15.6 Hz). |
| 5(5d) | 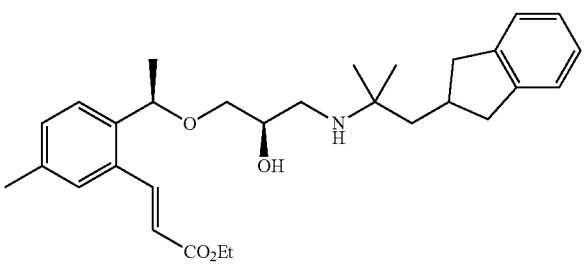 | ¹H-NMR (CDCl₃) δ: 1.10 (6H, s), 1.34 (3H, t, J = 7.1 Hz), 1.44 (3H, d, J = 6.6 Hz), 1.66 (2H, d, J = 5.9 Hz), 2.33 (3H, s), 2.52-2.61 (4H, m), 2.70 (1H, dd, J = 11.7, 3.9 Hz), 3.03-3.07 (2H, m), 3.29-3.37 (2H, m), 3.73-3.75 (1H, m), 4.26 (2H, q, J = 7.1 Hz), 4.78-4.80 (1H, m), 6.32 (1H, d, J = 15.6 Hz), 7.09-7.20 (5H, m), 7.34-7.35 (2H, m), 8.08 (1H, d, J = 15.6 Hz). |

TABLE 6

| 5(5e) | 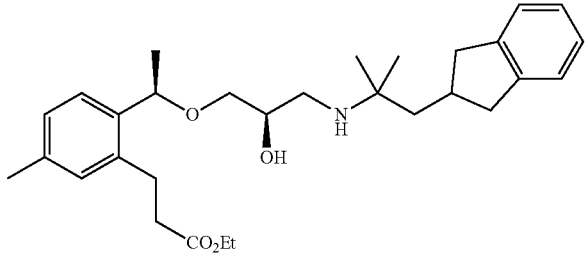 | ¹H-NMR (CDCl₃) δ: 1.10 (6H, s), 1.25 (3H, t, J = 7.2 Hz), 1.43 (3H, d, J = 6.3 Hz), 1.66 (2H, d, J = 5.9 Hz), 2.29 (3H, s), 2.51-2.61 (6H, m), 2.68 (1H, dd, J = 11.7, 4.1 Hz), 2.94 (2H, t, J = 8.2 Hz), 3.05 (2H, dd, J = 14.4, 6.6 Hz), 3.26-3.34 (2H, m), 3.72-3.75 (1H, m), 4.14 (2H, q, J = 7.2 Hz), 4.70-4.72 (1H, m), 6.96 (1H, s), 7.04 (1H, d, J = 8.0 Hz), 7.11-7.15 (4H, m), 7.31 (1H, d, J = 7.8 Hz). |
| --- | --- | --- |

TABLE 6-continued

5(5f) 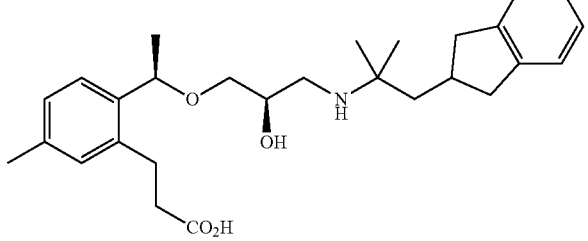

¹H-NMR (CDCl₃) δ: 1.41-1.43 (9H, m), 1.99 (2H, d, J = 6.3 Hz), 2.28 (3H, s), 2.55-2.64 (5H, m), 2.90-3.20 (6H, m), 3.49-3.52 (1H, m), 3.58-3.61 (1H, m), 4.28-4.30 (1H, m), 4.95-4.97 (1H, m), 6.98 (2H, d, J = 8.1 Hz), 7.09-7.15 (4H, m), 7.19 (1H, d, J = 7.8 Hz).

6(6a) 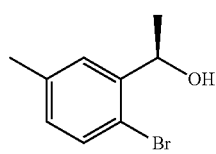

¹H-NMR (CDCl₃) δ: 1.48 (3H, d, J = 6.4 Hz), 1.94-1.97 (1H, m), 2.33 (3H, s), 5.19-5.22 (1H, m), 6.94 (1H, d, J = 8.3 Hz), 7.38-7.39 (2H, m).

6(6b) 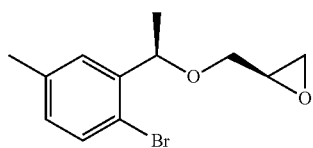

¹H-NMR (CDCl₃) δ: 1.42 (3H, d, J = 6.3 Hz), 2.32 (3H, s), 2.55-2.57 (1H, m), 2.77 (1H, t, J = 4.5 Hz), 3.14-3.15 (1H, m), 3.31 (1H, dd, J = 11.2, 5.9 Hz), 3.60 (1H, dd, J = 11.2, 3.2 Hz), 4.86 (1H, q, J = 6.3 Hz), 6.94 (1H, d, J = 8.1, 2.2 Hz), 7.31 (1H, d, J = 2.2 Hz), 7.38 (1H, d, J = 8.1 Hz).

6(6c) 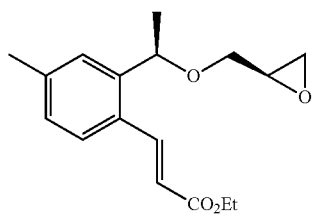

¹H-NMR (CDCl₃) δ: 1.34 (3H, t, J = 7.1 Hz), 1.45 (3H, d, J = 6.3 Hz), 2.38 (3H, s), 2.52-2.54 (1H, m), 2.76 (1H, t, J = 4.6 Hz), 3.13-3.17 (1H, m), 3.28 (1H, dd, J = 11.2, 6.2 Hz), 3.58 (1H, dd, J = 11.2, 3.1 Hz), 4.27 (2H, q, J = 7.1 Hz), 4.86 (1H, q, J = 6.2 Hz), 6.30 (1H, d, J = 15.9 Hz), 7.10 (1H, d, J = 7.8 Hz), 7.29 (1H, s), 7.45 (1H, d, J = 7.8 Hz), 8.06 (1H, d, J = 15.9 Hz).

6(6d) 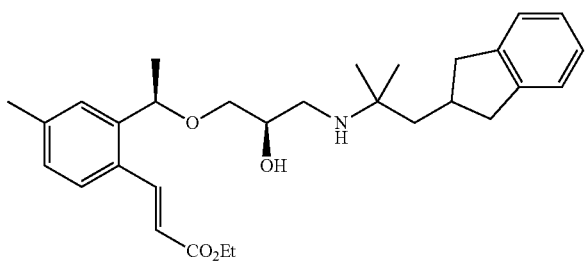

¹H-NMR (CDCl₃) δ: 1.10 (6H, s), 1.33 (3H, t, J = 7.2 Hz), 1.45 (3H, d, J = 6.3 Hz), 1.67-1.70 (2H, m), 2.37 (3H, s), 2.52-2.63 (4H, m), 2.72 (1H, dd, J = 11.7, 3.9 Hz), 3.06 (2H, dd, J = 14.8, 7.0 Hz), 3.32-3.39 (2H, m), 3.74-3.77 (1H, m), 4.26 (2H, q, J = 7.2 Hz), 4.80 (1H, q, J = 6.4 Hz), 6.30 (1H, d, J = 15.6 Hz), 7.11-7.14 (6H, m), 7.45 (1H, d, J = 8.0 Hz), 8.08 (1H, d, J = 15.6 Hz).

6(6e) 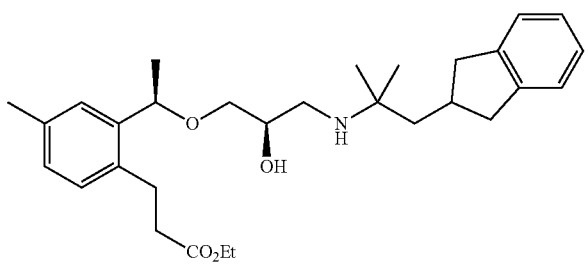

¹H-NMR (CDCl₃) δ: 1.10 (6H, s), 1.24 (3H, t, J = 7.2 Hz), 1.44 (3H, d, J = 6.4 Hz), 1.67 (2H, d, J = 5.6 Hz), 2.32 (3H, s), 2.50-2.63 (6H, m), 2.70 (1H, dd, J = 11.6, 4.0 Hz), 2.93 (2H, t, J = 8.1 Hz), 3.06 (2H, dd, J = 14.5, 7.0 Hz), 3.30-3.33 (2H, m), 3.74-3.76 (1H, m), 4.13 (2H, q, J = 7.2 Hz), 4.71 (1H, q, J = 6.4 Hz), 7.00-7.04 (2H, m), 7.09-7.13 (2H, m), 7.15-7.16 (2H, m), 7.23 (1H, s).

TABLE 7

| | | |
|---|---|---|
| 6(6f) | 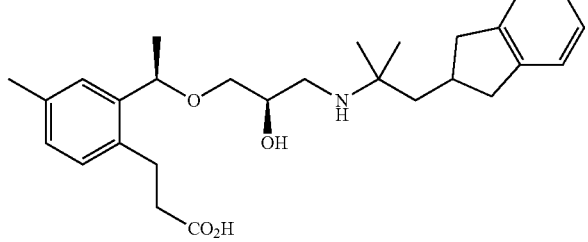 | $^1$H-NMR (CDCl$_3$) δ: 1.37-1.47 (10H, m), 1.98-2.06 (2H, m), 2.30 (3H, s), 2.38-2.67 (6H, m), 3.01-3.13 (6H, m), 3.55-3.58 (1H, m), 3.66-3.68 (1H, m), 4.15-4.18 (1H, m), 4.97-4.99 (1H, m), 7.00-7.14 (5H, m). |
| 7(7a) | 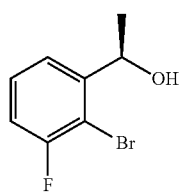 | $^1$H-NMR (CDCl$_3$) δ: 1.49 (3H, d, J = 6.3 Hz), 4.06-4.11 (1H, m), 5.26-5.28 (1H, m), 7.03-7.05 (1H, m), 7.31-7.33 (1H, m), 7.40 (1H, d, J = 7.8 Hz). |
| 7(7b) | 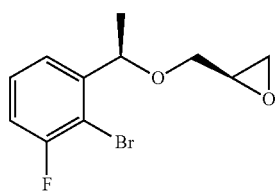 | $^1$H-NMR (CDCl$_3$) δ: 1.43 (3H, d, J = 6.3 Hz), 2.56-2.57 (1H, m), 2.77-2.78 (1H, m), 3.13-3.17 (1H, m), 3.31 (1H, dd, J = 11.2, 6.0 Hz), 3.61 (1H, dd, J = 11.2, 3.2 Hz), 4.92 (1H, q, J = 6.3 Hz), 7.02-7.06 (1H, m), 7.29-7.33 (2H, m). |
| 7(7c) | 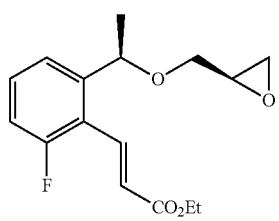 | $^1$H-NMR (CDCl$_3$) δ: 1.35 (3H, t, J = 7.2 Hz), 1.46 (3H, d, J = 6.3 Hz), 2.54 (1H, dd, J = 5.1, 2.7 Hz), 2.77 (1H, t, J = 4.6 Hz), 3.13-3.16 (1H, m), 3.28 (1H, dd, J = 11.2, 5.9 Hz), 3.60 (1H, dd, J = 11.2, 3.2 Hz), 4.28 (2H, q, J = 7.2 Hz), 4.86 (1H, q, J = 6.3 Hz), 6.51 (1H, dd, J = 16.1, 1.6 Hz), 7.00-7.06 (1H, m), 7.31-7.35 (2H, m), 7.80 (1H, d, J = 16.1 Hz). |
| 7(7d) | 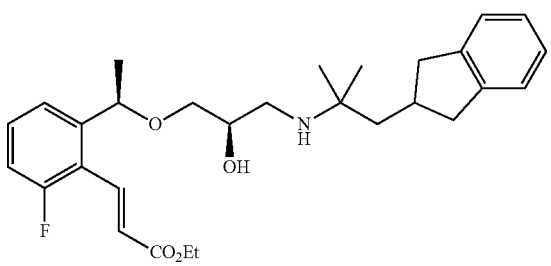 | $^1$H-NMR (CDCl$_3$) δ: 1.11 (6H, s), 1.34 (3H, t, J = 7.1 Hz), 1.45 (3H, d, J = 6.4 Hz), 1.68 (2H, d, J = 5.5 Hz), 2.55-2.62 (4H, m), 2.72 (1H, dd, J = 11.5, 4.1 Hz), 3.06 (2H, d, J = 15.4, 7.1 Hz), 3.35-3.36 (2H, m), 3.73-3.76 (1H, m), 4.27 (2H, q, J = 7.1 Hz), 4.80 (1H, q, J = 6.4 Hz), 6.52 (1H, dd, J = 16.0, 1.6 Hz), 7.00-7.03 (1H, m), 7.11-7.15 (4H, m), 7.30-7.33 (2H, m), 7.82 (1H, d, J = 16.0 Hz). |
| 7(7e) | 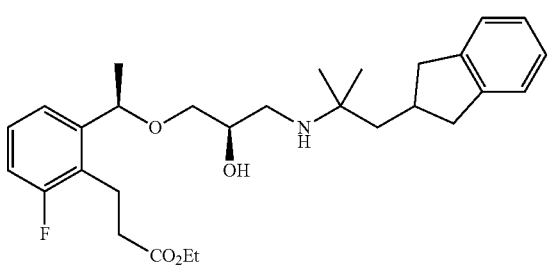 | $^1$H-NMR (CDCl$_3$) δ: 1.10 (6H, s), 1.26 (3H, t, J = 7.2 Hz), 1.44 (3H, d, J = 6.4 Hz), 1.67 (2H, d, J = 6.0 Hz), 2.52-2.64 (6H, m), 2.70 (1H, dd, J = 11.7, 3.9 Hz), 2.91-3.10 (4H, m), 3.28-3.36 (2H, m), 3.72-3.77 (1H, m), 4.14 (2H, q, J = 7.2 Hz), 4.75 (1H, q, J = 6.4 Hz), 6.91-6.95 (1H, m), 7.10-7.23 (6H, m). |

TABLE 7-continued

7(7f) 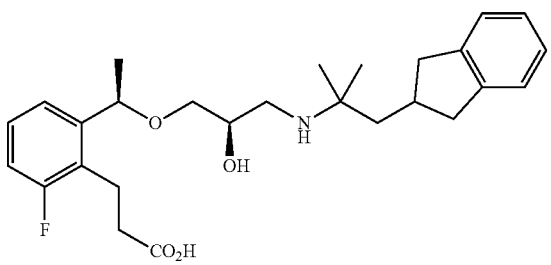
¹H-NMR (CDCl₃) δ: 1.46 (6H, s), 2.02-2.07 (3H, m), 2.38-2.67 (6H, m), 2.97-3.16 (7H, m), 3.55-3.58 (1H, m), 3.70-3.72 (1H, m), 4.16-4.19 (1H, m), 4.98-5.00 (1H, m), 6.94 (1H, t, J = 8.7 Hz), 7.02-7.04 (1H, m), 7.08-7.14 (6H, m).

TABLE 8

8(8a) 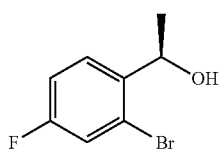
¹H-NMR (CDCl₃) δ: 1.47-1.48 (3H, m), 1.95-1.97 (1H, m), 5.21-5.23 (1H, m), 7.06-7.08 (1H, m), 7.25-7.28 (1H, m), 7.57-7.60 (1H, m).

8(8b) 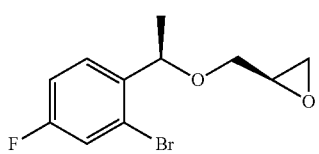
¹H-NMR (CDCl₃) δ: 1.41 (3H, d, J = 6.4 Hz), 2.56 (1H, dd, J = 4.3, 3.2 Hz), 2.77 (1H, t, J = 4.6 Hz), 3.12-3.14 (1H, m), 3.30 (1H, dd, J = 11.2, 5.9 Hz), 3.58 (1H, dd, J = 11.2, 3.2 Hz), 4.86 (1H, q, J = 6.4 Hz), 7.06-7.08 (1H, m), 7.26-7.28 (1H, m), 7.48 (1H, dd, J = 8.7, 6.2 Hz).

8(8c) 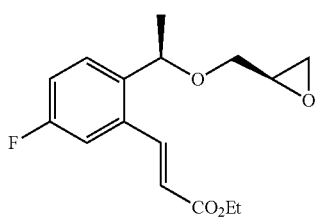
¹H-NMR (CDCl₃) δ: 1.35 (3H, t, J = 7.1 Hz), 1.44 (3H, d, J = 6.3 Hz), 2.54 (1H, dd, J = 4.6, 2.7 Hz), 2.77 (1H, t, J = 4.6 Hz), 3.14 (1H, dt, J = 9.3, 3.2 Hz), 3.25-3.28 (1H, m), 3.59 (1H, dd, J = 11.2, 3.2 Hz), 4.28 (2H, q, J = 7.1 Hz), 4.85 (1H, q, J = 6.3 Hz), 6.31 (1H, d, J = 15.6 Hz), 7.09 (1H, td, J = 8.5, 2.7 Hz), 7.21 (1H, dd, J = 9.8, 2.7 Hz), 7.47 (1H, dd, J = 8.5, 5.9 Hz), 8.03 (1H, d, J = 15.6 Hz).

8(8d) 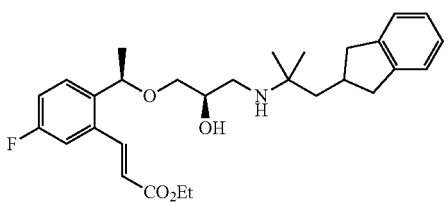
¹H-NMR (CDCl₃) δ: 1.12 (6H, s), 1.34 (3H, t, J = 7.2 Hz), 1.43 (3H, d, J = 6.3 Hz), 1.67 (2H, d, J = 5.9 Hz), 2.51-2.64 (4H, m), 2.71 (1H, dd, J = 11.7, 4.1 Hz), 3.06 (2H, dd, J = 11.7, 7.0 Hz), 3.32-3.37 (2H, m), 3.72-3.76 (1H, m), 4.27 (2H, q, J = 7.2 Hz), 4.79 (1H, q, J = 6.3 Hz), 6.31 (1H, d, J = 15.6 Hz), 7.04-7.18 (5H, m), 7.21 (1H, dd, J = 9.8, 2.7 Hz), 7.44 (1H, dd, J = 8.7, 5.7 Hz), 8.04 (1H, d, J = 15.6 Hz).

8(8e) 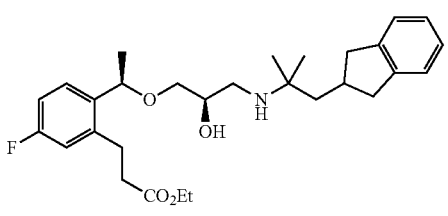
¹H-NMR (CDCl₃) δ: 1.10 (6H, s), 1.25 (3H, t, J = 7.2 Hz), 1.43 (3H, d, J = 6.3 Hz), 1.67 (2H, d, J = 5.6 Hz), 2.50-2.72 (7H, m), 2.96 (2H, t, J = 7.9 Hz), 3.06 (2H, dd, J = 14.3, 7.2 Hz), 3.26-3.34 (2H, m), 3.72-3.74 (1H, m), 4.14 (2H, q, J = 7.2 Hz), 4.71 (1H, q, J = 6.3 Hz), 6.85 (1H, dd, J = 9.9, 2.6 Hz), 6.92 (1H, dd, J = 9.9, 7.0 Hz), 7.11-7.15 (5H, m), 7.39 (1H, dd, J = 8.5, 6.1 Hz).

8(8f) 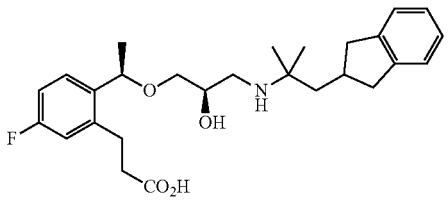
¹H-NMR (CDCl₃) δ: 1.40 (6H, d, J = 7.1 Hz), 1.47-1.50 (3H, m), 1.97-2.04 (2H, m), 2.44-2.46 (2H, m), 2.56-2.67 (3H, m), 3.00-3.14 (6H, m), 3.54-3.57 (1H, m), 3.65-3.67 (1H, m), 4.11-4.13 (1H, m), 4.97-4.99 (1H, m), 6.83 (1H, td, J = 8.3, 2.7 Hz), 6.92 (1H, dd, J = 10.0, 2.7 Hz), 7.10-7.13 (4H, m), 7.21-7.22 (1H, m).

TABLE 8-continued

| 9(9a) | 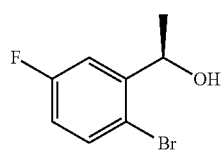 | ¹H-NMR (CDCl₃) δ: 1.47 (3H, d, J = 6.4 Hz), 1.99 (1H, m), 5.16-5.21 (1H, m), 6.85-6.87 (1H, m), 7.34 (1H, dd, J = 9.6, 3.1 Hz), 7.46 (1H, dd, J = 8.7, 5.2 Hz). |

TABLE 9

| 9(9b) | 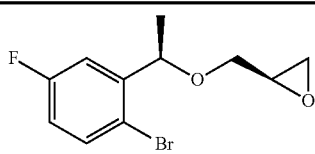 | ¹H-NMR (CDCl₃) δ: 1.42 (3H, d, J = 6.3 Hz), 2.56 (1H, dd, J = 5.1, 2.7 Hz), 2.78 (1H, t, J = 4.5 Hz), 3.15-3.16 (1H, m), 3.31 (1H, dd, J = 11.3, 6.0 Hz), 3.62 (1H, dd, J = 11.3, 3.0 Hz), 4.83 (1H, q, J = 6.3 Hz), 6.86 (1H, td, J = 8.2, 3.2 Hz), 7.22-7.26 (1H, m), 7.47 (1H, dd, J = 8.8, 5.4 Hz). |
| 9(9c) | 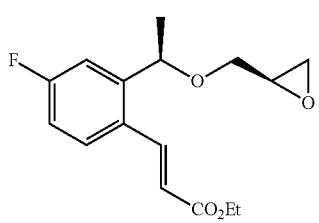 | ¹H-NMR (CDCl₃) δ: 1.38 (3H, t, J = 7.2 Hz), 1.47 (3H, d, J = 6.3 Hz), 2.58 (1H, dd, J = 4.9, 2.7 Hz), 2.81 (1H, dd, J = 4.9, 4.1 Hz), 3.19-3.21 (1H, m), 3.32 (1H, dd, J = 11.2, 6.1 Hz), 3.66 (1H, dd, J = 11.2, 3.2 Hz), 4.31 (2H, q, J = 7.2 Hz), 4.91 (1H, dd, J = 12.4, 7.2 Hz), 6.32 (1H, d, J = 15.6 Hz), 7.01 (1H, td, J = 8.8, 2.7 Hz), 7.26 (1H, dd, J = 8.8, 2.7 Hz), 7.56 (1H, dd, J = 8.8, 5.6 Hz), 8.00 (1H, d, J = 15.6 Hz). |
| 9(9d) | 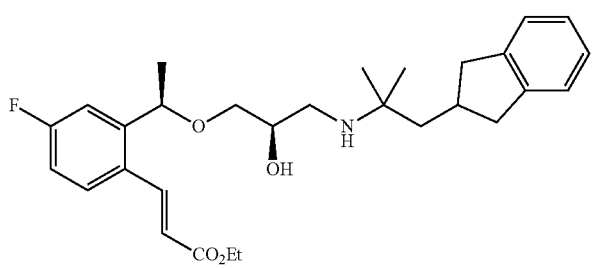 | ¹H-NMR (CDCl₃) δ: 1.11 (6H, s), 1.34 (3H, t, J = 7.2 Hz), 1.43 (3H, d, J = 6.4 Hz), 1.68 (2H, d, J = 6.0 Hz), 2.50-2.65 (4H, m), 2.73 (1H, dd, J = 11.9, 4.1 Hz), 3.06 (2H, dd, J = 14.4, 7.1 Hz), 3.35-3.39 (2H, m), 3.73-3.79 (1H, m), 4.26 (2H, q, J = 7.2 Hz), 4.82 (1H, d, J = 6.4 Hz), 6.28 (1H, d, J = 16.0 Hz), 6.95-6.99 (1H, m), 7.10-7.22 (5H, m), 7.52 (1H, dd, J = 8.7, 5.5 Hz), 7.97 (1H, d, J = 16.0 Hz). |
| 9(9e) | 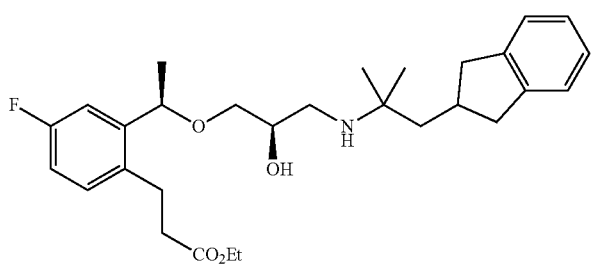 | ¹H-NMR (CDCl₃) δ: 1.11 (6H, s), 1.24 (3H, t, J = 7.2 Hz), 1.42 (3H, d, J = 6.0 Hz), 1.67 (2H, d, J = 6.0 Hz), 2.50-2.64 (6H, m), 2.72 (1H, dd, J = 11.9, 4.1 Hz), 2.92 (2H, t, J = 8.0 Hz), 3.06 (2H, dd, J = 14.4, 7.1 Hz), 3.29-3.34 (2H, m), 3.73-3.78 (1H, m), 4.13 (2H, q, J = 7.2 Hz), 4.71-4.72 (1H, m), 6.88 (1H, td, J = 8.3, 2.8 Hz), 7.10-7.15 (6H, m). |
| 9(9f) | 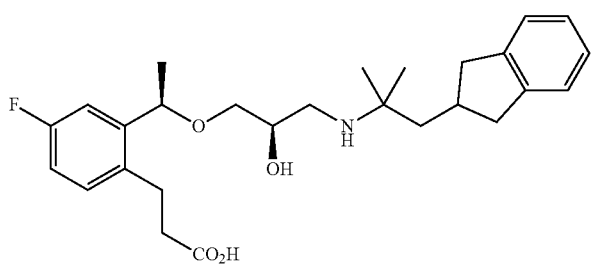 | ¹H-NMR (CDCl₃) δ: 1.41-1.45 (9H, m), 2.00-2.04 (3H, m), 2.43-2.45 (2H, m), 2.63-2.66 (3H, m), 3.01-3.14 (6H, m), 3.55-3.57 (1H, m), 3.65-3.67 (1H, m), 4.14 (1H, br s), 4.97-5.00 (1H, m), 6.88-6.90 (1H, m), 6.94-6.96 (1H, m), 7.09-7.17 (5H, m). |
| 10(10a) | 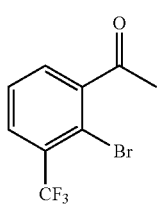 | ¹H-NMR (CDCl₃) δ: 2.63 (3H, s), 7.43-7.51 (2H, m), 7.76 (1H, dd, J = 7.6, 1.7 Hz). |

TABLE 9-continued

| 10(10b) | 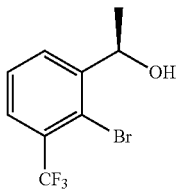 | ¹H-NMR (CDCl₃) δ: 1.50 (3H, d, J = 7.2 Hz), 4.06-4.07 (1H, m), 5.39-5.41 (1H, m), 7.46 (1H, t, J = 7.8 Hz), 7.63 (1H, d, J = 7.8 Hz), 7.83 (1H, d, J = 7.8 Hz). |
| --- | --- | --- |
| 10(10c) | 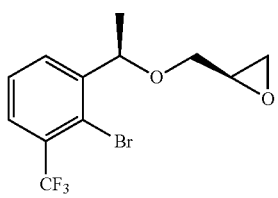 | ¹H-NMR (CDCl₃) δ: 1.45 (3H, d, J = 6.3 Hz), 2.59 (1H, dd, J = 4.6, 2.7 Hz), 2.78 (1H, t, J = 4.6 Hz), 3.13-3.16 (1H, m), 3.32 (1H, dd, J = 11.2, 5.9 Hz), 3.60 (1H, dd, J = 11.2, 2.9 Hz), 5.04 (1H, q, J = 6.3 Hz), 7.45 (1H, t, J = 7.7 Hz), 7.63 (1H, d, J = 7.7 Hz), 7.72 (1H, d, J = 7.7 Hz). |

TABLE 10

| 10(10d) | 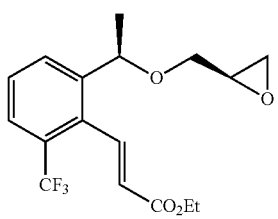 | ¹H-NMR (CDCl₃) δ: 1.35 (3H, t, J = 7.2 Hz), 1.42 (3H, d, J = 6.4 Hz), 2.52 (1H, dd, J = 4.9, 2.7 Hz), 2.76 (1H, dd, J = 4.9, 4.1 Hz), 3.09-3.11 (1H, m), 3.20 (1H, dd, J = 11.2, 6.1 Hz), 3.53 (1H, dd, J = 11.2, 2.9 Hz), 4.29 (2H, q, J = 7.2 Hz), 4.75 (1H, q, J = 6.4 Hz), 5.99 (1H, d, J = 16.3 Hz), 7.48 (1H, t, J = 7.8 Hz), 7.63 (1H, d, J = 7.8 Hz), 7.76 (1H, d, J = 7.8 Hz), 7.87 (1H, d, J = 16.3 Hz). |
| --- | --- | --- |
| 10(10e) | 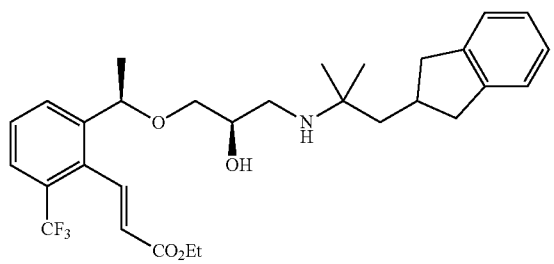 | ¹H-NMR (CDCl₃) δ: 1.11 (6H, s), 1.35 (3H, t, J = 7.1 Hz), 1.40 (3H, d, J = 6.4 Hz), 1.68 (2H, d, J = 6.0 Hz), 2.50-2.64 (4H, m), 2.70 (1H, dd, J = 11.9, 4.1 Hz), 3.04-3.08 (2H, m), 3.24-3.29 (2H, m), 3.70-3.72 (1H, m), 4.29 (2H, q, J = 7.1 Hz), 4.69 (1H, q, J = 6.4 Hz), 5.99 (1H, d, J = 16.5 Hz), 7.11-7.16 (4H, m), 7.46 (1H, t, J = 7.8 Hz), 7.62 (1H, d, J = 7.8 Hz), 7.74 (1H, d, J = 7.8 Hz), 7.86 (1H, d, J = 16.4 Hz). |
| 10(10f) | 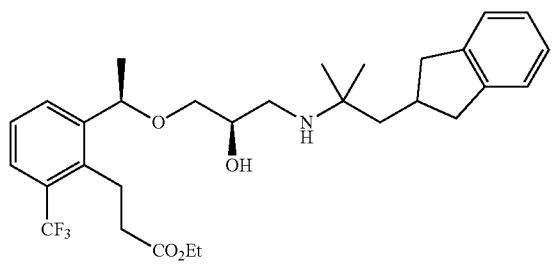 | ¹H-NMR (CDCl₃) δ: 1.11 (6H, s), 1.29 (3H, t, J = 7.2 Hz), 1.46 (3H, d, J = 6.4 Hz), 1.68 (2H, d, J = 6.0 Hz), 2.54-2.62 (6H, m), 2.71 (1H, dd, J = 11.7, 3.9 Hz), 3.04-3.08 (3H, m), 3.15-3.17 (1H, m), 3.26 (1H, dd, J = 9.4, 4.4 Hz), 3.33-3.35 (1H, m), 3.72-3.75 (1H, m), 4.18 (2H, q, J = 7.2 Hz), 4.81 (1H, d, J = 6.4 Hz), 7.11-7.14 (4H, m), 7.35 (1H, t, J = 7.8 Hz), 7.57 (1H, d, J = 7.8 Hz), 7.70 (1H, d, J = 7.8 Hz). |
| 10(10g) | 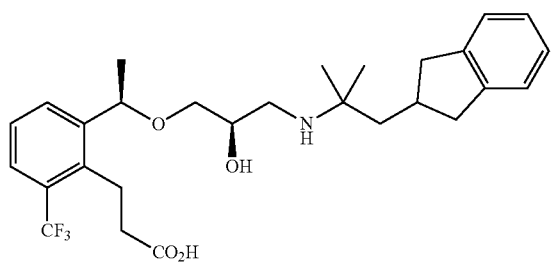 | ¹H-NMR (CDCl₃) δ: 1.44-1.46 (9H, m), 2.00-2.12 (2H, m), 2.44-2.48 (1H, m), 2.58-2.69 (4H, m), 3.05-3.11 (5H, m), 3.26-3.31 (1H, m), 3.65-3.72 (2H, m), 4.15-4.23 (1H, m), 5.20-5.29 (1H, m), 7.10-7.13 (4H, m), 7.27-7.28 (2H, m), 7.42-7.44 (1H, m), 7.56 (1H, d, J = 7.8 Hz). |

TABLE 10-continued

| | | |
|---|---|---|
| 11(11a) | 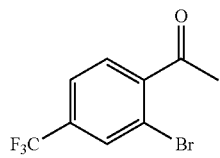 | $^1$H-NMR (CDCl$_3$) δ: 2.65 (3H, s), 7.53 (1H, d, J = 7.8 Hz), 7.64 (1H, d, J = 7.3 Hz), 7.88 (1H, s). |
| 11(11b) | 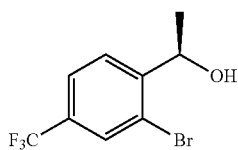 | $^1$H-NMR (CDCl$_3$) δ: 1.50 (3H, d, J = 6.4 Hz), 2.02 (1H, d, J = 3.7 Hz), 5.26-5.27 (1H, m), 7.61 (1H, d, J = 8.3 Hz), 7.75 (1H, d, J = 8.3 Hz), 7.78 (1H, s). |
| 11(11c) | 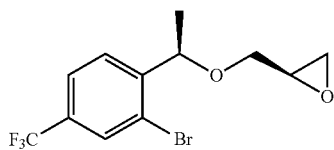 | $^1$H-NMR (CDCl$_3$) δ: 1.44 (3H, d, J = 6.4 Hz), 2.58-2.59 (1H, m), 2.78-2.79 (1H, m), 3.14-3.16 (1H, m), 3.31 (1H, dd, J = 11.5, 6.0 Hz), 3.63 (1H, dd, J = 11.5, 2.8 Hz), 4.92 (1H, q, J = 6.4 Hz), 7.63 (2H, q, J = 8.4 Hz), 7.79 (1H, s). |

TABLE 11

| | | |
|---|---|---|
| 11(11d) | 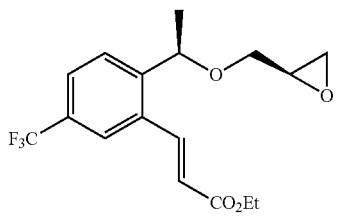 | $^1$H-NMR (CDCl$_3$) δ: 1.35 (3H, t, J = 7.2 Hz), 1.46 (3H, d, J = 6.4 Hz), 2.55 (1H, dd, J = 5.0, 2.8 Hz), 2.78 (1H, t, J = 4.6 Hz), 3.15-3.17 (1H, m), 3.28 (1H, dd, J = 11.2, 6.2 Hz), 3.63 (1H, dd, J = 11.2, 3.0 Hz), 4.29 (2H, q, J = 7.2 Hz), 4.93 (1H, q, J = 6.4 Hz), 6.40 (1H, d, J = 16.0 Hz), 7.64-7.65 (2H, m), 7.76 (1H, s), 8.04 (1H, d, J = 16.0 Hz). |
| 11(11e) | 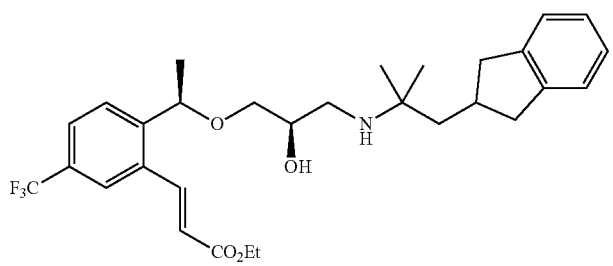 | $^1$H-NMR (CDCl$_3$) δ: 1.11 (6H, s), 1.35 (3H, t, J = 7.2 Hz), 1.45 (3H, d, J = 6.4 Hz), 1.68 (2H, d, J = 6.0 Hz), 2.52-2.64 (4H, m), 2.73 (1H, dd, J = 11.5, 4.1 Hz), 3.06 (2H, dd, J = 14.4, 7.1 Hz), 3.34-3.39 (2H, m), 3.74-3.76 (1H, m), 4.28 (2H, q, J = 7.2 Hz), 4.86 (1H, q, J = 6.4 Hz), 6.39 (1H, d, J = 15.6 Hz), 7.11-7.14 (4H, m), 7.62-7.63 (2H, m), 7.76 (1H, s), 8.04 (1H, d, J = 15.6 Hz). |
| 11(11f) | 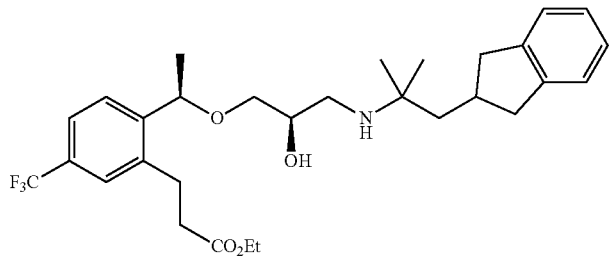 | $^1$H-NMR (CDCl$_3$) δ: 1.10 (6H, s), 1.24 (3H, t, J = 7.3 Hz), 1.45 (3H, d, J = 6.4 Hz), 1.67 (2H, d, J = 6.0 Hz), 2.50-2.65 (6H, m), 2.71 (1H, dd, J = 11.5, 4.1 Hz), 3.00-3.10 (4H, m), 3.28-3.36 (2H, m), 3.73-3.76 (1H, m), 4.14 (2H, q, J = 7.3 Hz), 4.80 (1H, q, J = 6.4 Hz), 7.10-7.18 (4H, m), 7.41 (1H, s), 7.49 (1H, d, J = 8.3 Hz), 7.57 (1H, d, J = 8.3 Hz). |
| 11(11g) | 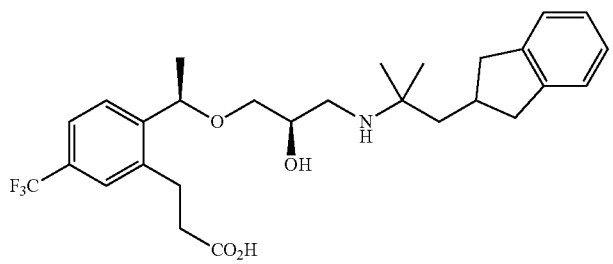 | $^1$H-NMR (CDCl$_3$) δ: 1.41 (3H, s), 1.43 (3H, s), 1.47 (3H, d, J = 6.4 Hz), 2.00-2.04 (2H, m), 2.44-2.46 (2H, m), 2.63-2.65 (3H, m), 2.99-3.14 (6H, m), 3.57-3.60 (1H, m), 3.67-3.69 (1H, m), 4.13-4.18 (1H, m), 5.03-5.05 (1H, m), 7.09-7.10 (4H, m), 7.36 (1H, d, J = 8.3 Hz), 7.41-7.43 (2H, m). |

TABLE 11-continued

| 12(12a) | 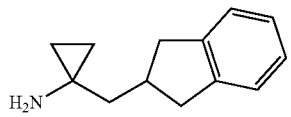 | ¹H-NMR (CDCl₃) δ: 0.69 (2H, t, J = 6.7 Hz), 1.22-1.28 (2H, m), 1.87 (2H, d, J = 7.6 Hz), 2.62 (2H, dd, J = 15.4, 7.3 Hz), 2.76-2.84 (1H, m), 3.20 (2H, dd, J = 15.2, 7.7 Hz), 7.09-7.12 (2H, m), 7.14-7.18 (2H, m), 8.30 (2H, br s). |
|---|---|---|
| 12(12b) | 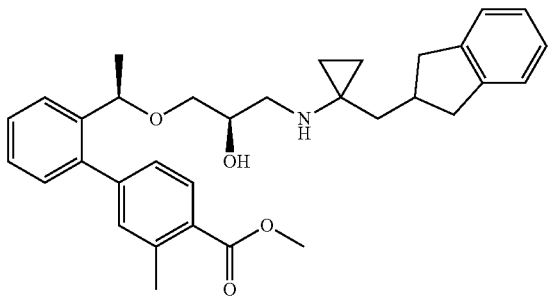 | ¹H-NMR (CDCl₃) δ: 0.35-0.40 (2H, m), 0.52-0.56 (2H, m), 1.35 (3H, d, J = 6.3 Hz), 1.52 (1H, dd, J = 14.6, 6.6 Hz), 1.74 (1H, dd, J = 14.6, 6.0 Hz), 2.60-2.68 (4H, m), 2.64 (3H, s), 2.77 (1H, dd, J = 12.0, 4.0 Hz), 3.02-3.08 (2H, m), 3.13 (1H, dd, J = 9.5, 6.0 Hz), 3.19 (1H, dd, J = 9.2, 4.6 Hz), 3.63-3.67 (1H, m), 3.92 (3H, s), 4.47 (1H, q, J = 6.3 Hz), 7.11-7.20 (7H, m), 7.29 (1H, td, J = 7.6, 1.5 Hz), 7.38 (1H, td, J = 7.7, 1.1 Hz), 7.55 (1H, d, J = 6.3 Hz), 7.95 (1H, d, J = 8.0 Hz). |

TABLE 12

| 12(12c) | 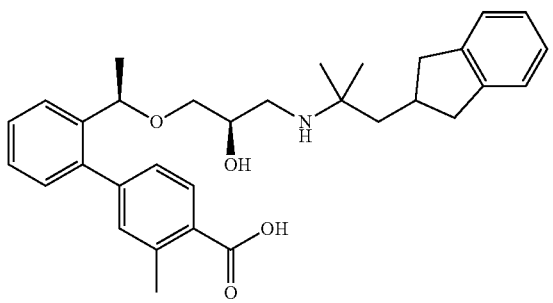 | ¹H-NMR (CDCl₃) δ: 0.51-0.60 (2H, m), 0.93-1.01 (2H, m), 1.33 (3H, d, J = 6.4 Hz), 1.59 (1H, dd, J = 14.7, 6.9 Hz), 1.92 (1H, dd, J = 14.7, 5.5 Hz), 2.54 (3H, s), 2.60-2.71 (3H, m), 2.85 (1H, dd, J = 11.9, 8.7 Hz), 3.04 (1H, dd, J = 12.2, 3.4 Hz), 3.07-3.14 (2H, m), 3.21-3.29 (2H, m), 3.92-3.98 (1H, m), 4.41 (2H, br s), 4.53 (1H, q, J = 6.3 Hz), 7.05-7.07 (2H, m), 7.10-7.13 (2H, m), 7.14-7.17 (3H, m), 7.28 (1H, t, J = 8.3 Hz), 7.38 (1H, t, J = 7.6 Hz), 7.54 (1H, d, J = 6.9 Hz), 7.85 (1H, d, J = 8.3 Hz). |
|---|---|---|
| 13(13a) | 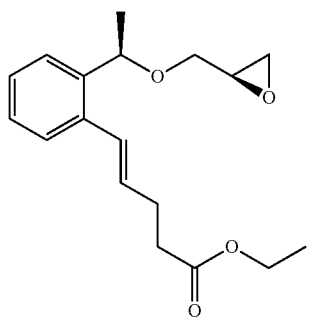 | ¹H-NMR (CDCl₃) δ: 1.27 (3H, t, J = 7.2 Hz), 1.43 (3H, d, J = 6.9 Hz), 2.47-2.51 (3H, m), 2.54-2.58 (2H, m), 2.75 (1H, t, J = 4.6 Hz), 3.13-3.16 (1H, m), 3.22 (1H, dd, J = 11.2, 6.0 Hz), 3.57 (1H, dd, J = 11.5, 3.4 Hz), 4.15 (2H, q, J = 7.1 Hz), 4.80 (1H, q, J = 6.5 Hz), 6.03 (1H, dt, J = 15.7, 6.7 Hz), 6.75 (1H, d, J = 15.5 Hz), 7.19-7.27 (2H, m), 7.38 (2H, ddd, J = 12.7, 7.6, 1.6 Hz). |
| 13(13b) | 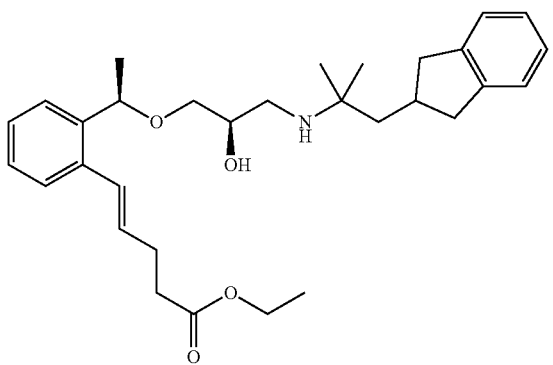 | ¹H-NMR (CDCl₃) δ: 1.10 (6H, s), 1.26 (3H, t, J = 7.2 Hz), 1.42 (3H, d, J = 6.3 Hz), 1.66 (2H, d, J = 6.3 Hz), 2.46-2.63 (9H, m), 2.69 (1H, dd, J = 11.5, 4.0 Hz), 3.03-3.08 (3H, m), 3.31 (1H, d, J = 5.7 Hz), 3.73-3.78 (1H, m), 4.15 (2H, q, J = 6.7 Hz), 4.73 (1H, q, J = 6.3 Hz), 6.03 (1H, dt, J = 15.7, 6.7 Hz), 6.74 (1H, d, J = 15.5 Hz), 7.10-7.13 (3H, m), 7.14-7.17 (2H, m), 7.22 (1H, ddd, J = 12.6, 7.4, 1.7 Hz), 7.36-7.39 (2H, m). |

TABLE 12-continued

13(13c) 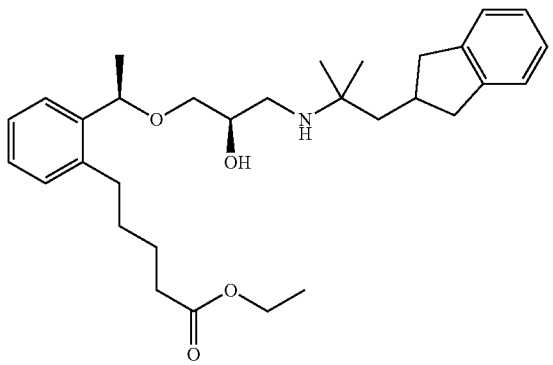

¹H-NMR (CDCl₃) δ: 1.10 (6H, s), 1.25 (3H, t, J = 7.2 Hz), 1.43 (3H, d, J = 6.9 Hz), 1.57-1.75 (6H, m), 2.33 (2H, t, J = 7.4 Hz), 2.49-2.55 (2H, m), 2.56-2.65 (4H, m), 2.69 (1H, dd, J = 12.0, 4.0 Hz), 3.05 (2H, dd, J = 14.6, 7.2 Hz), 3.25-3.32 (2H, m), 3.72-3.77 (1H, m), 4.12 (2H, q, J = 7.3 Hz), 4.72 (1H, q, J = 6.5 Hz), 7.10-7.12 (3H, m), 7.14-7.23 (4H, m), 7.42 (1H, dd, J = 7.4, 1.7 Hz).

13(13d) 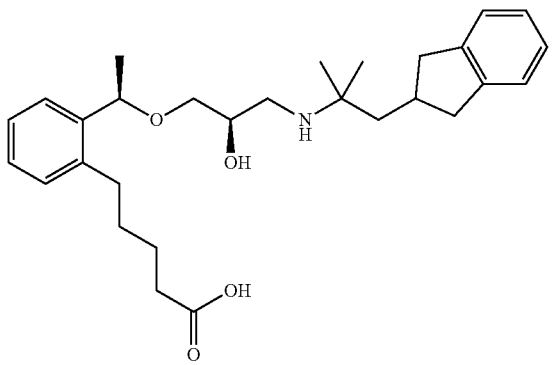

¹H-NMR (CDCl₃) δ: 1.31 (6H, d, J = 5.2 Hz), 1.36-1.38 (1H, m), 1.40 (3H, d, J = 6.3 Hz), 1.47-1.57 (2H, br m), 1.63-1.74 (2H, br m), 1.87 (2H, t, J = 6.0 Hz), 2.17 (1H, dq, J = 14.6, 4.1 Hz), 2.33 (1H, dq, J = 14.7, 4.0 Hz), 2.41-2.50 (2H, m), 2.53-2.59 (2H, m), 2.65-2.71 (1H, m), 2.84 (1H, dd, J = 12.3, 10.0 Hz), 3.00-3.09 (3H, m), 3.30 (1H, dd, J = 10.9, 8.6 Hz), 3.56 (1H, dd, J = 10.6, 5.4 Hz), 4.26-4.31 (1H, m), 4.77 (1H, q, J = 6.3 Hz), 7.08 (1H, dd, J = 7.4, 1.7 Hz), 7.11-7.20 (6H, m), 7.35 (1H, dd, J = 7.4, 1.7 Hz).

TABLE 13

14(14a) 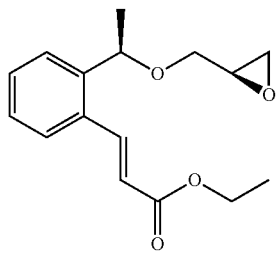

¹H-NMR (CDCl₃) δ: 1.35 (3H, t, J = 7.2 Hz), 1.46 (3H, d, J = 6.3 Hz), 2.53 (1H, dd, J = 5.2, 2.9 Hz), 2.76 (1H, t, J = 4.6 Hz), 3.15 (1H, td, J = 6.6, 2.9 Hz), 3.29 (1H, dd, J = 11.2, 6.0 Hz), 3.59 (1H, dd, J = 11.5, 2.9 Hz), 4.28 (2H, q, J = 7.1 Hz), 4.89 (1H, q, J = 6.5 Hz), 6.33 (1H, d, J = 15.5 Hz), 7.29 (1H, t, J = 7.4 Hz), 7.40 (1H, t, J = 7.7 Hz), 7.49 (1H, d, J = 8.0 Hz), 7.54 (1H, d, J = 8.0 Hz), 8.09 (1H, d, J = 15.5 Hz).

14(14b) 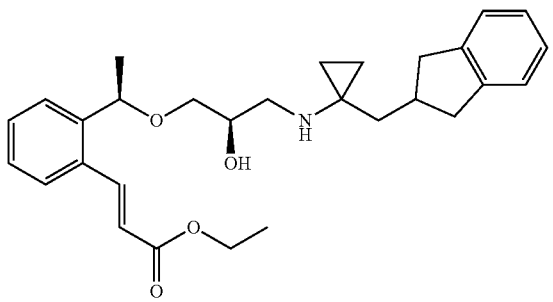

¹H-NMR (CDCl₃) δ: 0.36-0.40 (2H, m), 0.54-0.58 (2H, m), 1.34 (2H, t, J = 7.2 Hz), 1.44 (3H, d, J = 6.3 Hz), 1.49-1.58 (2H, m), 1.74 (1H, dd, J = 14.6, 6.0 Hz), 2.62-2.69 (4H, m), 2.82 (1H, dd, J = 12.0, 4.0 Hz), 3.02-3.10 (2H, m), 3.30-3.35 (2H, m), 3.72-3.76 (1H, m), 4.26 (2H, q, J = 7.3 Hz), 4.81 (1H, q, J = 6.5 Hz), 6.32 (1H, d, J = 16.0 Hz), 7.10-7.14 (2H, m), 7.17-7.19 (2H, m), 7.25-7.28 (1H, m), 7.36 (1H, t, J = 8.0 Hz), 7.45 (1H, d, J = 9.2 Hz), 7.52 (1H, d, J = 7.4 Hz), 8.08 (1H, d, J = 16.0 Hz).

TABLE 13-continued

| | | |
|---|---|---|
| 14(14c) | 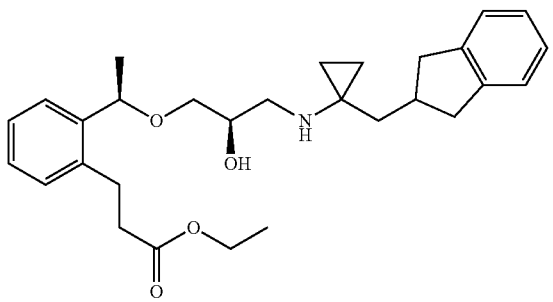 | ¹H-NMR (CDCl₃) δ: 0.36-0.40 (2H, m), 0.54-0.58 (2H, m), 1.24 (3H, t, J = 7.2 Hz), 1.43 (3H, d, J = 6.3 Hz), 1.52-1.55 (1H, m), 1.74 (1H, dd, J = 14.6, 6.0 Hz), 2.57 (2H, td, J = 7.9, 2.3 Hz), 2.62-2.69 (4H, m), 2.80 (1H, dd, J = 11.7, 4.3 Hz), 2.96 (2H, dd, J = 8.6, 7.4 Hz), 3.02-3.10 (2H, m), 3.28-3.29 (2H, m), 3.71-3.76 (1H, m), 4.13 (2H, q, J = 7.1 Hz), 4.73 (1H, q, J = 6.3 Hz), 7.11-7.15 (3H, m), 7.16-7.22 (4H, m), 7.41 (1H, dd, J = 7.4, 1.7 Hz). |
| 14(14d) | 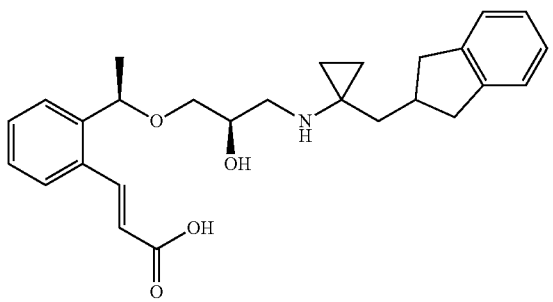 | ¹H-NMR (CDCl₃) δ: 0.50-0.54 (1H, m), 0.56-0.60 (1H, m), 0.93-0.97 (1H, m), 1.00-1.04 (1H, m), 1.47 (3H, d, J = 6.3 Hz), 1.64 (1H, dd, J = 14.6, 7.2 Hz), 1.83 (1H, dd, J = 14.9, 6.3 Hz), 2.47 (2H, t, J = 7.7 Hz), 2.58-2.66 (4H, m), 2.91-3.06 (4H, m), 3.11 (2H, dd, J = 14.0, 6.0 Hz), 3.48 (1H, dd, J = 10.9, 5.2 Hz), 3.60 (1H, dd, J = 10.3, 5.2 Hz), 3.94-3.99 (1H, m), 4.93 (1H, q, J = 6.5 Hz), 7.08-7.12 (2H, m), 7.13-7.20 (5H, m), 7.32-7.34 (1H, m). |

As intermediates for producing the compounds of the Examples, the following compounds were produced. The production was performed according to the production steps of Example 4. Specifically, the Example 4(4a)-2 described below indicates that the production is carried out according to the same steps as Example 4(4a). The other compounds described with a number behind the hyphen indicate that the compounds are produced according to the same steps as those described in the Example on which they are based.

TABLE 14

| Example No. | Structure | Data |
|---|---|---|
| 4(4a)-2 | 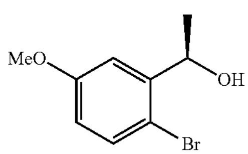 | ¹H-NMR (CDCl₃) δ: 1.47 (3H, d, J = 6.0 Hz), 1.94-1.98 (1H, m), 3.81 (3H, s), 5.15-5.23 (1H, m), 6.69 (1H, dd, J = 8.7, 3.2 Hz), 7.16 (1H, d, J = 3.2 Hz), 7.39 (1H, d, J = 8.7 Hz). Optical purity: 95.6% ee |
| 4(4b)-2 | 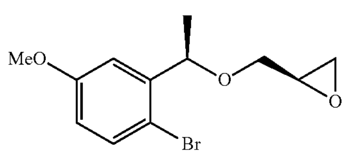 | ¹H-NMR (CDCl₃) δ: 1.43 (3H, dd, J = 6.4, 2.8 Hz), 2.57-2.61 (1H, m), 2.76-2.80 (1H, m), 3.12-3.19 (1H, m), 3.29-3.36 (1H, m), 3.60-3.65 (1H, m), 3.81 (3H, s), 4.80-4.87 (1H, m), 6.71 (1H, dt, J = 8.7, 2.8 Hz), 7.07 (1H, t, J = 2.8 Hz), 7.40 (1H, dd, J = 8.7, 2.8 Hz). |
| 4(4c)-2 | 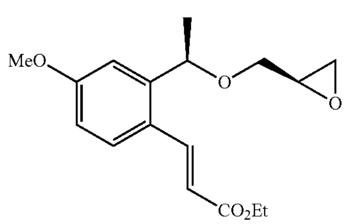 | ¹H-NMR (CDCl₃) δ: 1.34 (3H, t, J = 7.2 Hz), 1.45 (3H, d, J = 6.6 Hz), 2.55-2.58 (1H, m), 2.75-2.79 (1H, m), 3.14-3.17 (1H, m), 3.31 (1H, dd, J = 11.4, 5.9 Hz), 3.62 (1H, dd, J = 11.4, 3.1 Hz), 3.85 (3H, s), 4.26 (2H, q, J = 7.2 Hz), 4.89 (1H, q, J = 6.6 Hz), 6.26 (1H, d, J = 15.6 Hz), 6.82 (1H, dd, J = 8.5, 2.7 Hz), 7.04 (1H, d, J = 2.7 Hz), 7.53 (1H, d, J = 8.5 Hz), 7.99 (1H, d, J = 15.6 Hz). |
| 4(4a)-3 | 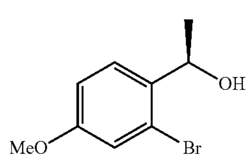 | ¹H-NMR (CDCl₃) δ: 1.47 (3H, d, J = 6.8 Hz), 1.87-1.97 (1H, m), 3.79 (3H, s), 5.16-5.24 (1H, m), 6.90 (1H, dd, J = 8.5, 2.4 Hz), 7.07 (1H, d, J = 2.4 Hz), 7.48 (1H, d, J = 8.5 Hz). Optical purity: 93.9% ee |

TABLE 14-continued

| Example No. | Structure | Data |
| --- | --- | --- |
| 4(4b)-3 | 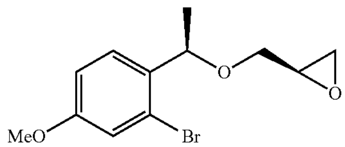 | ¹H-NMR (CDCl₃) δ: 1.41 (3H, d, J = 6.3 Hz), 2.54-2.57 (1H, m), 2.75-2.78 (1H, m), 3.10-3.16 (1H, m), 3.30 (1H, dd, J = 11.9, 6.0 Hz), 3.56 (1H, dd, J = 11.9, 3.2 Hz), 3.80 (3H, s), 4.84 (1H, q, J = 6.3 Hz), 6.91 (1 H, dd, J = 8.7, 2.8 Hz), 7.06 (1H, d, J = 1.8 Hz), 7.40 (1H, d, J = 8.7 Hz). |
| 4(4c)-3 | 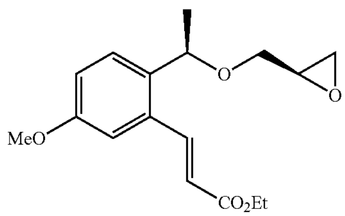 | ¹H-NMR (CDCl₃) δ: 1.35 (3H, t, J = 7.3 Hz), 1.45 (3H, d, J = 6.9 Hz), 2.51-2.54 (1H, m), 2.74-2.78 (1H, m), 3.11-3.17 (1H, m), 3.24-3.30 (1H, m), 3.53-3.59 (1H, m), 3.83 (3H, s), 4.25-4.32 (2H, m), 4.83 (1 H, q, J = 6.4 Hz), 6.32 (1H, d, J = 15.6 Hz), 6.96 (1H, d, J = 8.3 Hz), 7.03 (1H, s), 7.40 (1H, d, J = 7.3 Hz), 8.08 (1H, d, J = 15.6 Hz). |
| 4(4a)-4 | 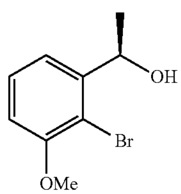 | ¹H-NMR (CDCl₃) δ: 1.48 (3H, d, J = 6.3 Hz), 1.98-2.02 (1H, m), 3.90 (3H, s), 5.27-5.36 (1H, m), 6.83 (1H, dd, J = 7.9, 1.5 Hz), 7.22 (1H, dd, J = 7.9, 1.5 Hz), 7.31 (1H, t, J = 7.9 Hz). Optical purity: 95.1% ee |

TABLE 15

| Example No. | Structure | Data |
| --- | --- | --- |
| 4(4b)-4 | 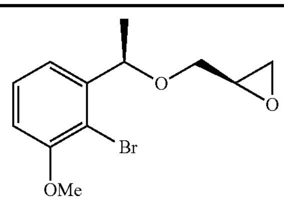 | ¹H-NMR (CDCl₃) δ: 1.43 (3H, d, J = 6.4 Hz), 2.56 (1H, dd, J = 4.9, 2.7 Hz), 2.77 (1H, t, J = 4.5 Hz), 3.11-3.18 (1H, m), 3.31 (1H, dd, J = 11.2, 5.9 Hz), 3.59 (1H, dd, J = 11.2, 3.2 Hz), 3.90 (3H, s), 4.96 (1H, q, J = 6.4 Hz), 6.82 (1H, d, J = 7.9 Hz), 7.13 (1H, d, J = 7.9 Hz), 7.31 (1H, t, J = 7.9 Hz). |
| 4(4c)-4 | 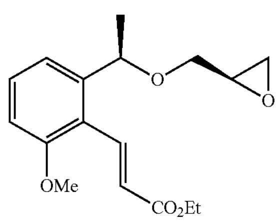 | ¹H-NMR (CDCl₃) δ: 1.35 (3H, t, J = 7.2 Hz), 1.46 (3H, d, J = 6.4 Hz), 2.53 (1H, dd, J = 5.1, 2.7 Hz), 2.75 (1H, t, J = 4.6 Hz), 3.11-3.15 (1H, m), 3.26 (1H, dd, J = 11.2, 5.9 Hz), 3.53 (1H, dd, J = 11.2, 2.7 Hz), 3.87 (3H, s), 4.27 (2H, q, J = 7.2 Hz), 4.88 (1H, q, J = 6.4 Hz), 6.52 (1H, d, J = 16.1 Hz), 6.85 (1H, d, J = 8.0 Hz), 7.16 (1H, d, J = 8.0 Hz), 7.34 (1H, t, J = 8.0 Hz), 7.88 (1H, d, J = 16.1 Hz). |
| 4(4a)-5 | 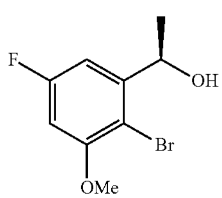 | ¹H-NMR (CDCl₃) δ: 1.46 (3H, d, J = 6.4 Hz), 1.99 (1H, d, J = 3.2 Hz), 3.89 (3H, s), 5.25-5.32 (1H, m), 6.57 (1H, dd, J = 10.1, 2.7 Hz), 6.99 (1H, dd, J = 9.7, 2.7 Hz). Optical purity: 97.2% ee |
| 4(4b)-5 | 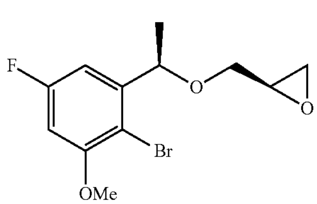 | ¹H-NMR (CDCl₃) δ: 1.41 (3H, d, J = 6.0 Hz), 2.56 (1H, dd, J = 5.2, 2.9 Hz), 2.78 (1H, t, J = 4.6 Hz), 3.13-3.18 (1H, m), 3.29 (1H, dd, J = 11.5, 6.0 Hz), 3.61 (1H, dd, J = 11.5, 3.4 Hz), 3.89 (3H, s), 4.94 (1H, q, J = 6.5 Hz), 6.57 (1H, dd, J = 9.7, 2.9 Hz), 6.88 (1H, dd, J = 9.2, 2.9 Hz). |

TABLE 15-continued

| | | |
|---|---|---|
| 4(4c)-5 | 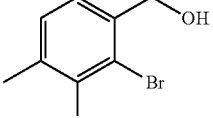 | ¹H-NMR (CDCl₃) δ: 1.34 (3H, t, J = 7.1 Hz), 1.43 (3H, d, J = 6.3 Hz), 2.54 (1H, dd, J = 4.9, 2.6 Hz), 2.77 (1H, t, J = 4.6 Hz), 3.13-3.16 (1H, m), 3.26 (1H, dd, J = 10.9, 6.0 Hz), 3.57 (1H, dd, J = 10.9, 2.9 Hz), 3.86 (3H, s), 4.27 (2H, q, J = 7.1 Hz), 4.88 (1H, q, J = 6.3 Hz), 6.50 (1H, d, J = 16.0 Hz), 6.57 (1H, dd, J = 10.3, 2.6 Hz), 6.90 (1H, dd, J = 9.5, 2.6 Hz), 7.77 (1H, d, J = 16.0 Hz). |
| 4(4a)-6 | | ¹H-NMR (CDCl₃) δ: 1.49 (3H, d, J = 6.9 Hz), 1.84 (1H, d, J = 5.0 Hz), 2.33 (3H, d, J = 2.3 Hz), 5.12-5.18 (1H, m), 7.21 (1H, t, J = 8.0 Hz), 7.34 (1H, d, J = 8.3 Hz). Optical purity: 92.5% ee |
| 4(4b)-6 | | ¹H-NMR (CDCl₃) δ: 1.45 (3H, d, J = 6.3 Hz), 2.33 (3H, d, J = 2.4 Hz), 2.55 (1H, dd, J = 5.1, 2.4 Hz), 2.77 (1H, dd, J = 4.9, 4.2 Hz), 3.12-3.16 (1H, m), 3.29 (1H, dd, J = 11.4, 6.1 Hz), 3.61 (1H, dd, J = 11.4, 3.1 Hz), 4.81 (1H, q, J = 6.3 Hz), 7.15 (1H, t, J = 7.9 Hz), 7.35 (1H, d, J = 8.3 Hz). |
| 4(4c)-6 | 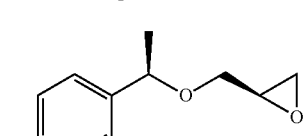 | ¹H-NMR (CDCl₃) δ: 1.35 (3H, t, J = 7.1 Hz), 1.47 (3H, d, J = 6.4 Hz), 2.33 (3H, d, J = 2.4 Hz), 2.56 (1H, dd, J = 4.9, 2.7 Hz), 2.78 (1H, t, J = 4.6 Hz), 3.14-3.17 (1H, m), 3.31 (1H, dd, J = 11.4, 6.0 Hz), 3.62 (1H, dd, J = 11.2, 3.2 Hz), 4.28 (2H, q, J = 7.1 Hz), 4.86 (1H, q, J = 6.4 Hz), 6.36 (1H, d, J = 15.9 Hz), 7.29 (1H, d, J = 7.3 Hz), 7.36 (1H, d, J = 8.3 Hz), 7.91 (1H, d, J = 15.9 Hz). |

TABLE 16

| | | |
|---|---|---|
| 4(4a)-7 | | ¹H-NMR (CDCl₃) δ: 1.45 (3H, d, J = 6.3 Hz), 1.75 (1H, d, J = 4.0 Hz), 2.27 (3H, d, J = 2.3 Hz), 5.05-5.11 (1H, m), 7.21 (1H, d, J = 8.6 Hz), 7.40 (1H, t, J = 7.7 Hz). Optical purity: 94.0% ee |
| 4(4b)-7 | | ¹H-NMR (CDCl₃) δ: 1.41 (3H, d, J = 6.3 Hz), 2.27 (3H, d, J = 2.3 Hz), 2.50-2.51 (1H, m), 2.76-2.78 (1H, m), 3.13-3.19 (2H, m), 3.61-3.66 (1H, m), 4.73 (1H, q, J = 6.3 Hz), 7.10 (1H, d, J = 9.2 Hz), 7.39 (1H, t, J = 7.7 Hz). |
| 4(4c)-7 | 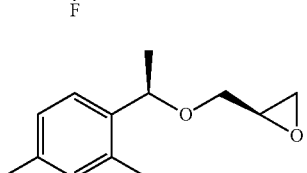 | ¹H-NMR (CDCl₃) δ: 1.34 (3H, t, J = 7.2 Hz), 1.42 (3H, d, J = 6.5 Hz), 2.25 (3H, d, J = 2.3 Hz), 2.51 (1H, dd, J = 5.2, 2.3 Hz), 2.75-2.79 (1H, m), 3.14-3.21 (2H, m), 3.62-3.67 (1H, m), 4.27 (2H, q, J = 7.2 Hz), 4.77 (1H, q, J = 6.5 Hz), 6.50 (1H, d, J = 16.0 Hz), 7.23 (1H, d, J = 7.7 Hz), 7.40 (1H, t, J = 7.7 Hz), 7.81 (1H, d, J = 16.0 Hz). |

TABLE 16-continued

| | | |
|---|---|---|
| 4(4a)-8 | 4-cyano-2-bromo-α-methylbenzyl alcohol structure | $^1$H-NMR (CDCl$_3$) δ: 1.49 (3H, d, J = 6.9 Hz), 2.03 (1H, d, J = 4.0 Hz), 5.22-5.28 (1H, m), 7.65 (1H, dd, J = 8.0, 1.1 Hz), 7.76 (1H, d, J = 8.0 Hz), 7.81 (1H, d, J = 1.1 Hz). Optical purity: 94.8% ee |
| 4(4b)-8 | glycidyl ether structure | $^1$H-NMR (CDCl$_3$) δ: 1.44 (3H, d, J = 6.4 Hz), 2.58-2.60 (1H, m), 2.78-2.82 (1H, m), 3.13-3.19 (1H, m), 3.28-3.34 (1H, m), 3.62-3.67 (1H, m), 4.90 (1H, q, J = 6.4 Hz), 7.64-7.67 (2H, m), 7.83 (1H, s). |
| 4(4c)-8 | glycidyl ether with cinnamate structure | $^1$H-NMR (CDCl$_3$) δ: 1.35 (3H, t, J = 7.1 Hz), 1.44 (3H, d, J = 6.5 Hz), 2.55 (1H, dd, J = 4.6, 2.9 Hz), 2.76-2.80 (1H, m), 3.13-3.18 (1H, m), 3.26 (1H, dd, J = 11.5, 6.3 Hz), 3.65 (1H, dd, J = 11.5, 2.9 Hz), 4.29 (2H, q, J = 7.1 Hz), 4.91 (1H, q, J = 6.5 Hz), 6.37 (1H, d, J = 16.0 Hz), 7.63-7.69 (2H, m), 7.79 (1H, s), 7.97 (1H, d, J = 16.0 Hz). |
| 4(4a)-9 | 4,5-difluoro-2-bromo-α-methylbenzyl alcohol structure | $^1$H-NMR (CDCl$_3$) δ: 1.45 (3H, d, J = 6.3 Hz), 1.98 (1H, d, J = 3.4 Hz), 5.12-5.18 (1H, m), 7.35 (1H, dd, J = 9.7, 7.4 Hz), 7.46 (1H, dd, J = 11.5, 8.0 Hz). Optical purity: 93.6% ee |
| 4(4b)-9 | glycidyl ether structure | $^1$H-NMR (CDCl$_3$) δ: 1.40 (3H, d, J = 6.3 Hz), 2.57 (1H, dd, J = 4.9, 2.6 Hz), 2.79 (1H, t, J = 4.5 Hz), 3.13-3.17 (1H, m), 3.29 (1H, dd, J = 11.5, 5.7 Hz), 3.62 (1H, dd, J = 11.5, 2.9 Hz), 4.80 (1H, q, J = 6.3 Hz), 7.32-7.37 (2H, m). |
| 4(4c)-9 | glycidyl ether with cinnamate structure | $^1$H-NMR (CDCl$_3$) δ: 1.34 (3H, t, J = 7.2 Hz), 1.42 (3H, d, J = 6.9 Hz), 2.55 (1H, dd, J = 5.2, 2.9 Hz), 2.78 (1H, t, J = 4.6 Hz), 3.14-3.17 (1H, m), 3.27 (1H, dd, J = 11.5, 5.7 Hz), 3.64 (1H, dd, J = 11.5, 2.9 Hz), 4.28 (2H, q, J = 7.1 Hz), 4.85 (1H, q, J = 6.3 Hz), 6.26 (1H, d, J = 15.5 Hz), 7.31-7.35 (2H, m), 7.91 (1H, d, J = 15.5 Hz). |

TABLE 17

| | | |
|---|---|---|
| 4(4a)-10 | 3,5-difluoro-2-bromo-α-methylbenzyl alcohol structure | $^1$H-NMR (CDCl$_3$) δ: 1.47 (3H, d, J = 6.3 Hz), 1.98 (1H, d, J = 3.4 Hz), 5.21-5.27 (1H, m), 6.82 (1H, td, J = 8.2, 3.1 Hz), 7.19-7.23 (1H, m). Optical purity: 94.1% ee |
| 4(4b)-10 | glycidyl ether structure | $^1$H-NMR (CDCl$_3$) δ: 1.42 (3H, d, J = 6.5 Hz), 2.57 (1H, dd, J = 4.6, 2.6 Hz), 2.79 (1H, t, J = 4.6 Hz), 3.14-3.18 (1H, m), 3.29 (1H, dd, J = 11.5, 5.7 Hz), 3.65 (1H, dd, J = 11.5, 2.9 Hz), 4.90 (1H, q, J = 6.5 Hz), 6.82 (1H, td, J = 8.3, 2.9 Hz), 7.08-7.13 (1H, m). |

TABLE 17-continued

| | | |
|---|---|---|
| 4(4c)-10 | [structure: 2,4-difluorophenyl with CH(CH₃)-O-CH₂-epoxide and CH=CH-CO₂Et] | $^1$H-NMR (CDCl$_3$) δ: 1.35 (3H, t, J = 7.1 Hz), 1.43 (3H, d, J = 6.3 Hz), 2.55 (1H, dd, J = 4.6, 2.6 Hz), 2.79 (1H, t, J = 4.6 Hz), 3.14-3.18 (1H, m), 3.27 (1H, dd, J = 11.2, 6.0 Hz), 3.64 (1H, dd, J = 11.2, 2.9 Hz), 4.28 (2H, q, J = 7.1 Hz), 4.86 (1H, q, J = 6.3 Hz), 6.48 (1H, dd, J = 16.0, 1.7 Hz), 6.76-6.82 (1H, m), 7.08-7.12 (1H, m), 7.69 (1H, d, J = 16.0 Hz). |
| 4(4a)-11 | [structure: 4-chloro-5-fluoro-2-bromophenyl with CH(CH₃)OH] | $^1$H-NMR (CDCl$_3$) δ: 1.45 (3H, d, J = 6.3 Hz), 2.00 (1H, d, J = 3.4 Hz), 5.11-5.18 (1H, m), 7.43 (1H, d, J = 9.7 Hz), 7.56 (1H, d, J = 6.9 Hz). Optical purity: 94.0% ee |
| 4(4b)-11 | [structure: 4-chloro-5-fluoro-2-bromophenyl with CH(CH₃)-O-CH₂-epoxide] | $^1$H-NMR (CDCl$_3$) δ: 1.41 (3H, d, J = 6.3 Hz), 2.57 (1H, dd, J = 4.9, 2.6 Hz), 2.79 (1H, t, J = 4.6 Hz), 3.13-3.17 (1H, m), 3.29 (1H, dd, J = 11.5, 5.7 Hz), 3.64 (1H, dd, J = 11.5, 2.9 Hz), 4.80 (1H, q, J = 6.3 Hz), 7.32 (1H, d, J = 10.3 Hz), 7.57 (1H, d, J = 6.9 Hz). |
| 4(4c)-11 | [structure: 4-chloro-5-fluorophenyl with CH(CH₃)-O-CH₂-epoxide and CH=CH-CO₂Et] | $^1$H-NMR (CDCl$_3$) δ: 1.34 (3H, t, J = 7.3 Hz), 1.42 (3H, d, J = 6.9 Hz), 2.55 (1H, dd, J = 4.9, 2.6 Hz), 2.78 (1H, t, J = 4.6 Hz), 3.13-3.18 (1H, m), 3.27 (1H, dd, J = 11.5, 6.0 Hz), 3.64 (1H, dd, J = 11.5, 2.9 Hz), 4.28 (2H, q, J = 7.3 Hz), 4.84 (1H, q, J = 6.3 Hz), 6.29 (1H, d, J = 16.0 Hz), 7.31 (1H, d, J = 10.3 Hz), 7.57 (1H, d, J = 7.4 Hz), 7.89 (1H, d, J = 16.0 Hz). |
| 4(4a)-12 | [structure: 5-CF₃, 2-Br phenyl with CH(CH₃)OH] | $^1$H-NMR (CDCl$_3$) δ: 1.50 (3H, d, J = 6.4 Hz), 5.24-5.30 (1H, m), 7.38 (1H, d, J = 7.8 Hz), 7.64 (1H, d, J = 7.8 Hz), 7.90 (1H, s). Optical purity: 94% ee |
| 4(4b)-12 | [structure: 5-CF₃, 2-Br phenyl with CH(CH₃)-O-CH₂-epoxide] | $^1$H-NMR (CDCl$_3$) δ: 1.45 (3H, d, J = 6.4 Hz), 2.54 (1H, dd, J = 4.8, 2.5 Hz), 2.79 (1H, t, J = 4.8 Hz), 3.15-3.19 (1H, m), 3.33 (1H, dd, J = 11.2, 6.2 Hz), 3.60 (1H, dd, J = 11.2, 3.2 Hz), 4.92 (1H, q, J = 6.4 Hz), 7.38 (1H, dd, J = 8.3, 2.3 Hz), 7.65 (1H, d, J = 8.3 Hz), 7.78 (1H, s). |
| 4(4c)-12 | [structure: 5-CF₃ phenyl with CH(CH₃)-O-CH₂-epoxide and CH=CH-COOEt] | $^1$H-NMR (CDCl$_3$) δ: 1.36 (3H, t, J = 7.1 Hz), 1.47 (3H, d, J = 6.4 Hz), 2.52 (1H, dd, J = 4.8, 2.5 Hz), 2.78 (1H, t, J = 4.4 Hz), 3.15-3.19 (1H, m), 3.30 (1H, dd, J = 11.2, 6.2 Hz), 3.61 (1H, dd, J = 11.2, 2.8 Hz), 4.29 (2H, q, J = 7.1 Hz), 4.92 (1H, q, J = 6.4 Hz), 6.38 (1H, d, J = 15.6 Hz), 7.54 (1H, d, J = 8.3 Hz), 7.62 (1H, d, J = 8.3 Hz), 7.77 (1H, s), 8.04 (1H, d, J = 15.6 Hz). |

TABLE 18

| | | |
|---|---|---|
| 4(4a)-13 | [structure: 5-ethoxy-2-bromophenyl with CH(CH₃)OH] | $^1$H-NMR (CDCl$_3$) δ: 1.41 (3H, t, J = 7.0 Hz), 1.47 (3H, d, J = 6.3 Hz), 4.03 (2H, q, J = 7.0 Hz), 5.18 (1H, q, J = 6.3 Hz), 6.68 (1H, dd, J = 8.7, 3.0 Hz), 7.15 (1H, d, J = 3.0 Hz), 7.38 (1H, d, J = 8.7 Hz). Optical purity: 90.8% ee |

TABLE 18-continued

| | | |
|---|---|---|
| 4(4b)-13 | (structure: 2-bromo-5-ethoxyphenyl with CH(CH3)-O-CH2-epoxide) | ¹H-NMR (CDCl₃) δ: 1.42 (3H, t, J = 7.0 Hz), 1.42 (3H, d, J = 6.4 Hz), 2.58 (1H, dd, J = 4.8, 2.8 Hz), 2.77 (1H, t, J = 4.8 Hz), 3.12-3.17 (1H, m), 3.31 (1H, dd, J = 11.1, 6.0 Hz), 3.62 (1H, dd, J = 11.1, 3.0 Hz), 4.03 (2H, q, J = 7.0 Hz), 4.82 (1H, q, J = 6.4 Hz), 6.69 (1H, dd, J = 8.7, 2.8 Hz), 7.05 (1H, d, J = 2.8 Hz), 7.38 (1H, d, J = 8.7 Hz). |
| 4(4c)-13 | (structure: 4-ethoxyphenyl with CH(CH3)-O-CH2-epoxide and CH=CH-CO2Et) | ¹H-NMR (CDCl₃) δ: 1.34 (3H, t, J = 7.1 Hz), 1.43 (3H, t, J = 7.1 Hz), 1.44 (3H, d, J = 6.4 Hz), 2.56 (1H, dd, J = 4.7, 2.5 Hz), 2.77 (1H, t, J = 4.7 Hz), 3.13-3.17 (1H, m), 3.29 (1H, dd, J = 11.3, 6.0 Hz), 3.62 (1H, dd, J = 11.3, 3.0 Hz), 4.08 (2H, q, J = 7.1 Hz), 4.26 (2H, q, J = 7.1 Hz), 4.88 (1H, q, J = 6.4 Hz), 6.25 (1H, d, J = 15.6 Hz), 6.81 (1H, dd, J = 8.5, 2.5 Hz), 7.03 (1H, d, J = 2.5 Hz), 7.52 (1H, d, J = 8.5 Hz), 7.98 (1H, d, J = 15.6 Hz). |
| 4(4a)-14 | (structure: 2-bromo-5-chlorophenyl with CH(CH3)-O-CH2-epoxide) | ¹H-NMR (CDCl₃) δ: 1.47 (3H, d, J = 6.3 Hz), 1.98 (1H, d, J = 3.4 Hz), 5.16-5.21 (1H, m), 7.11 (1H, dd, J = 8.6, 2.6 Hz), 7.43 (1H, d, J = 8.6 Hz), 7.60 (1H, d, J = 2.6 Hz). Optical purity: 93.3% ee |
| 4(4b)-14 | (structure: 2-bromo-5-chlorophenyl with CH(CH3)-O-CH2-epoxide) | ¹H-NMR (CDCl₃) δ: 1.42 (3H, d, J = 6.6 Hz), 2.56 (1H, dd, J = 4.6, 2.6 Hz), 2.79 (1H, t, J = 4.6 Hz), 3.14-3.18 (1H, m), 3.30 (1H, dd, J = 11.2, 6.0 Hz), 3.63 (1H, dd, J = 11.2, 3.2 Hz), 4.84 (1H, q, J = 6.6 Hz), 7.11 (1H, dd, J = 8.3, 2.6 Hz), 7.44 (1H, d, J = 8.3 Hz), 7.49 (1H, d, J = 2.6 Hz). |
| 4(4c)-14 | (structure: 4-chlorophenyl with CH(CH3)-O-CH2-epoxide and CH=CH-CO2Et) | ¹H-NMR (CDCl₃) δ: 1.34 (3H, t, J = 6.9 Hz), 1.44 (3H, d, J = 6.3 Hz), 2.53-2.55 (1H, m), 2.79 (1H, t, J = 4.6 Hz), 3.15-3.18 (1H, m), 3.28 (1H, dd, J = 11.5, 6.0 Hz), 3.63 (1H, dd, J = 11.5, 2.3 Hz), 4.28 (2H, q, J = 6.9 Hz), 4.86 (1H, q, J = 6.5 Hz), 6.31 (1H, d, J = 16.0 Hz), 7.25-7.28 (1H, m), 7.45-7.51 (2H, m), 7.98 (1H, d, J = 16.0 Hz). |
| 4(4a)-15 | (structure: 2-bromo-4-chlorophenyl with CH(CH3)-OH) | ¹H-NMR (CDCl₃) δ: 1.46 (3H, d, J = 6.4 Hz), 1.97 (1H, d, J = 3.7 Hz), 5.17-5.23 (1H, m), 7.33 (1H, dd, J = 8.3, 1.8 Hz), 7.52-7.56 (2H, m). Optical purity: 93.4% ee |
| 4(4b)-15 | (structure: 2-bromo-4-chlorophenyl with CH(CH3)-O-CH2-epoxide) | ¹H-NMR (CDCl₃) δ: 1.41 (3H, d, J = 6.4 Hz), 2.57 (1H, q, J = 2.9 Hz), 2.77 (1H, t, J = 4.6 Hz), 3.12-3.15 (1H, m), 3.29 (1H, dd, J = 11.5, 5.7 Hz), 3.59 (1H, dd, J = 11.5, 3.4 Hz), 4.84 (1H, q, J = 6.4 Hz), 7.33 (1H, dd, J = 8.6, 2.3 Hz), 7.44 (1H, d, J = 8.6 Hz), 7.53 (1H, d, J = 2.3 Hz). |

TABLE 19

| | | |
|---|---|---|
| 4(4c)-15 | (structure: 4-chlorophenyl with CH(CH3)-O-CH2-epoxide and CH=CH-CO2Et) | ¹H-NMR (CDCl₃) δ: 1.35 (3H, t, J = 7.3 Hz), 1.43 (3H, d, J = 6.4 Hz), 2.54 (1H, dd, J = 5.2, 2.9 Hz), 2.77 (1H, t, J = 4.6 Hz), 3.12-3.16 (1H, m), 3.26 (1H, dd, J = 11.5, 5.7 Hz), 3.60 (1H, dd, J = 11.5, 3.2 Hz), 4.28 (2H, q, J = 7.3 Hz), 4.85 (1H, q, J = 6.4 Hz), 6.33 (1H, d, J = 15.5 Hz), 7.36 (1H, dd, J = 8.0, 2.3 Hz), 7.44 (1H, d, J = 8.0 Hz), 7.50 (1H, d, J = 2.3 Hz), 7.99 (1H, d, J = 15.5 Hz). |

TABLE 19-continued

| | | |
|---|---|---|
| 4(4a)-16 | 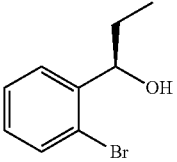 | $^1$H-NMR (CDCl$_3$) δ: 1.01 (3H, t, J = 7.4 Hz), 1.66-1.78 (1H, m), 1.79-1.90 (1H, m), 1.94 (1H, d, J = 3.2 Hz), 4.99-5.05 (1H, m), 7.10-7.15 (1H, m), 7.31-7.36 (1H, m), 7.50-7.56 (2H, m). Optical purity: 80.1% ee |
| 4(4b)-16 | 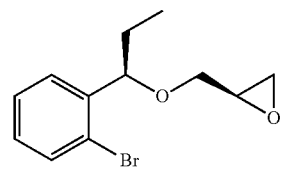 | $^1$H-NMR (CDCl$_3$) δ: 0.99 (3H, t, J = 7.3 Hz), 1.68-1.79 (2H, m), 2.55 (1H, dd, J = 5.1, 2.7 Hz), 2.73-2.77 (1H, m), 3.10-3.16 (1H, m), 3.30 (1H, dd, J = 11.3, 5.9 Hz), 3.58 (1H, dd, J = 11.3, 3.3 Hz), 4.70 (1H, dd, J = 7.3, 5.2 Hz), 7.12 (1H, td, J = 7.6, 1.7 Hz), 7.33 (1H, t, J = 7.6 Hz), 7.46 (1H, dd, J = 7.6, 1.7 Hz), 7.51 (1H, dd, J = 7.6, 1.0 Hz). |
| 4(4c)-16 | 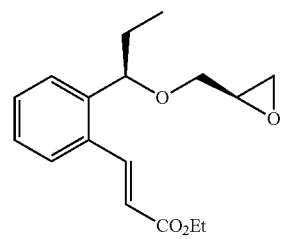 | $^1$H-NMR (CDCl$_3$) δ: 0.92 (3H, t, J = 7.3 Hz), 1.35 (3H, t, J = 7.2 Hz), 1.64-1.75 (1H, m), 1.77-1.87 (1H, m), 2.52 (1H, dd, J = 4.9, 2.7 Hz), 2.74 (1H, dd, J = 5.4, 4.6 Hz), 3.11-3.16 (1H, m), 3.25 (1H, dd, J = 11.2, 6.0 Hz), 3.58 (1H, dd, J = 11.2, 3.2 Hz), 4.28 (2H, q, J = 7.2 Hz), 4.65 (1H, dd, J = 7.6, 5.4 Hz), 6.32 (1H, d, J = 15.6 Hz), 7.26-7.31 (1H, m), 7.36-7.41 (1H, m), 7.45 (1H, dd, J = 7.8, 2.0 Hz), 7.54 (1H, d, J = 7.8 Hz), 8.12 (1H, d, J = 15.6 Hz). |
| 4(4a)-17 | 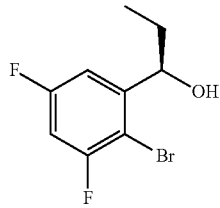 | $^1$H-NMR (CDCl$_3$) δ: 1.02 (3H, t, J = 7.3 Hz), 1.61-1.72 (1H, m), 1.78-1.88 (1H, m), 2.00 (1H, d, J = 3.7 Hz), 5.01-5.05 (1H, m), 6.82 (1H, td, J = 8.2, 2.9 Hz), 7.16 (1H, dq, J = 9.5, 1.5 Hz). Optical purity: 96.8% ee |
| 4(4b)-17 | 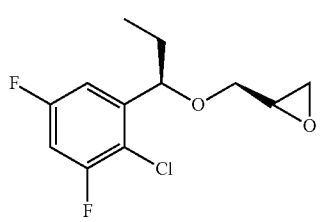 | $^1$H-NMR (CDCl$_3$) δ: 1.00 (3H, t, J = 7.3 Hz), 1.62-1.80 (2H, m), 2.56 (1H, dd, J = 5.0, 2.8 Hz), 2.78 (1H, t, J = 4.6 Hz), 3.13-3.17 (1H, m), 3.27 (1H, dd, J = 11.5, 6.0 Hz), 3.64 (1H, dd, J = 11.5, 3.0 Hz), 4.72 (1H, dd, J = 6.9, 4.6 Hz), 6.82 (1H, td, J = 8.3, 3.2 Hz), 7.05 (1H, dq, J = 9.3, 1.5 Hz). |
| 4(4c)-17 | 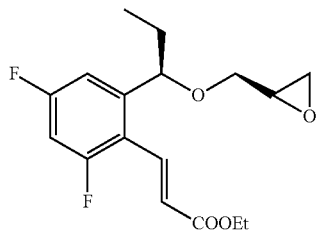 | $^1$H-NMR (CDCl$_3$) δ: 0.95 (3H, t, J = 7.6 Hz), 1.34 (3H, t, J = 7.1 Hz), 1.63-1.81 (2H, m), 2.54 (1H, dd, J = 4.8, 2.5 Hz), 2.77 (1H, t, J = 4.1 Hz), 3.13-3.17 (1H, m), 3.24 (1H, dd, J = 11.5, 6.0 Hz), 3.64 (1H, dd, J = 11.5, 2.3 Hz), 4.28 (2H, q, J = 7.1 Hz), 4.65 (1H, t, J = 6.2 Hz), 6.48 (1H, d, J = 16.5 Hz), 6.76-6.82 (1H, m), 7.06 (1H, d, J = 9.6 Hz), 7.71 (1H, d, J = 16.5 Hz). |

TABLE 20

| | | |
|---|---|---|
| 4(4a)-18 | 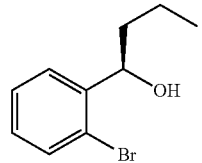 | $^1$H-NMR (CDCl$_3$) δ: 0.94-1.00 (3H, m), 1.38-1.61 (2H, m), 1.63-1.80 (2H, m), 1.93 (1H, brs), 5.06-5.13 (1H, m), 7.10-7.14 (1H, m), 7.34 (1H, t, J = 7.3 Hz), 7.48-7.58 (2H, m). Optical purity: 97.0% ee |

TABLE 20-continued

| | | |
|---|---|---|
| 4(4b)-18 | *[structure: 2-bromophenyl with propyl chain, ether-linked glycidyl ether]* | ¹H-NMR (CDCl₃) δ: 0.94 (3H, t, J = 7.2 Hz), 1.37-1.48 (1H, m), 1.50-1.59 (1H, m), 1.62-1.73 (2H, m), 2.55 (1H, dd, J = 4.6, 2.6 Hz), 2.75 (1H, t, J = 4.6 Hz), 3.10-3.14 (1H, m), 3.29 (1H, dd, J = 11.2, 6.0 Hz), 3.57 (1H, dd, J = 11.2, 2.9 Hz), 4.77 (1H, dd, J = 7.7, 4.9 Hz), 7.10-7.14 (1H, m), 7.31-7.35 (1H, m), 7.46 (1H, dd, J = 8.0, 1.5 Hz), 7.51 (1H, dd, J = 8.0, 1.1 Hz). |
| 4(4c)-18 | *[structure: 2-(ethoxycarbonylvinyl)phenyl with propyl chain, ether-linked glycidyl ether]* | ¹H-NMR (CDCl₃) δ: 0.92 (3H, t, J = 7.4 Hz), 1.29-1.40 (4H, m), 1.47 (1H, dtt, J = 24.2, 8.6, 2.9 Hz), 1.55-1.64 (1H, m), 1.76-1.84 (1H, m), 2.51 (1H, dd, J = 5.2, 2.9 Hz), 2.74 (1H, t, J = 4.6 Hz), 3.12-3.15 (1H, m), 3.24 (1H, dd, J = 11.2, 6.0 Hz), 3.58 (1H, dd, J = 10.9, 2.9 Hz), 4.24-4.31 (2H, m), 4.73 (1H, dd, J = 8.0, 5.7 Hz), 6.33 (1H, d, J = 15.8 Hz), 7.26-7.31 (1H, m), 7.37-7.41 (1H, m), 7.46 (1H, dd, J = 7.4, 1.1 Hz), 7.54 (1H, d, J = 7.4 Hz), 8.11 (1H, d, J = 15.8 Hz). |
| 4(4a)-19 | *[structure: 5-fluoro-2-bromophenyl with propyl-CHOH]* | ¹H-NMR (CDCl₃) δ: 0.97 (3H, t, J = 7.3 Hz), 1.36-1.80 (4H, m), 1.98 (1H, br s), 5.02-5.05 (1H, m), 6.85 (1H, dq, J = 9.9, 2.9 Hz), 7.30 (1H, dd, J = 9.9, 3.2 Hz), 7.46 (1H, dd, J = 8.7, 5.5 Hz). Optical purity: 87.3% ee |
| 4(4b)-19 | *[structure: 5-fluoro-2-bromophenyl with propyl chain, ether-linked glycidyl ether]* | ¹H-NMR (CDCl₃) δ: 0.95 (3H, t, J = 7.3 Hz), 1.37-1.48 (1H, m), 1.50-1.59 (1H, m), 1.61-1.68 (2H, m), 2.55 (1H, dd, J = 4.8, 2.5 Hz), 2.77 (1H, t, J = 4.4 Hz), 3.12-3.16 (1H, m), 3.27 (1H, dd, J = 11.5, 6.0 Hz), 3.61 (1H, dd, J = 11.5, 3.0 Hz), 4.72 (1H, t, J = 7.3 Hz), 6.86 (1H, td, J = 8.1, 3.1 Hz), 7.20 (1H, dd, J = 9.6, 3.1 Hz), 7.47 (1H, dd, J = 8.7, 5.5 Hz). |
| 4(4c)-19 | *[structure: 5-fluoro-2-(ethoxycarbonylvinyl)phenyl with propyl chain, ether-linked glycidyl ether]* | ¹H-NMR (CDCl₃) δ: 0.92 (3H, t, J = 7.1 Hz), 1.31-1.39 (1H, m), 1.34 (3H, t, J = 7.1 Hz), 1.42-1.52 (1H, m), 1.53-1.62 (1H, m), 1.71-1.80 (1H, m), 2.52 (1H, dd, J = 4.0, 2.5 Hz), 2.76 (1H, t, J = 4.8 Hz), 3.13-3.17 (1H, m), 3.23 (1H, dd, J = 11.5, 6.0 Hz), 3.62 (1H, dd, J = 11.5, 3.0 Hz), 4.27 (2H, q, J = 7.1 Hz), 4.74 (1H, dd, J = 7.1, 5.3 Hz), 6.28 (1H, d, J = 16.0 Hz), 6.98 (1H, td, J = 8.3, 2.8 Hz), 7.19 (1H, dd, J = 9.6, 2.8 Hz), 7.53 (1H, dd, J = 8.7, 5.5 Hz), 7.99 (1H, d, J = 16.0 Hz). |
| 4(4a)-20 | *[structure: 3-methyl-2-bromophenyl with propyl-CHOH]* | ¹H-NMR (CDCl₃) δ: 0.97 (3H, t, J = 7.3 Hz), 1.39-1.59 (2H, m), 1.59-1.70 (1H, m), 1.72-1.80 (1H, m), 1.94 (1H, d, J = 3.7 Hz), 2.42 (3H, s), 5.14-5.18 (1H, m), 7.15 (1H, d, J = 7.3 Hz), 7.23 (1H, t, J = 7.6 Hz), 7.38 (1H, d, J = 7.3 Hz). Optical purity: 90% ee |

TABLE 21

| | | |
|---|---|---|
| 4(4b)-20 | [structure: 1-(2-bromo-3-methylphenyl)butyl glycidyl ether] | ¹H-NMR (CDCl₃) δ: 0.94 (3H, t, J = 7.3 Hz), 1.40-1.48 (1H, m), 1.52-1.60 (1H, m), 1.63-1.69 (2H, m), 2.42 (3H, s), 2.54 (1H, dd, J = 5.0, 2.8 Hz), 2.75 (1H, t, J = 4.6 Hz), 3.11-3.15 (1H, m), 3.27 (1H, dd, J = 11.5, 6.0 Hz), 3.57 (1H, dd, J = 11.5, 3.2 Hz), 4.85 (1H, t, J = 6.2 Hz), 7.15 (1H, d, J = 6.0 Hz), 7.22 (1H, t, J = 7.3 Hz), 7.28 (1H, t, J = 8.0 Hz). |
| 4(4c)-20 | [structure: with CO₂Et cinnamate group] | ¹H-NMR (CDCl₃) δ: 0.90 (3H, t, J = 7.1 Hz), 1.35 (3H, t, J = 7.1 Hz), 1.44-1.59 (3H, m), 1.71-1.80 (1H, m), 2.32 (3H, s), 2.49 (1H, dd, J = 5.0, 3.0 Hz), 2.73 (1H, t, J = 4.6 Hz), 3.08-3.12 (1H, m), 3.17 (1H, dd, J = 11.5, 6.0 Hz), 3.52 (1H, dd, J = 11.5, 3.0 Hz), 4.29 (2H, q, J = 7.1 Hz), 4.60 (1H, dd, J = 8.3, 4.1 Hz), 5.96 (1H, d, J = 15.6 Hz), 7.14 (1H, d, J = 7.3 Hz), 7.25 (1H, t, J = 7.6 Hz), 7.34 (1H, d, J = 7.3 Hz), 7.85 (1H, d, J = 15.6 Hz). |
| 4(4a)-21 | [structure: 1-(2-bromo-3-fluorophenyl)butan-1-ol] | ¹H-NMR (CDCl₃) δ: 0.98 (3H, q, J = 7.5 Hz), 1.18-1.30 (1H, m), 1.42-1.59 (1H, m), 1.61-1.81 (2H, m), 1.98 (1H, br s), 5.10-5.15 (1H, m), 7.02-7.07 (1H, m), 7.30-7.38 (2H, m). Optical purity: 93% ee |
| 4(4b)-21 | [structure: with Br, F and glycidyl ether] | ¹H-NMR (CDCl₃) δ: 0.95 (3H, t, J = 7.3 Hz), 1.38-1.48 (1H, m), 1.49-1.59 (1H, m), 1.60-1.70 (2H, m), 2.55 (1H, dd, J = 5.0, 3.0 Hz), 2.76 (1H, t, J = 4.6 Hz), 3.10-3.16 (1H, m), 3.27 (1H, dd, J = 11.5, 6.0 Hz), 3.59 (1H, dd, J = 11.5, 3.0 Hz), 4.75-4.82 (1H, m), 7.03 (1H, td, J = 8.0, 1.8 Hz), 7.25-7.33 (2H, m). |
| 4(4c)-21 | [structure: with F, CO₂Et cinnamate and glycidyl ether] | ¹H-NMR (CDCl₃) δ: 0.93 (3H, t, J = 7.3 Hz), 1.34-1.39 (1H, m), 1.35 (3H, t, J = 7.3 Hz), 1.44-1.51 (1H, m), 1.53-1.64 (1H, m), 1.73-1.82 (1H, m), 2.53 (1H, dd, J = 5.0, 2.8 Hz), 2.75 (1H, t, J = 4.6 Hz), 3.11-3.15 (1H, m), 3.23 (1H, dd, J = 11.0, 6.0 Hz), 3.60 (1H, dd, J = 11.0, 3.0 Hz), 4.28 (2H, q, J = 7.3 Hz), 4.72 (1H, dd, J = 8.0, 4.8 Hz), 6.52 (1H, d, J = 16.0 Hz), 7.00-7.05 (1H, m), 7.27-7.35 (2H, m), 7.82 (1H, d, J = 16.0 Hz). |
| 4(4a)-22 | [structure: 1-(2-bromo-4-methylphenyl)butan-1-ol] | ¹H-NMR (CDC: 0.96 (3H, t, J = 7.3 Hz), 1.35-1.54 (2H, m), 1.55-1.58 (1H, m), 1.63-1.77 (1H, m), 1.88-1.91 (1H, m), 2.31 (3H, s), 5.03-5.07 (1H, m), 7.14 (1H, d, J = 7.8 Hz), 7.34 (1H, s), 7.41 (1H, d, J = 7.8 Hz). Optical purity: 92.7% ee |

TABLE 21-continued

| | | |
|---|---|---|
| 4(4b)-22 | 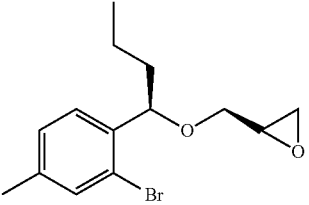 | ¹H-NMR (CDCl₃) δ: 0.93 (3H, t, J = 7.3 Hz), 1.33-1.44 (1H, m), 1.46-1.59 (1H, m), 1.60-1.74 (2H, m), 2.31 (3H, s), 2.54 (1H, dd, J = 5.0, 2.8 Hz), 2.74 (1H, t, J = 4.6 Hz), 3.09-3.13 (1H, m), 3.28 (1H, dd, J = 11.2, 5.7 Hz), 3.55 (1H, dd, J = 11.2, 3.2 Hz), 4.74 (1H, dd, J = 7.8, 4.6 Hz), 7.14 (1H, d, J = 7.8 Hz), 7.33 (2H, d, J = 8.3 Hz). |

TABLE 22

| | | |
|---|---|---|
| 4(4c)-22 | 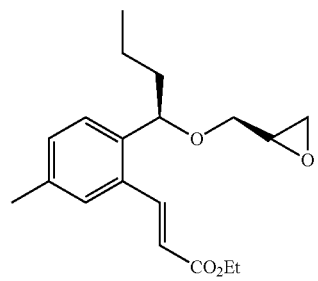 | ¹H-NMR (CDCl₃) δ: 0.91 (3H, t, J = 7.3 Hz), 1.31-1.39 (1H, m), 1.34 (3H, t, J = 7.1 Hz), 1.40-1.51 (1H, m), 1.54-1.62 (1H, m), 1.75-1.84 (1H, m), 2.35 (3H, s), 2.50 (1H, dd, J = 5.0, 2.8 Hz), 2.74 (1H, t, J = 4.6 Hz), 3.10-3.14 (1H, m), 3.22 (1H, dd, J = 11.5, 6.0 Hz), 3.56 (1H, dd, J = 11.5, 3.2 Hz), 4.27 (2H, q, J = 7.1 Hz), 4.69 (1H, dd, J = 8.0, 5.3 Hz), 6.32 (1H, d, J = 15.6 Hz), 7.20 (1H, d, J = 7.8 Hz), 7.34 (1H, d, J = 7.8 Hz), 7.35 (1H, s), 8.09 (1H, d, J = 15.6 Hz). |
| 4(4a)-23 | 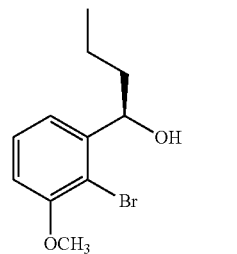 | ¹H-NMR (CDCl₃) δ: 0.96 (3H, t, J = 7.3 Hz), 1.37-1.59 (2H, m), 1.61-1.82 (2H, m), 1.92-1.97 (1H, m), 3.90 (3H, s), 5.14-5.18 (1H, m), 6.82 (1H, d, J = 7.8 Hz), 7.17 (1H, d, J = 7.8 Hz), 7.30 (1H, t, J = 8.0 Hz). Optical purity: 96.7% ee |
| 4(4b)-23 | 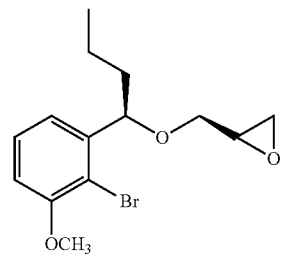 | ¹H-NMR (CDCl₃) δ: 0.94 (3H, t, J = 6.9 Hz), 1.39-1.49 (1H, m), 1.51-1.61 (1H, m), 1.62-1.70 (2H, m), 2.54-2.56 (1H, m), 2.75 (1H, t, J = 4.6 Hz), 3.10-3.14 (1H, m), 3.29 (1H, dd, J= 11.5, 6.0 Hz), 3.57 (1H, dd, J = 11.5, 3.2 Hz), 3.90 (3H, s), 4.85 (1H, t, J = 6.4 Hz), 6.81 (1H, d, J = 8.3 Hz), 7.09 (1H, d, J = 7.8 Hz), 7.29 (1 H, t, J = 7.8 Hz). |
| 4(4c)-23 | 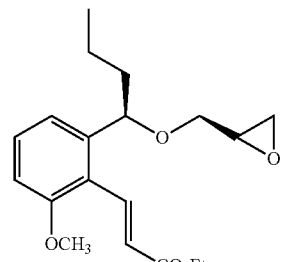 | ¹H-NMR (CDCl₃) δ: 0.93 (3H, t, J = 7.1 Hz), 1.34 (3H, t, J = 7.3 Hz), 1.38-1.44 (1H, m), 1.45-1.64 (2H, m), 1.73-1.82 (1H, m), 2.52 (1H, dd, J = 5.0, 2.8 Hz), 2.74 (1H, t, J = 4.6 Hz), 3.10-3.14 (1H, m), 3.23 (1H, dd, J = 11.0, 6.0 Hz), 3.54 (1H, dd, J = 11.0, 3.2 Hz), 3.87 (3H, s), 4.27 (2H, q, J = 7.3 Hz), 4.75 (1H, dd, J = 8.5, 4.4 Hz), 6.57 (1H, d, J = 16.0 Hz), 6.85 (1H, d, J = 8.3 Hz), 7.13 (1H, d, J = 8.0 Hz), 7.32 (1H, t, J = 8.0 Hz), 7.89 (1H, d, J = 16.0 Hz). |
| 4(4a)-24 | 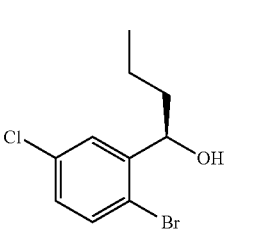 | ¹H-NMR (CDCl₃) δ: 0.97 (3H, t, J = 7.3 Hz), 1.38-1.60 (2H, m), 1.61-1.67 (1H, m), 1.68-1.77 (1H, m), 1.99 (1H, d, J = 4.1 Hz), 5.01-5.05 (1H, m), 7.10 (1H, dd, J = 8.7, 2.8 Hz), 7.43 (1H, d, J = 8.7 Hz), 7.55 (1H, d, J = 2.8 Hz). Optical purity: 93.7% ee |

TABLE 22-continued

| | | |
|---|---|---|
| 4(4b)-24 | 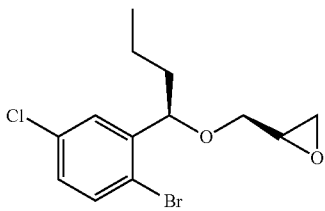 | $^1$H-NMR (CDCl$_3$) δ: 0.95 (3H, t, J = 7.2 Hz), 1.38-1.48 (1H, m), 1.50-1.58 (1H, m), 1.60-1.70 (2H, m), 2.53-2.55 (1H, m), 2.77 (1H, t, J = 4.6 Hz), 3.12-3.16 (1H, m), 3.26 (1H, dd, J = 11.5, 6.0 Hz), 3.61 (1H, dd, J = 11.5, 2.9 Hz), 4.73 (1H, dd, J = 7.2, 4.9 Hz), 7.10 (1H, dd, J = 8.3, 2.0 Hz), 7.43 (1H, s), 7.45 (1H, t, J = 2.6 Hz). |

TABLE 23

| | | |
|---|---|---|
| 4(4c)-24 | 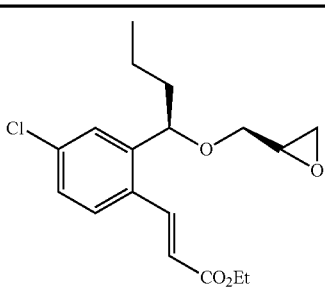 | $^1$H-NMR (CDCl$_3$) δ: 0.92 (3H, t, J = 7.3 Hz), 1.34 (3H, t, J = 7.1 Hz), 1.30-1.48 (2H, m), 1.52-1.59 (1H, m), 1.72-1.81 (1H, m), 2.51 (1H, dd, J = 4.4, 2.5 Hz), 2.76 (1H, t, J = 4.4 Hz), 3.13-3.17 (1H, m), 3.21 (1H, dd, J = 11.0, 6.2 Hz), 3.62 (1H, dd, J = 11.0, 2.8 Hz), 4.27 (2H, q, J = 7.1 Hz), 4.71 (1H, dd, J = 8.0, 4.8 Hz), 6.30 (1H, d, J = 16.0 Hz), 7.24 (1H, d, J = 2.3 Hz), 7.46 (1H, s), 7.47 (1H, d, J = 10.5 Hz), 8.00 (1H, d, J = 16.0 Hz). |
| 4(4a)-25 | 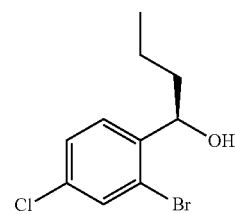 | $^1$H-NMR (CDCl$_3$) δ: 0.96 (3H, t, J = 7.3 Hz), 1.36-1.60 (2H, m), 1.61-1.76 (2H, m), 1.93-1.96 (1H, m), 5.02-5.06 (1H, m), 7.31 (1H, dd, J = 8.3, 2.3 Hz), 7.49 (1H, d, J = 8.3 Hz), 7.52 (1H, d, J = 2.3 Hz). Optical purity: 90.6% ee |
| 4(4b)-25 | 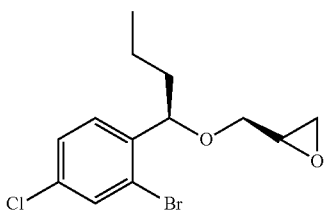 | $^1$H-NMR (CDCl$_3$) δ: 0.94 (3H, t, J = 7.3 Hz), 1.35-1.45 (1H, m), 1.48-1.59 (1H, m), 1.59-1.68 (2H, m), 2.55 (1H, dd, J = 5.0, 2.8 Hz), 2.76 (1H, t, J = 4.6 Hz), 3.09-3.13 (1H, m), 3.26 (1H, dd, J = 11.5, 6.0 Hz), 3.58 (1H, dd, J = 11.5, 2.8 Hz), 4.73 (1H, dd, J = 7.6, 4.8 Hz), 7.32 (1H, dd, J = 8.3, 1.8 Hz), 7.40 (1H, d, J = 8.3 Hz), 7.53 (1H, d, J = 1.8 Hz). |
| 4(4c)-25 | 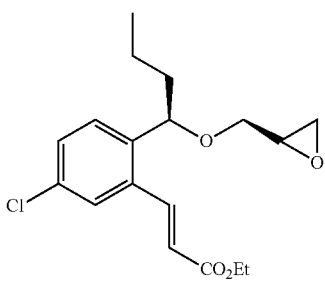 | $^1$H-NMR (CDCl$_3$) δ: 0.91 (3H, t, J = 7.3 Hz), 1.35 (3H, t, J = 7.1 Hz), 1.38-1.49 (1H, m), 1.52-1.61 (2H, m), 1.72-1.81 (1H, m), 2.51 (1H, dd, J = 5.0, 2.8 Hz), 2.75 (1H, t, J = 4.6 Hz), 3.10-3.14 (1H, m), 3.21 (1H, dd, J = 11.5, 6.0 Hz), 3.59 (1H, dd, J = 11.5, 2.8 Hz), 4.28 (2H, q, J = 7.1 Hz), 4.70 (1H, dd, J = 7.8, 5.0 Hz), 6.32 (1H, d, J = 16.0 Hz), 7.35 (1H, d, J = 8.3 Hz), 7.40 (1H, d, J = 8.3 Hz), 7.50 (1H, s), 8.02 (1H, d, J = 16.0 Hz). |
| 4(4a)-26 | 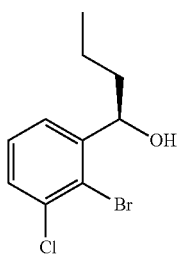 | $^1$H-NMR (CDCl$_3$) δ: 0.97 (3H, t, J = 7.3 Hz), 1.40-1.68 (3H, m), 1.71-1.79 (1H, m), 1.99-2.01 (1H, m), 5.12-5.16 (1H, m), 7.29 (1H, d, J = 7.8 Hz), 7.38 (1H, d, J = 7.8 Hz), 7.47 (1H, d, J = 7.8 Hz). Optical purity: 92% ee |

TABLE 23-continued

| 4(4b)-26 | 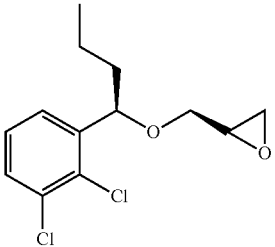 | $^1$H-NMR (CDCl$_3$) δ: 0.95 (3H, t, J = 7.3 Hz), 1.39-1.60 (2H, m), 1.62-1.68 (2H, m), 2.55-2.57 (1H, m), 2.76 (1H, t, J = 4.6 Hz), 3.11-3.15 (1H, m), 3.27 (1H, dd, J = 11.5, 6.0 Hz), 3.60 (1H, dd, J = 11.5, 2.8 Hz), 4.83 (1H, t, J = 6.0 Hz), 7.29 (1H, d, J = 7.8 Hz), 7.37-7.39 (2H, m). |
|---|---|---|
| 4(4c)-26 | 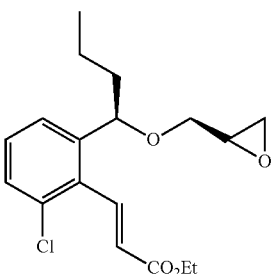 | $^1$H-NMR (CDCl$_3$) δ: 0.91 (3H, t, J = 7.2 Hz), 1.34-1.38 (1H, m), 1.35 (3H, t, J = 7.2 Hz), 1.44-1.58 (2H, m), 1.69-1.78 (1H, m), 2.50 (1H, dd, J = 5.2, 2.9 Hz), 2.74 (1H, dd, J = 5.2, 4.0 Hz), 3.08-3.11 (1H, m), 3.16 (1H, dd, J = 11.5, 6.3 Hz), 3.55 (1H, dd, J = 11.5, 2.9 Hz), 4.30 (2H, q, J = 7.2 Hz), 4.63 (1H, dd, J = 8.6, 4.0 Hz), 6.16 (1H, d, J = 16.6 Hz), 7.29 (1H, t, J = 8.0 Hz), 7.35 (1H, dd, J = 8.0, 1.1 Hz), 7.43 (1H, dd, J = 7.7, 1.4 Hz), 7.76 (1H, d, J = 16.6 Hz). |

TABLE 24

| 4(4a)-27 | 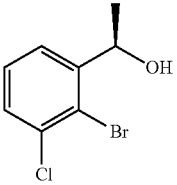 | $^1$H-NMR (CDCl$_3$) δ: 1.48 (3H, d, J = 6.3 Hz), 5.29 (1H, q, J = 6.3 Hz), 7.29 (1H, t, J = 7.7 Hz), 7.39 (1H, dd, J = 7.7, 1.4 Hz), 7.52 (1H, dd, J = 7.7, 1.4 Hz). Optical purity: 93.8% ee |
|---|---|---|
| 4(4b)-27 | 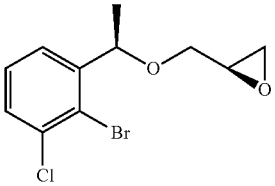 | $^1$H-NMR (CDCl$_3$) δ: 1.43 (3H, d, J = 6.4 Hz), 2.57 (1H, dd, J = 4.9, 2.6 Hz), 2.78 (1H, t, J = 4.6 Hz), 3.13-3.16 (1H, m), 3.30 (1H, dd, J = 11.2, 6.0 Hz), 3.61 (1H, dd, J = 11.5, 2.9 Hz), 4.94 (1H, q, J = 6.4 Hz), 7.29 (1H, t, J = 7.8 Hz), 7.39 (1H, dd, J = 7.8, 1.6 Hz), 7.42 (1H, dd, J = 7.8, 1.6 Hz). |
| 4(4c)-27 | 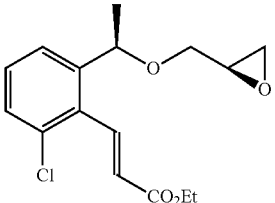 | $^1$H-NMR (CDCl$_3$) δ: 1.36 (3H, t, J = 7.1 Hz), 1.43 (3H, d, J = 6.3 Hz), 2.51 (1H, dd, J = 4.9, 2.6 Hz), 2.75 (1H, t, J = 4.6 Hz), 3.09-3.12 (1H, m), 3.20 (1H, dd, J = 11.5, 6.3 Hz), 3.53 (1H, dd, J = 11.5, 2.9 Hz), 4.30 (2H, q, J = 7.1 Hz), 4.76 (1H, q, J = 6.3 Hz), 6.14 (1H, d, J = 16.0 Hz), 7.30 (4H, t, J = 7.6 Hz), 7.35 (4H, dd, J = 7.6, 1.3 Hz), 7.47 (1H, dd, J = 7.6, 1.3 Hz), 7.78 (1H, d, J = 16.0 Hz). |
| 4(4a)-28 | 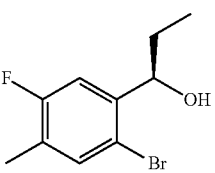 | $^1$H-NMR (CDCl$_3$) δ: 1.00 (3H, t, J = 7.3 Hz), 1.62-1.73 (1H, m), 1.75-1.85 (1H, m), 1.93 (1H, d, J = 3.7 Hz), 2.24 (3H, s), 4.90-4.95 (1H, m), 7.20 (1H, d, J = 10.5 Hz), 7.33 (1H, d, J = 6.9 Hz). Optical purity: 86.6% ee |
| 4(4b)-28 | 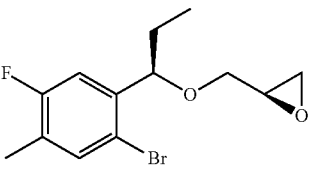 | $^1$H-NMR (CDCl$_3$) δ: 0.97 (3H, t, J = 7.3 Hz), 1.65-1.76 (2H, m), 2.24 (3H, s), 2.55 (1H, dd, J = 5.0, 2.8 Hz), 2.76 (1H, t, J = 4.6 Hz), 3.11-3.16 (1H, m), 3.28 (1H, dd, J = 11.0, 6.0 Hz), 3.59 (1H, dd, J = 11.5, 3.2 Hz), 4.61 (1H, t, J = 6.2 Hz), 7.11 (1H, d, J = 10.5 Hz), 7.34 (1H, d, J = 6.9 Hz). |

TABLE 24-continued

| | | |
|---|---|---|
| 4(4c)-28 | 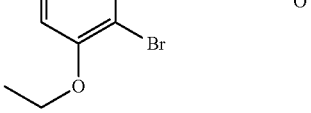 | ¹H-NMR (CDCl₃) δ: 0.91 (3H, t, J = 7.3 Hz), 1.34 (3H, t, J = 7.1 Hz), 1.61 -1.72 (1H, m), 1.72-1.84 (1H, m), 2.27 (3H, s), 2.52 (1H, dd, J = 4.8, 2.5 Hz), 2.76 (1H, t, J = 4.6 Hz), 3.12-3.17 (1H, m), 3.24 (1H, dd, J = 11.0, 6.0 Hz), 3.60 (1H, dd, J = 11.2, 3.0 Hz), 4.27 (2H, q, J = 7.1 Hz), 4.62 (1H, t, J = 6.4 Hz), 6.27 (1H, d, J = 15.8 Hz), 7.11 (1H, d, J = 10.5 Hz), 7.38 (1H, d, J = 7.3 Hz), 7.98 (1H, d, J = 15.8 Hz). |
| 4(4a)-29 | 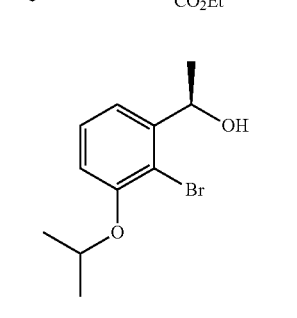 | ¹H-NMR (CDCl₃) δ: 1.48 (3H, t, J = 7.1 Hz), 1.48 (3H, d, J = 6.3 Hz), 2.00 (1H, d, J = 3.4 Hz), 4.11 (2H, q, J = 7.1 Hz), 5.28-5.33 (1H, m), 6.81 (1H, dd, J = 7.9, 1.6 Hz), 7.20 (1H, dd, J = 7.9, 1.6 Hz), 7.28 (1H, t, J = 7.9 Hz). Optical purity: 92.7% ee |

TABLE 25

| | | |
|---|---|---|
| 4(4b)-29 | 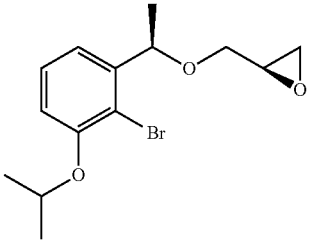 | ¹H-NMR (CDCl₃) δ: 1.43 (3H, d, J = 6.3 Hz), 1.48 (3H, t, J = 7.0 Hz), 2.55 (1H, dd, J = 5.2, 2.9 Hz), 2.76 (1H, t, J = 4.6 Hz), 3.13-3.16 (1H, m), 3.31 (1H, dd, J = 11.5, 5.7 Hz), 3.58 (1H, dd, J = 11.5, 3.4 Hz), 4.10 (2H, q, J = 7.0 Hz), 4.97 (1H, q, J = 6.3 Hz), 6.80 (1H, dd, J = 7.7, 1.6 Hz), 7.11 (1H, dd, J = 7.7, 1.6 Hz), 7.28 (2H, t, J = 7.7 Hz). |
| 4(4c)-29 |  | ¹H-NMR (CDCl₃) δ: 1.35 (3H, t, J = 7.1 Hz), 1.46 (6H, d, J = 6.3 Hz), 1.47 (6H, t, J = 6.6 Hz), 2.53 (1H, dd, J = 4.9, 2.6 Hz), 2.75 (1H, t, J = 4.6 Hz), 3.11-3.15 (1H, m), 3.26 (1H, dd, J = 11.5, 5.7 Hz), 3.54 (1H, dd, J = 10.9, 3.4 Hz), 4.07-4.12 (2H, m), 4.27 (2H, q, J = 7.1 Hz), 4.89 (1H, q, J = 6.3 Hz), 6.58 (1H, d, J = 16.0 Hz), 6.83 (1H, d, J = 8.0 Hz), 7.14 (1H, d, J = 8.0 Hz), 7.31 (1H, t, J = 8.0 Hz), 7.89 (1H, d, J = 16.0 Hz). |
| 4(4a)-30 | | ¹H-NMR (CDCl₃) δ: 1.38 (3H, d, J = 5.7 Hz), 1.39 (3H, d, J = 6.3 Hz), 1.48 (3H, d, J = 6.3 Hz), 1.99 (1H, d, J = 3.4 Hz), 4.52-4.59 (1H, m), 5.27-5.32 (1H, m), 6.84 (1H, dd, J = 7.8, 1.6 Hz), 7.19 (1H, dd, J = 7.8, 1.6 Hz), 7.27 (1H, t, J = 7.8 Hz). Optical purity: 92.7% ee |
| 4(4b)-30 | | ¹H-NMR (CDCl₃) δ: 1.39 (6H, d, J = 6.3 Hz), 1.43 (3H, d, J = 6.3 Hz), 2.56 (1H, dd, J = 5.2, 2.3 Hz), 2.75-2.78 (1H, m), 3.13-3.16 (1H, m), 3.32 (1H, dd, J = 11.2, 6.0 Hz), 3.58 (1H, dd, J = 11.5, 3.4 Hz), 4.51-4.59 (1H, m), 4.95 (1H, q, J = 6.3 Hz), 6.82 (1H, dd, J = 7.9, 1.3 Hz), 7.10 (1H, dd, J = 7.9, 1.3 Hz), 7.26 (1H, t, J = 7.9 Hz). |

TABLE 25-continued

| 4(4c)-30 | [structure] | $^1$H-NMR (CDCl$_3$) δ: 1.34 (3H, t, J = 7.1 Hz), 1.37 (3H, d, J = 5.7 Hz), 1.38 (3H, d, J = 6.3 Hz), 1.46 (3H, d, J = 6.4 Hz), 2.53 (1H, dd, J = 4.9, 2.6 Hz), 2.74-2.77 (1H, m), 3.11-3.15 (1H, m), 3.27 (1H, dd, J = 10.9, 5.7 Hz), 3.54 (1H, dd, J = 10.9, 3.4 Hz), 4.27 (2H, q, J = 7.1 Hz), 4.56-4.63 (1H, m), 4.88 (1H, q, J = 6.4 Hz), 6.55 (1H, d, J = 16.0 Hz), 6.84 (1H, d, J = 8.0 Hz), 7.12 (1H, d, J = 8.0 Hz), 7.30 (1H, t, J = 8.0 Hz), 7.87 (1H, d, J = 16.0 Hz). |
|---|---|---|
| 4(4a)-31 | [structure] | $^1$H-NMR (CDCl$_3$) δ: 1.45 (3H, d, J = 6.3 Hz), 1.95 (1H, d, J = 4.0 Hz), 2.24 (3H, d, J = 1.7 Hz), 5.11-5.18 (1H, m), 7.26 (1H, d, J = 10.3 Hz), 7.33 (1H, d, J = 8.0 Hz). Optical purity: 94.2% ee |
| 4(4b)-31 | [structure] | $^1$H-NMR (CDCl$_3$) δ: 1.40 (3H, d, J = 6.6 Hz), 2.24 (3H, d, J = 1.8 Hz), 2.56 (1H, dd, J = 5.0, 2.8 Hz), 2.78 (1H, t, J = 4.6 Hz), 3.12-3.17 (1H, m), 3.30 (1H, dd, J = 11.5, 6.0 Hz), 3.60 (1H, dd, J = 11.5, 3.2 Hz), 4.79 (1H, q, J = 6.6 Hz), 7.15 (1H, d, J = 10.1 Hz), 7.33 (1H, d, J = 7.3 Hz). |
| 4(4c)-31 | [structure] | $^1$H-NMR (CDCl$_3$) δ: 1.34 (3H, t, J = 7.1 Hz), 1.42 (3H, d, J = 6.6 Hz), 2.27 (3H, s), 2.54 (1H, dd, J = 5.2, 2.9 Hz), 2.76-2.78 (1H, m), 3.13-3.17 (1H, m), 3.27 (1H, dd, J = 11.2, 6.0 Hz), 3.60 (1H, dd, J = 11.2, 3.2 Hz), 4.27 (2H, q, J = 7.1 Hz), 4.84 (1H, q, J = 6.6 Hz), 6.27 (1H, d, J = 15.8 Hz), 7.14 (1H, d, J = 10.3 Hz), 7.38 (1H, d, J = 8.0 Hz), 7.95 (1H, d, J = 15.8 Hz). |

TABLE 26

| 4(4a)-32 | [structure] | $^1$H-NMR (CDCl$_3$) δ: 1.45 (3H, d, J = 6.3 Hz), 2.01 (1H, d, J = 3.4 Hz), 5.13-5.18 (1H, m), 7.35 (1H, dd, J = 9.5, 7.2 Hz), 7.46 (1H, dd, J = 11.2, 8.3 Hz). Optical purity: 93.0% ee |
|---|---|---|
| 4(4b)-32 | [structure] | $^1$H-NMR (CDCl$_3$) δ: 1.40 (3H, d, J = 6.4 Hz), 2.57 (1H, dd, J = 5.0, 2.8 Hz), 2.79 (1H, t, J = 4.6 Hz), 3.13-3.17 (1H, m), 3.29 (1H, dd, J = 11.5, 6.0 Hz), 3.62 (1H, dd, J = 11.2, 3.0 Hz), 4.80 (1H, q, J = 6.4 Hz), 7.32-7.38 (2H, m). |
| 4(4c)-32 | [structure] | $^1$H-NMR (CDCl$_3$) δ: 1.34 (6H, t, J = 7.1 Hz), 1.42 (6H, d, J = 6.4 Hz), 2.55 (1H, dd, J = 4.9, 2.6 Hz), 2.78 (1H, t, J = 4.6 Hz), 3.13-3.17 (1H, m), 3.27 (1H, dd, J = 11.2, 6.0 Hz), 3.64 (1H, dd, J = 11.5, 2.9 Hz), 4.28 (2H, q, J = 7.1 Hz), 4.85 (1H, q, J = 6.4 Hz), 6.26 (1H, d, J = 15.8 Hz), 7.30-7.35 (2H, m), 7.91 (1H, d, J = 15.8 Hz). |

TABLE 26-continued

| | | |
|---|---|---|
| 4(4a)-33 | 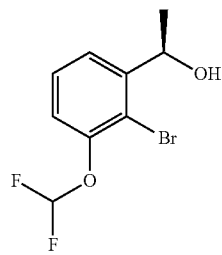 | $^1$H-NMR (CDCl$_3$) δ: 1.49 (3H, d, J = 6.9 Hz), 2.00 (1H, d, J = 3.4 Hz), 5.27-5.32 (1H, m), 6.52 (1H, t, J = 73.6 Hz), 7.12-7.15 (1H, m), 7.35 (1H, t, J = 7.9 Hz), 7.51 (1H, dd, J = 7.9, 1.4 Hz). Optical purity: 94.6% ee |
| 4(4b)-33 | 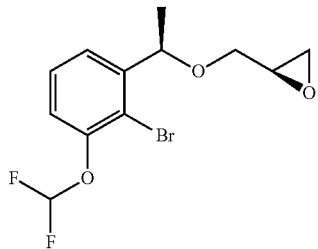 | $^1$H-NMR (CDCl$_3$) δ: 1.44 (3H, d, J = 6.4 Hz), 2.57 (1H, dd, J = 4.9, 2.6 Hz), 2.78 (1H, t, J = 4.3 Hz), 3.13-3.16 (1H, m), 3.31 (1H, dd, J = 11.5, 5.7 Hz), 3.61 (1H, dd, J = 11.5, 2.9 Hz), 4.94 (1H, q, J = 6.4 Hz), 6.53 (1H, t, J = 73.6 Hz), 7.12-7.15 (1H, m), 7.35 (1H, t, J = 7.9 Hz), 7.40 (1H, dd, J = 7.9, 1.7 Hz). |
| 4(4c)-33 | 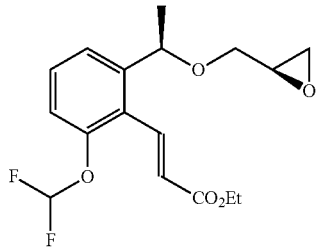 | $^1$H-NMR (CDCl$_3$) δ: 1.35 (3H, t, J = 7.1 Hz), 1.45 (3H, d, J = 6.4 Hz), 2.54 (1H, dd, J = 4.9, 2.6 Hz), 2.76 (1H, dd, J = 5.2, 4.0 Hz), 3.11-3.14 (1H, m), 3.25 (1H, dd, J = 11.2, 6.0 Hz), 3.56 (1H, dd, J = 11.2, 3.2 Hz), 4.28 (2H, q, J = 7.1 Hz), 4.83 (1H, q, J = 6.4 Hz), 6.35 (1H, d, J = 16.3 Hz), 6.49 (1H, t, J = 73.3 Hz), 7.08-7.11 (1H, m), 7.37 (1H, t, J = 7.7 Hz), 7.43 (1H, dd, J = 7.7, 1.4 Hz), 7.78 (1H, d, J = 16.3 Hz). |
| 4(4a)-34 | 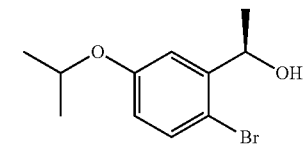 | $^1$H-NMR (CDCl$_3$) δ: 1.33 (3H, d, J = 6.0 Hz), 1.33 (3H, d, J = 6.0 Hz), 1.47 (3H, d, J = 6.4 Hz), 1.94 (1H, d, J = 3.2 Hz), 4.50-4.59 (1H, m), 5.14-5.21 (1H, m), 6.67 (1H, dd, J = 8.7, 3.0 Hz), 7.14 (1H, d, J = 3.0 Hz), 7.37 (1H, d, J = 8.7 Hz). Optical purity: of 91.6% ee |
| 4(4b)-34 | 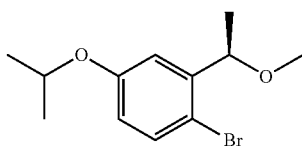 | $^1$H-NMR (CDCl$_3$) δ: 1.33 (6H, d, J = 6.4 Hz), 1.42 (3H, d, J = 6.3 Hz), 2.57 (1H, dd, J = 5.0, 2.8 Hz), 2.78 (1H, t, J = 4.6 Hz), 3.13-3.17 (1H, m), 3.31 (1H, dd, J = 11.0, 6.0 Hz), 3.62 (1H, dd, J = 11.2, 3.0 Hz), 4.49-4.58 (1H, m), 4.82 (1H, q, J = 6.3 Hz), 6.68 (1H, dd, J = 8.7, 3.2 Hz), 7.04 (1H, d, J = 3.2 Hz), 7.37 (1H, d, J = 8.7 Hz). |

TABLE 27

| | | |
|---|---|---|
| 4(4c)-34 | 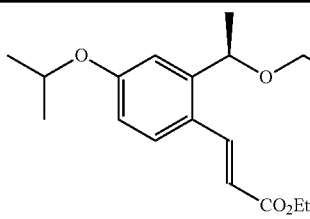 | $^1$H-NMR (CDCl$_3$) δ: 1.34 (3H, t, J = 7.1 Hz), 1.36 (6H, d, J = 6.0 Hz), 1.44 (3H, d, J = 6.5 Hz), 2.55 (1H, dd, J = 4.8, 2.5 Hz), 2.77 (1H, t, J = 4.6 Hz), 3.13-3.18 (1H, m), 3.29 (1H, dd, J = 11.5, 6.0 Hz), 3.62 (1H, dd, J = 11.2, 3.0 Hz), 4.26 (2H, q, J = 7.1 Hz), 4.57-4.66 (1H, m), 4.88 (1H, q, J = 6.5 Hz), 6.25 (1H, d, J = 15.8 Hz), 6.79 (1H, dd, J = 8.7, 2.8 Hz), 7.01 (1H, d, J = 2.8 Hz), 7.51 (1H, d, J = 8.7 Hz), 7.98 (1H, d, J = 15.8 Hz). |
| 4(4b)-35 | 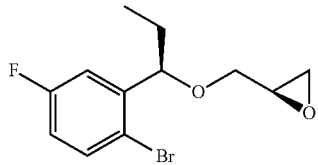 | $^1$H-NMR (CDCl$_3$) δ: 0.99 (3H, t, J = 7.8 Hz), 1.62-1.81 (2H, m), 2.53-2.59 (1H, m), 2.75-2.82 (1H, m), 3.12-3.18 (1H, m), 3.29 (1H, dd, J = 11.2, 5.7 Hz), 3.62 (1H, dd, J = 11.5, 3.2 Hz), 4.59-4.69 (1H, m), 6.83-6.90 (1H, m), 7.17-7.22 (1H, m), 7.44-7.50 (1H, m). |

TABLE 27-continued

| | | |
|---|---|---|
| 4(4c)-35 | 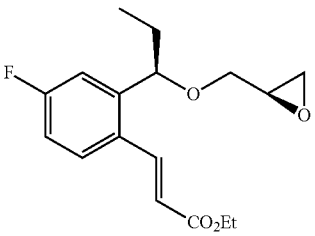 | ¹H-NMR (CDCl₃) δ: 0.93 (3H, t, J = 8.9 Hz), 1.35 (3H, t, J = 7.1 Hz), 1.62-1.87 (2H, m), 2.49-2.58 (1H, m), 2.72-2.84 (1H, m), 3.10-3.31 (2H, m), 3.53-3.70 (1H, m), 4.27 (2H, q, J = 7.1 Hz), 4.66 (1H, t, J = 6.2 Hz), 6.28 (1H, d, J = 15.6 Hz), 6.93-7.04 (1H, m), 7.15-7.24 (1H, m), 7.49-7.60 (1H, m), 7.99 (1H, d, J = 15.6 Hz). |
| 4(4b)-35 | 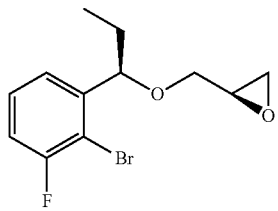 | ¹H-NMR (CDCl₃) δ: 0.99 (3H, t, J = 7.5 Hz), 1.65-1.80 (2H, m), 2.54-2.58 (1H, m), 2.76 (1H, t, J = 4.6 Hz), 3.10-3.18 (1H, m), 3.26-3.32 (1H, m), 3.60 (1H, dd, J = 11.2, 3.0 Hz), 4.70-4.76 (1H, m), 7.01-7.07 (1H, m), 7.23-7.35 (2H, m). |
| 4(4c)-35 | 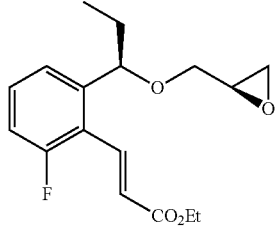 | ¹H-NMR (CDCl₃) δ: 0.94 (3H, t, J = 7.6 Hz), 1.35 (3H, t, J = 7.1 Hz), 1.63-1.86 (2H, m), 2.51-2.55 (1H, m), 2.76 (1H, t, J = 4.6 Hz), 3.11-3.17 (1H, m), 3.22-3.28 (1H, m), 3.60 (1H, dd, J = 11.5, 2.8 Hz), 4.28 (2H, q, J = 7.1 Hz), 4.61-4.67 (1H, m), 6.52 (1H, d, J = 14.7 Hz), 6.99-7.07 (1H, m), 7.22-7.40 (2H, m), 7.83 (1H, d, J = 14.7 Hz). |
| 4(4b)-36 | 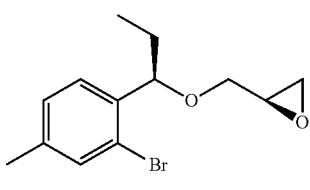 | ¹H-NMR (CDCl₃) δ: 0.97 (3H, t, J = 7.8 Hz), 1.68-1.77 (2H, m), 2.31 (3H, s), 2.53-2.56 (1H, m), 2.72-2.76 (1H, m), 3.08-3.14 (1H, m), 3.26-3.32 (1H, m), 3.56 (1H, dd, J = 10.1, 5.0 Hz), 4.66 (1H, t, J = 6.4 Hz), 7.13 (1H, d, J = 7.8 Hz), 7.30-7.37 (2H, m). |
| 4(4c)-36 | 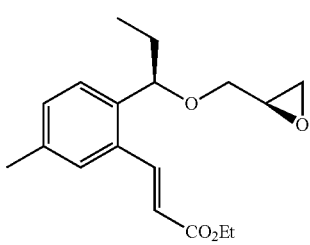 | ¹H-NMR (CDCl₃) δ: 0.90 (3H, t, J = 7.3 Hz), 1.34 (3H, t, J = 7.1 Hz), 1.60-1.73 (1H, m), 1.76-1.88 (1H, m), 2.35 (3H, s), 2.49-2.52 (1H, m), 2.74 (1H, t, J = 4.6 Hz), 3.10-3.15 (1H, m), 3.24 (1H, dd, J = 11.0, 6.0 Hz), 3.56 (1H, dd, J = 11.2, 3.0 Hz), 4.27 (2H, q, J = 7.2 Hz), 4.61 (1H, t, J = 6.6 Hz), 6.32 (1H, d, J = 15.6 Hz), 7.20 (1H, d, J = 7.8 Hz), 7.31-7.38 (2H, m), 8.10 (1H, d, J = 15.6 Hz). |

TABLE 28

| | | |
|---|---|---|
| 4(4b)-37 | 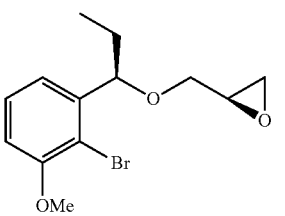 | ¹H-NMR (CDCl₃) δ: 0.99 (3H, t, J = 7.3 Hz), 1.66-1.82 (2H, m), 2.53-2.57 (1H, m), 2.73-2.77 (1H, m), 3.10-3.17 (1H, m), 3.27-3.33 (1H, m), 3.57 (1H, dd, J = 11.5, 3.2 Hz), 3.90 (3H, s), 4.78 (1H, dd, J = 7.3, 5.0 Hz), 6.80-6.84 (1H, m), 7.06-7.11 (1H, m), 7.26-7.32 (1H, m). |

TABLE 28-continued

| | | |
|---|---|---|
| 4(4c)-37 | 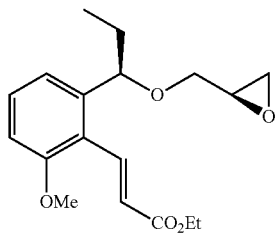 | ¹H-NMR (CDCl₃) δ: 0.96 (3H, t, J = 7.4 Hz), 1.35 (3H, t, J = 7.2 Hz), 1.65-1.85 (2H, m), 2.50-2.54 (1H, m), 2.72-2.76 (1H, m), 3.10-3.14 (1H, m), 3.24 (1H, dd, J = 11.5, 5.7 Hz), 3.55 (1H, dd, J = 11.2, 3.2 Hz), 3.87 (3H, s), 4.27 (2H, q, J = 7.4 Hz), 4.63-4.68 (1H, m), 6.56 (1H, d, J = 16.0 Hz), 6.85 (1H, d, J = 8.0 Hz), 7.12 (1H, d, J = 6.9 Hz), 7.33 (1H, t, J = 8.0 Hz), 7.90 (1H, d, J = 16.0 Hz). |
| 4(4b)-38 | 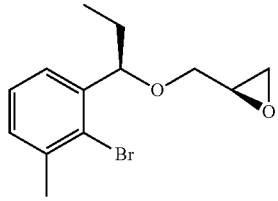 | ¹H-NMR (CDCl₃) δ: 1.00 (3H, t, J = 7.3 Hz), 1.63-1.82 (2H, m), 2.42 (3H, s), 2.53-2.57 (1H, m), 2.75 (1H, t, J = 4.6 Hz), 3.11-3.16 (1H, m), 3.29 (1H, dd, J = 11.5, 5.7 Hz), 3.58 (1H, dd, J = 11.5, 3.2 Hz), 4.78 (1H, q, J = 7.8 Hz), 7.15 (1H, d, J = 7.8 Hz), 7.19-7.32 (2H, m). |
| 4(4c)-38 | 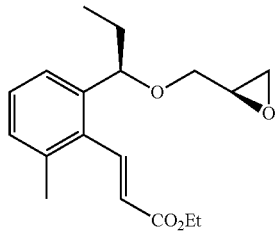 | ¹H-NMR (CDCl₃) δ: 0.93 (3H, t, J = 7.3 Hz), 1.35 (3H, t, J = 7.1 Hz), 1.60-1.71 (1H, m), 1.71-1.83 (1H, m), 2.32 (3H, s), 2.47-2.52 (1H, m), 2.71-2.75 (1H, m), 3.08-3.13 (1H, m), 3.19 (1H, dd, J = 11.5, 6.0 Hz), 3.52 (1H, dd, J = 11.5, 3.0 Hz), 4.29 (2H, q, J = 7.3 Hz), 4.51 (1H, dd, J = 7.8, 5.0 Hz), 5.95 (1H, d, J = 16.0 Hz), 7.14 (1H, d, J = 7.3 Hz), 7.21-7.29 (1H, m), 7.33 (1H, d, J = 7.3 Hz), 7.86 (1H, d, J = 16.0 Hz). |
| 4(4b)-39 | 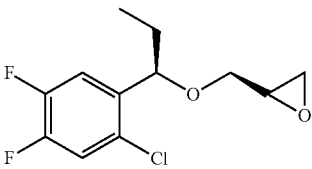 | ¹H-NMR (CDCl₃) δ: 0.98 (3H, t, J = 7.3 Hz), 1.63-1.76 (2H, m), 2.56 (1H, dd, J = 4.8, 2.5 Hz), 2.77 (1H, t, J = 4.8 Hz), 3.11-3.15 (1H, m), 3.27 (1H, dd, J = 11.5, 6.0 Hz), 3.61 (1H, dd, J = 11.5, 2.8 Hz), 4.62 (1H, t, J = 6.0 Hz), 7.30 (1H, dd, J = 11.0, 8.3 Hz), 7.36 (1H, dd, J = 9.6, 7.3 Hz). |
| 4(4c)-39 | 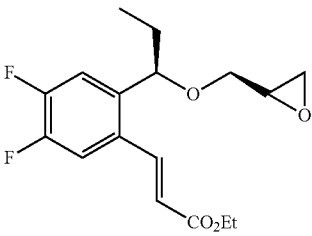 | ¹H-NMR (CDCl₃) δ: 0.91 (3H, t, J = 7.3 Hz), 1.34 (3H, t, J = 7.1 Hz), 1.60-1.69 (1H, m), 1.70-1.82 (1H, m), 2.53 (1H, dd, J = 4.8, 2.5 Hz), 2.77 (1H, t, J = 4.8 Hz), 3.12-3.16 (1H, m), 3.22 (1H, dd, J = 11.2, 6.2 Hz), 3.63 (1H, dd, J = 11.2, 2.7 Hz), 4.27 (2H, q, J = 7.1 Hz), 4.63 (1H, t, J = 6.4 Hz), 6.25 (1H, d, J = 15.6 Hz), 7.28-7.36 (2H, m), 7.94 (1H, d, J = 15.6 Hz). |
| 4(4b)-40 | 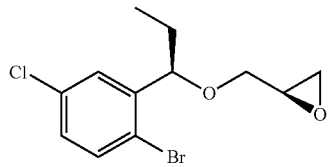 | ¹H-NMR (CDCl₃) δ: 0.99 (3H, t, J = 6.6 Hz), 1.63-1.81 (2H, m), 2.53-2.57 (1H, m), 2.75-2.80 (1H, m), 3.12-3.18 (1H, m), 3.27 (1H, dd, J = 11.5, 6.0 Hz), 3.62 (1H, dd, J = 11.5, 3.2 Hz), 4.63-4.68 (1H, m), 7.11 (1H, dd, J = 5.7, 3.0 Hz), 7.44 (2H, dd, J = 5.7, 3.0 Hz). |
| 4(4c)-40 | 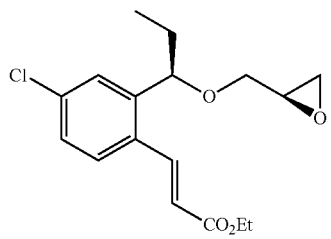 | ¹H-NMR (CDCl₃) δ: 0.92 (3H, t, J = 8.7 Hz), 1.34 (3H, t, J = 7.3 Hz), 1.58-1.86 (2H, m), 2.49-2.54 (1H, m), 2.72-2.81 (1H, m), 3.10-3.19 (1H, m), 3.20-3.28 (1H, m), 3.62 (1H, dd, J = 11.2, 2.1 Hz), 4.27 (2H, q, J = 7.3 Hz), 4.63 (1H, t, J = 6.4 Hz), 6.31 (1H, d, J = 16.0 Hz), 7.22-7.30 (1H, m), 7.43-7.52 (2H, m), 8.00 (1H, d, J = 16.0 Hz). |

TABLE 29

| | | |
|---|---|---|
| 4(4b)-41 | | ¹H-NMR (CDCl₃) δ: 0.97 (3H, t, J = 7.4 Hz), 1.64-1.78 (2H, m), 2.54-2.57 (1H, m), 2.74-2.77 (1H, m), 3.09-3.16 (1H, m), 3.27 (1H, dd, J = 11.5, 4.9 Hz), 3.58 (1H, dd, J = 11.5, 3.4 Hz), 4.64-4.68 (1H, m), 7.32 (1H, dd, J = 8.6, 1.7 Hz), 7.39 (1H, d, J = 8.0 Hz), 7.52-7.55 (1H, m). |
| 4(4c)-41 | | ¹H-NMR (CDCl₃) δ: 0.90 (3H, t, J = 7.3 Hz), 1.34 (3H, t, J = 7.1 Hz), 1.59-1.73 (1H, m), 1.73-1.87 (1H, m), 2.50-2.54 (1H, m), 2.72-2.80 (1H, m), 3.09-3.16 (1H, m), 3.22 (1H, dd, J = 10.1, 6.0 Hz), 3.59 (1H, dd, J = 10.1, 5.0 Hz), 4.28 (2H, q, J = 7.1 Hz), 4.59-4.66 (1H, m), 6.33 (1H, d, J = 15.6 Hz), 7.31-7.44 (2H, m), 7.49-7.52 (1H, m), 8.02 (1H, d, J = 15.6 Hz). |
| 4(4b)-42 | | ¹H-NMR (CDCl₃) δ: 1.00 (3H, t, J = 7.8 Hz), 1.61-1.83 (2H, m), 2 54-2.61 (1H, m), 2.74-2.78 (1H, m), 3.10-3.18 (1H, m), 3.25-3.32 (1H, m), 3.58-3.64 (1H, m), 4.73-4.79 (1H, m), 7.25-7.31 (1H, m), 7.34-7.41 (2H, m). |
| 4(4c)-42 | | ¹H-NMR (CDCl₃) δ: 0.94 (3H, t, J = 7.3 Hz), 1.36 (3H, t, J = 7.1 Hz), 1.57-1.82 (2H, m), 2.49-2.54 (1H, m), 2.74 (1H, t, J = 4.4 Hz), 3.07-3.13 (1H, m), 3.18 (1H, dd, J = 11.0, 6.0 Hz), 3.55 (1H, dd, J = 11.5, 2.8 Hz), 4.30 (2H, q, J = 7.0 Hz), 4.51-4.57 (1H, m), 6.15 (1H, d, J = 16.5 Hz), 7.30 (1H, d, J = 7.3 Hz), 7.35 (1H, d, J = 7.3 Hz), 7.42 (1H, d, J = 7.3 Hz), 7.77 (1H, d, J = 16.5 Hz). |
| 4(4b)-43 | | ¹H-NMR (CDCl₃) δ: 0.40-0.54 (3H, m), 0.56-0.62 (1H, m), 1.17-1.24 (1H, m), 2.58 (1H, dd, J = 4.6, 2.6 Hz), 2.78 (1H, t, J = 4.6 Hz), 3.11-3.16 (1H, m), 3.34 (1H, dd, J = 11.2, 5.4 Hz), 3.54 (1H, dd, J = 11.2, 3.7 Hz), 4.45 (1H, d, J = 6.9 Hz), 7.12-7.16 (1H, m), 7.35 (1H, t, J = 7.4 Hz), 7.51-7.54 (2H, m). |
| 4(4c)-43 | | ¹H-NMR (CDCl₃) δ: 0.23-0.30 (1H, m), 0.41-0.50 (2H, m), 0.60-0.67 (1H, m), 1.17-1.24 (1H, m), 1.35 (3H, t, J = 7.2 Hz), 2.61 (1H, dd, J = 4.9, 2.6 Hz), 2.76-2.78 (1H, m), 3.11-3.15 (1H, m), 3.39 (1H, dd, J = 11.5, 5.2 Hz), 3.60 (1H, dd, J = 11.5, 3.4 Hz), 4.20-4.26 (1H, m), 4.27 (2H, q, J = 7.3 Hz), 6.34 (1H, d, J = 15.5 Hz), 7.28-7.33 (1H, m), 7.37-7.42 (1H, m), 7.48 (1H, d, J = 6.3 Hz), 7.56 (1H, d, J = 6.9 Hz), 8.14 (1H, d, J = 15.5 Hz). |
| 4(4b)-44 | | ¹H-NMR (CDCl₃) δ: 0.40-0.63 (4H, m), 1.18-1.25 (1H, m), 2.52 (1H, dd, J = 4.9, 2.6 Hz), 2.73-2.75 (1H, m), 3.10-3.14 (1H, m), 3.34 (1H, dd, J = 11.2, 6.0 Hz), 3.52 (1H, dd, J = 11.2, 3.4 Hz), 4.45 (1H, d, J = 7.4 Hz), 7.14 (1H, td, J = 7.7, 1.5 Hz), 7.32-7.36 (1H, m), 7.50-7.54 (2H, m). |

TABLE 30

| | | |
|---|---|---|
| 4(4c)-44 | (cyclopropyl-CH(O-CH2-epoxide)-phenyl with ortho CH=CH-CO2Et) | ¹H-NMR (CDCl₃) δ: 0.24-0.30 (1H, m), 0.41-0.52 (2H, m), 0.63-0.69 (1H, m), 1.19-1.27 (1H, m), 1.35 (3H, t, J = 7.2 Hz), 2.50 (1H, dd, J = 4.9, 2.6 Hz), 2.74 (1H, t, J = 4.6 Hz), 3.13-3.17 (1H, m), 3.34 (1H, dd, J = 11.5, 6.0 Hz), 3.57 (1H, dd, J = 11.5, 3.4 Hz), 4.20-4.30 (3H, m), 6.34 (1H, d, J = 16.0 Hz), 7.28-7.33 (1H, m), 7.37-7.41 (1H, m), 7.47 (1H, d, J = 8.0 Hz), 7.56 (1H, d, J = 6.9 Hz), 8.16 (1H, d, J = 16.0 Hz). |
| 4(4b)-45 | F, Br substituted phenyl-CH(CH3)-O-CH2-epoxide | ¹H-NMR (CDCl₃) δ: 1.58-1.62 (3.0H, m), 2.51 (0.5H, dd, J = 4.9, 2.6 Hz), 2.65 (0.5H, dd, J = 5.2, 2.3 Hz), 2.74-2.79 (1.0H, m), 3.10-3.17 (1.0H, m), 3.35-3.42 (1.0H, m), 3.50 (0.5H, dd, J = 11.2, 3.7 Hz), 3.58 (0.5H, dd, J = 11.5, 3.4 Hz), 5.09-5.16 (1.0H, m), 7.01-7.06 (1.0H, m), 7.10-7.15 (1.0H, m), 7.35 (1.0H, d, J = 8.0 Hz). |
| 4(4c)-45 | F substituted phenyl-CH(CH3)-O-CH2-epoxide with CH=CH-CO2Et | ¹H-NMR (CDCl₃) δ: 1.35 (3.0H, t, J = 7.3 Hz), 1.53-1.57 (3.0H, m), 2.50 (0.5H, dd, J = 5.2, 2.9 Hz), 2.69 (0.5H, dd, J = 5.2, 2.9 Hz), 2.72-2.77 (1.0H, m), 3.06 (0.5H, s), 3.11-3.15 (0.5H, m), 3.32 (0.5H, dd, J = 11.2, 6.0 Hz), 3.38 (0.5H, dd, J = 11.5, 4.6 Hz), 3.49 (0.5H, dd, J = 10.9, 3.4 Hz), 3.56 (0.5H, dd, J = 11.5, 3.4 Hz), 4.28 (2.0H, q, J = 7.3 Hz), 5.07-5.15 (1.0H, m), 6.27 (1.0H, d, J = 16.0 Hz), 7.03-7.09 (1.0H, m), 7.23-7.28 (1.0H, m), 7.32-7.36 (1.0H, m), 8.41-8.46 (1.0H, m). |
| 4(4b)-46 | CH3, Br substituted phenyl-CH(CH3)-O-CH2-epoxide | ¹H-NMR (CDCl₃) δ: 1.50-1.54 (3.0H, m), 2.51 (3.0H, s), 2.54 (0.5H, dd, J = 4.9, 2.6 Hz), 2.58 (0.5H, dd, J = 4.9, 2.6 Hz), 2.29-2.29 (1.0H, m), 3.11-3.16 (1.0H, m), 3.20-3.30 (1.0H, m), 3.47-3.55 (1.0H, m), 5.26 (1.0H, q, J = 6.9 Hz), 6.99 (1.0H, t, J = 8.0 Hz), 7.09 (1.0H, d, J = 8.0 Hz), 7.39 (1.0H, d, J = 8.0 Hz). |
| 4(4c)-46 | CH3 substituted phenyl-CH(CH3)-O-CH2-epoxide with CH=CH-CO2Et | ¹H-NMR (CDCl₃) δ: 1.32-1.36 (3.0H, m), 1.51-1.55 (3.0H, m), 2.39 (3.0H, s), 2.44-2.47 (0.5H, m), 2.70 (0.5H, dd, J = 5.2, 2.9 Hz), 2.72-2.75 (1.0H, m), 3.05-3.08 (0.5H, m), 3.10-3.14 (0.5H, m), 3.17 (0.5H, dd, J = 10.9, 6.3 Hz), 3.33 (0.5H, dd, J = 11.5, 4.6 Hz), 3.48-3.52 (1.0H, m), 4.27 (2.0H, q, J = 7.3 Hz), 4.99 (0.5H, q, J = 6.7 Hz), 5.05 (0.5H, q, J = 6.7 Hz), 6.17 (0.5H, d, J = 2.3 Hz), 6.21 (0.5H, d, J = 2.3 Hz), 7.14-7.19 (2.0H, m), 7.34-7.38 (1.0H, m), 8.46-8.54 (1.0H, m). |
| 4(4b)-47 | Cl, Br substituted phenyl-CH(CH3)-O-CH2-epoxide | ¹H-NMR (CDCl₃) δ: 1.60-1.63 (3.0H, m), 2.52 (0.5H, dd, J = 5.2, 2.9 Hz), 2.67 (0.5H, dd, J = 5.2, 2.3 Hz), 2.75-2.79 (1.0H, m), 3.12-3.15 (0.5H, m), 3.17-3.20 (0.5H, m), 3.28 (0.5H, dd, J = 11.2, 6.3 Hz), 3.37 (0.5H, dd, J = 11.2, 4.6 Hz), 3.43 (0.5H, dd, J = 11.2, 3.7 Hz), 3.48 (0.5H, dd, J = 11.2, 3.7 Hz), 5.30-5.36 (1.0H, m), 7.03-7.07 (1.0H, m), 7.34 (1.0H, d, J = 8.0 Hz), 7.50 (1.0H, d, J = 8.0 Hz). |

TABLE 31

| | | |
|---|---|---|
| 4(4c)-47 | Cl substituted phenyl-CH(CH3)-O-CH2-epoxide with CH=CH-CO2Et | ¹H-NMR (CDCl₃) δ: 1.34 (3.0H, t, J = 7.1 Hz), 1.52-1.58 (3.0H, m), 2.50 (0.5H, dd, J = 5.2, 2.9 Hz), 2.69 (0.5H, dd, J = 5.2, 2.9 Hz), 2.72-2.75 (1.0H, m), 3.05-3.13 (1.0H, m), 3.30 (0.5H, dd, J = 10.9, 5.7 Hz), 3.35 (0.5H, dd, J = 10.9, 4.6 Hz), 3.44 (0.5H, dd, J = 11.5, 3.4 Hz), 3.52 (0.5H, dd, J = 11.5, 3.4 Hz), 4.27 (2.0H, q, J = 7.1 Hz), 5.27-5.33 (1.0H, m), 6.21 (1.0H, d, J = 16.0 Hz), 7.19-7.23 (1.0H, m), 7.37 (1.0H, d, J = 8.0 Hz), 7.43 (1.0H, d, J = 7.4 Hz), 8.52-8.57 (1.0H, m). |

TABLE 31-continued

| | | |
|---|---|---|
| 4(4b)-48 | (structure: 2,3-difluoro-6-bromophenyl with CH(CH₃)-O-CH₂-epoxide) | ¹H-NMR (CDCl₃) δ: 1.60 (3.0H, t, J = 7.4 Hz), 2.53 (0.5H, dd, J = 4.8, 2.5 Hz), 2.66 (0.5H, dd, J = 5.0, 2.8 Hz), 2.78 (1.0H, q, J = 4.7 Hz), 3.10-3.18 (1.0H, m), 3.33-3.43 (1.0H, m), 3.54 (0.5H, dd, J = 11.0, 3.7 Hz), 3.62 (0.5H, dd, J = 11.5, 3.7 Hz), 5.04-5.12 (1.0H, m), 6.97-7.04 (1.0H, m), 7.28-7.33 (1.0H, m). |
| 4(4c)-48 | (structure with CO₂Et vinyl substituent) | ¹H-NMR (CDCl₃) δ: 1.34 (3.0H, t, J = 7.2 Hz), 1.54-1.59 (3.0H, m), 2.51 (0.5H, dd, J = 5.2, 2.9 Hz), 2.68 (0.5H, dd, J = 5.2, 2.3 Hz), 2.75 (1.0H, q, J = 4.6 Hz), 3.06-3.10 (0.5H, m), 3.11-3.15 (0.5H, m), 3.30-3.38 (1.0H, m), 3.52 (0.5H, dd, J = 11.2, 3.2 Hz), 3.60 (0.5H, dd, J = 11.5, 3.4 Hz), 4.27 (2.0H, q, J = 7.3 Hz), 5.06-5.14 (1.0H, m), 6.23 (1.0H, d, J = 15.5 Hz), 7.07-7.12 (1.0H, m), 7.28-7.32 (1.0H, m), 8.33-8.37 (1.0H, m). |
| 4(4c)-49 | (structure) | ¹H-NMR (CDCl₃) δ: 1.25-1.28 (3H, m), 1.37-1.41 (3H, m), 2.46-2.57 (4H, m), 2.76-2.80 (1H, m), 3.12-3.17 (2H, m), 3.59-3.64 (1H, m), 4.11-4.18 (2H, m), 4.70-4.77 (1H, m), 5.96-6.02 (1H, m), 6.58-6.62 (1H, m), 7.16 (1H, dd, J = 11.5, 7.7 Hz), 7.22 (1H, dd, J = 11.5, 9.2 Hz). |
| 4(4c)-50 | (structure with OMe) | ¹H-NMR (CDCl₃) δ: 1.18-1.32 (3H, m), 1.39-1.48 (3H, m), 2.46-2.53 (3H, m), 2.54-2.64 (1H, m), 2.70-2.79 (1H, m), 3.07-3.23 (2H, m), 3.38-3.54 (2H, m), 3.81 (3H, s), 4.15 (2H, q, J = 6.4 Hz), 4.85 (1H, q, J = 6.4 Hz), 5.81-5.91 (1H, m), 6.42 (1H, d, J = 16.0 Hz), 6.75-6.81 (1H, m), 7.04-7.16 (1H, m), 7.19-7.31 (1H, m). |
| 4(4c)-51 | (structure with methyl) | ¹H-NMR (CDCl₃) δ: 1.27 (3H, t, J = 7.2 Hz), 1.42 (3H, d, J = 6.4 Hz), 2.32 (3H, s) 2.45-2.51 (3H, m), 2.54 (2H, t, J = 6.4 Hz), 2.75 (1H, t, J= 4.4 Hz), 3.11-3.16 (1H, m), 3.20 (1H, dd, J = 11.0, 6.0 Hz), 3.56 (1H, dd, J = 11.0, 2.8 Hz), 4.15 (2H, q, J = 7.2 Hz), 4.76 (1H, q, J = 6.4 Hz), 6.03 (1H, dt, J = 15.6, 6.6 Hz), 6.74 (1H, d, J = 15.6 Hz), 7.07 (1H, d, J = 8.3 Hz), 7.19 (1H, s), 7.28 (1H, d, J = 8.3 Hz) |
| 4(4c)-52 | (structure with F) | ¹H-NMR (CDCl₃) δ: 1.27 (3H, t, J = 7.2 Hz), 1.42 (3H, d, J = 6.1 Hz), 2.46-2.53 (3H, m), 2.56 (2H, t, J = 6.1 Hz), 2.73-2.80 (1H, m), 3.09-3.17 (1H, m), 3.18-3.24 (1H, m), 3.54-3.61 (1H, m), 4.14 (2H, q, J = 7.2 Hz), 4.77 (1H, q, J = 6.1 Hz), 6.05 (1H, dt, J = 15.6, 5.6 Hz), 6.73 (1H, d, J = 15.6 Hz), 6.94 (1H, dd, J = 10.3, 5.7 Hz), 7.07 (1H, dd, J = 10.3, 2.8 Hz), 7.32-7.40 (1H, m). |

TABLE 32

| | | |
|---|---|---|
| 4(4c)-53 | | ¹H-NMR (CDCl₃) δ: 1.27 (3H, t, J = 7.8 Hz), 1.40 (3H, d, J = 6.9 Hz), 2.44-2.65 (5H, m), 2.77 (1H, t, J = 4.1 Hz), 3.10-3.19 (1H, m), 3.22 (1H, dd, J = 11.0, 5.5 Hz), 3.61 (1H, dd, J = 11.0, 2.5 Hz), 4.14 (2H, q, J = 7.8 Hz), 4.77 (1H, q, J = 6.9 Hz), 5.98 (1H, dt, J = 11.9, 6.3 Hz), 6.63 (1H, d, J = 15.6 Hz), 6.87-6.92 (1H, m), 7.07-7.16 (1H, m), 7.33 (1H, dd, J = 8.5, 5.7 Hz). |
| 4(4c)-54 | | ¹H-NMR (CDCl₃) δ: 1.26 (3H, t, J = 7.1 Hz), 1.42 (3H, d, J = 6.4 Hz), 2.33 (3H, s), 2.42-2.56 (5H, m), 2.76 (1H, t, J = 3.9 Hz), 3.09-3.18 (1H, m), 3.22 (1H, dd, J = 10.8, 6.6 Hz), 3.58 (1H, dd, J = 10.8, 2.3 Hz), 4.14 (2H, q, J = 7.1 Hz), 4.77 (1H, q, J = 6.4 Hz), 5.99 (1H, dt, J = 15.4, 7.0 Hz), 6.72 (1H, d, J = 15.4 Hz), 7.03 (2H, d, J = 4.6 Hz), 7.20 (1H, s). |
| 4(4c)-55 | | ¹H-NMR (CDCl₃) δ: 1.26 (3H, t, J = 7.1 Hz), 1.42 (3H, d, J = 6.3 Hz), 2.29 (3H, s), 2.47-2.52 (2H, m), 2.55-2.60 (1H, m), 2.73-2.75 (1H, m), 2.99 (1H, dd, J = 7.2, 1.4 Hz), 3.09-3.18 (2H, m), 3.40 (1H, dd, J = 13.7, 6.3 Hz), 3.52 (1H, d, J = 8.0 Hz), 4.10 (2H, q, J = 7.1 Hz), 4.76 (1H, q, J = 6.3 Hz), 5.33-5.39 (1H, m), 5.63-5.68 (1H, m), 7.08 (1H, d, J = 7.4 Hz), 7.15-7.20 (1H, m), 7.33 (1H, d, J = 7.4 Hz). |
| 4(4c)-56 | | ¹H-NMR (CDCl₃) δ: 1.23 (3H, t, J = 7.5 Hz), 1.43 (3H, d, J = 6.0 Hz), 2.49-2.53 (2H, m), 2.59 (1H, dd, J = 14.4, 7.1 Hz), 2.76 (1H, t, J = 4.1 Hz), 3.01 (1H, d, J = 6.9 Hz), 3.10-3.17 (2H, m), 3.44 (1H, dd, J = 15.1, 6.0 Hz), 3.55 (1H, d, J = 10.8 Hz), 4.10 (2H, q, J = 7.5 Hz), 4.76 (1H, q, J = 6.0 Hz), 5.45-5.53 (1H, m), 5.63-5.70 (1H, m), 6.95 (1H, t, J = 9.9 Hz), 7.20-7.25 (2H, m). |
| 4(4c)-57 | | ¹H-NMR (CDCl₃) δ: 1.27 (3H, t, J = 6.2 Hz), 1.44 (3H, d, J = 6.4 Hz), 2.48-2.53 (3H, m), 2.58 (2H, t, J = 6.6 Hz), 2.76-2.78 (1H, m), 3.15-3.19 (1H, m), 3.21-3.26 (1H, m), 3.58 (1H, dd, J = 11.2, 2.5 Hz), 4.15 (2H, q, J = 6.2 Hz), 4.84 (1H, q, J = 6.4 Hz), 6.11-6.18 (1H, m), 6.74 (1H, d, J = 15.6 Hz), 7.47 (2H, br s), 7.68 (1H, s). |
| 4(4c)-58 | | ¹H-NMR (CDCl₃) δ: 1.26 (3H, t, J = 7.1 Hz), 1.41 (3H, t, J = 7.1 Hz), 1.41 (3H, d, J = 6.7 Hz), 2.43-2.55 (4H, m), 2.76 (1H, t, J = 4.6 Hz), 3.10-3.19 (2H, m), 3.22 (1H, dd, J = 11.2, 6.2 Hz), 3.60 (1H, dd, J = 11.2, 3.0 Hz), 4.04 (2H, q, J = 7.1 Hz), 4.15 (2H, q, J = 7.1 Hz), 4.76 (1H, q, J = 6.7 Hz), 5.93 (1H, dt, J = 15.5, 6.5 Hz), 6.64 (1H, d, J = 15.5 Hz), 6.75 (1H, dd, J = 8.6, 2.6 Hz), 6.95 (1H, d, J = 2.6 Hz), 7.30 (1H, d, J = 8.6 Hz). |

TABLE 33

| | | |
|---|---|---|
| 4(4c)-59 | | ¹H-NMR (CDCl₃) δ: 1.26 (3H, t, J = 7.0 Hz), 1.33 (6H, d, J = 6.0 Hz), 1.41 (3H, d, J = 6.4 Hz), 2.43-2.55 (4H, m), 2.76 (1H, t, J = 4.6 Hz), 3.10-3.18 (2H, m), 3.22 (1H, dd, J = 11.0, 6.0 Hz), 3.60 (1H, dd, J = 11.2, 3.0 Hz), 4.14 (2H, q, J = 7.0 Hz), 4.51-4.60 (1H, m), 4.76 (1H, q, J = 6.3 Hz), 5.93 (1H, dt, J = 15.4, 6.5 Hz), 6.64 (1H, d, J = 15.4 Hz), 6.74 (1H, dd, J = 8.5, 2.8 Hz), 6.94 (1H, d, J = 2.8 Hz), 7.29 (1H, d, J = 8.5 Hz). |
| 4(4c)-60 | | ¹H-NMR (CDCl₃) δ: 1.27 (3H, t, J = 7.4 Hz), 1.39 (3H, d, J = 6.9 Hz), 2.23-2.25 (2H, m), 2.44-2.57 (3H, m), 2.75-2.78 (2H, m), 3.13-3.16 (1H, m), 3.20 (1H, dd, J = 11.2, 6.0 Hz), 3.59 (1H, dd, J = 11.2, 3.4 Hz), 4.13-4.18 (2H, m), 4.71-4.76 (1H, m), 5.93-5.99 (1H, m), 6.62 (1H, d, J = 16.0 Hz), 7.05 (1H, d, J = 10.9 Hz), 7.18 (1H, d, J = 7.4 Hz). |
| 4(4c)-61 | | ¹H-NMR (CDCl₃) δ: 0.91 (3H, t, J = 7.3 Hz), 1.27 (3H, t, J = 7.3 Hz), 1.58-1.80 (2H, m), 2.24 (3H, s), 2.75 (1H, t, J = 4.4 Hz), 3.09-3.19 (3H, m), 3.58 (1H, dd, J = 10.8, 2.5 Hz), 4.15 (2H, q, J = 7.3 Hz), 4.51 (1H, t, J = 6.4 Hz), 5.95 (1H, dt, J = 15.6, 6.4 Hz), 6.63 (1H, d, J = 15.6 Hz), 7.01 (1H, d, J = 11.0 Hz), 7.18 (1H, d, J = 7.8 Hz). |
| 4(4c)-62 | | ¹H-NMR (CDCl₃) δ: 1.27 (3H, t, J = 7.1 Hz), 1.41 (3H, t, J = 6.9 Hz), 1.42 (3H, d, J = 6.3 Hz), 2.47-2.52 (3H, m), 2.56-2.60 (1H, m), 2.73 (1H, t, J = 4.6 Hz), 3.08-3.14 (2H, m), 3.18 (1H, dd, J = 11.2, 6.0 Hz), 3.47 (1H, dd, J = 11.2, 3.2 Hz), 4.01 (2H, q, J = 6.9 Hz), 4.15 (2H, q, J = 7.1 Hz), 4.84 (1H, q, J = 6.3 Hz), 5.95 (1H, dt, J = 16.0, 6.6 Hz), 6.43 (1H, d, J = 16.0 Hz), 6.76 (1H, d, J = 8.0 Hz), 7.09 (1H, d, J = 8.0 Hz), 7.20 (1H, t, J = 8.0 Hz). |
| 4(4c)-63 | | ¹H-NMR (CDCl₃) δ: 1.27 (3H, t, J = 7.0 Hz), 1.32 (6H, d, J = 5.7 Hz), 1.42 (3H, d, J = 6.3 Hz), 2.47-2.51 (3H, m), 2.55-2.59 (1H, m), 2.73 (1H, t, J = 4.9 Hz), 3.08-3.14 (2H, m), 3.18 (1H, q, J = 5.7 Hz), 3.47 (1H, dd, J = 10.9, 3.4 Hz), 4.15 (2H, q, J = 7.0 Hz), 4.45-4.52 (1H, m), 4.83 (1H, q, J = 6.3 Hz), 5.91 (1H, dt, J = 16.0, 6.6 Hz), 6.40 (1H, d, J = 16.0 Hz), 6.78 (1H, d, J = 7.7 Hz), 7.08 (1H, d, J = 7.7 Hz), 7.18 (1H, t, J = 7.7 Hz). |
| 4(4c)-64 | | ¹H-NMR (CDCl₃) δ: 1.26 (3H, q, J = 7.4 Hz), 1.40 (3H, d, J = 6.3 Hz), 2.46-2.52 (2H, m), 2.53-2.58 (1H, m), 2.74-2.77 (1H, m), 3.03-3.07 (1H, m), 3.09-3.16 (2H, m), 3.17-3.22 (1H, m), 3.36-3.42 (1H, m), 3.58 (1H, dd, J = 11.5, 2.9 Hz), 4.11-4.18 (2H, m), 4.73-4.78 (1H, m), 6.02-6.10 (1H, m), 6.68 (1H, d, J = 15.5 Hz), 7.20-7.24 (1H, m), 7.34-7.36 (1H, m). |

TABLE 33-continued

| | | |
|---|---|---|
| 4(4c)-65 | 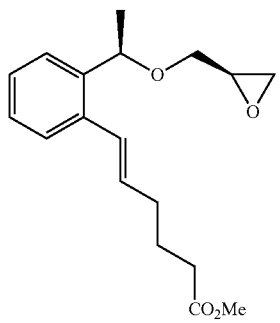 | $^1$H-NMR (CDCl$_3$) δ: 1.44 (3H, d, J = 6.4 Hz), 1.78-1.87 (2H, m), 2.24-2.41 (5H, m), 2.47-2.53 (1H, m), 2.73-2.77 (1H, m), 3.10-3.26 (3H, m), 3.54-3.70 (1H, m), 3.68 (3H, s), 4.75-4.84 (1H, m), 5.22 (0H, s), 5.96-6.05 (1H, m), 6.71 (1H, d, J = 15.6 Hz), 7.17-7.28 (2H, m), 7.39 (1H, t, J = 6.9 Hz). |

TABLE 34

| | | |
|---|---|---|
| 4(4c)-66 | 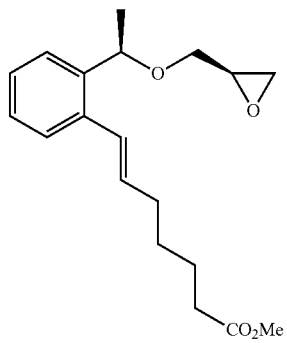 | $^1$H-NMR (CDCl3) δ: 1.40-1.54 (2H, m), 1.44 (3H, d, J = 6.0 Hz), 1.63-1.75 (2H, m), 2.20-2.40 (5H, m), 2.47-2.52 (1H, m), 2.72-2.77 (1H, m), 3.08-3.25 (3H, m), 3.52-3.70 (1H, m), 3.67 (3H, s), 4.75-4.86 (1H, m), 5.97-6.07 (1H, m), 6.69 (1H, d, J = 15.6 Hz), 7.18-7.28 (2H, m), 7.39 (1H, t, J = 7.1 Hz). |

The compounds of the Examples described below were produced with reference to the steps that are described in Examples 1 to 14 above. In Examples 15 to 68, for instance, the production steps are carried out in the order of (1) coupling reaction, (2) olefin hydrogenation, and (3) ester hydrolysis, like the production steps 1(a), 1(b), and 1(c) of Example 1.

TABLE 35

| Example No. | Structure | Data |
|---|---|---|
| 15(15a) | 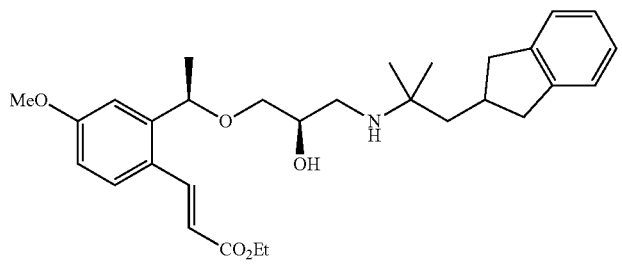 | $^1$H-NMR (CDCl$_3$) δ: 1.10 (6H, s), 1.33 (3H, t, J = 7.2 Hz), 1.44 (3H, d, J = 6.6 Hz), 1.66-1.69 (2H, m), 2.49-2.66 (5H, m), 2.72 (1H, dd, J = 11.7, 3.9 Hz), 3.06 (2H, dd, J = 14.9, 7.3 Hz), 3.37 (2H, d, J = 5.1 Hz), 3.72-3.78 (1H, m), 3.83 (3H, s), 4.25 (2H, q, J = 7.1 Hz), 4.83 (1H, q, J = 6.3 Hz), 6.25 (1H, d, J = 15.6 Hz), 6.81 (1H, dd, J = 8.8, 2.7 Hz), 7.02-7.04 (1H, m), 7.09-7.19 (5H, m), 7.52 (1H, d, J = 8.8 Hz), 8.00 (1H, d, J = 15.6 Hz). |
| 15(15b) | 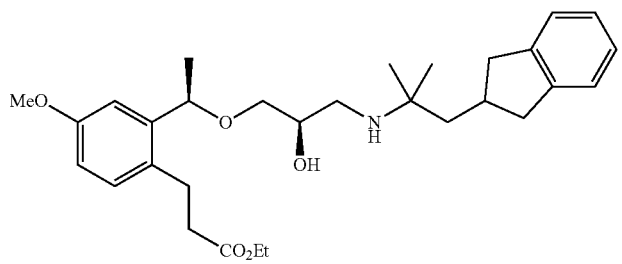 | $^1$H-NMR (CDCl$_3$) δ: 1.10 (6H, s), 1.24 (3H, t, J = 7.2 Hz), 1.43 (3H, d, J = 6.3 Hz), 1.65-1.69 (2H, m), 2.48-2.65 (6H, m), 2.70 (1H, dd, J = 11.7, 3.9 Hz), 2.87-2.94 (2H, m), 3.02-3.09 (2H, m), 3.28-3.37 (2H, m), 3.71-3.77 (1H, m), 3.78 (3H, s), 4.13 (2H, q, J = 7.2 Hz), 4.71 (1H, q, J = 6.3 Hz), 6.74 (1H, dd, J = 8.5, 2.9 Hz), 6.99 (1H, d, J = 2.9 Hz), 7.05-7.18 (5H, m). |

TABLE 35-continued

| Example No. | Structure | Data |
|---|---|---|
| 15(15c) | 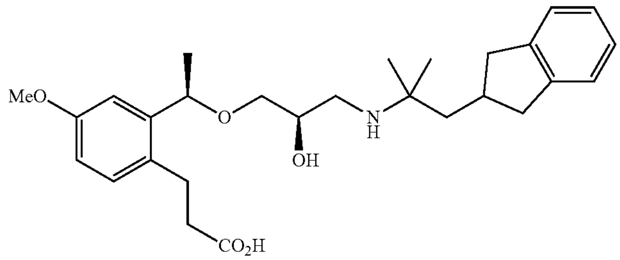 | ¹H-NMR (CDCl₃) δ: 1.41 (6H, s), 1.46 (3H, d, J = 6.4 Hz), 1.96-2.10 (2H, m), 2.40-2.69 (6H, m), 2.95-3.14 (7H, m), 3.53-3.63 (1H, m), 3.67-3.73 (1H, m), 3.77 (3H, s), 4.13-4.21 (1H, m), 4.93-5.03 (1H, m), 6.74-6.78 (1H, m), 6.80 (1H, s), 7.08-7.14 (6H, m). |
| 16(16a) | 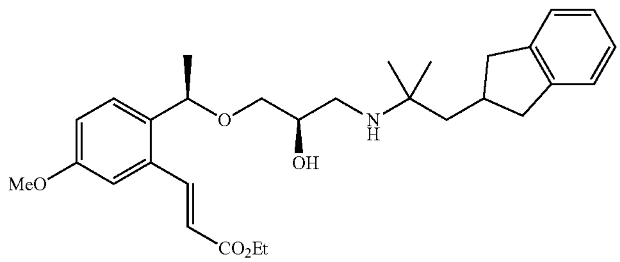 | ¹H-NMR (CDCl₃) δ: 1.10 (6H, s), 1.24-1.30 (1H, m), 1.32-1.37 (3H, m), 1.42-1.46 (3H, m), 1.65-1.69 (2H, m), 2.50-2.73 (5H, m), 3.01-3.10 (2H, m), 3.28-3.38 (2H, m), 3.71-3.78 (1H, m), 3.81 (3H, s), 4.24-4.31 (2H, m), 4.74-4.82 (1H, m), 6.32 (1H, dd, J = 16.0, 4.6 Hz), 6.91-6.96 (1H, m), 7.02-7.06 (1H, m), 7.09-7.19 (4H, m), 7.38 (1H, dd, J = 8.7, 4.1 Hz), 8.09 (1H, dd, J = 16.0, 4.6 Hz). |
| 16(16b) | 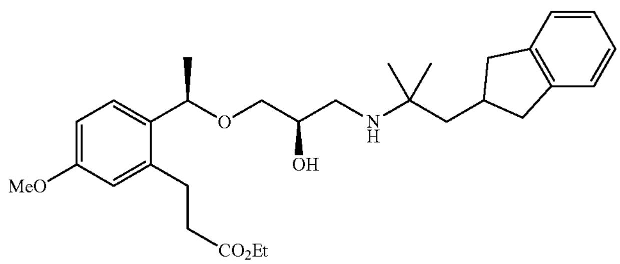 | ¹H-NMR (CDCl₃) δ: 1.10 (6H, s), 1.25 (3H, t, J = 7.2 Hz), 1.43 (3H, d, J = 6.4 Hz), 1.65-1.68 (2H, m), 2.50-2.64 (6H, m), 2.68 (1H, dd, J = 11.7, 4.1 Hz), 2.95 (2H, t, J = 8.0 Hz), 3.06 (2H, dd, J = 14.6, 6.8 Hz), 3.25-3.33 (2H, m), 3.70-3.75 (1H, m), 3.76 (3H, s), 4.14 (2H, q, J = 7.2 Hz), 4.69 (1H, q, J = 6.4 Hz), 6.68 (1H, d, J = 2.4 Hz), 6.78 (1H, dd, J = 8.5, 2.4 Hz), 7.09-7.13 (2H, m), 7.13-7.18 (2H, m), 7.33 (1H, d, J = 8.5 Hz). |
| 16(16c) | 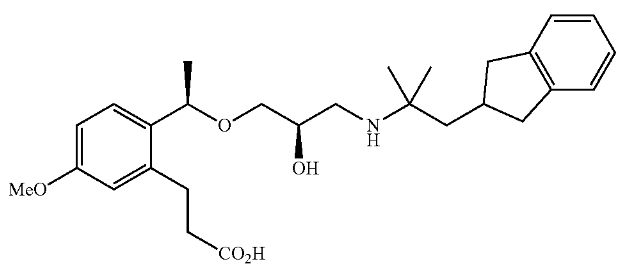 | ¹H-NMR (CDCl₃) δ: 1.40-1.44 (6H, m), 1.45-1.48 (3H, m), 1.95-2.09 (2H, m), 2.47-2.67 (5H, m), 2.97-3.15 (6H, m), 3.49-3.60 (1H, m), 3.65-3.71 (1H, m), 3.77 (3H, s), 4.09-4.21 (1H, m), 4.87-4.97 (1H, m), 6.67-6.72 (1H, m), 6.77 (1H, s), 7.07-7.20 (5H, m). |

TABLE 36

| | | |
|---|---|---|
| 17(17a) | | ¹H-NMR (CDCl₃) δ: 1.10 (6H, s), 1.34 (3H, t, J = 7.2 Hz), 1.45 (3H, d, J = 6.3 Hz), 1.67 (2H, d, J = 5.9 Hz), 2.48-2.65 (4H, m), 2.69 (1H, dd, J = 11.7, 4.1 Hz), 3.02-3.09 (2H, m), 3.28-3.35 (2H, m), 3.69-3.80 (1H, m), 3.86 (3H, s), 4.26 (2H, q, J = 7.1 Hz), 4.83 (1H, q, J = 6.3 Hz), 6.53 (1H, d, J = 16.1 Hz), 6.83 (1H, d, J = 8.3 Hz), 7.08-7.19 (5H, m), 7.29-7.35 (1H, m), 7.91 (1H, d, J = 16.1 Hz). |

TABLE 36-continued

17(17b) 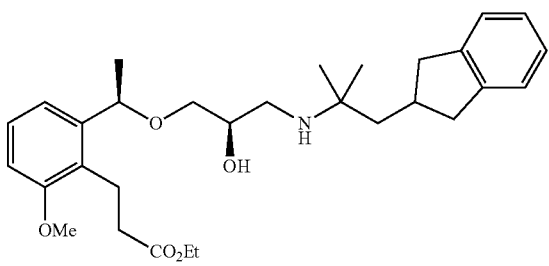
$^1$H-NMR (CDCl$_3$) δ: 1.09-1.10 (6H, m), 1.26 (3H, t, J = 7.8 Hz), 1.43 (3H, d, J = 6.3 Hz), 1.66 (2H, d, J = 5.9 Hz), 2.48-2.64 (6H, m), 2.68 (1H, dd, J = 11.6, 4.0 Hz), 2.88-3.09 (4H, m), 3.26-3.34 (2H, m), 3.71-3.78 (1H, m), 3.81 (3H, s), 4.15 (2H, q, J = 7.2 Hz), 4.76 (1H, q, J = 6.3 Hz), 6.75 (1H, d, J = 8.0 Hz), 7.05 (1H, d, J = 6.8 Hz), 7.09-7.23 (5H, m).

17(17c) 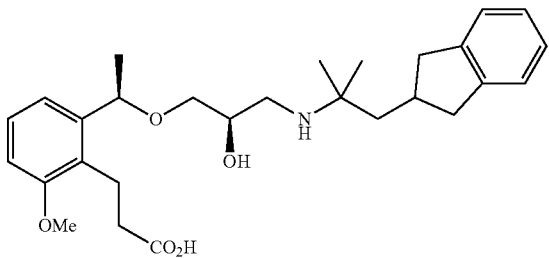
$^1$H-NMR (CDCl$_3$) δ: 1.40-1.48 (9H, m), 1.98-2.11 (2H, m), 2.39-2.60 (3H, m), 2.60-2.70 (2H, m), 2.89-3.14 (6H, m), 3.49-3.59 (1H, m), 3.63-3.69 (1H, m), 3.78 (3H, s), 4.23-4.30 (1H, m), 5.00-5.10 (1H, m), 6.74-6.78 (1H, m), 6.87-6.92 (1H, m), 7.08-7.17 (5H, m).

18(18a) 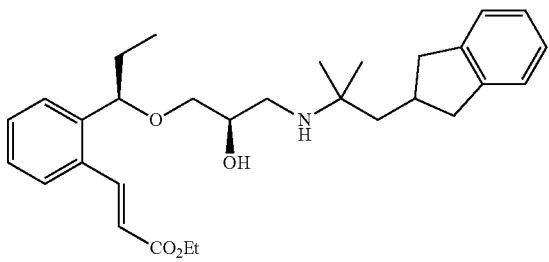
$^1$H-NMR (CDCl$_3$) δ: 0.91 (3H, t, J = 7.1 Hz), 1.10 (6H, s), 1.34 (3H, t, J = 7.2 Hz), 1.65-1.74 (3H, m), 1.77-1.87 (1H, m), 2.48-2.65 (4H, m), 2.71 (1H, dd, J = 11.6, 4.0 Hz), 3.01-3.11 (2H, m), 3.29-3.36 (2H, m), 3.71-3.78 (1H, m), 4.26 (2H, q, J = 7.1 Hz), 4.55-4.60 (1H, m), 6.32 (1H, d, J = 15.9 Hz), 7.09-7.13 (2H, m), 7.13-7.17 (2H, m), 7.27-7.29 (1H, m), 7.35-7.40 (1H, m), 7.41-7.44 (1H, m), 7.54 (1H, d, J = 7.6 Hz), 8.12 (1H, d, J = 15.9 Hz).

18(18b) 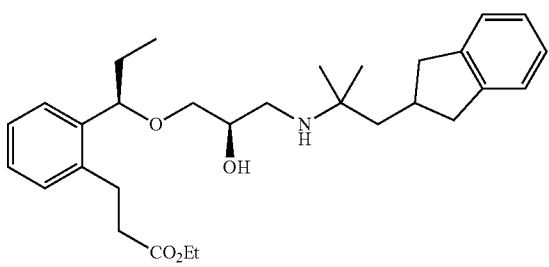
$^1$H-NMR (CDCl$_3$) δ: 0.97 (3H, t, J = 7.3 Hz), 1.10 (6H, s), 1.24 (3H, t, J = 7.1 Hz), 1.61-1.72 (3H, m), 1.75-1.85 (1H, m), 2.49-2.65 (6H, m), 2.69 (1H, dd, J = 11.6, 4.0 Hz), 2.90-3.08 (4H, m), 3.26-3.33 (2H, m), 3.72-3.78 (1H, m), 4.14 (2H, q, J = 7.3 Hz), 4.49 (1H, dd, J = 7.9, 5.0 Hz), 7.10-7.24 (7H, m), 7.39 (1H, dd, J = 7.3, 2.2 Hz).

18(18c) 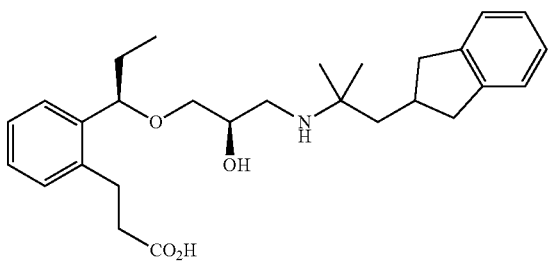
$^1$H-NMR (CDCl$_3$) δ: 0.67-0.79 (3H, m), 1.23-1.40 (8H, m), 1.62-1.75 (1H, m), 1.87-2.07 (4H, m), 2.42-2.67 (4H, m), 2.90-3.13 (4H, m), 3.52-3.69 (2H, m), 4.13-4.25 (1H, m), 4.78-4.89 (1H, m), 7.09-7.26 (8H, m).

19(19a) 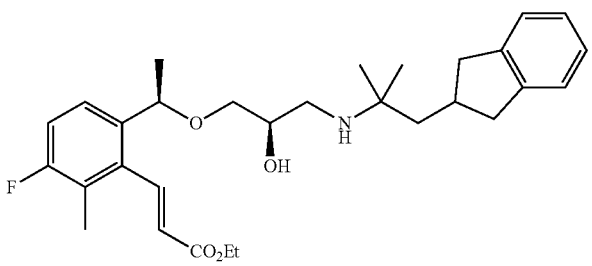
$^1$H-NMR (CDCl$_3$) δ: 1.11 (6H, s), 1.35 (3H, t, J = 7.2 Hz), 1.45 (3H, d, J = 6.6 Hz), 1.65-1.69 (2H, m), 2.32 (3H, d, J = 2.0 Hz), 2.50-2.65 (4H, m), 2.71 (1H, dd, J = 11.6, 4.0 Hz), 3.02-3.09 (2H, m), 3.34-3.41 (2H, m), 3.72-3.78 (1H, m), 4.27 (2H, q, J = 7.1 Hz), 4.80 (1H, q, J = 6.3 Hz), 6.34 (1H, d, J = 15.9 Hz), 7.08-7.18 (4H, m), 7.23-7.26 (1H, m), 7.34 (1H, d, J = 8.3 Hz), 7.89 (1H, d, J = 15.9 Hz).

TABLE 36-continued

| 19(19b) | 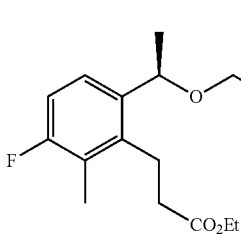 | ¹H-NMR (CDCl₃) δ: 1.10 (6H, s), 1.25 (3H, t, J = 7.0 Hz), 1.44 (3H, d, J = 6.4 Hz), 1.67 (2H, d, J = 6.0 Hz), 2.21 (3H, d, J = 2.3 Hz), 2.51-2.64 (6H, m), 2.70 (1H, dd, J = 11.5, 4.1 Hz), 2.90-2.94 (2H, m), 3.03-3.09 (2H, m), 3.33-3.39 (2H, m), 3.71-3.77 (1H, m), 4.14 (2H, q, J = 7.0 Hz), 4.77 (1H, q, J = 6.4 Hz), 6.93 (1H, d, J = 8.3 Hz), 7.10-7.18 (5H, m). |

TABLE 37

| 19(19c) | 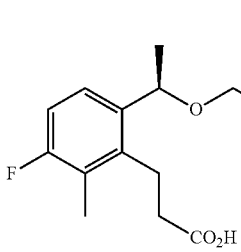 | ¹H-NMR (CDCl₃) δ: 1.28 (3H, s), 1.30 (3H, s), 1.41 (3H, d, J = 6.9 Hz), 1.87 (2H, d, J = 6.9 Hz), 2.20 (3H, s), 2.43-2.54 (4H, m), 2.61-2.69 (2H, m), 2.72-2.79 (1H, m), 2.88-2.94 (2H, m), 3.01-3.14 (3H, m), 3.43 (1H, dd, J = 10.3, 5.7 Hz), 3.55-3.64 (1H, m), 4.78 (1H, q, J = 6.3 Hz), 6.92 (1H, d, J = 8.0 Hz), 6.96-7.00 (1H, m), 7.12-7.15 (2H, m), 7.17-7.21 (2H, m). |
| 20(20a) | 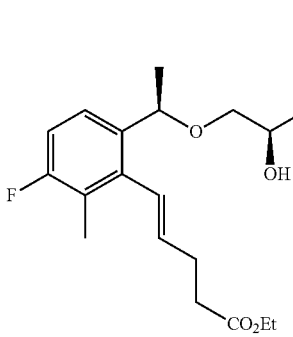 | ¹H-NMR (CDCl₃) δ: 1.10 (6H, s), 1.26 (3H, t, J = 7.0 Hz), 1.44 (3H, d, J = 6.4 Hz), 1.67 (2H, d, J = 6.0 Hz), 2.19-2.22 (3H, m), 2.37-2.74 (9H, m), 3.02-3.10 (2H, m), 3.32-3.39 (2H, m), 3.71-3.77 (1H, m), 4.15 (2H, q, J = 7.0 Hz), 4.78 (1H, q, J = 6.4 Hz), 6.03-6.11 (1H, m), 6.56 (1H, d, J = 15.6 Hz), 7.09-7.19 (6H, m). |
| 20(20b) | 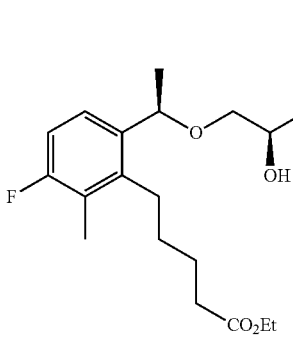 | ¹H-NMR (CDCl₃) δ: 1.10 (6H, s), 1.25 (3H, t, J = 7.2 Hz), 1.44 (3H, d, J = 6.4 Hz), 1.53-1.61 (2H, m), 1.65-1.74 (4H, m), 2.17-2.19 (3H, m), 2.33 (2H, t, J = 7.1 Hz), 2.50-2.65 (6H, m), 2.70 (1H, dd, J = 11.7, 3.9 Hz), 3.02-3.10 (2H, m), 3.33-3.40 (2H, m), 3.71-3.78 (1H, m), 4.13 (2H, q, J = 7.2 Hz), 4.76 (1H, q, J = 6.4 Hz), 6.90 (1H, d, J = 8.3 Hz), 7.09-7.18 (5H, m). |
| 20(20c) | 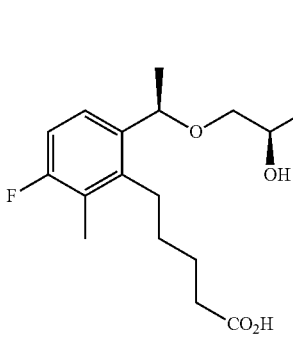 | ¹H-NMR (CDCl₃) δ: 1.22-1.28 (2H, m), 1.31 (6H, s), 1.44 (3H, d, J = 6.3 Hz), 1.50-1.60 (4H, m), 1.88 (2H, d, J = 6.3 Hz), 2.05-2.15 (2H, m), 2.16 (3H, s), 2.47-2.67 (6H, m), 2.90-2.95 (1H, m), 3.02-3.11 (2H, m), 3.18-3.22 (1H, m), 3.45-3.49 (1H, m), 3.90-3.94 (1H, m), 4.71 (1H, q, J = 6.3 Hz), 6.88 (1H, d, J = 8.0 Hz), 7.07-7.17 (5H, m). |

TABLE 37-continued

| 21(21a) | 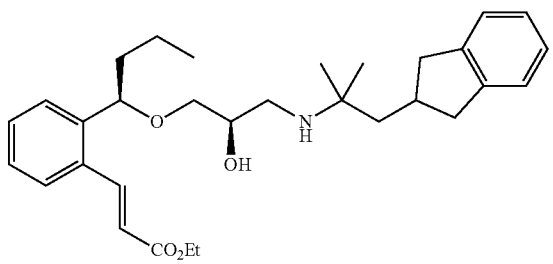 | $^1$H-NMR (CDCl$_3$) δ: 0.91 (3H, t, J = 7.4 Hz), 1.10 (6H, s), 1.30-1.37 (4H, m), 1.41-1.52 (1H, m), 1.56-1.63 (1H, m), 1.67 (2H, d, J = 5.7 Hz), 1.76-1.84 (1H, m), 2.49-2.64 (4H, m), 2.70 (1H, dd, J = 11.7, 4.3 Hz), 3.03-3.08 (2H, m), 3.28-3.35 (2H, m), 3.72-3.77 (1H, m), 4.22-4.31 (2H, m), 4.65 (1H, dd, J = 8.0, 5.2 Hz), 6.32 (1H, d, J = 16.0 Hz), 7.09-7.12 (2H, m), 7.14-7.17 (2H, m), 7.25-7.29 (2H, m), 7.37 (1H, t, J = 6.9 Hz), 7.43 (1H, d, J = 7.4 Hz), 7.54 (1H, d, J = 7.4 Hz), 8.11 (1H, d, J = 16.0 Hz). |
| --- | --- | --- |
| 21(21b) | 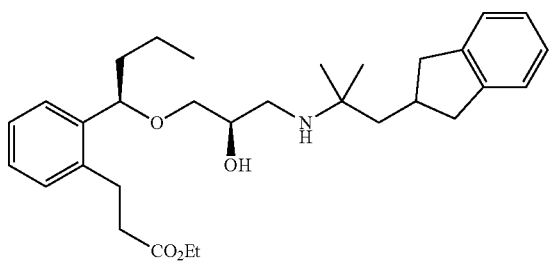 | $^1$H-NMR (CDCl$_3$) δ: 0.92 (3H, t, J = 6.9 Hz), 1.10 (6H, s), 1.24 (3H, t, J = 7.1 Hz), 1.33-1.43 (2H, m), 1.48-1.61 (2H, m), 1.65-1.68 (2H, m), 1.75-1.82 (1H, m), 2.50-2.64 (6H, m), 2.68 (1H, dd, J = 11.5, 4.1 Hz), 2.90-3.00 (2H, m), 3.02-3.08 (2H, m), 3.24-3.32 (2H, m), 3.71-3.77 (1H, m), 4.14 (2H, q, J = 7.3 Hz), 4.57 (1H, dd, J = 8.3, 3.7 Hz), 7.09-7.24 (7H, m), 7.39 (1H, d, J = 7.3 Hz). |
| 21(21c) | 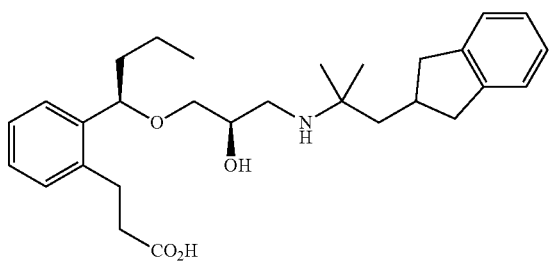 | $^1$H-NMR (CDCl$_3$) δ: 0.84 (3H, t, J = 7.3 Hz), 1.05-1.15 (1H, m), 1.16-1.25 (1H, m), 1.35-1.38 (6H, m), 1.64-1.72 (1H, m), 1.91-2.03 (3H, m), 2.46-2.57 (3H, m), 2.62 (2H, dd, J = 14.9, 9.7 Hz), 2.95-3.11 (6H, m), 3.57-3.68 (2H, m), 4.14-4.20 (1H, m), 4.86-4.95 (1H, m), 7.10-7.23 (9H, m). |

TABLE 38

| 22(22a) | 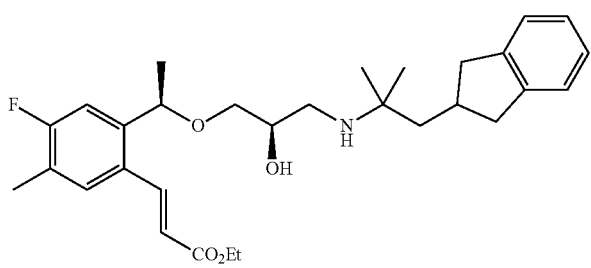 | $^1$H-NMR (CDCl$_3$) δ: 1.12 (6H, d, J = 5.7 Hz), 1.34 (3H, t, J = 7.2 Hz), 1.42 (3H, d, J = 6.4 Hz), 1.68 (2H, d, J = 6.3 Hz), 2.26 (3H, s), 2.50-2.64 (4H, m), 2.72 (1H, dd, J = 11.5, 4.0 Hz), 3.06 (2H, dd, J = 14.6, 7.2 Hz), 3.32-3.39 (2H, m), 3.73-3.78 (1H, m), 4.27 (2H, q, J = 7.2 Hz), 4.79 (1H, q, J = 6.4 Hz), 6.28 (1H, d, J = 16.0 Hz), 7.10-7.17 (5H, m), 7.38 (1H, d, J = 7.4 Hz), 7.96 (1H, d, J = 16.0 Hz). |
| --- | --- | --- |
| 22(22b) | 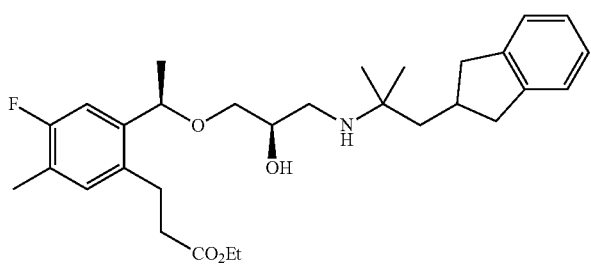 | $^1$H-NMR(CDCl$_3$) δ: 1.10 (6H, s), 1.22-1.27 (3H, m), 1.39-1.42 (3H, m), 1.65-1.68 (2H, m), 2.21 (3H, s), 2.50-2.64 (6H, m), 2.68-2.72 (1H, m), 2.86-2.90 (2H, m), 3.02-3.08 (2H, m), 3.25-3.29 (1H, m), 3.30-3.34 (1H, m), 3.71-3.77 (1H, m), 4.10-4.16 (2H, m), 4.64-4.69 (1H, m), 6.92-6.97 (1H, m), 7.04-7.08 (1H, m), 7.09-7.17 (4H, m). |

TABLE 38-continued

| | | |
|---|---|---|
| 22(22c) | 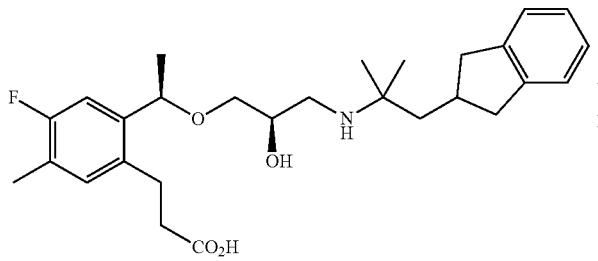 | $^1$H-NMR (CDCl$_3$) δ: 1.40-1.43 (9H, m), 1.96-2.05 (2H, m), 2.21 (3H, s), 2.41-2.48 (2H, m), 2.52-2.59 (1H, m), 2.60-2.67 (2H, m), 2.86-3.13 (6H, m), 3.60-3.66 (1H, m), 3.61-3.66 (1H, m), 4.18-4.24 (1H, m), 4.90-4.97 (1H, m), 6.91 (1H, d, J = 10.3 Hz), 6.99 (1H, d, J = 7.4 Hz), 7.09-7.14 (4H, m). |
| 23(23a) | 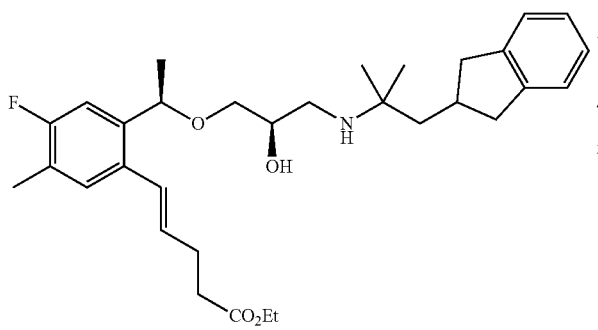 | $^1$H-NMR (CDCl$_3$) δ: 1.10 (6H, s), 1.26 (3H, t, J = 7.3 Hz), 1.38 (3H, d, J = 6.3 Hz), 1.67 (2H, d, J = 6.3 Hz), 2.23 (3H, s), 2.43-2.72 (9H, m), 3.03-3.08 (2H, m), 3.25-3.34 (2H, m), 3.71-3.78 (1H, m), 4.12-4.17 (2H, m), 4.63-4.70 (1H, m), 5.93-5.98 (1H, m), 6.60 (1H, d, J = 15.5 Hz), 7.02-7.18 (6H, m). |
| 23(23b) | 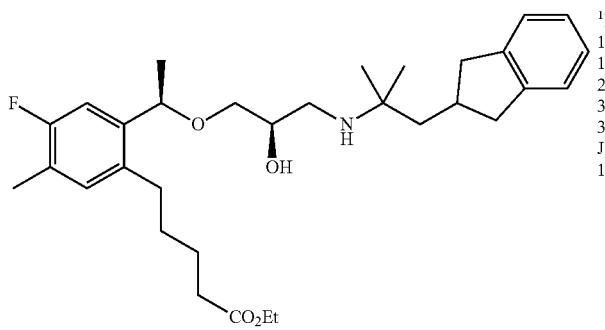 | $^1$H-NMR(CDCl$_3$) δ: 1.10 (6H, s), 1.24-1.27 (3H, m), 1.39 (3H, d, J = 6.3 Hz), 1.53-1.61 (2H, m), 1.65-1.73 (4H, m), 2.21 (3H, s), 2.33 (2H, t, J = 7.4 Hz), 2.51-2.63 (6H, m), 2.70 (1H, dd, J = 12.0, 4.0 Hz), 3.05 (2H, dd, J = 14.9, 7.4 Hz), 3.24-3.31 (2H, m), 3.71-3.77 (1H, m), 4.10-4.14 (2H, m), 4.64 (1H, q, J = 6.1 Hz), 6.91 (1H, d, J = 7.4 Hz), 7.05 (1H, d, J = 10.9 Hz), 7.09-7.13 (2H, m), 7.14-7.18 (2H, m). |
| 23(23c) | 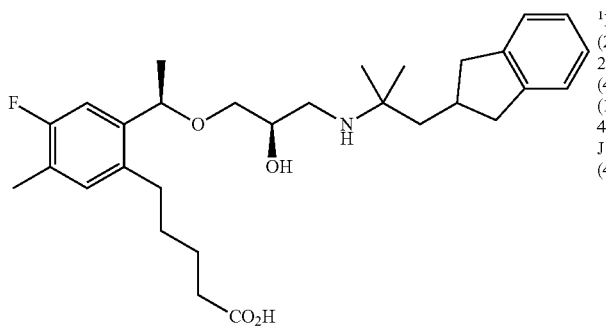 | $^1$H-NMR (CDCl$_3$) δ: 1.32-1.37 (9H, m), 1.44-1.53 (2H, m), 1.60-1.73 (2H, m), 1.88-1.91 (2H, m), 2.15-2.23 (4H, m), 2.28-2.40 (2H, m), 2.45-2.63 (4H, m), 2.83-2.87 (1H, m), 3.01-3.11 (3H, m), 3.29 (1H, dd, J = 10.9, 8.6 Hz), 3.51-3.56 (1H, m), 4.25-4.31 (1H, m), 4.69 (1H, q, J = 6.3 Hz), 6.88 (1H, d, J = 8.0 Hz), 6.99 (1H, d, J = 10.3 Hz), 7.10-7.17 (4H, m). |
| 24(24a) | 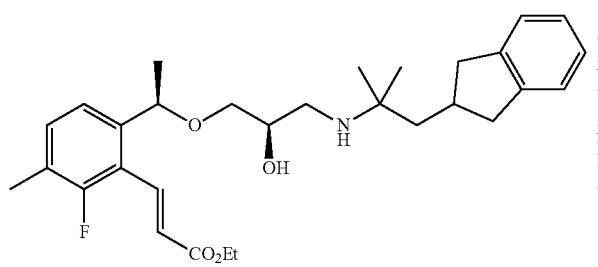 | $^1$H-NMR (CDCl$_3$) δ: 1.11 (6H, s), 1.34 (3H, t, J = 7.3 Hz), 1.41 (3H, d, J = 6.3 Hz), 1.64-1.71 (2H, m), 2.24 (3H, d, J = 2.3 Hz), 2.49-2.64 (4H, m), 2.71 (1H, dd, J = 12.0, 4.0 Hz), 3.05 (2H, dd, J = 14.9, 6.9 Hz), 3.31-3.36 (2H, m), 3.73-3.77 (1H, m), 4.27 (2H, q, J = 7.3 Hz), 4.68 (1H, q, J = 6.3 Hz), 6.49 (1H, d, J = 16.0 Hz), 7.10-7.17 (4H, m), 7.21 (1H, d, J = 7.4 Hz), 7.37 (1H, t, J = 7.4 Hz), 7.80 (1H, d, J = 16.0 Hz). |

TABLE 39

24(24b) 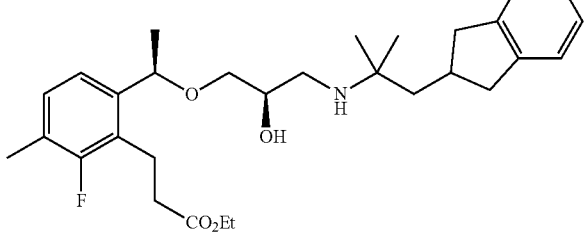
¹H-NMR (CDCl₃) δ: 1.10 (6H, s), 1.24 (3H, t, J = 7.1 Hz), 1.40 (3H, d, J = 6.3 Hz), 1.65-1.69 (2H, m), 2.21 (3H, d, J = 1.7 Hz), 2.51-2.63 (6H, m), 2.70 (1H, dd, J = 11.7, 4.3 Hz), 2.93 (2H, t, J = 7.7 Hz), 3.03-3.08 (2H, m), 3.28-3.35 (2H, m), 3.72-3.76 (1H, m), 4.13 (2H, q, J = 7.1 Hz), 4.64 (1H, q, J = 6.3 Hz), 7.01-7.04 (1H, m), 7.07-7.17 (5H, m).

24(24c) 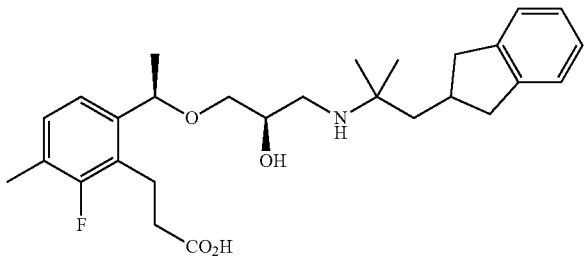
¹H-NMR (CDCl₃) δ: 1.30 (3H, s), 1.31 (3H, s), 1.39 (3H, d, J = 6.5 Hz), 1.85-1.91 (2H, m), 2.18 (3H, d, J = 1.7 Hz), 2.48-2.67 (6H, m), 2.74-2.80 (1H, m), 2.86-2.90 (1H, m), 2.92-2.98 (1H, m), 3.06-3.12 (3H, m), 3.39 (1H, dd, J = 10.3, 5.2 Hz), 3.65-3.73 (1H, m), 4.67 (1H, q, J = 6.5 Hz), 6.98-7.02 (2H, m), 7.11-7.14 (2H, m), 7.15-7.19 (2H, m).

25(25a) 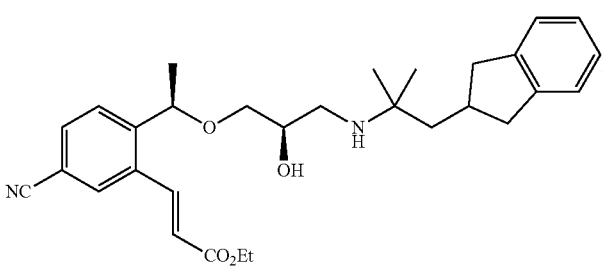
¹H-NMR (CDCl₃) δ: 1.11 (6H, s), 1.35 (3H, t, J = 7.1 Hz), 1.43 (3H, d, J = 6.5 Hz), 1.66-1.71 (2H, m), 2.50-2.56 (2H, m), 2.59-2.64 (2H, m), 2.73 (1H, dd, J = 12.0, 4.0 Hz), 3.06 (2H, dd, J = 14.9, 7.4 Hz), 3.34 (1H, dd, J = 10.0, 4.0 Hz), 3.39 (1H, dd, J = 10.0, 5.0 Hz), 3.72-3.76 (1H, m), 4.28 (2H, q, J = 7.1 Hz), 4.84 (1H, q, J = 6.5 Hz), 6.36 (1H, d, J = 15.5 Hz), 7.10-7.13 (2H, m), 7.14-7.18 (2H, m), 7.62-7.66 (2H, m), 7.78 (1H, s), 7.97 (1H, d, J = 15.5 Hz).

25(25b) 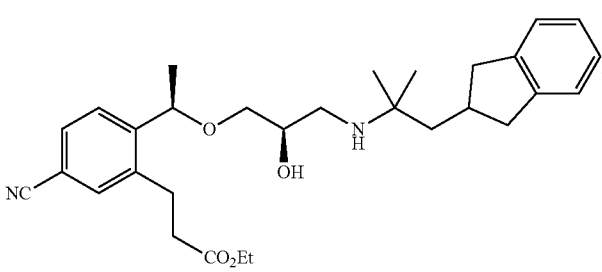
¹H-NMR (CDCl₃) δ: 1.11 (6H, s), 1.25 (3H, t, J = 7.1 Hz), 1.43 (3H, d, J = 6.5 Hz), 1.65-1.70 (2H, m), 2.49-2.57 (2H, m), 2.58-2.64 (4H, m), 2.71 (1H, dd, J = 11.5, 4.0 Hz), 2.93-3.03 (2H, m), 3.03-3.08 (2H, m), 3.29 (1H, dd, J = 9.7, 4.3 Hz), 3.35 (1H, dd, J = 9.7, 5.7 Hz), 3.71-3.75 (1H, m), 4.14 (2H, q, J = 7.1 Hz), 4.79 (1H, q, J = 6.5 Hz), 7.11-7.13 (2H, m), 7.15-7.17 (2H, m), 7.45 (1H, s), 7.52 (1H, dd, J = 8.3, 1.4 Hz), 7.57 (1H, d, J = 8.3 Hz).

25(25c) 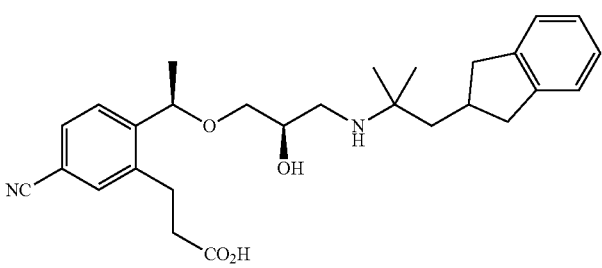
¹H-NMR (CDCl₃) δ: 1.41 (3H, s), 1.43 (3H, s), 1.46 (3H, d, J = 6.3 Hz), 1.97 (2H, dd, J = 13.7, 6.0 Hz), 2.04 (1H, dd, J = 13.7, 5.7 Hz), 2.39-2.47 (2H, m), 2.54-2.66 (3H, m), 2.95-3.14 (6H, m), 3.54-3.60 (1H, m), 3.65-3.69 (1H, m), 4.13-4.18 (1H, m), 5.01-5.08 (1H, m), 7.09-7.14 (4H, m), 7.33-7.36 (1H, m), 7.44-7.48 (2H, m).

26(26a) 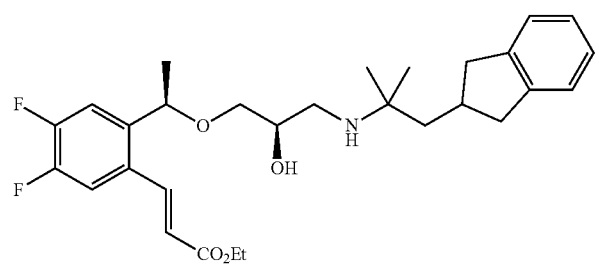
¹H-NMR (CDCl₃) δ: 1.11 (6H, s), 1.34 (3H, t, J = 7.1 Hz), 1.41 (3H, d, J = 6.3 Hz), 1.66-1.71 (2H, m), 2.51-2.64 (4H, m), 2.73 (1H, dd, J = 12.0, 4.0 Hz), 3.04-3.08 (2H, m), 3.33-3.40 (2H, m), 3.72-3.77 (1H, m), 4.27 (2H, q, J = 7.1 Hz), 4.79 (1H, q, J = 6.3 Hz), 6.25 (1H, d, J = 15.5 Hz), 7.10-7.13 (2H, m), 7.14-7.18 (2H, m), 7.29-7.35 (2H, m), 7.91 (1H, d, J = 14.9 Hz).

TABLE 39-continued

26(26b) 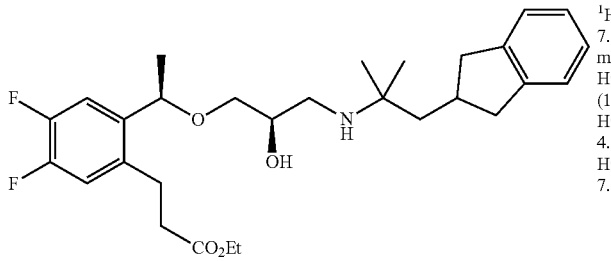
¹H-NMR (CDCl₃) δ: 1.11 (6H, s), 1.25 (3H, t, J = 7.3 Hz), 1.40 (3H, d, J = 6.3 Hz), 1.64-1.71 (2H, m), 2.50-2.64 (6H, m), 2.72 (1H, dd, J = 11.5, 4.0 Hz), 2.85-2.95 (2H, m), 3.04-3.09 (2H, m), 3.29 (1H, dd, J = 9.7, 4.6 Hz), 3.33 (1H, dd, J = 9.7, 5.7 Hz), 3.72-3.76 (1H, m), 4.14 (2H, q, J = 7.1 Hz), 4.68 (1H, q, J = 6.3 Hz), 6.95 (1H, dd, J = 11.5, 8.0 Hz), 7.10-7.13 (2H, m), 7.14-7.18 (2H, m), 7.21-7.25 (1H, m).

26(26c) 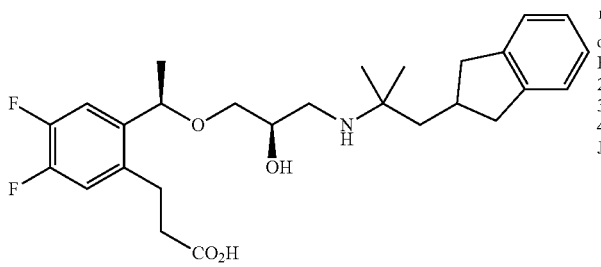
¹H-NMR (CDCl₃) δ: 1.40-1.44 (9H, m), 1.97 (1H, dd, J = 13.7, 6.3 Hz), 2.03 (1H, dd, J = 13.7, 5.7 Hz), 2.41-2.45 (2H, m), 2.53-2.67 (3H, m), 2.88-2.94 (1H, m), 2.97-3.04 (3H, m), 3.06-3.14 (2H, m), 3.49-3.56 (1H, m), 3.62 (1H, dd, J = 10.9, 2.9 Hz), 4.12-4.18 (1H, m), 4.91-4.97 (1H, m), 6.99 (1H, dd, J = 11.2, 8.3 Hz), 7.05-7.15 (6H, m).

TABLE 40

27(27a) 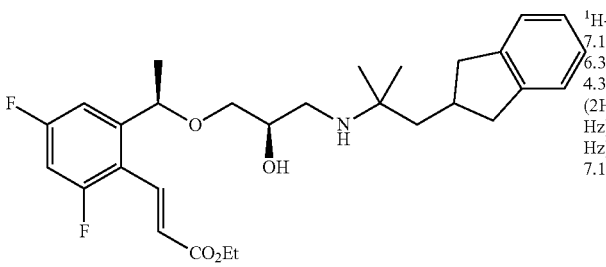
¹H-NMR (CDCl₃) δ: 1.12 (6H, s), 1.34 (3H, t, J = 7.1 Hz), 1.43 (3H, d, J = 6.5 Hz), 1.69 (2H, d, J = 6.3 Hz), 2.50-2.65 (4H, m), 2.75 (1H, dd, J = 11.7, 4.3 Hz), 3.07 (2H, dd, J = 15.2, 7.2 Hz), 3.34-3.40 (2H, m), 3.74-3.79 (1H, m), 4.27 (2H, q, J = 7.1 Hz), 4.80 (1H, q, J = 6.5 Hz), 6.48 (1H, d, J = 16.6 Hz), 6.75-6.80 (1H, m), 7.07-7.13 (3H, m), 7.15-7.17 (2H, m), 7.70 (1H, d, J = 16.6 Hz).

27(27b) 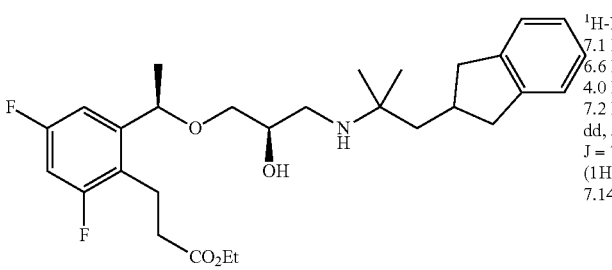
¹H-NMR (CDCl₃) δ: 1.12 (6H, s), 1.25 (3H, t, J = 7.1 Hz), 1.41 (3H, d, J = 6.3 Hz), 1.68 (2H, d, J = 6.6 Hz), 2.50-2.64 (6H, m), 2.72 (1H, dd, J = 12.0, 4.0 Hz), 2.86-3.00 (2H, m), 3.06 (2H, dd, J = 14.6, 7.2 Hz), 3.30 (1H, dd, J = 9.7, 4.0 Hz), 3.35 (1H, dd, J = 9.7, 5.2 Hz), 3.73-3.77 (1H, m), 4.14 (2H, q, J = 7.3 Hz), 4.75 (1H, q, J = 6.1 Hz), 6.67-6.71 (1H, m), 6.97-7.00 (1H, m), 7.10-7.13 (2H, m), 7.14-7.18 (2H, m).

27(27c) 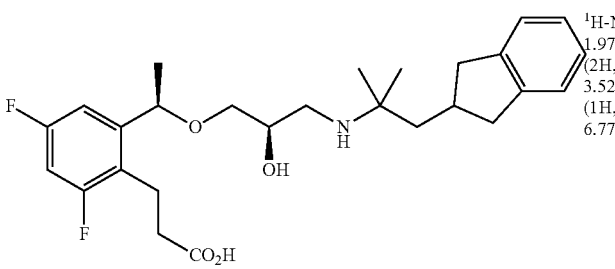
¹H-NMR (CDCl₃) δ: 1.23-1.26 (3H, m), 1.43 (6H, s), 1.97-2.03 (1H, m), 2.03-2.09 (1H, m), 2.35-2.48 (2H, m), 2.53-2.68 (3H, m), 2.91-3.15 (6H, m), 3.52-3.59 (1H, m), 3.67-3.74 (1H, m), 4.14-4.21 (1H, m), 4.94-5.02 (1H, m), 6.67-6.72 (1H, m), 6.77-6.81 (1H, m), 7.09-7.15 (6H, m).

TABLE 40-continued

| | | |
|---|---|---|
| 28(28a) | 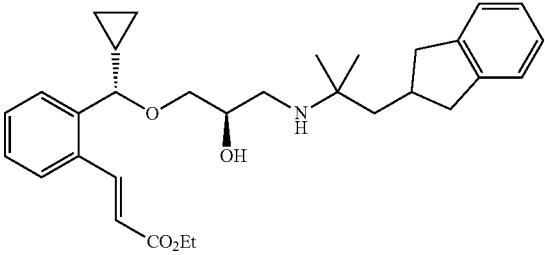 | $^1$H-NMR (CDCl$_3$) δ: 0.21-0.27 (1H, m), 0.41-0.50 (2H, m), 0.62-0.68 (1H, m), 1.10 (6H, s), 1.18-1.28 (1H, m), 1.33 (3H, t, J = 6.9 Hz), 1.65-1.70 (2H, m), 2.49-2.57 (1H, m), 2.58-2.63 (3H, m), 2.70 (1H, dd, J = 11.7, 4.3 Hz), 3.02-3.08 (2H, m), 3.37 (1H, dd, J = 9.7, 5.7 Hz), 3.47 (1H, dd, J = 9.7, 4.6 Hz), 3.72-3.76 (1H, m), 4.15 (1H, d, J = 8.0 Hz), 4.26 (2H, q, J = 7.3 Hz), 6.34 (1H, d, J = 16.0 Hz), 7.10-7.12 (2H, m), 7.14-7.17 (2H, m), 7.27-7.30 (1H, m), 7.35-7.38 (1H, m), 7.44 (1H, d, J = 6.3 Hz), 7.56 (1H, d, J = 6.9 Hz), 8.17 (1H, d, J = 16.0 Hz). |
| 28(28b) | 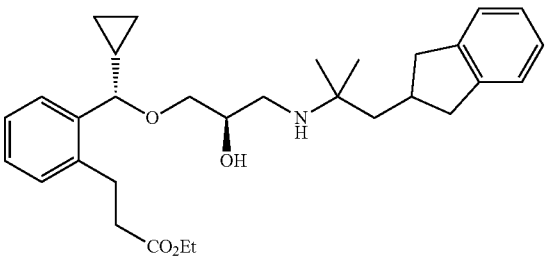 | $^1$H-NMR (CDCl$_3$) δ: 0.25-0.30 (1H, m), 0.39-0.49 (2H, m), 0.59-0.64 (1H, m), 1.11 (6H, s), 1.20-1.26 (4H, m), 1.65-1.71 (2H, m), 2.50-2.65 (6H, m), 2.70 (1H, dd, J = 11.5, 4.6 Hz), 2.94-3.09 (4H, m), 3.34 (1H, dd, J = 10.0, 5.7 Hz), 3.45 (1H, dd, J = 10.0, 4.3 Hz), 3.71-3.75 (1H, m), 4.13 (2H, q, J = 7.3 Hz), 4.20 (1H, d, J = 6.9 Hz), 7.10-7.13 (2H, m), 7.14-7.18 (3H, m), 7.19-7.23 (2H, m), 7.40-7.43 (1H, m). |
| 28(28c) | 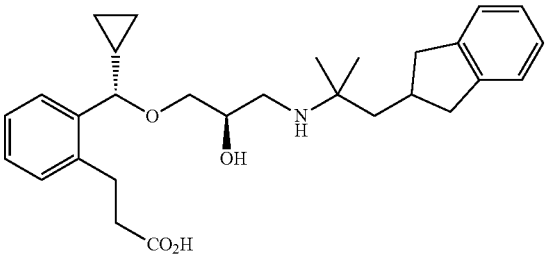 | $^1$H-NMR (CDCl$_3$) δ: 0.03-0.09 (1H, m), 0.41-0.48 (2H, m), 0.72-0.79 (1H, m), 1.17-1.25 (1H, m), 1.35-1.37 (6H, m), 1.96 (1H, dd, J = 13.7, 6.3 Hz), 2.05 (1H, dd, J = 13.7, 6.9 Hz), 2.35-2.42 (1H, m), 2.47-2.59 (2H, m), 2.59-2.65 (2H, m), 2.88-2.95 (1H, m), 3.02-3.11 (5H, m), 3.55-3.60 (1H, m), 3.91-3.99 (2H, m), 4.11-4.18 (1H, m), 7.09-7.15 (5H, m), 7.18-7.24 (2H, m), 7.30-7.38 (1H, m). |
| 29(29a) | 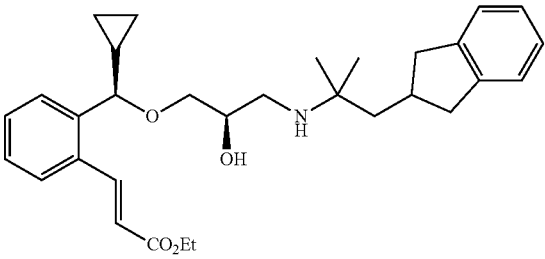 | $^1$H-NMR (CDCl$_3$) δ: 0.21-0.27 (1H, m), 0.41-0.50 (2H, m), 0.62-0.67 (1H, m), 1.09 (6H, s), 1.18-1.24 (1H, m), 1.33 (3H, t, J = 6.9 Hz), 1.66 (2H, d, J = 6.3 Hz), 2.48-2.62 (4H, m), 2.71 (1H, dd, J = 11.5, 4.0 Hz), 3.02-3.07 (2H, m), 3.33 (1H, dd, J = 9.5, 4.9 Hz), 3.44 (1H, dd, J = 9.5, 5.7 Hz), 3.73-3.78 (1H, m), 4.13 (1H, d, J = 8.6 Hz), 4.26 (2H, q, J = 7.3 Hz), 6.34 (1H, d, J = 16.0 Hz), 7.09-7.12 (2H, m), 7.14-7.17 (2H, m), 7.27-7.31 (1H, m), 7.37 (1H, t, J = 7.4 Hz), 7.44 (1H, d, J = 8.0 Hz), 7.56 (1H, d, J = 6.9 Hz), 8.17 (1H, d, J = 16.0 Hz). |

TABLE 41

| | | |
|---|---|---|
| 29(29b) | 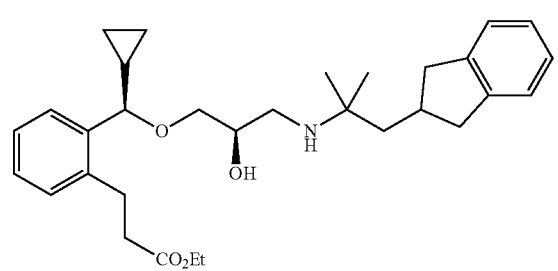 | $^1$H-NMR (CDCl$_3$) δ: 0.25-0.30 (1H, m), 0.39-0.49 (2H, m), 0.59-0.65 (1H, m), 1.09-1.11 (6H, m), 1.19-1.26 (4H, m), 1.66 (2H, d, J = 5.7 Hz), 2.54-2.62 (6H, m), 2.69 (1H, dd, J = 12.0, 4.0 Hz), 2.94-3.08 (4H, m), 3.31 (1H, dd, J = 9.5, 4.9 Hz), 3.41 (1H, dd, J = 9.5, 6.3 Hz), 3.74-3.78 (1H, m), 4.13 (2H, q, J = 7.3 Hz), 4.18 (1H, d, J = 7.4 Hz), 7.10-7.12 (2H, m), 7.14-7.17 (3H, m), 7.19-7.24 (2H, m), 7.40-7.43 (1H, m). |

TABLE 41-continued

| | | |
|---|---|---|
| 29(29c) | [structure] | ¹H-NMR (CDCl₃) δ: −0.08−−0.01 (1H, m), 0.31-0.38 (1H, m), 0.57-0.64 (1H, m), 0.73-0.80 (1H, m), 1.14-1.21 (1H, m), 1.23-1.27 (1H, m), 1.41-1.43 (6H, m), 2.01 (1H, dd, J = 13.5, 6.9 Hz), 2.11 (1H, dd, J = 13.5, 6.0 Hz), 2.39-2.46 (1H, m), 2.49-2.58 (2H, m), 2.62-2.68 (2H, m), 2.97-3.13 (6H, m), 3.79-4.08 (3H, m), 4.16-4.23 (1H, m), 7.08-7.21 (8H, m). |
| 30(30a) | [structure] | ¹H-NMR (CDCl₃) δ: 1.11 (6H, s), 1.24-1.28 (3H, m), 1.35-1.40 (3H, m), 1.66-1.71 (2H, m), 2.44-2.64 (8H, m), 2.70-2.75 (1H, m), 3.04-3.08 (2H, m), 3.30-3.35 (2H, m), 3.71-3.77 (1H, m), 4.10-4.19 (2H, m), 4.61-4.71 (1H, m), 5.95-6.01 (1H, m), 6.59 (1H, d, J = 15.5 Hz), 7.10-7.22 (6H, m). |
| 30(30b) | [structure] | ¹H-NMR (CDCl₃) δ: 1.11 (6H, s), 1.25 (3H, t, J = 7.3 Hz), 1.38 (3H, d, J = 6.3 Hz), 1.54-1.61 (2H, m), 1.66-1.72 (4H, m), 2.33 (2H, t, J = 7.4 Hz), 2.49-2.64 (6H, m), 2.72 (1H, dd, J = 12.0, 4.0 Hz), 3.03-3.09 (2H, m), 3.25-3.31 (2H, m), 3.71-3.76 (1H, m), 4.13 (2H, q, J = 7.3 Hz), 4.64 (1H, q, J = 6.3 Hz), 6.89-6.94 (1H, m), 7.10-7.13 (2H, m), 7.14-7.18 (2H, m), 7.22 (1H, dd, J = 11.7, 8.3 Hz). |
| 30(30c) | [structure] | ¹H-NMR (CDCl₃) δ: 1.34 (3H, d, J = 6.3 Hz), 1.37-1.46 (6H, m), 1.48-1.55 (2H, m), 1.59-1.73 (2H, m), 1.96 (2H, d, J = 6.3 Hz), 2.17-2.23 (1H, m), 2.30-2.38 (2H, m), 2.48-2.56 (1H, m), 2.58-2.66 (3H, m), 2.86-2.91 (1H, m), 3.05-3.11 (3H, m), 3.32 (1H, dd, J = 11.5, 7.2 Hz), 3.44 (1H, dd, J = 11.5, 6.3 Hz), 4.28-4.34 (1H, m), 4.72 (1H, q, J = 6.3 Hz), 6.85-6.89 (1H, m), 7.11-7.17 (5H, m). |

Example 31

3-{2-[(1R)-1-{[(2R)-3-{[1-(2,3-Dihydro-1H-inden-2-yl)-2-methylpropan-2-yl]amino}-2-hydroxypropyl]oxy}ethyl]-3-fluorophenyl}propanoic acid and 3-{2-[(1S)-1-{[(2R)-3-{[1-(2,3-dihydro-1H-inden-2-yl)-2-methylpropan-2-yl]amino-}-2-hydroxypropyl]oxy}ethyl]-3-fluorophenyl}propanoic acid (31c)

Ethyl 3-[2-(1-{[(2R)-3-{[1-(2,3-dihydro-1H-inden-2-yl)-2-methylpropan-2-yl]amino}-2-hydroxypropyl]oxy}ethyl)-3-fluorophenyl]propanoate (115 mg, 0.25 mmol) which had been obtained in Example 31(31b) was dissolved in a mixture solution of tetrahydrofuran-methanol-water (4:1:1, 1 mL), added with 4 N aqueous sodium hydroxide solution (62 μL, 0.25 mmol), and then stirred at room temperature for 4 hours. After neutralization by adding 1 N aqueous hydrogen chloride solution (0.25 mmol), the mixture was extracted with ethyl acetate. The organic layer was washed with saturated brine and dried over anhydrous magnesium sulfate. The solvent was distilled off under reduced pressure. The residue was purified by diolsilica gel (SHOKO SCIENTIFIC CO., LTD.) column chromatography (dichloromethane/methanol=20/1) to give 53 mg of 3-{2-[(1R)-1-{[(2R)-3-{[1-(2,3-dihydro-1H-inden-2-yl)-2-methylpropan-2-yl]amino}-2-hydroxypropyl]oxy}ethyl]-3-fluorophenyl}propanoic acid (low polarity, yield 46%) and 44 mg of 3-{2-[(1S)-1-{[(2R)-3-{[1-(2,3-dihydro-1H-inden-2-yl)-2-methylpropan-2-yl]amino}-2-hydroxypropyl]oxy}ethyl]-3-fluorophenyl}propanoic acid (high polarity, yield 39%), each as a colorless amorphous substance.

TABLE 42

| | | |
|---|---|---|
| 31(31a) | 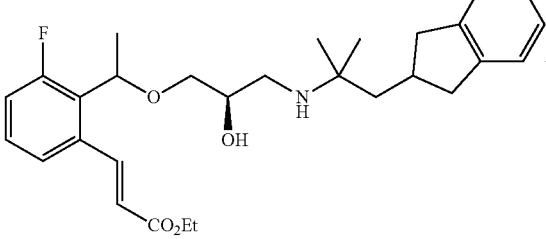 | ¹H-NMR (CDCl₃) δ: 1.08-1.10 (6H, m), 1.32 (3H, t, J = 7.2 Hz), 1.54-1.56 (3H, m), 1.64-1.68 (2H, m), 2.48-2.72 (5H, m), 3.02-3.07 (2H, m), 3.24-3.30 (1H, m), 3.41-3.46 (1H, m), 3.70-3.75 (1H, m), 4.21-4.27 (2H, m), 5.08 (1H, q, J = 6.7 Hz), 6.26-6.31 (2H, m), 7.02-7.06 (1H, m), 7.10-7.12 (2.0H, m), 7.14-7.17 (2.0H, m), 7.21-7.25 (1.0H, m), 7.32-7.35 (1.0H, m), 8.44 (1.0H, d, J = 16.0 Hz). |
| 31(31b) | 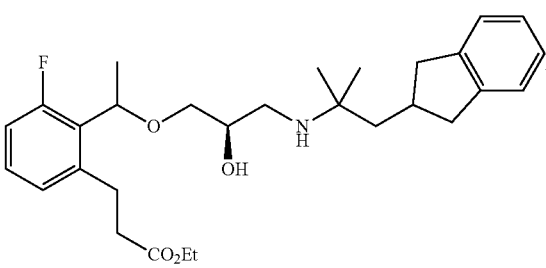 | ¹H-NMR (CDCl₃) δ: 1.09-1.10 (6H, m), 1.24 (3H, t, J = 7.1 Hz), 1.57 (3H, d, J = 6.3 Hz), 1.65-1.69 (2H, m), 2.51-2.63 (6H, m), 2.65-2.70 (1H, m), 3.03-3.10 (3H, m), 3.12-3.20 (1H, m), 3.28-3.31 (1H, m), 3.43-3.49 (1H, m), 3.71-3.77 (1H, m), 4.13 (2H, q, J = 7.1 Hz), 4.92-4.97 (1H, m), 6.86-6.90 (1H, m), 6.96 (1H, d, J = 7.4 Hz), 7.10-7.18 (5H, m). |
| 31(31c) | 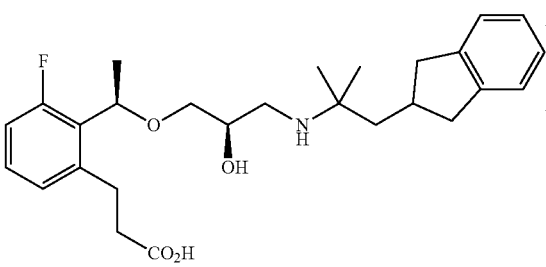 | A less polar: ¹H-NMR (CDCl₃) δ: 1.38 (6H, s), 1.50 (3H, d, J = 6.3 Hz), 1.94 (1H, dd, J = 13.7, 6.3 Hz), 2.05 (1H, dd, J = 13.7, 6.3 Hz), 2.34-2.41 (1H, m), 2.50-2.65 (4H, m), 2.85-2.91 (1H, m), 3.01-3.11 (4H, m), 3.36-3.47 (2H, m), 3.70-3.74 (1H, m), 4.11-4.16 (1H, m), 5.05 (1H, q, J = 6.5 Hz), 6.76-6.81 (1H, m), 7.07-7.16 (6H, m). |
| 31(31c) | 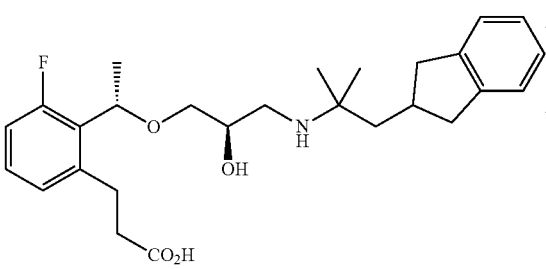 | A more polar: ¹H-NMR (CDCl₃) δ: 1.44 (6H, s), 1.51 (3H, d, J = 6.3 Hz), 2.01 (1H, dd, J = 13.7, 6.3 Hz), 2.09 (1H, dd, J = 13.7, 6.3 Hz), 2.33-2.42 (1H, m), 2.47-2.68 (4H, m), 2.87-2.95 (1H, m), 2.99-3.15 (5H, m), 3.56-3.68 (1H, m), 3.69-3.76 (1H, m), 4.15-4.22 (1H, m), 5.32-5.42 (1H, m), 6.84-6.88 (1H, m), 6.94 (1H, d, J = 6.9 Hz), 7.08-7.16 (6H, m). |
| 32(32a) | 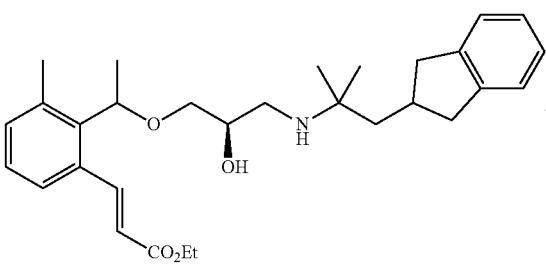 | ¹H-NMR (CDCl₃) δ: 1.08-1.10 (6H, m), 1.30-1.34 (3H, m), 1.53 (3H, d, J = 6.9 Hz), 1.64-1.70 (2H, m), 2.38 (3H, s), 2.48-2.70 (5H, m), 3.02-3.08 (2H, m), 3.21-3.28 (1H, m), 3.32-3.38 (1H, m), 3.68-3.75 (1H, m), 4.20-4.27 (2H, m), 4.96-5.00 (1H, m), 6.19-6.23 (1H, m), 7.09-7.18 (6H, m), 7.35-7.40 (1H, m), 8.52-8.57 (1H, m). |
| 32(32b) | 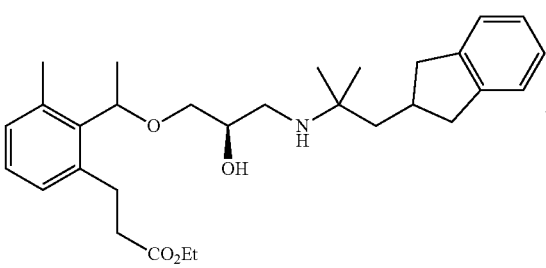 | ¹H-NMR (CDCl₃) δ: 1.10-1.11 (6H, m), 1.23-1.26 (3H, m), 1.53-1.54 (3H, m), 1.66-1.68 (2H, m), 2.41-2.43 (3H, m), 2.49-2.64 (6H, m), 2.66-2.71 (1H, m), 3.03-3.09 (3H, m), 3.27-3.31 (1H, m), 3.33-3.40 (1H, m), 3.72-3.79 (1H, m), 4.11-4.16 (2H, m), 4.92-4.97 (1H, m), 6.99-7.02 (2H, m), 7.07-7.12 (3H, m), 7.14-7.17 (2H, m). |

TABLE 43

| | | |
|---|---|---|
| 32(32c) | 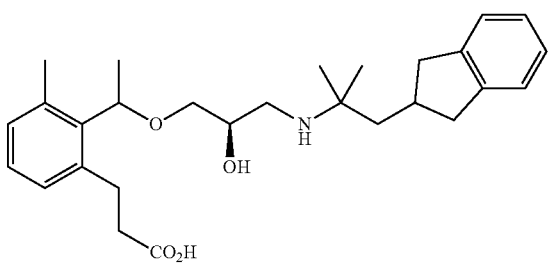 | ¹H-NMR (CDCl₃) δ: 1.41-1.46 (9H, m), 1.97-2.02 (1H, m), 2.05-2.12 (1H, m), 2.32-2.48 (3H, m), 2.51-2.58 (2H, m), 2.61-2.67 (2H, m), 2.77-2.90 (1H, m), 2.90-3.02 (1H, m), 3.03-3.16 (2H, m), 3.18-3.29 (1H, m), 3.38-3.43 (1H, m), 3.43-3.55 (1H, m), 3.68-3.77 (2H, m), 4.11-4.17 (1H, m), 4.21-4.27 (1H, m), 4.97 (1H, q, J = 6.5 Hz), 6.90-6.97 (1H, m), 7.01-7.15 (6H, m). |
| 33(33a) | 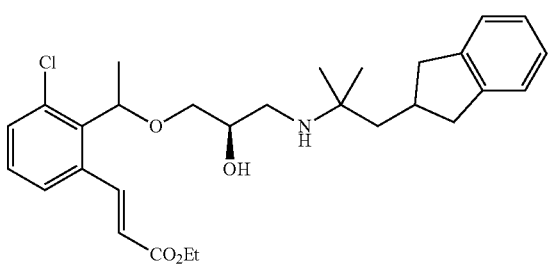 | ¹H-NMR (CDCl₃) δ: 1.08 (6H, s), 1.29-1.34 (3H, m), 1.52-1.56 (3H, m), 1.64-1.68 (2H, m), 2.48-2.71 (5H, m), 3.01-3.07 (2H, m), 3.21-3.29 (1H, m), 3.38-3.43 (1H, m), 3.69-3.76 (1H, m), 4.20-4.27 (2H, m), 5.25-5.31 (1H, m), 6.19-6.26 (1H, m), 7.09-7.21 (5H, m), 7.36 (1H, d, J = 7.8 Hz), 7.42-7.46 (1H, m), 8.54-8.60 (1H, m). |
| 33(33b) | 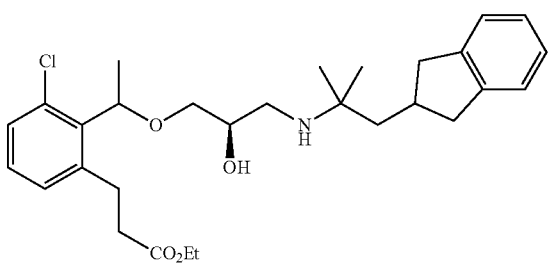 | ¹H-NMR (CDCl₃) δ: 1.10 (6H, s), 1.22-1.26 (3H, m), 1.66-1.69 (4H, m), 2.50-2.71 (8H, m), 3.03-3.19 (3H, m), 3.24-3.33 (2H, m), 3.42-3.46 (1H, m), 3.74-3.80 (1H, m), 4.11-4.16 (2H, m), 5.22 (1H, q, J = 6.5 Hz), 7.09-7.22 (7H, m). |
| 33(33c) | 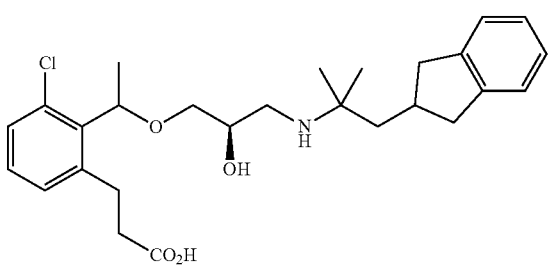 | ¹H-NMR (CDCl₃) δ: 1.40-1.49 (9.0H, m), 1.97-2.13 (2.5H, m), 2.26-2.37 (0.5H, m), 2.46-2.67 (5.0H, m), 2.72-2.97 (2.0H, m), 3.03-3.19 (3.0H, m), 3.32-3.41 (1.0H, m), 3.65-3.79 (1.0H, m), 4.01-4.10 (0.5H, m), 4.21-4.30 (0.5H, m), 5.26-5.31 (1.0H, m), 7.06-7.22 (7.0H, m). |
| 34(34a) | 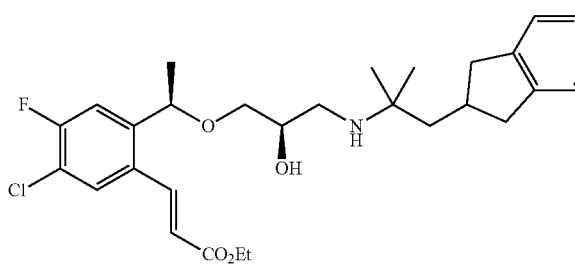 | ¹H-NMR (CDCl₃) δ: 1.11 (6H, s), 1.34 (3H, t, J = 7.1 Hz), 1.41 (3H, d, J = 6.6 Hz), 1.68 (2H, d, J = 5.9 Hz), 2.50-2.65 (4H, m), 2.73 (1H, dd, J = 11.8, 4.0 Hz), 3.03-3.10 (2H, m), 3.32-3.41 (2H, m), 3.71-3.78 (1H, m), 4.27 (2H, q, J = 7.1 Hz), 4.78 (1H, q, J = 6.6 Hz), 6.28 (1H, d, J = 15.6 Hz), 7.10-7.18 (4H, m), 7.28-7.31 (1H, m), 7.57 (1H, d, J = 7.3 Hz), 7.89 (1H, d, J = 15.6 Hz). |
| 34(34b) | 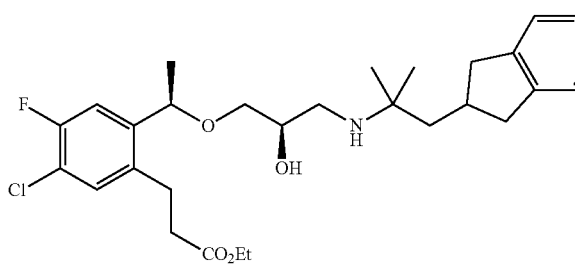 | ¹H-NMR (CDCl₃) δ: 1.11 (6H, s), 1.25 (3H, t, J = 7.2 Hz), 1.41 (3H, d, J = 6.4 Hz), 1.68 (2H, d, J = 5.5 Hz), 2.48-2.65 (6H, m), 2.72 (1H, dd, J = 11.7, 3.9 Hz), 2.87-2.92 (2H, m), 3.02-3.10 (2H, m), 3.27-3.36 (2H, m), 3.71-3.77 (1H, m), 4.14 (2H, q, J = 7.2 Hz), 4.69 (1H, q, J = 6.4 Hz), 7.10-7.24 (6H, m). |

TABLE 43-continued

| 34(34c) | 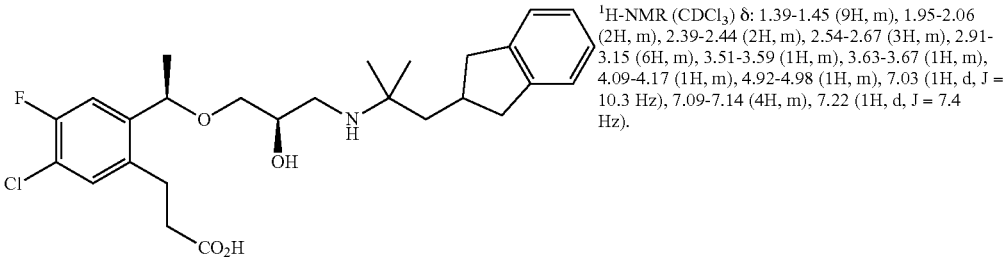 | ¹H-NMR (CDCl₃) δ: 1.39-1.45 (9H, m), 1.95-2.06 (2H, m), 2.39-2.44 (2H, m), 2.54-2.67 (3H, m), 2.91-3.15 (6H, m), 3.51-3.59 (1H, m), 3.63-3.67 (1H, m), 4.09-4.17 (1H, m), 4.92-4.98 (1H, m), 7.03 (1H, d, J = 10.3 Hz), 7.09-7.14 (4H, m), 7.22 (1H, d, J = 7.4 Hz). |
|---|---|---|
| 35(35a) | 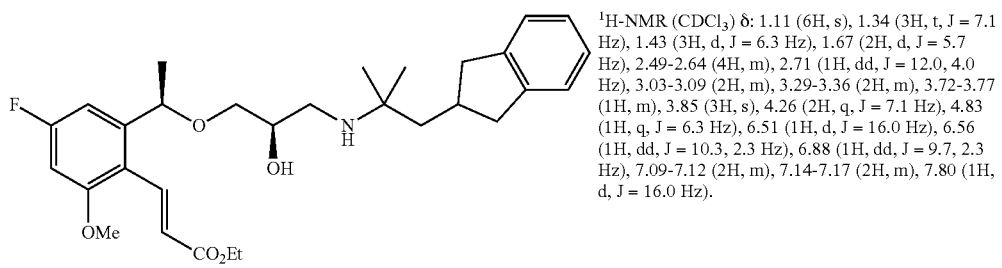 | ¹H-NMR (CDCl₃) δ: 1.11 (6H, s), 1.34 (3H, t, J = 7.1 Hz), 1.43 (3H, d, J = 6.3 Hz), 1.67 (2H, d, J = 5.7 Hz), 2.49-2.64 (4H, m), 2.71 (1H, dd, J = 12.0, 4.0 Hz), 3.03-3.09 (2H, m), 3.29-3.36 (2H, m), 3.72-3.77 (1H, m), 3.85 (3H, s), 4.26 (2H, q, J = 7.1 Hz), 4.83 (1H, q, J = 6.3 Hz), 6.51 (1H, d, J = 16.0 Hz), 6.56 (1H, dd, J = 10.3, 2.3 Hz), 6.88 (1H, dd, J = 9.7, 2.3 Hz), 7.09-7.12 (2H, m), 7.14-7.17 (2H, m), 7.80 (1H, d, J = 16.0 Hz). |

TABLE 44

| 35(35b) | 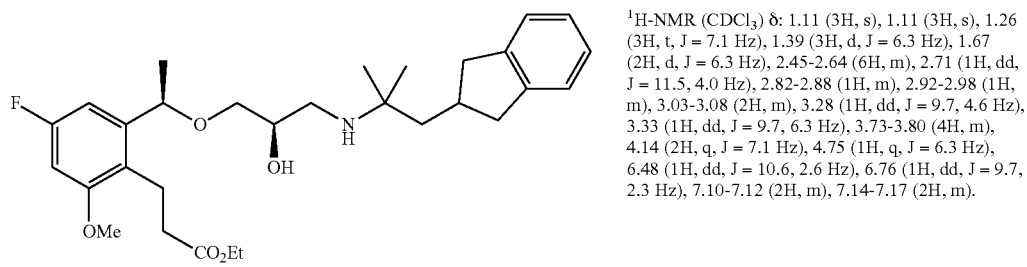 | ¹H-NMR (CDCl₃) δ: 1.11 (3H, s), 1.11 (3H, s), 1.26 (3H, t, J = 7.1 Hz), 1.39 (3H, d, J = 6.3 Hz), 1.67 (2H, d, J = 6.3 Hz), 2.45-2.64 (6H, m), 2.71 (1H, dd, J = 11.5, 4.0 Hz), 2.82-2.88 (1H, m), 2.92-2.98 (1H, m), 3.03-3.08 (2H, m), 3.28 (1H, dd, J = 9.7, 4.6 Hz), 3.33 (1H, dd, J = 9.7, 6.3 Hz), 3.73-3.80 (4H, m), 4.14 (2H, q, J = 7.1 Hz), 4.75 (1H, q, J = 6.3 Hz), 6.48 (1H, dd, J = 10.6, 2.6 Hz), 6.76 (1H, dd, J = 9.7, 2.3 Hz), 7.10-7.12 (2H, m), 7.14-7.17 (2H, m). |
|---|---|---|
| 35(35c) | 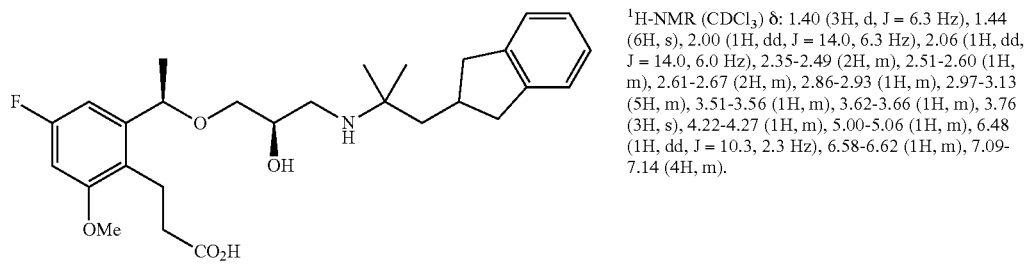 | ¹H-NMR (CDCl₃) δ: 1.40 (3H, d, J = 6.3 Hz), 1.44 (6H, s), 2.00 (1H, dd, J = 14.0, 6.3 Hz), 2.06 (1H, dd, J = 14.0, 6.0 Hz), 2.35-2.49 (2H, m), 2.51-2.60 (1H, m), 2.61-2.67 (2H, m), 2.86-2.93 (1H, m), 2.97-3.13 (5H, m), 3.51-3.56 (1H, m), 3.62-3.66 (1H, m), 3.76 (3H, s), 4.22-4.27 (1H, m), 5.00-5.06 (1H, m), 6.48 (1H, dd, J = 10.3, 2.3 Hz), 6.58-6.62 (1H, m), 7.09-7.14 (4H, m). |
| 36(36a) | 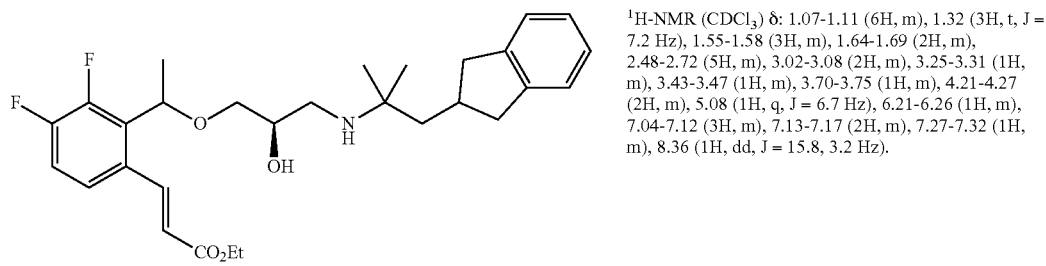 | ¹H-NMR (CDCl₃) δ: 1.07-1.11 (6H, m), 1.32 (3H, t, J = 7.2 Hz), 1.55-1.58 (3H, m), 1.64-1.69 (2H, m), 2.48-2.72 (5H, m), 3.02-3.08 (2H, m), 3.25-3.31 (1H, m), 3.43-3.47 (1H, m), 3.70-3.75 (1H, m), 4.21-4.27 (2H, m), 5.08 (1H, q, J = 6.7 Hz), 6.21-6.26 (1H, m), 7.04-7.12 (3H, m), 7.13-7.17 (2H, m), 7.27-7.32 (1H, m), 8.36 (1H, dd, J = 15.8, 3.2 Hz). |

TABLE 44-continued
| | | |
|---|---|---|
| 36(36b) | 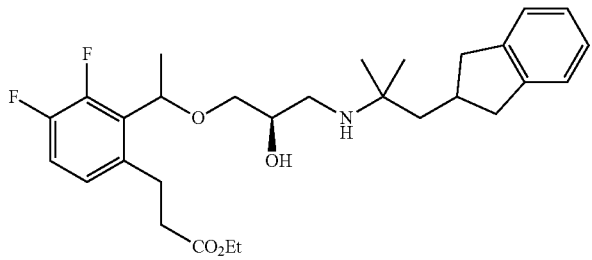 | ¹H-NMR (CDCl₃) δ: 1.09-1.12 (6H, m), 1.22-1.26 (3H, m), 1.58 (3H, d, J = 6.9 Hz), 1.66-1.69 (2H, m), 2.50-2.65 (6H, m), 2.68-2.72 (1H, m), 2.99-3.14 (4H, m), 3.29-3.32 (1H, m), 3.44-3.50 (1H, m), 3.71-3.77 (1H, m), 4.13 (2H, q, J = 7.1 Hz), 4.90-4.95 (1H, m), 6.87-6.91 (1H, m), 6.96-7.02 (1H, m), 7.10-7.12 (2H, m), 7.14-7.18 (2H, m). |
| 36(36c) | 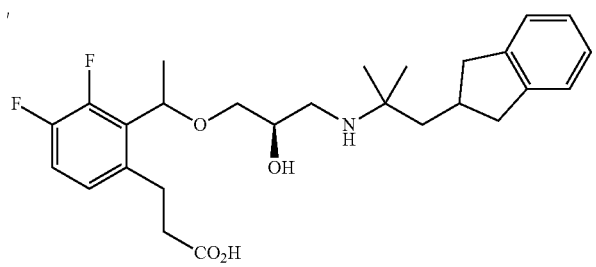 | ¹H-NMR (CDCl₃) δ: 1.42-1.46 (6.0H, m), 1.49-1.53 (3.0H, m), 1.97-2.09 (2.0H, m), 2.34-2.60 (3.0H, m), 2.61-2.68 (1.0H, m), 2.81-2.90 (1.0H, m), 2.91-2.98 (0.5H, m), 3.03-3.14 (3.0H, m), 3.18-3.27 (0.5H, m), 3.47 (0.5H, dd, J = 10.3, 4.6 Hz), 3.54-3.66 (1.5H, m), 3.68-3.72 (1.0H, m), 4.17-4.26 (1.5H, m), 4.97-5.02 (0.5H, m), 5.22-5.32 (1.0H, m), 6.85-6.88 (1.0H, m), 6.92-6.99 (2.0H, m), 7.09-7.16 (4.0H, m). |
| 37(37a) | 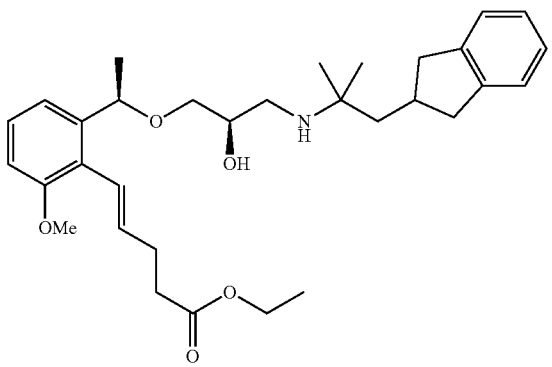 | ¹H-NMR (CDCl₃) δ: 1.11 (6H, s), 1.19-1.31 (3H, m), 1.37-1.44 (3H, m), 1.64-1.71 (2H, m), 2.45-2.79 (7H, m), 2.96-3.11 (3H, m), 3.18-3.33 (2H, m), 3.34-3.52 (1H, m), 3.68-3.83 (4H, m), 4.05-4.23 (2H, m), 4.76-4.85 (1H, m), 5.81-5.92 (1H, m), 6.42 (1H, d, J = 15.6 Hz), 6.73-6.81 (1H, m), 7.02-7.32 (6H, m). |
| 37(37b) | 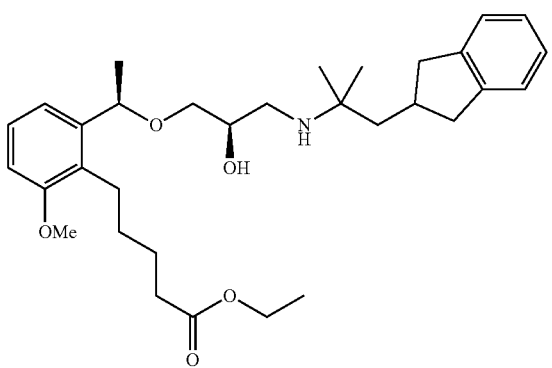 | ¹H-NMR (CDCl₃) δ: 1.10 (6H, s), 1.21-1.28 (3H, m), 1.42 (3H, d, J = 6.4 Hz), 1.46-1.55 (2H, m), 1.64-1.76 (4H, m), 2.34 (2H, t, J = 7.6 Hz), 2.46-2.65 (5H, m), 2.65-2.75 (2H, m), 3.00-3.10 (2H, m), 3.23-3.32 (2H, m), 3.71-3.81 (4H, m), 4.12 (2H, q, J = 7.2 Hz), 4.71 (1H, q, J = 6.4 Hz), 6.74 (1H, d, J = 7.8 Hz), 7.04 (1H, d, J = 8.3 Hz), 7.08-7.21 (5H, m). |

TABLE 45

| 37(37c) | 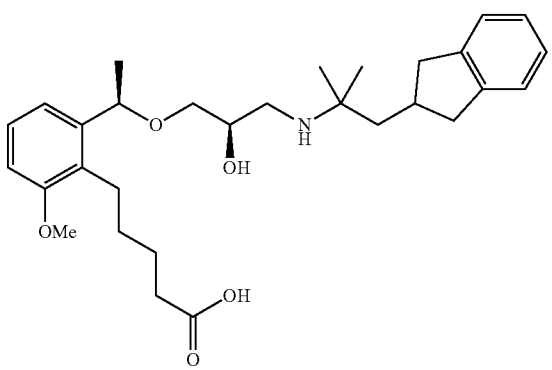 | ¹H-NMR (CDCl₃) δ: 1.37 (3H, d, J = 4.6 Hz), 1.43 (6H, s), 1.52-1.81 (3H, m), 1.94-2.00 (3H, m), 2.19-2.28 (1H, m), 2.30-2.43 (2H, m), 2.44-2.68 (3H, m), 2.75-2.86 (1H, m), 2.87-2.96 (1H, m), 3.00-3.18 (3H, m), 3.27-3.35 (1H, m), 3.38-3.47 (1H, m), 3.77 (3H, s), 4.28-4.38 (1H, m), 4.74-4.84 (1H, m), 6.72 (1H, d, J = 8.3 Hz), 6.98 (1H, d, J = 7.8 Hz), 7.09-7.20 (5H, m). |
|---|---|---|
| 38(38a) | 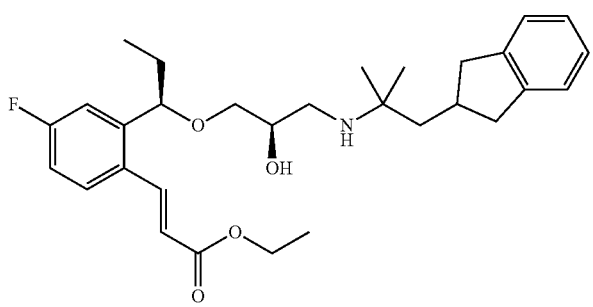 | ¹H-NMR (CDCl₃) δ: 0.92 (3H, t, J = 7.3 Hz), 1.11 (6H, s), 1.34 (3H, t, J = 7.1 Hz), 1.62-1.82 (4H, m), 2.48-2.66 (4H, m), 2.73 (1H, dd, J = 11.5, 4.1 Hz), 3.06 (2H, dd, J = 14.9, 7.1 Hz), 3.31-3.38 (2H, m), 3.72-3.80 (1H, m), 4.26 (2H, q, J = 7.1 Hz), 4.55-4.60 (1H, m), 6.27 (1H, d, J = 15.6 Hz), 6.97 (1H, td, J = 8.3, 2.8 Hz), 7.08-7.19 (5H, m), 7.53 (1H, dd, J = 8.7, 5.5 Hz), 7.98 (1H, d, J = 15.6 Hz). |
| 38(38b) | 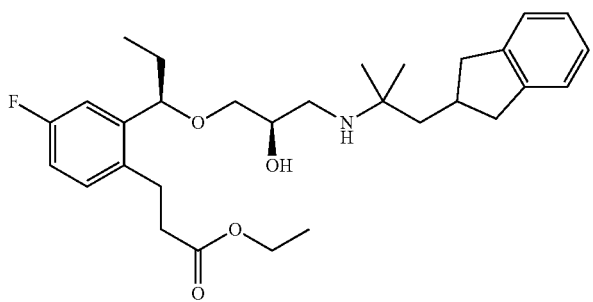 | ¹H-NMR (CDCl₃) δ: 0.97 (3H, t, J = 7.6 Hz), 1.11 (6H, s), 1.24 (3H, t, J = 7.3 Hz), 1.59-1.80 (4H, m), 2.47-2.67 (6H, m), 2.72 (1H, dd, J = 11.5, 5.7 Hz), 2.84-2.99 (2H, m), 3.06 (2H, dd, J = 14.4, 7.1 Hz), 3.30 (2H, d, J = 5.5 Hz), 3.70-3.80 (1H, m), 4.13 (2H, q, J = 7.3 Hz), 4.44-4.51 (1H, m), 6.88 (1H, td, J = 8.3, 2.8 Hz), 7.07-7.17 (6H, m). |
| 38(38c) | 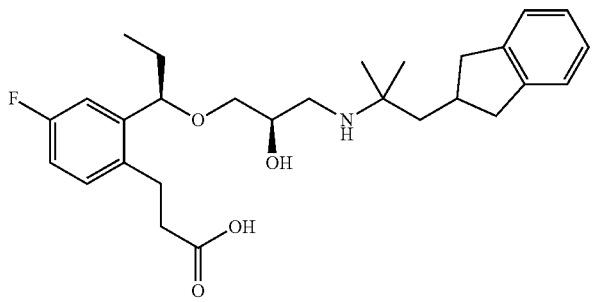 | ¹H-NMR (CDCl₃) δ: 0.90 (3H, t, J = 7.6 Hz), 1.43 (6H, s), 1.53-1.66 (1H, m), 1.69-1.84 (1H, m), 1.95-2.00 (2H, m), 2.45-2.67 (5H, m), 2.72-2.82 (1H, m), 2.82-2.91 (1H, m), 2.94-3.05 (1H, m), 3.09 (2H, dd, J = 14.9, 7.1 Hz), 3.20-3.27 (1H, m), 3.40-3.47 (1H, m), 3.47-3.54 (1H, m), 4.34-4.42 (1H, m), 4.76-4.83 (1H, m), 6.83-6.90 (1H, m), 6.99-7.04 (1H, m), 7.09-7.18 (5H, m). |
| 39(39a) | 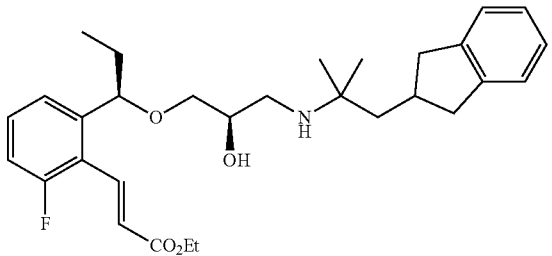 | ¹H-NMR (CDCl₃) δ: 0.93 (3H, t, J = 1.3 Hz), 1.11 (6H, s), 1.34 (3H, t, J = 7.2 Hz), 1.64-1.85 (4H, m), 2.47-2.66 (4H, m), 2.72 (1H, dd, J = 11.5, 3.2 Hz), 3.06 (2H, dd, J = 14.7, 6.9 Hz), 3.28-3.38 (2H, m), 3.71-3.78 (1H, m), 4.27 (2H, q, J = 7.2 Hz), 4.56 (1H, t, J = 6.4 Hz), 6.52 (1H, d, J = 16.5 Hz), 6.98-7.05 (1H, m), 7.07-7.19 (4H, m), 7.21-7.35 (2H, m), 7.84 (1H, d, J = 16.0 Hz). |

TABLE 45-continued

| | | |
|---|---|---|
| 39(39b) | 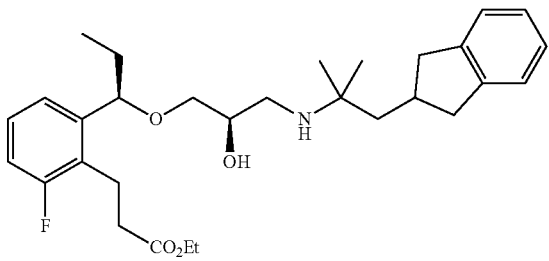 | ¹H-NMR (CDCl₃) δ: 0.96 (3H, t, J = 7.3 Hz), 1.11 (6H, s), 1.26 (3H, t, J = 7.3 Hz), 1.59-1.71 (3H, m), 1.72-1.85 (1H, m), 2.46-2.67 (6H, m), 2.71 (1H, dd, J = 11.5, 4.1 Hz), 2.91-3.11 (4H, m), 3.26-3.35 (2H, m), 3.70-3.79 (1H, m), 4.14 (2H, q, J = 7.3 Hz), 4.47-4.53 (1H, m), 6.89-6.96 (1H, m), 7.08-7.23 (6H, m). |
| 39(39c) | 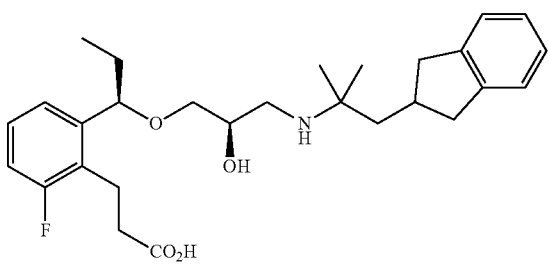 | ¹H-NMR (CDCl₃) δ: 0.89 (3H, t, J = 6.6 Hz), 1.44 (6H, s), 1.55-1.68 (1H, m), 1.70-1.84 (1H, m), 1.93-2.06 (2H, m), 2.43-2.69 (5H, m), 2.80-3.16 (5H, m), 3.17-3.27 (1H, m), 3.37-3.56 (2H, m), 4.33-4.44 (1H, m), 4.76-4.89 (1H, m), 6.87-6.94 (1H, m), 7.07-7.19 (6H, m). |

TABLE 46

| | | |
|---|---|---|
| 40(40a) | 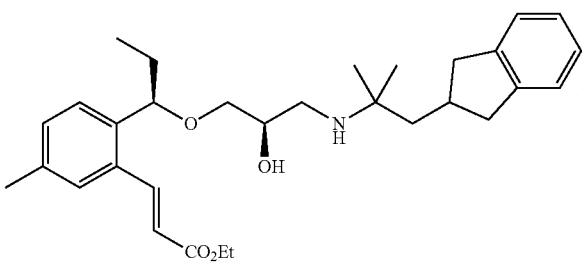 | ¹H-NMR (CDCl₃) δ: 0.90 (3H, t, J = 7.3 Hz), 1.10 (6H, s), 1.34 (3H, t, J = 7.2 Hz), 1.61-1.73 (3H, m), 1.76-1.86 (1H, m), 2.34 (3H, s), 2.46-2.65 (4H, m), 2.70 (1H, dd, J = 11.7, 3.9 Hz), 3.01-3.10 (2H, m), 3.27-3.35 (2H, m), 3.71-3.79 (1H, m), 4.26 (2H, q, J = 7.2 Hz), 4.53 (1H, t, J = 6.4 Hz), 6.32 (1H, d, J = 16.0 Hz), 7.07-7.21 (5H, m), 7.28-7.33 (1H, m), 7.36 (1H, s), 8.10 (1H, d, J = 16.0 Hz). |
| 40(40b) | 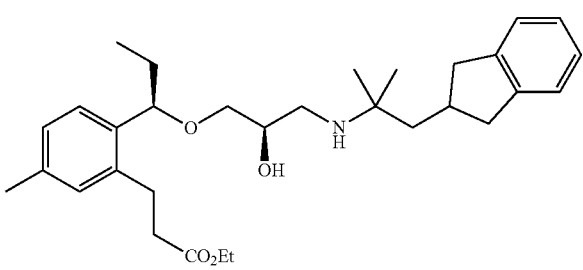 | ¹H-NMR (CDCl₃) δ: 0.96 (3H, t, J = 7.4 Hz), 1.10 (6H, d, J = 1.7 Hz), 1.25 (3H, t, J = 7.4 Hz), 1.60-1.70 (3H, m), 1.75-1.85 (1H, m), 2.29 (3H, s), 2.48-2.64 (6H, m), 2.65-2.70 (1H, m), 2.87-3.00 (2H, m), 3.01-3.09 (2H, m), 3.25-3.32 (2H, m), 3.71-3.77 (1H, m), 4.14 (2H, q, J = 7.4 Hz), 4.43-4.47 (1H, m), 6.96 (1H, s), 7.03 (1H, d, J = 8.0 Hz), 7.08-7.13 (2H, m), 7.13-7.18 (2H, m), 7.27 (1H, s). |
| 40(40c) | 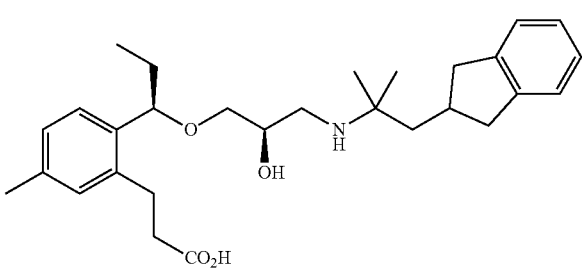 | ¹H-NMR (CDCl₃) δ: 0.88 (3H, t, J = 7.3 Hz), 1.43 (6H, s), 1.56-1.67 (1H, m), 1.76-1.88 (1H, m), 1.97 (2H, d, J = 6.0 Hz), 2.28 (3H, s), 2.49-2.67 (5H, m), 2.75-2.90 (2H, m), 2.95-3.13 (3H, m), 3.21-3.28 (1H, m), 3.39-3.46 (1H, m), 3.49-3.56 (1H, m), 4.35-4.43 (1H, m), 4.77 (1H, t, J = 6.4 Hz), 6.97-7.01 (2H, m), 7.09-7.20 (5H, m). |

TABLE 46-continued

| | | |
|---|---|---|
| 41(41a) | 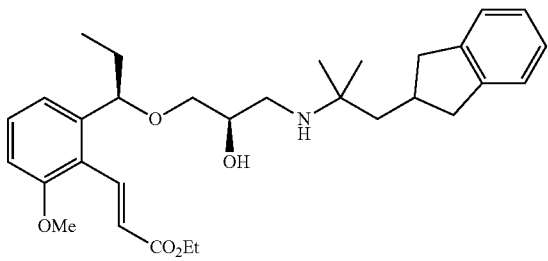 | ¹H-NMR (CDCl₃) δ: 0.95 (3H, t, J = 7.3 Hz), 1.11 (6H, s), 1.34 (3H, t, J = 7.1 Hz), 1.63-1.86 (4H, m), 2.46-2.66 (4H, m), 2.70 (1H, dd, J = 11.7, 3.9 Hz), 3.01-3.10 (2H, m), 3.26-3.36 (2H, m), 3.70-3.78 (1H, m), 3.86 (3H, s), 4.26 (2H, q, J = 7.1 Hz), 4.59 (1H, t, J = 6.4 Hz), 6.57 (1H, d, J = 16.0 Hz), 6.84 (1H, d, J = 8.3 Hz), 7.05-7.19 (4H, m), 7.31 (2H, t, J = 7.8 Hz), 7.93 (1H, d, J = 16.0 Hz). |
| 41(41b) | 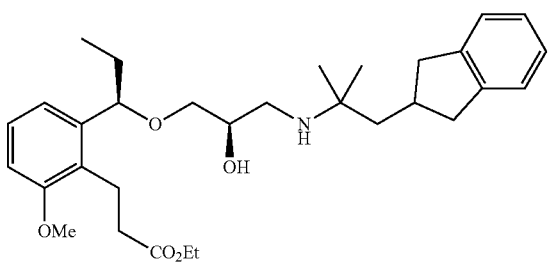 | ¹H-NMR (CDCl₃) δ: 0.96 (3H, t, J = 7.3 Hz), 1.10 (6H, s), 1.26 (3H, t, J = 7.3 Hz), 1.58-1.71 (3H, m), 1.71-1.84 (1H, m), 2.45-2.65 (6H, m), 2.69 (1H, dd, J = 11.7, 3.9 Hz), 2.86-3.11 (4H, m), 3.24-3.35 (2H, m), 3.71-3.79 (1H, m), 3.80 (3H, s), 4.15 (2H, q, J = 7.3 Hz), 4.47-4.53 (1H, m), 6.74 (1H, d, J = 8.3 Hz), 7.00 (1H, d, J = 7.8 Hz), 7.08-7.22 (5H, m). |
| 41(41c) | 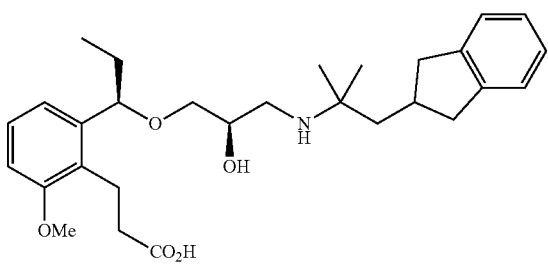 | ¹H-NMR (CDCl₃) δ: 0.92 (3H, t, J = 7.3 Hz), 1.44 (6H, s), 1.54-1.66 (1H, m), 1.71-1.82 (1H, m), 1.95-2.02 (2H, m), 2.45-2.67 (5H, m), 2.79-2.90 (2H, m), 3.01-3.14 (3H, m), 3.21-3.28 (1H, m), 3.37-3.45 (1H, m), 3.49-3.57 (1H, m), 3.79 (3H, s), 4.38-4.48 (1H, m), 4.84-4.91 (1H, m), 6.72 (1H, d, J = 8.3 Hz), 6.93 (1H, d, J = 7.8 Hz), 7.09-7.19 (5H, m). |
| 42(42a) | 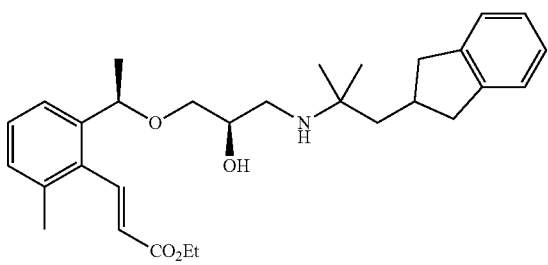 | ¹H-NMR (CDCl₃) δ: 0.92 (3H, t, J = 7.3 Hz), 1.10 (6H, s), 1.35 (3H, t, J = 7.1 Hz), 1.59-1.70 (3H, m), 1.70-1.82 (1H, m), 2.29 (3H, d, J = 17.4 Hz), 2.47-2.65 (4H, m), 2.69 (1H, dd, J = 11.5, 4.1 Hz), 3.06 (2H, dd, J = 14.7, 6.9 Hz), 3.22-3.32 (2H, m), 3.69-3.76 (1H, m), 4.28 (2H, q, J = 7.1 Hz), 4.41-4.47 (1H, m), 5.95 (1H, d, J = 16.0 Hz), 7.07-7.19 (4H, m), 7.20-7.34 (3H, m), 7.85 (1H, d, J = 16.0 Hz). |

TABLE 47

| | | |
|---|---|---|
| 42(42b) | 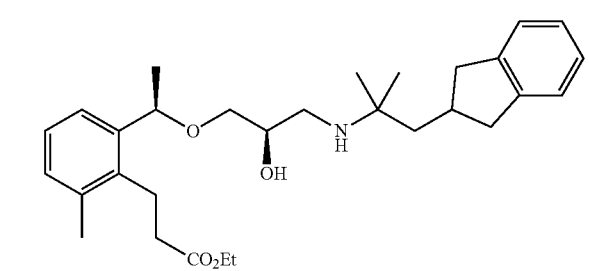 | ¹H-NMR (CDCl₃) δ: 0.99 (3H, t, J = 7.3 Hz), 1.10 (6H, s), 1.28 (3H, t, J = 7.0 Hz), 1.59-1.71 (3H, m), 1.72-1.84 (1H, m), 2.33 (3H, s), 2.39-2.66 (6H, m), 2.70 (1H, dd, J = 11.7, 3.9 Hz), 2.89-3.01 (2H, m), 3.06 (2H, dd, J = 14.7, 6.9 Hz), 3.24-3.34 (2H, m), 3.71-3.79 (1H, m), 4.17 (2H, q, J = 7.0 Hz), 4.45-4.51 (1H, m), 7.04-7.18 (5H, m), 7.23-7.28 (2H, m). |

TABLE 47-continued

| 42(42c) | 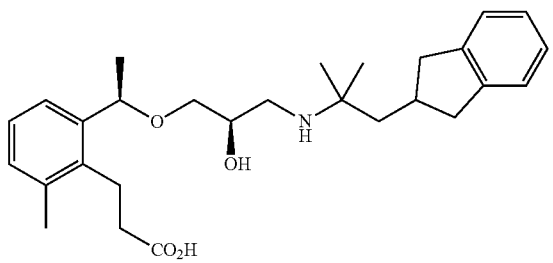 | ¹H-NMR (CDCl₃) δ: 0.93 (3H, t, J = 7.1 Hz), 1.48 (6H, s), 1.56-1.68 (1H, m), 1.74-1.89 (1H, m), 1.95-2.07 (2H, m), 2.32 (3H, s), 2.46-2.69 (5H, m), 2.81-3.06 (3H, m), 3.06-3.16 (2H, m), 3.25-3.33 (1H, m), 3.39-3.57 (2H, m), 4.46-4.56 (1H, m), 4.83-4.91 (1H, m), 7.03-7.07 (1H, m), 7.09-7.21 (6H, m). |
|---|---|---|
| 43(43a) | 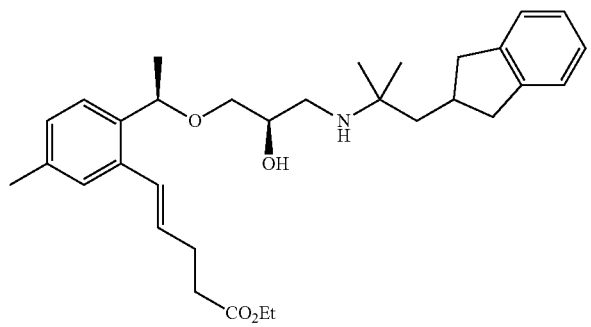 | ¹H-NMR (CDCl₃) δ: 1.10 (6H, s), 1.26 (3H, t, J = 7.1 Hz), 1.40 (3H, d, J = 6.4 Hz), 1.67 (2H, d, J = 5.5 Hz), 2.31 (3H, s), 2.46-2.69 (10H, m), 3.04 (1H, d, J = 6.0 Hz), 3.07 (1H, d, J = 6.9 Hz), 3.25-3.31 (2H, m), 3.71-3.76 (1H, m), 4.15 (2H, q, J = 7.1 Hz), 4.68-4.73 (1H, m), 5.99-6.06 (1H, m), 6.73 (1H, d, J = 15.6 Hz), 7.05 (1H, d, J = 7.8 Hz), 7.10-7.19 (6H, m). |
| 43(43b) | 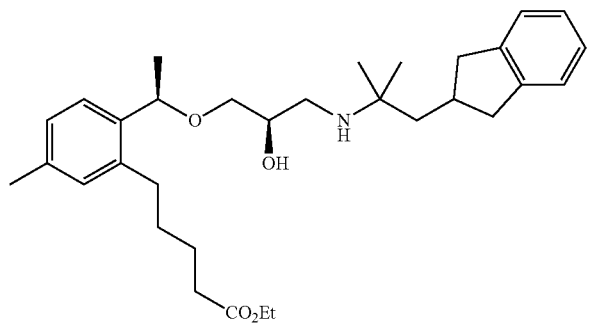 | ¹H-NMR (CDCl₃) δ: 1.09 (3H, s), 1.25 (3H, t, J = 7.1 Hz), 1.41 (3H, d, J = 6.4 Hz), 1.55-1.63 (2H, m), 1.66 (2H, d, J = 5.5 Hz), 1.67-1.75 (2H, m), 2.29 (3H, s), 2.33 (2H, t, J = 7.6 Hz), 2.50-2.63 (6H, m), 2.67 (1H, dd, J = 11.7, 3.4 Hz), 3.03 (1H, d, J = 6.9 Hz), 3.07 (1H, d, J = 7.3 Hz), 3.23-3.30 (2H, m), 3.71-3.76 (1H, m), 4.12 (2H, q, J = 7.1 Hz), 4.68 (1H, q, J = 6.4 Hz), 6.93 (1H, s), 7.02 (1H, d, J = 7.8 Hz), 7.09-7.17 (4H, m), 7.30 (1H, d, J = 7.8 Hz). |
| 43(43c) | 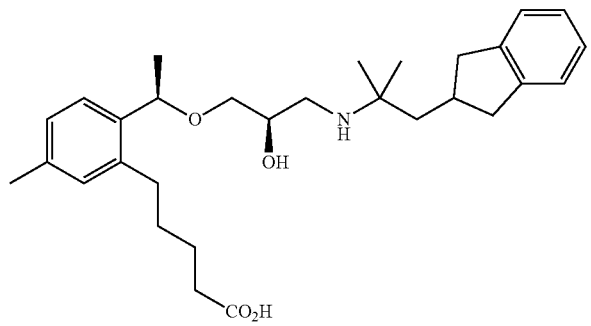 | ¹H-NMR (CDCl₃) δ: 1.34-1.40 (1H, m), 1.38 (3H, d, J = 6.1 Hz), 1.45 (6H, s), 1.53-1.76 (4H, m), 2.00 (2H, d, J = 5.5 Hz), 2.28 (3H, s), 2.33-2.45 (3H, m), 2.51-2.57 (1H, m), 2.60-2.67 (3H, m), 2.90 (1H, t, J = 10.5 Hz), 3.09 (2H, dd, J = 14.7, 7.3 Hz), 3.17 (1H, d, J = 11.9 Hz), 3.31-3.36 (1H, m), 3.42-3.46 (1H, m), 4.28-4.33 (1H, m), 4.79 (1H, q, J = 6.1 Hz), 6.91 (1H, s), 7.01 (1H, d, J = 7.8 Hz), 7.11-7.16 (4H, m), 7.24 (1H, d, J = 7.8 Hz). |
| 44(44a) | 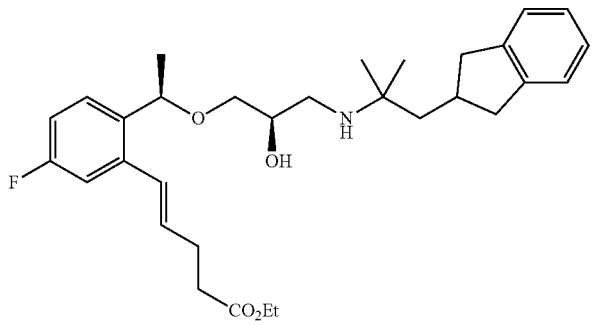 | ¹H-NMR (CDCl₃) δ: 1.10 (6H, s), 1.26 (3H, t, J = 6.9 Hz), 1.40 (3H, d, J = 6.4 Hz), 1.67 (2H, d, J = 5.5 Hz), 2.46-2.72 (10H, m), 3.06 (2H, dd, J = 14.7, 6.9 Hz), 3.26-3.31 (2H, m), 3.71-3.75 (1H, m), 4.14 (2H, q, J = 6.9 Hz), 4.70 (1H, q, J = 6.4 Hz), 6.02-6.08 (1H, m), 6.71 (1H, d, J = 15.6 Hz), 6.92 (1H, t, J = 8.5 Hz), 7.06 (1H, d, J = 10.5 Hz), 7.10-7.17 (4H, m), 7.34 (1H, t, J =7.3 Hz). |

TABLE 47-continued

| | | |
|---|---|---|
| 44(44b) | 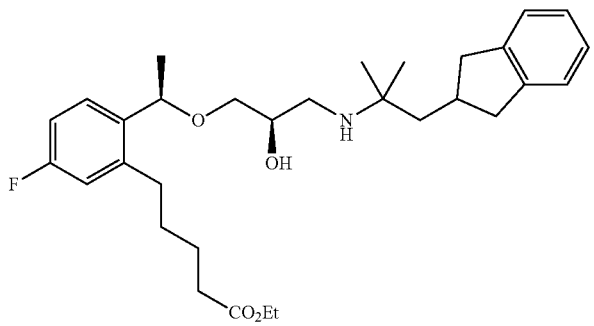 | $^1$H-NMR (CDCl$_3$) δ: 1.10 (6H, s), 1.26 (3H, t, J = 7.1 Hz), 1.41 (3H, d, J = 6.2 Hz), 1.58-1.64 (2H, m), 1.66-1.73 (4H, m), 2.34 (2H, t, J = 7.2 Hz), 2.49-2.55 (2H, m), 2.58-2.65 (4H, m), 2.67-2.72 (1H, m), 3.06 (2H, dd, J = 14.9, 5.7 Hz), 3.26-3.29 (2H, m), 3.71-3.75 (1H, br m), 4.13 (2H, q, J = 7.1 Hz), 4.66-4.70 (1H, m), 6.83 (1H, d, J = 10.1 Hz), 6.90 (1H, t, J = 8.5 Hz), 7.10-7.17 (4H, m), 7.36-7.40 (1H, m). |

TABLE 48

| | | |
|---|---|---|
| 44(44c) | 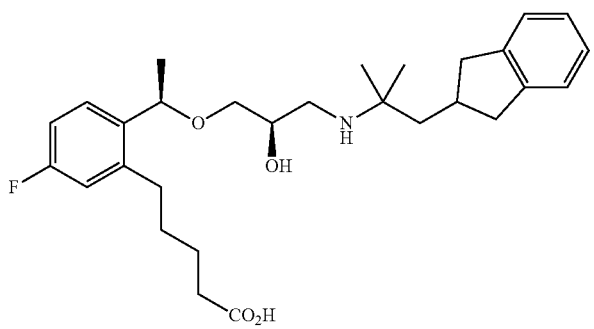 | $^1$H-NMR (CDCl$_3$) δ: 1.37 (3H, d, J = 4.1 Hz), 1.41-1.46 (1H, m), 1.43 (6H, s), 1.53-1.73 (4H, m), 1.98 (2H, d, J = 4.6 Hz), 2.19-2.26 (1H, m), 2.31-2.46 (2H, m), 2.50-2.57 (1H, m), 2.58-2.70 (3H, m), 2.90 (1H, t, J = 10.1 Hz), 3.05-3.13 (3H, m), 3.32 (1H, t, J = 8.3 Hz), 3.41-3.45 (1H, m), 4.29-4.34 (1H, br m), 4.74-4.79 (1H, m), 6.79 (1H, d, J = 9.6 Hz), 6.87 (1H, t, J = 8.5 Hz), 7.11-7.16 (4H, m), 7.31 (1H, t, J = 6.2 Hz). |
| 45(45a) | 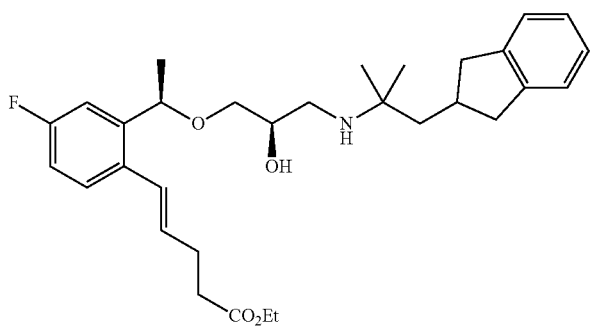 | $^1$H-NMR (CDCl$_3$) δ: 1.11 (6H, s), 1.26 (3H, t, J = 7.3 Hz), 1.39 (3H, d, J = 6.4 Hz), 1.67 (2H, d, J = 5.5 Hz), 2.44-2.64 (9H, m), 2.71 (1H, dd, J = 11.5, 4.1 Hz), 3.06 (2H, dd, J = 15.1, 6.9 Hz), 3.27-3.36 (2H, m), 3.72-3.78 (1H, m), 4.15 (2H, q, J = 7.3 Hz), 4.70 (1H, q, J = 6.4 Hz), 5.97 (1H, dt, J = 15.6, 6.4 Hz), 6.61 (1H, d, J = 15.6 Hz), 6.86-6.91 (1H, m), 7.09-7.17 (5H, m), 7.32 (1H, dd, J = 8.7, 6.0 Hz). |
| 45(45b) | 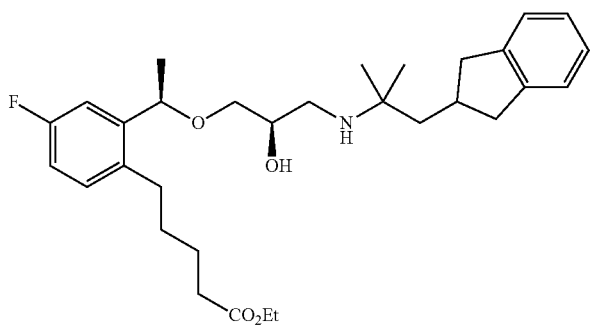 | $^1$H-NMR (CDCl$_3$) δ: 1.11 (6H, s), 1.25 (3H, t, J = 7.1 Hz), 1.41 (3H, d, J = 6.0 Hz), 1.54-1.62 (2H, m), 1.66-1.72 (2H, m), 1.67 (2H, d, J = 6.0 Hz), 2.33 (2H, t, J = 7.3 Hz), 2.50-2.64 (6H, m), 2.71 (1H, dd, J = 11.9, 3.7 Hz), 3.06 (2H, dd, J = 14.7, 6.9 Hz), 3.25-3.33 (2H, m), 3.72-3.78 (1H, m), 4.12 (2H, q, J = 7.1 Hz), 4.68 (1H, q, J = 6.0 Hz), 6.86 (1H, td, J = 8.5, 2.8 Hz), 7.05-7.17 (6H, m). |

TABLE 48-continued

| 45(45c) | 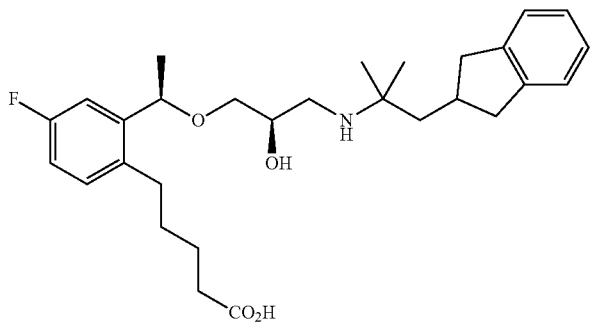 | ¹H-NMR (CDCl₃) δ: 1.36 (3H, d, J = 6.3 Hz), 1.39-1.50 (1H, m), 1.45 (6H, s), 1.52-1.58 (2H, m), 1.59-1.73 (2H, m), 2.01 (2H, d, J = 6.9 Hz), 2.20-2.26 (1H, m), 2.32-2.43 (2H, m), 2.50-2.57 (1H, m), 2.63 (3H, dd, J = 14.6, 9.5 Hz), 2.91 (1H, t, J = 11.2 Hz), 3.07-3.15 (3H, m), 3.36 (1H, dd, J = 11.5, 6.3 Hz), 3.42 (1H, dd, J = 10.9, 5.7 Hz), 4.31-4.36 (1H, m), 4.78 (1H, q, J = 6.3 Hz), 6.83 (1H, td, J = 8.3, 2.9 Hz), 7.02 (1H, dd, J = 8.6, 5.7 Hz), 7.06 (1H, dd, J = 9.7, 2.9 Hz), 7.11-7.15 (4H, m). |
|---|---|---|
| 46(46a) | 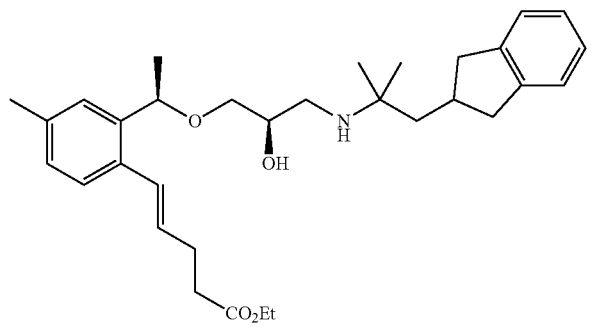 | ¹H-NMR (CDCl₃) δ: 1.10 (6H, s), 1.26 (3H, t, J = 7.1 Hz), 1.41 (3H, d, J = 6.4 Hz), 1.67 (2H, d, J = 5.5 Hz), 2.32 (3H, s), 2.42-2.63 (9H, m), 2.70 (1H, dd, J = 11.5, 4.1 Hz), 3.06 (2H, dd, J = 14.7, 6.9 Hz), 3.27-3.33 (2H, m), 3.72-3.78 (1H, m), 4.14 (2H, q, J = 7.1 Hz), 4.70 (1H, q, J = 6.4 Hz), 5.99 (1H, dt, J = 15.4, 6.5 Hz), 6.71 (1H, d, J = 15.4 Hz), 7.00-7.03 (2H, m), 7.10-7.13 (2H, m), 7.15-7.18 (3H, m). |
| 46(46b) | 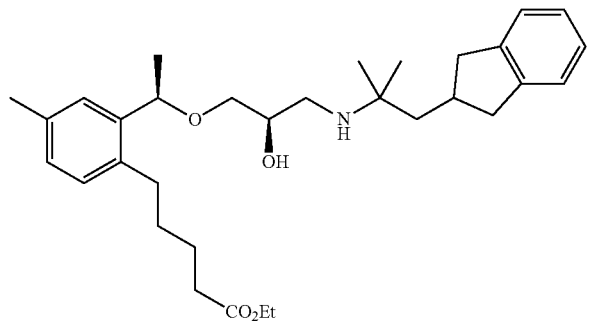 | ¹H-NMR (CDCl₃) δ: 1.10 (6H, s), 1.25 (3H, t, J = 6.4 Hz), 1.42 (3H, d, J = 6.4 Hz), 1.55-1.63 (2H, m), 1.65-1.72 (4H, m), 2.31 (3H, s), 2.32-2.35 (2H, m), 2.49-2.64 (6H, m), 2.70 (1H, d, J = 11.5 Hz), 3.06 (2H, dd, J = 14.9, 6.6 Hz), 3.29 (2H, d, J = 4.6 Hz), 3.72-3.77 (1H, m), 4.12 (2H, q, J = 6.4 Hz), 4.66-4.71 (1H, m), 6.99-7.01 (2H, br m), 7.10-7.15 (4H, m), 7.22 (1H, s). |
| 46(46c) | 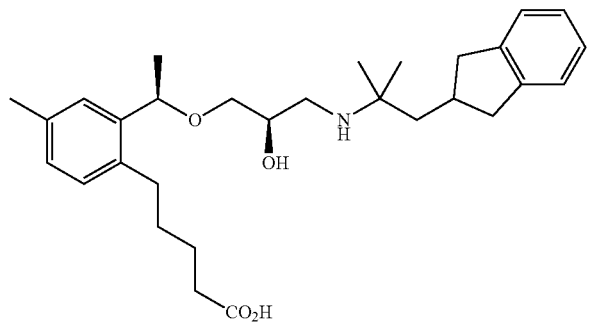 | ¹H-NMR (CDCl₃) δ: 1.34 (3H, d, J = 6.3 Hz), 1.39 (6H, d, J = 6.3 Hz), 1.46-1.54 (2H, m), 1.63-1.73 (2H, m), 1.88-1.91 (2H, m), 2.14-2.20 (1H, m), 2.28-2.33 (1H, m), 2.28 (3H, s), 2.38-2.44 (1H, m), 2.47-2.52 (1H, m), 2.55-2.65 (3H, m), 2.83 (1H, t, J = 10.6 Hz), 3.02-3.10 (4H, m), 3.31 (1H, t, J = 9.7 Hz), 3.53-3.57 (1H, m), 4.26-4.30 (1H, m), 4.75 (1H, q, J = 6.3 Hz), 6.94-6.98 (2H, m), 7.11-7.16 (5H, m). |

TABLE 49

| | | |
|---|---|---|
| 47(47a) | [structure] | ¹H-NMR (CDCl₃) δ: 1.10 (6H, s), 1.22 (3H, t, J = 7.1 Hz), 1.40 (3H, d, J = 6.4 Hz), 1.67 (2H, d, J = 4.1 Hz), 2.29 (3H, s), 2.50-2.71 (8H, m), 3.00 (1H, d, J = 6.9 Hz), 3.06 (2H, dd, J = 14.7, 6.9 Hz), 3.25 (2H, d, J = 5.5 Hz), 3.38-3.41 (1H, m), 3.71-3.76 (1H, br m), 4.09 (2H, q, J = 7.1 Hz), 4.70 (1H, q, J = 6.4 Hz), 5.32-5.39 (1H, m), 5.62-5.68 (1H, m), 7.06-7.16 (6H, m), 7.31 (1H, d, J = 7.8 Hz). |
| 47(47b) | [structure] | ¹H-NMR (CDCl₃) δ: 1.10 (6H, s), 1.25 (3H, t, J = 7.1 Hz), 1.43 (3H, d, J = 6.4 Hz), 1.48-1.54 (2H, m), 1.66 (2H, d, J = 5.5 Hz), 1.73-1.81 (2H, m), 2.31 (3H, s), 2.36 (2H, t, J = 7.6 Hz), 2.51-2.70 (7H, m), 3.05 (2H, dd, J = 14.7, 6.9 Hz), 3.23-3.31 (2H, m), 3.72-3.78 (1H, m), 4.13 (2H, q, J = 7.1 Hz), 4.72 (1H, q, J =6.4 Hz), 7.05 (1H, d, J = 7.3 Hz), 7.10-7.17 (5H, m), 7.29 (1H, d, J = 7.8 Hz). |
| 47(47c) | [structure] | ¹H-NMR (CDCl₃) δ: 1.39 (3H, d, J = 6.4 Hz), 1.42-1.61 (3H, m), 1.50 (6H, s), 1.71-1.81 (2H, m), 2.05 (2H, d, J = 6.4 Hz), 2.30 (3H, s), 2.31-2.34 (1H, m), 2.40-2.44 (1H, m), 2.45-2.68 (5H, m), 2.93 (1H, dd, J = 11.9, 9.6 Hz), 3.08-3.15 (2H, m), 3.28 (1H, dd, J = 12.2, 2.5 Hz), 3.37 (1H, dd, J = 11.2, 6.6 Hz), 3.42-3.49 (1H, m), 4.31-4.37 (1H, m), 4.80 (1H, q, J = 6.4 Hz), 7.04 (1H, d, J = 7.3 Hz), 7.08-7.17 (5H, m), 7.23 (1H, d, J = 7.3 Hz). |
| 48(48a) | [structure] | ¹H-NMR (CDCl₃) δ: 1.10 (6H, s), 1.27 (3H, t, J = 7.1 Hz), 1.41 (3H, d, J = 6.4 Hz), 1.67 (2H, d, J = 5.0 Hz), 2.50-2.64 (7H, m), 2.70 (1H, dd, J = 11.5, 2.8 Hz), 2.99-3.09 (3H, m), 3.26-3.29 (2H, m), 3.38-3.48 (1H, m), 3.72-3.75 (1H, br m), 4.12 (2H, q, J = 7.1 Hz), 4.68-4.73 (1H, m), 5.44-5.52 (1H, m), 5.63-5.69 (1H, m), 6.94 (1H, t, J = 8.3 Hz), 7.10-7.25 (6H, m). |
| 48(48b) | [structure] | ¹H-NMR (CDCl₃) δ: 1.10 (6H, s), 1.25 (3H, t, J = 7.1 Hz), 1.42 (3H, d, J = 6.4 Hz), 1.53-1.60 (2H, m), 1.66-1.77 (3H, m), 2.34 (2H, t, J = 7.1 Hz), 2.50-2.64 (6H, m), 2.70 (2H, dd, J = 11.7, 3.9 Hz), 3.06 (2H, dd, J = 14.4, 7.1 Hz), 3.26-3.32 (2H, m), 3.71-3.77 (1H, m), 4.12 (2H, q, J = 7.1 Hz), 4.69 (1H, q, J = 6.4 Hz), 6.91 (1H, t, J = 8.9 Hz), 7.10-7.17 (5H, m), 7.21 (1H, t, J = 6.0 Hz). |

TABLE 49-continued

| | | |
|---|---|---|
| 48(48c) | 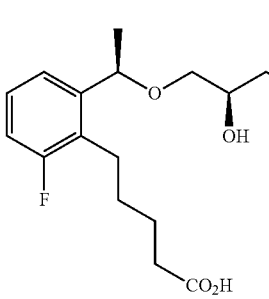 | ¹H-NMR (CDCl₃) δ: 1.39 (3H, d, J = 5.0 Hz), 1.49 (6H, s), 1.61-1.78 (3H, m), 2.04 (2H, d, J = 6.0 Hz), 2.28-2.49 (3H, m), 2.53-2.68 (4H, m), 2.73-2.79 (1H, m), 2.94 (1H, t, J = 11.0 Hz), 3.07-3.15 (3H, m), 3.21 (1H, d, J = 12.4 Hz), 3.34-3.45 (2H, m), 4.31-4.36 (1H, br m), 4.77-4.82 (1H, m), 6.88-6.93 (1H, m), 7.15 (6H, s). |

TABLE 50

| | | |
|---|---|---|
| 49(49a) | 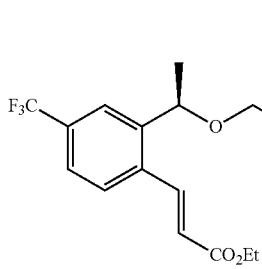 | ¹H-NMR (CDCl₃) δ: 1.11 (6H, s), 1.35 (3H, t, J = 7.2 Hz), 1.46 (3H, d, J = 6.4 Hz), 1.67 (2H, d, J = 6.0 Hz), 2.49-2.68 (4H, m), 2.76 (1H, dd, J = 11.7, 3.0 Hz), 3.06 (2H, dd, J = 14.0, 6.6 Hz), 3.32 (1H, dd, J = 8.9, 3.9 Hz), 3.43 (1H, dd, J = 8.9, 6.6 Hz), 3.73-3.79 (1H, m), 4.29 (2H, q, J = 7.2 Hz), 4.85 (1H, q, J = 6.4 Hz), 6.38 (1H, d, J = 15.6 Hz), 7.10-7.17 (4H, m), 7.53 (1H, d, J = 8.3 Hz), 7.62 (1H, d, J = 8.3 Hz), 7.75 (1H, s), 8.04 (1H, d, J = 15.6 Hz). |
| 49(49b) | 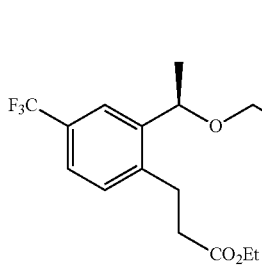 | ¹H-NMR (CDCl₃) δ: 1.10 (6H, s), 1.25 (3H, t, J = 7.0 Hz), 1.45 (3H, d, J = 6.4 Hz), 1.67 (2H, d, J = 6.0 Hz), 2.46-2.64 (6H, m), 2.76 (1H, dd, J = 11.7, 3.9 Hz), 2.99-3.09 (4H, m), 3.26 (1H, dd, J = 9.4, 4.8 Hz), 3.38 (1H, dd, J = 9.4, 6.2 Hz), 3.72-3.78 (1H, m), 4.13 (2H, q, J = 7.0 Hz), 4.79 (1H, q, J = 6.4 Hz), 7.10-7.17 (4H, m), 7.27 (1H, d, J = 8.3 Hz), 7.44 (1H, d, J = 8.3 Hz), 7.71 (1H, s). |
| 49(49c) | 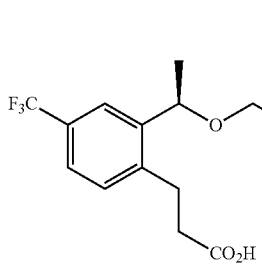 | ¹H-NMR (CDCl₃) δ: 1.41 (3H, d, J = 6.4 Hz), 1.43 (3H, s), 1.44 (3H, s), 2.00 (2H, d, J = 6.0 Hz), 2.50-2.66 (5H, m), 2.84-2.95 (2H, m), 3.02-3.12 (3H, m), 3.21 (1H, d, J = 10.1 Hz), 3.46 (1H, dd, J = 10.5, 6.4 Hz), 3.56 (1H, dd, J = 10.5, 4.4 Hz), 4.33-4.37 (1H, br m), 5.01 (1H, q, J = 6.4 Hz), 7.10-7.16 (4H, m), 7.27 (1H, d, J = 9.2 Hz), 7.43 (1H, d, J = 7.8 Hz), 7.60 (1H, s). |
| 50(50a) | 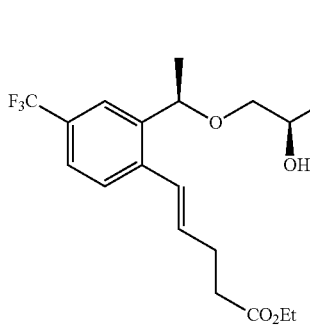 | ¹H-NMR (CDCl₃) δ: 1.10 (6H, s), 1.27 (3H, t, J = 7.1 Hz), 1.42 (3H, d, J = 6.4 Hz), 1.67 (2H, d, J = 6.0 Hz), 2.48-2.53 (3H, m), 2.55-2.64 (4H, m), 2.75 (1H, dd, J = 11.7, 3.9 Hz), 3.02-3.09 (2H, m), 3.29 (1H, dd, J = 9.4, 4.8 Hz), 3.37 (1H, dd, J = 9.4, 6.0 Hz), 3.42-3.48 (1H, m), 3.73-3.77 (1H, m), 4.14 (2H, q, J = 7.1 Hz), 4.76 (1H, q, J = 6.4 Hz), 6.13 (1H, dt, J = 15.3, 6.6 Hz), 6.72 (1H, d, J = 15.3 Hz), 7.10-7.13 (2H, m), 7.14-7.17 (2H, m), 7.45-7.46 (2H, m), 7.66 (1H, s). |

TABLE 50-continued

| | | |
|---|---|---|
| 50(50b) | 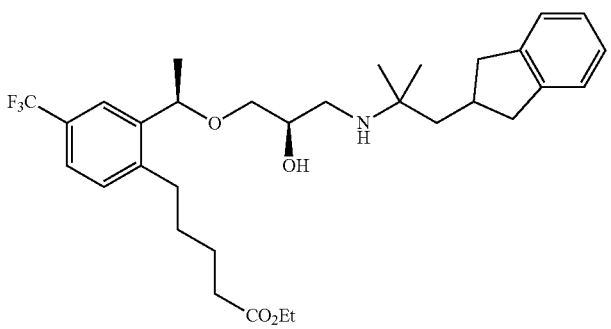 | ¹H-NMR (CDCl₃) δ: 1.10 (6H, s), 1.26 (3H, t, J = 7.1 Hz), 1.43 (3H, d, J = 6.0 Hz), 1.59-1.76 (6H, m), 2.34 (2H, t, J = 7.1 Hz), 2.48 (1H, dd, J = 12.2, 7.6 Hz), 2.52-2.64 (3H, m), 2.68 (2H, t, J = 7.8 Hz), 2.76 (1H, dd, J = 11.7, 3.9 Hz), 3.02-3.09 (2H, m), 3.24 (1H, dd, J = 8.9, 4.8 Hz), 3.35 (1H, dd, J = 8.9, 6.0 Hz), 3.72-3.78 (1H, m), 4.13 (2H, q, J = 7.1 Hz), 4.75 (1H, q, J = 6.0 Hz), 7.10-7.13 (2H, m), 7.15 (2H, s), 7.24 (1H, d, J = 8.3 Hz), 7.43 (1H, d, J = 7.8 Hz), 7.70 (1H, s). |
| 50(50c) | 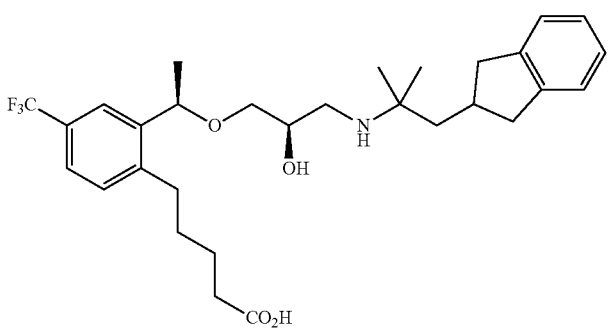 | ¹H-NMR (CDCl₃) δ: 1.38 (3H, d, J = 3.7 Hz), 1.43-1.50 (1H, m), 1.48 (6H, s), 1.56-1.73 (4H, m), 2.03 (2H, d, J = 5.5 Hz), 2.23-2.29 (1H, m), 2.32-2.39 (1H, m), 2.47-2.74 (5H, m), 2.91 (1H, t, J = 9.9 Hz), 3.06-3.17 (3H, m), 3.35-3.42 (2H, m), 4.34-4.39 (1H, m), 4.83-4.89 (1H, m), 7.10-7.20 (5H, m), 7.41 (1H, d, J = 7.8 Hz), 7.63 (1H, s). |

TABLE 51

| | | |
|---|---|---|
| 51(51a) | 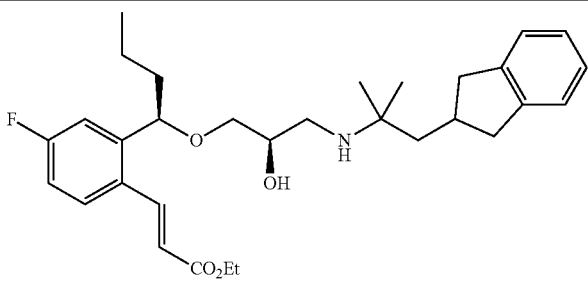 | ¹H-NMR (CDCl₃) δ: 0.92 (3H, t, J = 7.3 Hz), 1.11 (6H, s), 1.30-1.39 (1H, m), 1.34 (3H, t, J = 7.1 Hz), 1.41-1.61 (2H, m), 1.68 (2H, d, J = 6.0 Hz), 1.69-1.80 (1H, m), 2.49-2.64 (4H, m), 2.73 (1H, dd, J = 11.9, 4.1 Hz), 3.06 (2H, dd, J = 14.9, 7.1 Hz), 3.29-3.37 (2H, m), 3.73-3.78 (1H, m), 4.26 (2H, q, J = 7.1 Hz), 4.65 (1H, dd, J = 7.8, 4.6 Hz), 6.27 (1H, d, J = 16.0 Hz), 6.96 (1H, td, J = 8.3, 2.8 Hz), 7.10-7.13 (2H, m), 7.14-7.19 (3H, m), 7.53 (1H, dd, J = 8.3, 5.5 Hz), 7.98 (1H, d, J = 16.0 Hz). |
| 51(51b) | 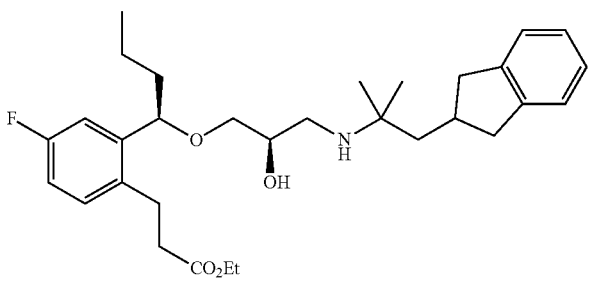 | ¹H-NMR (CDCl₃) δ: 0.93 (3H, t, J = 6.9 Hz), 1.11 (6H, s), 1.24 (3H, t, J = 7.2 Hz), 1.32-1.44 (1H, m), 1.50-1.58 (2H, m), 1.67 (2H, d, J = 6.0 Hz), 1.69-1.78 (1H, m), 2.50-2.64 (6H, m), 2.71 (1H, dd, J = 11.7, 3.9 Hz), 2.85-2.98 (2H, m), 3.06 (2H, dd, J = 14.9, 7.1 Hz), 3.26-3.34 (2H, m), 3.72-3.78 (1H, m), 4.13 (2H, q, J = 7.2 Hz), 4.54 (1H, d, J = 6.9 Hz), 6.87 (1H, td, J = 8.3, 2.8 Hz), 7.08-7.13 (4H, m), 7.14-7.17 (2H, m). |
| 51(51c) | 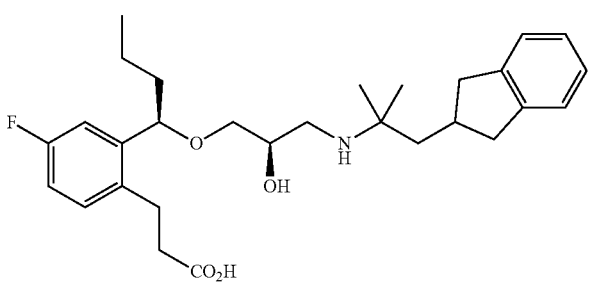 | ¹H-NMR (CDCl₃) δ: 0.88 (3H, t, J = 7.3 Hz), 1.28-1.35 (1H, m), 1.37-1.55 (2H, m), 1.44 (6H, s), 1.68-1.77 (1H, m), 1.99 (2H, t, J = 6.0 Hz), 2.47-2.66 (5H, m), 2.73-2.88 (2H, m), 2.93-3.01 (1H, m), 3.06-3.13 (2H, m), 3.23 (1H, d, J = 11.0 Hz), 3.37-3.42 (1H, m), 3.47 (1H, dd, J = 11.0, 4.6 Hz), 4.38-4.43 (1H, br m), 4.83-4.87 (1H, m), 6.85 (1H, td, J = 8.3, 2.8 Hz), 7.01 (1H, dd, J = 10.3, 3.0 Hz), 7.09-7.17 (5H, m). |

TABLE 51-continued

| | | |
|---|---|---|
| 52(52a) | 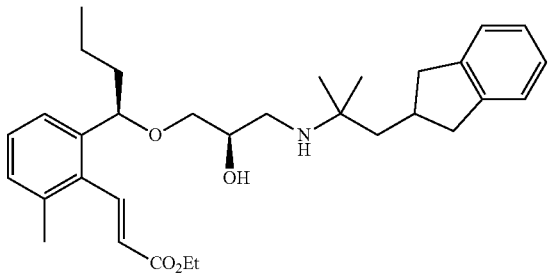 | $^1$H-NMR (CDCl$_3$) δ: 0.89 (3H, t, J = 7.3 Hz), 1.10 (6H, s), 1.29-1.40 (1H, m), 1.35 (3H, t, J = 7.1 Hz), 1.42-1.59 (2H, m), 1.66 (1H, d, J = 6.0 Hz), 1.72-1.79 (1H, m), 2.31 (3H, s), 2.47-2.69 (6H, m), 3.06 (2H, dd, J = 15.8, 6.6 Hz), 3.25 (2H, dd, J = 13.5, 5.3 Hz), 3.69-3.74 (1H, m), 4.28 (2H, q, J = 7.1 Hz), 4.53 (1H, dd, J = 8.5, 4.4 Hz), 5.96 (1H, d, J = 16.5 Hz), 7.08-7.19 (5H, m), 7.23 (1H, d, J = 7.8 Hz), 7.32 (1H, d, J = 7.8 Hz), 7.84 (1H, d, J = 16.5 Hz). |
| 52(52b) | 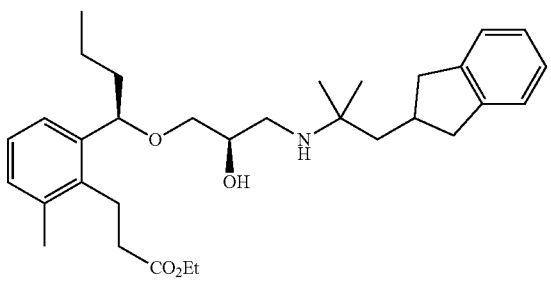 | $^1$H-NMR (CDCl$_3$) δ: 0.93 (3H, t, J = 6.9 Hz), 1.10 (6H, s), 1.28 (3H, t, J = 7.6 Hz), 1.36-1.46 (1H, m), 1.50-1.59 (2H, m), 1.66 (2H, d, J = 6.0 Hz), 1.72-1.80 (1H, m), 2.33 (3H, s), 2.45 (2H, t, J = 8.5 Hz), 2.50-2.64 (5H, m), 2.68 (1H, dd, J = 11.9, 4.1 Hz), 2.89-3.00 (2H, m), 3.06 (2H, dd, J = 14.7, 6.9 Hz), 3.23-3.31 (2H, m), 3.71-3.77 (1H, m), 4.17 (2H, q, J = 7.6 Hz), 4.56 (1H, dd, J = 8.5, 3.4 Hz), 7.06 (1H, d, J = 7.3 Hz), 7.10-7.17 (6H, m). |
| 52(52c) | 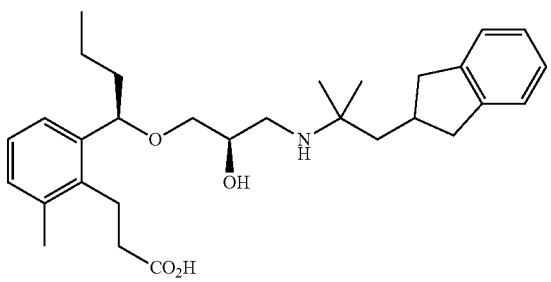 | $^1$H-NMR (CDCl$_3$) δ: 0.87 (3H, t, J = 6.9 Hz), 1.49 (6H, s), 1.69-1.77 (1H, m), 1.95-2.07 (4H, m), 2.31 (4H, s), 2.48-2.52 (2H, m), 2.59-2.67 (4H, m), 2.81-2.99 (3H, m), 3.07-3.15 (3H, m), 3.31 (1H, d, J = 11.0 Hz), 3.37-3.43 (1H, br m), 3.47-3.52 (1H, m), 4.51-4.56 (1H, br m), 4.89-4.94 (1H, br m), 7.04 (1H, d, J = 6.9 Hz), 7.09-7.16 (5H, m), 7.20 (1H, d, J = 7.8 Hz). |
| 53(53a) | 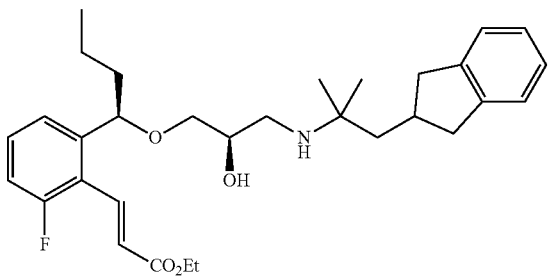 | $^1$H-NMR (CDCl$_3$) δ: 0.92 (3H, t, J = 7.2 Hz), 1.11 (6H, s), 1.31-1.41 (1H, m), 1.35 (3H, t, J = 7.0 Hz), 1.42-1.64 (2H, m), 1.69 (2H, d, J = 4.6 Hz), 1.72-1.82 (1H, m), 2.55-2.65 (4H, m), 2.69-2.74 (1H, m), 3.03-3.10 (2H, m), 3.28-3.38 (2H, m), 3.72-3.76 (1H, br m), 4.28 (2H, q, J = 7.0 Hz), 4.62-4.67 (1H, m), 6.54 (1H, d, J = 16.3 Hz), 7.02 (1H, t, J = 8.3 Hz), 7.10-7.18 (4H, m), 7.27-7.33 (2H, m), 7.84 (1H, d, J = 16.3 Hz). |

TABLE 52

| | | |
|---|---|---|
| 53(53b) | 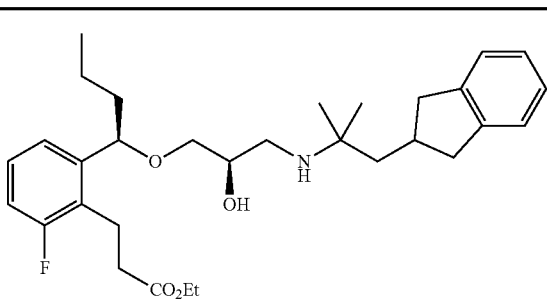 | $^1$H-NMR (CDCl$_3$) δ: 0.93 (3H, t, J = 7.1 Hz), 1.11 (6H, s), 1.26 (3H, t, J = 7.3 Hz), 1.30-1.43 (1H, m), 1.48-1.59 (2H, m), 1.67 (2H, d, J = 6.0 Hz), 1.73-1.80 (1H, m), 2.52-2.64 (6H, m), 2.70 (1H, dd, J = 11.5, 4.1 Hz), 2.91-3.09 (4H, m), 3.25-3.33 (2H, m), 3.71-3.77 (1H, m), 4.15 (2H, q, J = 7.3 Hz), 4.57 (1H, dd, J = 8.5, 3.9 Hz), 6.89-6.95 (1H, m), 7.10-7.13 (2H, m), 7.17 (4H, tt, J = 8.3, 3.1 Hz). |

TABLE 52-continued

| | | |
|---|---|---|
| 53(53c) | [structure] | ¹H-NMR (CDCl₃) δ: 0.87 (3H, t, J = 7.3 Hz), 1.22-1.30 (1H, m), 1.31-1.40 (1H, m), 1.44 (6H, s), 1.51-1.60 (1H, m), 1.75-1.83 (1H, br m), 2.00 (2H, dd, J = 10.3, 6.2 Hz), 2.49-2.67 (5H, m), 2.87-2.95 (2H, m), 3.01-3.18 (4H, m), 3.41-3.46 (1H, m), 3.49-3.54 (1H, m), 4.33-4.38 (1H, br m), 4.90-4.94 (1H, m), 6.90 (1H, t, J = 8.5 Hz), 7.07-7.16 (6H, m). |
| 54(54a) | [structure] | ¹H-NMR (CDCl₃) δ: 0.90 (3H, t, J = 7.3 Hz), 1.09 (6H, s), 1.30-1.36 (1H, m), 1.34 (3H, t, J = 7.1 Hz), 1.37-1.48 (1H, m), 1.50-1.62 (1H, m), 1.66 (2H, d, J = 6.0 Hz), 1.74-1.84 (1H, m), 2.33 (3H, s), 2.50-2.66 (4H, m), 2.69 (1H, dd, J = 11.5, 4.1 Hz), 3.02-3.08 (2H, m), 3.26-3.33 (2H, m), 3.71-3.76 (1H, m), 4.26 (2H, q, J = 7.1 Hz), 4.61 (1H, dd, J = 8.0, 5.3 Hz), 6.32 (1H, d, J = 15.6 Hz), 7.09-7.19 (5H, m), 7.31 (1H, d, J = 7.8 Hz), 7.35 (1H, s), 8.10 (1H, d, J = 15.6 Hz). |
| 54(54b) | [structure] | ¹H-NMR (CDCl₃) δ: 0.92 (3H, t, J = 7.1 Hz), 1.10 (6H, s), 1.25 (3H, t, J = 7.1 Hz), 1.31-1.41 (1H, m), 1.43-1.59 (2H, m), 1.66 (2H, d, J = 6.0 Hz), 1.74-1.82 (1H, m), 2.30 (3H, d, J = 7.8 Hz), 2.49-2.63 (6H, m), 2.67 (1H, dd, J = 11.5, 4.1 Hz), 2.87-3.00 (2H, m), 3.05 (2H, dd, J = 14.4, 6.6 Hz), 3.23-3.31 (2H, m), 3.71-3.76 (1H, m), 4.14 (2H, q, J = 7.1 Hz), 4.53 (1H, dd, J = 8.5, 4.4 Hz), 6.95 (1H, s), 7.03 (1H, d, J = 7.8 Hz), 7.10-7.17 (4H, m), 7.27 (1H, d, J = 8.7 Hz). |
| 54(54c) | [structure] | ¹H-NMR (CDCl₃) δ: 0.86 (3H, t, J = 7.3 Hz), 1.35-1.44 (2H, m), 1.42 (6H, s), 1.51-1.60 (1H, m), 1.75-1.84 (1H, m), 1.97 (2H, d, J = 5.0 Hz), 2.27 (3H, s), 2.51-2.65 (5H, m), 2.79-2.90 (2H, m), 2.98 (1H, dd, J = 14.4, 7.6 Hz), 3.08 (2H, td, J = 14.4, 7.2 Hz), 3.19 (1H, d, J = 11.9 Hz), 3.39-3.44 (1H, m), 3.48-3.53 (1H, m), 4.34-4.39 (1H, br m), 4.80-4.85 (1H, m), 6.98 (2H, s), 7.10-7.18 (5H, m). |
| 55(55a) | [structure] | ¹H-NMR (CDCl₃) δ: 0.92 (3H, t, J = 7.3 Hz), 1.10 (6H, s), 1.34 (3H, t, J = 7.1 Hz), 1.36-1.42 (1H, m), 1.46-1.51 (1H, m), 1.56-1.64 (1H, m), 1.67 (2H, d, J = 5.5 Hz), 1.76-1.79 (1H, m), 2.47-2.66 (4H, m), 2.69 (1H, dd, J = 11.5, 4.1 Hz), 3.02-3.09 (2H, m), 3.27 (1H, dd, J = 9.4, 5.7 Hz), 3.33 (1H, dd, J = 9.4, 4.4 Hz), 3.71-3.76 (1H, m), 3.86 (3H, s), 4.26 (2H, q, J = 7.1 Hz), 4.67 (1H, dd, J = 8.3, 4.6 Hz), 6.58 (1H, d, J = 16.0 Hz), 6.83 (1H, d, J = 8.3 Hz), 7.09-7.13 (3H, m), 7.15-7.18 (2H, m), 7.31 (1H, t, J = 8.0 Hz), 7.92 (1H, d, J = 16.0 Hz). |

TABLE 53

| | | |
|---|---|---|
| 55(55b) | 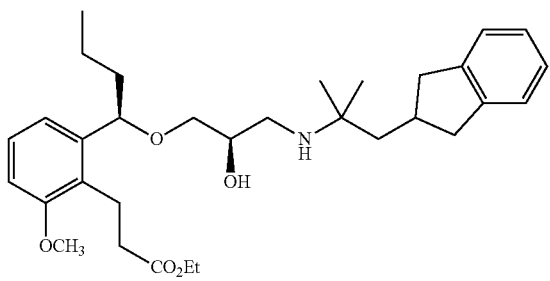 | ¹H-NMR(CDCl₃) δ: 0.92 (3H, t, J = 7.1 Hz), 1.10 (6H, s), 1.27 (3H, t, J = 7.1 Hz), 1.33-1.44 (1H, m), 1.48-1.59 (2H, m), 1.67 (2H, d, J = 5.5 Hz), 1.71-1.80 (1H, m), 2.49 (2H, t, J = 8.3 Hz), 2.52-2.64 (4H, m), 2.68 (1H, dd, J = 11.7, 3.9 Hz), 2.87-2.95 (1H, m), 2.98-3.09 (3H, m), 3.24-3.32 (2H, m), 3.71-3.77 (1H, m), 3.80 (3H, s), 4.15 (2H, q, J = 7.1 Hz), 4.58 (1H, dd, J = 8.5, 3.9 Hz), 6.74 (1H, d, J = 8.3 Hz), 7.01 (1H, d, J = 7.8 Hz), 7.10-7.21 (5H, m). |
| 55(55c) | 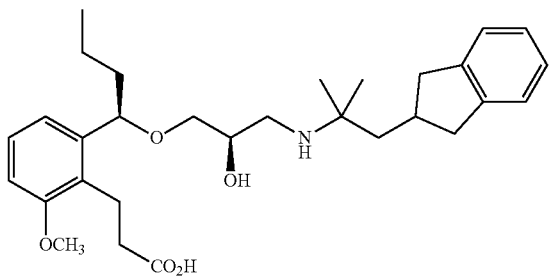 | ¹H-NMR (CDCl₃) δ: 0.88 (3H, t, J = 6.9 Hz), 1.31-1.40 (1H, m), 1.40-1.56 (2H, m), 1.47 (6H, s), 1.68-1.75 (1H, m), 2.00 (2H, d, J = 6.0 Hz), 2.50-2.67 (5H, m), 2.77-2.87 (2H, m), 3.03-3.14 (3H, m), 3.30 (1H, d, J = 10.1 Hz), 3.37 (1H, dd, J = 11.7, 8.5 Hz), 3.49 (1H, dd, J = 11.7, 4.8 Hz), 3.79 (3H, s), 4.45-4.50 (1H, m), 4.92 (1H, dd, J = 7.8, 4.1 Hz), 6.72 (1H, d, J = 8.3 Hz), 6.95 (1H, d, J = 7.3 Hz), 7.10-7.19 (5H, m). |
| 56(56a) | 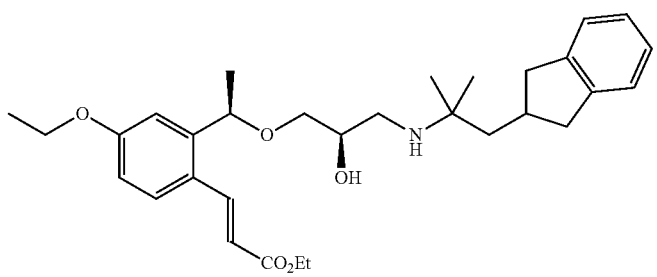 | ¹H-NMR (CDCl₃) δ: 1.10 (6H, s), 1.33 (3H, t, J = 7.1 Hz), 1.41 (3H, t, J = 7.0 Hz), 1.44 (3H, d, J = 6.5 Hz), 1.67 (2H, d, J = 5.5 Hz), 2.51-2.66 (4H, m), 2.72 (1H, dd, J = 11.9, 4.1 Hz), 3.05 (2H, dd, J = 14.9, 7.1 Hz), 3.36 (2H, d, J = 5.0 Hz), 3.72-3.78 (1H, m), 4.06 (2H, q, J = 7.1 Hz), 4.25 (2H, q, J = 7.0 Hz), 4.82 (1H, q, J = 6.5 Hz), 6.25 (1H, d, J = 15.8 Hz), 6.79 (1H, dd, J = 8.7, 2.8 Hz), 7.01 (1H, d, J = 2.8 Hz), 7.09-7.17 (4H, m), 7.51 (1H, d, J = 8.7 Hz), 8.00 (1H, d, J = 15.8 Hz). |
| 56(56b) | 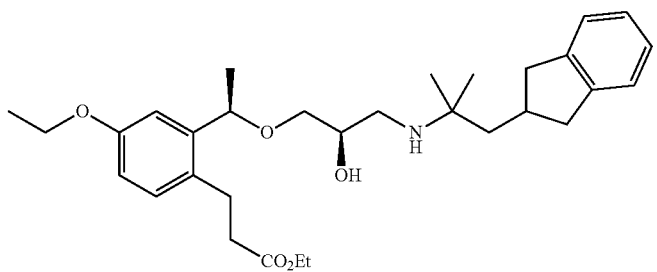 | ¹H-NMR (CDCl₃) δ: 1.10 (6H, s), 1.24 (3H, t, J = 7.1 Hz), 1.39 (3H, t, J = 7.1 Hz), 1.43 (3H, d, J = 6.4 Hz), 1.67 (2H, d, J = 5.5 Hz), 2.50-2.65 (6H, m), 2.70 (1H, dd, J = 11.7, 3.9 Hz), 2.87-2.92 (2H, m), 3.06 (2H, dd, J = 14.4, 7.1 Hz), 3.30-3.33 (2H, m), 3.72-3.78 (1H, m), 4.00 (2H, q, J = 7.1 Hz), 4.13 (2H, q, J = 7.1 Hz), 4.70 (1H, q, J = 6.4 Hz), 6.73 (1H, dd, J = 8.3, 2.8 Hz), 6.98 (1H, d, J = 3.2 Hz), 7.05 (1H, d, J = 8.3 Hz), 7.09-7.17 (4H, m). |
| 56(56c) | 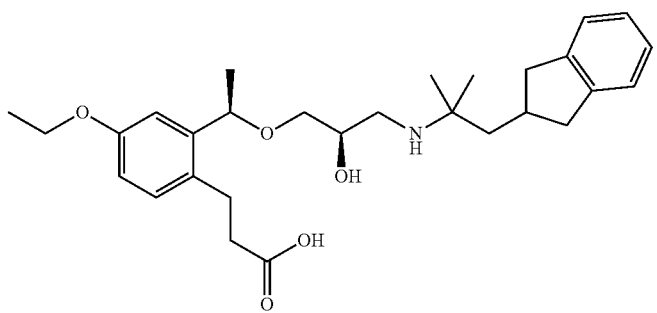 | ¹H-NMR (CDCl₃) δ: 1.37 (3H, t, J = 6.9 Hz), 1.39 (3H, d, J = 6.1 Hz), 1.44 (6H, s), 1.99 (2H, d, J = 6.0 Hz), 2.48-2.58 (3H, m), 2.59-2.68 (2H, m), 2.75-2.84 (1H, m), 2.88-2.99 (2H, m), 3.09 (2H, dd, J = 15.1, 7.3 Hz), 3.21-3.26 (1H, m), 3.47 (1H, dd, J = 11.2, 6.2 Hz), 3.56 (1H, dd, J = 11.2, 4.4 Hz), 3.94-4.01 (2H, m), 4.32-4.39 (1H, m), 4.94 (1H, q, J = 6.1 Hz), 6.72 (1H, dd, J = 8.3, 2.8 Hz), 6.89 (1H, d, J = 2.8 Hz), 7.07 (1H, d, J = 8.7 Hz), 7.10-7.17 (4H, m). |

TABLE 53-continued

57(57a) 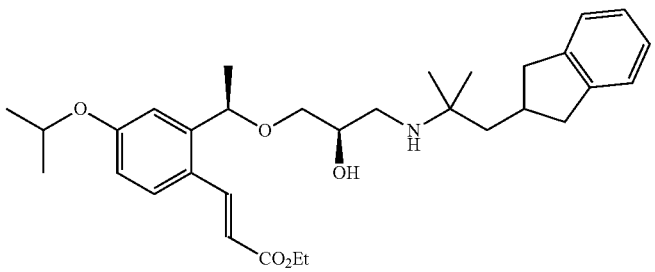

¹H-NMR (CDCl₃) δ: 1.10 (6H, s), 1.33 (3H, t, J = 7.2 Hz), 1.34 (6H, d, J = 6.0 Hz), 1.44 (3H, d, J = 6.6 Hz), 1.67 (2H, d, J = 5.5 Hz), 2.48-2.66 (4H, m), 2.72 (1H, dd, J = 11.9, 4.1 Hz), 3.06 (2H, dd, J = 14.7, 6.9 Hz), 3.37 (2H, d, J = 5.5 Hz), 3.72-3.79 (1H, m), 4.25 (2H, q, J = 7.2 Hz), 4.56-4.65 (1H, m), 4.82 (1H, q, J = 6.6 Hz), 6.24 (1H, d, J = 15.8 Hz), 6.78 (1H, dd, J = 8.7, 2.8 Hz), 6.99 (1H, d, J = 2.8 Hz), 7.09-7.17 (4H, m), 7.51 (1H, d, J = 8.7 Hz), 8.00 (1H, d, J = 15.8 Hz).

TABLE 54

57(57b) 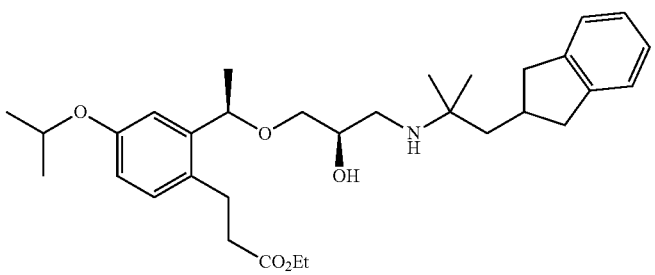

¹H-NMR (CDCl₃) δ: 1.11 (6H, s), 1.24 (3H, t, J = 7.1 Hz), 1.32 (6H, d, J = 6.0 Hz), 1.43 (3H, d, J = 6.1 Hz), 1.67 (2H, d, J = 6.0 Hz), 2.49-2.66 (6H, m), 2.71 (1H, dd, J = 11.5, 3.2 Hz), 2.86-2.92 (2H, m), 3.06 (2H, dd, J = 15.1, 6.9 Hz), 3.32 (2H, d, J = 4.6 Hz), 3.72-3.79 (1H, m), 4.13 (2H, q, J = 7.1 Hz), 4.48-4.57 (1H, m), 4.70 (1H, q, J = 6.1 Hz), 6.70-6.74 (1H, m), 6.96 (1H, s), 7.04 (1H, d, J = 8.3 Hz), 7.09-7.18 (4H, m).

57(57c) 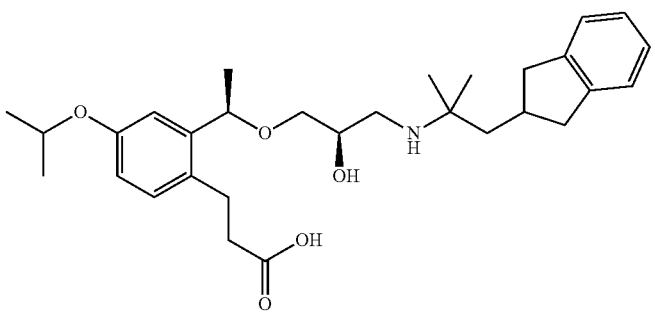

¹H-NMR (CDCl₃) δ: 1.30 (3H, d, J = 6.0 Hz), 1.31 (3H, d, J = 6.0 Hz), 1.40 (3H, d, J = 6.3 Hz), 1.43 (6H, s), 2.01 (2H, d, J = 6.0 Hz), 2.48-2.58 (3H, m), 2.59-2.68 (2H, m), 2.78-2.87 (1H, m), 2.89-2.99 (2H, m), 3.09 (2H, dd, J = 15.1, 7.3 Hz), 3.16-3.22 (1H, m), 3.47 (1H, dd, J = 11.2, 6.6 Hz), 3.57 (1H, dd, J = 11.0, 4.1 Hz), 4.29-4.38 (1H, m), 4.45-4.54 (1H, m), 4.95 (1H, q, J = 6.3 Hz), 6.72 (1H, dd, J = 8.5, 2.5 Hz), 6.86 (1H, d, J = 2.8 Hz), 7.06 (1H, d, J = 8.7 Hz), 7.09-7.17 (4H, m).

58(58a) 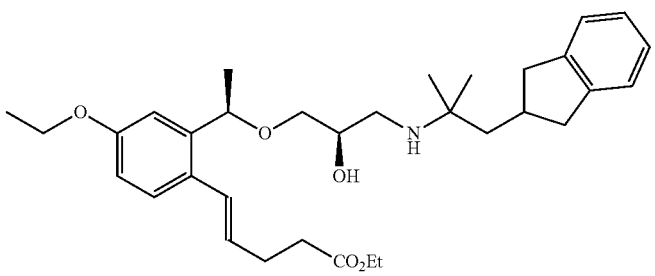

¹H-NMR (CDCl₃) δ: 1.10 (6H, s), 1.26 (3H, t, J = 7.2 Hz), 1.39 (3H, t, J = 6.5 Hz), 1.40 (3H, d, J = 6.5 Hz), 1.67 (2H, d, J = 6.0 Hz), 2.43-2.66 (7H, m), 2.70 (1H, dd, J = 11.7, 3.9 Hz), 3.06 (2H, dd, J = 14.4, 6.6 Hz), 3.26-3.34 (3H, m), 3.70-3.79 (1H, m), 4.02 (2H, q, J = 6.5 Hz), 4.14 (2H, q, J = 7.2 Hz), 4.70 (1H, q, J = 6.5 Hz), 5.93 (1H, dt, J = 15.4, 6.6 Hz), 6.63 (1H, d, J = 15.4 Hz), 6.74 (1H, dd, J = 8.3, 2.8 Hz), 6.93 (1H, d, J = 2.3 Hz), 7.07-7.18 (4H, m), 7.30 (1H, d, J = 8.7 Hz).

58(58b) 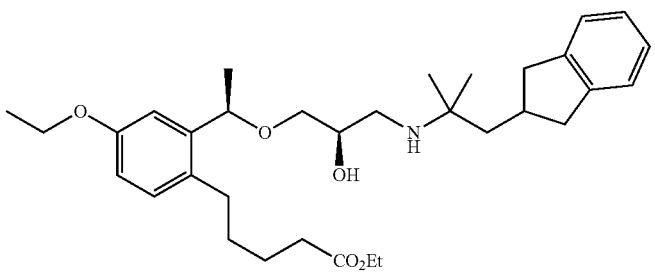

¹H-NMR (CDCl₃) δ: 1.10 (6H, s), 1.24 (3H, t, J = 7.0 Hz), 1.39 (3H, t, J = 7.1 Hz), 1.41 (3H, d, J = 6.3 Hz), 1.52-1.61 (2H, m), 1.65-1.73 (4H, m), 2.32 (2H, t, J = 7.3 Hz), 2.50-2.66 (6H, m), 2.70 (1H, dd, J = 11.7, 3.9 Hz), 3.05 (2H, dd, J = 14.4, 6.6 Hz), 3.29 (2H, d, J = 5.5 Hz), 3.70-3.79 (1H, m), 4.00 (2H, q, J = 7.0 Hz), 4.12 (2H, q, J = 7.1 Hz), 4.67 (1H, q, J = 6.3 Hz), 6.72 (1H, dd, J = 8.3, 2.8 Hz), 6.97 (1H, d, J = 2.8 Hz), 7.02 (1H, d, J = 8.3 Hz), 7.09-7.17 (4H, m).

TABLE 54-continued

| | | |
|---|---|---|
| 58(58c) | 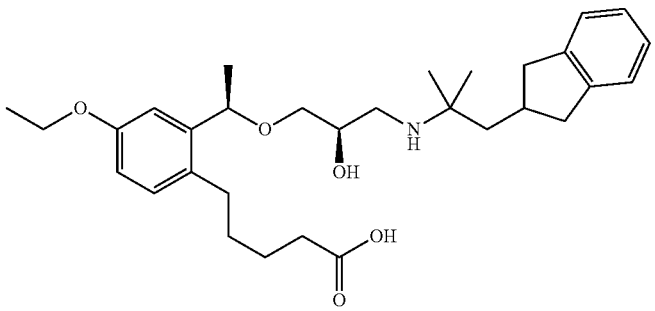 | $^1$H-NMR (CDCl$_3$) δ: 1.32 (3H, s), 1.33 (3H, s), 1.37 (3H, t, J = 7.0 Hz), 1.37 (3H, d, J = 6.3 Hz), 1.43-1.55 (2H, m), 1.59-1.73 (2H, m), 1.88 (2H, d, J = 5.5 Hz), 2.12-2.20 (1H, m), 2.28-2.42 (2H, m), 2.42-2.64 (4H, m), 2.82-2.89 (1H, m), 2.99-3.13 (3H, m), 3.31 (1H, dd, J = 11.0, 9.2 Hz), 3.57 (1H, dd, J = 11.0, 5.0 Hz), 3.96 (2H, q, J = 7.0 Hz), 4.25-4.34 (1H, m), 4.72 (1H, q, J = 6.3 Hz), 6.68 (1H, dd, J = 8.3, 2.8 Hz), 6.91 (1H, d, J = 2.8 Hz), 6.98 (1H, d, J = 8.3 Hz), 7.10-7.17 (4H, m). |
| 59(59a) | 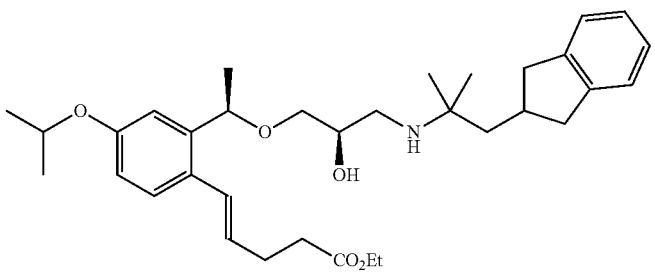 | $^1$H-NMR (CDCl$_3$) δ: 1.10 (6H, s), 1.26 (3H, t, J = 7.3 Hz), 1.32 (6H, d, J = 6.4 Hz), 1.40 (3H, d, J = 6.4 Hz), 1.67 (2H, d, J = 6.0 Hz), 2.42-2.65 (7H, m), 2.70 (1H, dd, J = 11.5, 4.1 Hz), 3.06 (2H, dd, J = 14.2, 6.9 Hz), 3.24-3.37 (3H, m), 3.69-3.79 (1H, m), 4.14 (2H, q, J = 7.3 Hz), 4.49-4.59 (1H, m), 4.69 (1H, q, J = 6.4 Hz), 5.92 (1H, dt, J = 15.5, 6.5 Hz), 6.63 (1H, d, J = 15.5 Hz), 6.73 (1H, dd, J = 8.5, 2.5 Hz), 6.92 (1H, d, J = 2.8 Hz), 7.09-7.17 (4H, m), 7.29 (1H, d, J = 8.7 Hz). |

TABLE 55

| | | |
|---|---|---|
| 59(59b) | 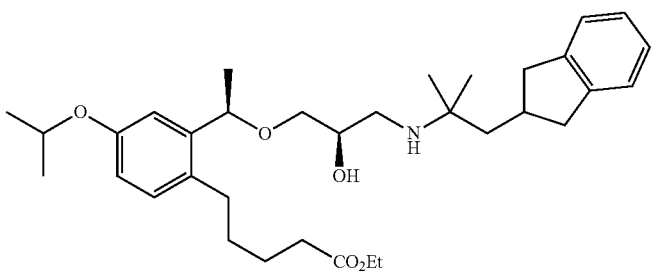 | $^1$H-NMR (CDCl$_3$) δ: 1.10 (6H, s), 1.25 (3H, t, J = 7.0 Hz), 1.31 (6H, d, J = 6.0 Hz), 1.41 (3H, d, J = 6.2 Hz), 1.52-1.61 (2H, m), 1.65-1.74 (4H, m), 2.32 (2H, t, J = 7.3 Hz), 2.47-2.65 (6H, m), 2.70 (1H, dd, J = 11.5, 3.7 Hz), 3.06 (2H, dd, J = 14.0, 6.6 Hz), 3.29 (2H, d, J = 5.5 Hz), 3.70-3.79 (1H, m), 4.12 (2H, q, J = 7.0 Hz), 4.47-4.56 (1H, m), 4.66 (1H, q, J = 6.2 Hz), 6.71 (1H, dd, J = 8.3, 2.8 Hz), 6.95 (1H, d, J = 2.8 Hz), 7.01 (1H, d, J = 8.3 Hz), 7.09-7.17 (4H, m). |
| 59(59c) | 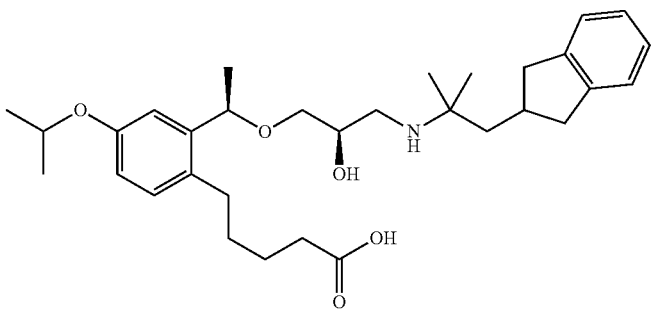 | $^1$H-NMR (CDCl$_3$) δ: 1.29 (3H, s), 1.30 (3H, s), 1.32 (6H, d, J = 7.3 Hz), 1.38 (3H, d, J = 6.1 Hz), 1.43-1.56 (2H, m), 1.59-1.74 (2H, m), 1.85-1.90 (2H, m), 2.11-2.20 (1H, m), 2.28-2.41 (2H, m), 2.42-2.64 (4H, m), 2.85 (1H, t, J = 11.0 Hz), 2.99-3.13 (3H, m), 3.30 (1H, t, J = 9.9 Hz), 3.58 (1H, dd, J = 11.0, 5.0 Hz), 4.25-4.34 (1H, m), 4.43-4.52 (1H, m), 4.72 (1H, q, J = 6.1 Hz), 6.68 (1H, dd, J = 8.3, 1.8 Hz), 6.90 (1H, d, J = 1.8 Hz), 6.96 (1H, d, J = 8.3 Hz), 7.10-7.17 (4H, m). |
| 60(60a) | 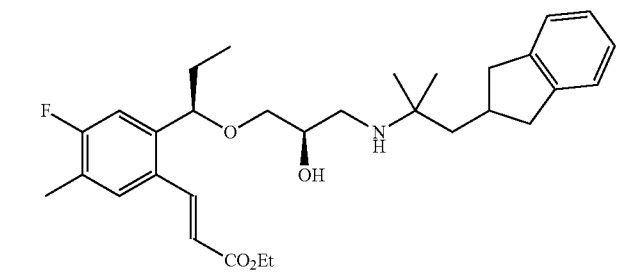 | $^1$H-NMR (CDCl$_3$) δ: 0.90 (3H, t, J = 7.4 Hz), 1.10 (6H, s), 1.33 (3H, t, J = 7.1 Hz), 1.62-1.71 (3H, m), 1.73-1.82 (1H, m), 2.26 (3H, s), 2.49-2.64 (4H, m), 2.71 (1H, dd, J = 11.5, 4.0 Hz), 3.02-3.08 (2H, m), 3.30-3.36 (2H, m), 3.72-3.77 (1H, m), 4.26 (2H, q, J = 7.1 Hz), 4.53 (1H, t, J = 6.6 Hz), 6.26 (1H, d, J = 15.8 Hz), 7.07-7.17 (5H, m), 7.38 (1H, d, J = 7.4 Hz), 7.97 (1H, d, J = 15.8 Hz). |

TABLE 55-continued

| 60(60b) | 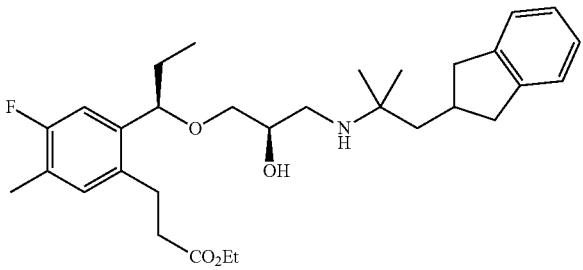 | ¹H-NMR (CDCl₃) δ: 0.95 (3H, t, J = 7.4 Hz), 1.10 (6H, s), 1.24 (3H, t, J = 7.0 Hz), 1.58-1.70 (1H, m), 1.67 (2H, d, J = 5.7 Hz), 1.71-1.80 (1H, m), 2.21 (3H, s), 2.51-2.63 (6H, m), 2.70 (1H, dd, J = 11.5, 4.0 Hz), 2.83-2.94 (2H, m), 3.05 (2H, dd, J = 15.2, 7.2 Hz), 3.28 (2H, d, J = 5.2 Hz), 3.72-3.78 (1H, m), 4.13 (2H, q, J = 7.0 Hz), 4.42 (1H, t, J = 6.0 Hz), 6.94 (1H, d, J = 7.4 Hz), 7.02 (1H, d, J = 10.9 Hz), 7.09-7.17 (4H, m). |
| --- | --- | --- |
| 60(60c) | 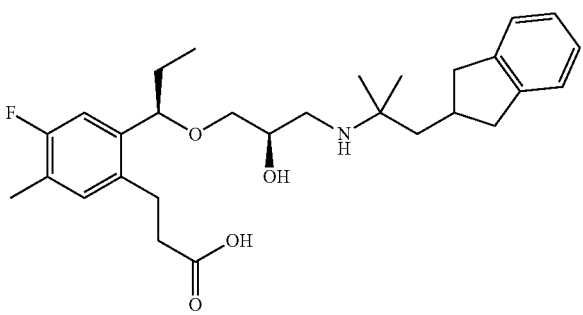 | ¹H-NMR (CDCl₃) δ: 0.83 (3H, t, J = 7.3 Hz), 1.40 (6H, s), 1.54-1.65 (1H, m), 1.79-1.91 (1H, m), 1.91-2.03 (2H, m), 2.20 (3H, s), 2.42-2.67 (5H, m), 2.73-2.83 (1H, m), 2.85-3.02 (2H, m), 3.03-3.17 (3H, m), 3.42-3.56 (2H, m), 4.26-4.35 (1H, m), 4.75 (1H, t, J = 6.2 Hz), 6.91 (1H, d, J = 11.0 Hz), 6.98 (1H, d, J = 7.8 Hz), 7.09-7.17 (4H, m). |
| 61(61a) | 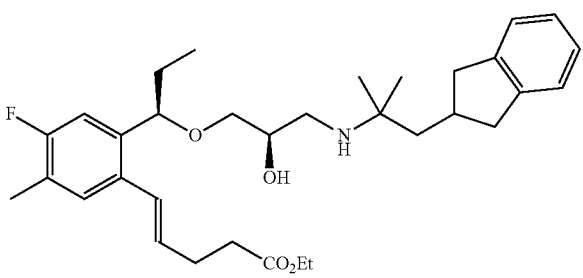 | ¹H-NMR (CDCl₃) δ: 0.90 (3H, t, J = 7.4 Hz), 1.10 (6H, s), 1.26 (3H, t, J = 6.9 Hz), 1.58-1.77 (2H, m), 1.67 (2H, d, J = 5.7 Hz), 2.23 (3H, s), 2.44-2.64 (7H, m), 2.70 (1H, dd, J = 11.5, 4.0 Hz), 3.05 (2H, dd, J = 16.3, 7.2 Hz), 3.22-3.34 (3H, m), 3.71-3.77 (1H, m), 4.15 (2H, q, J = 6.9 Hz), 4.43 (1H, t, J = 6.3 Hz), 5.95 (1H, dt, J = 15.5, 6.6 Hz), 6.62 (1H, d, J = 15.5 Hz), 6.99 (1H, d, J = 10.9 Hz), 7.09-7.19 (5H, m). |
| 61(61b) | 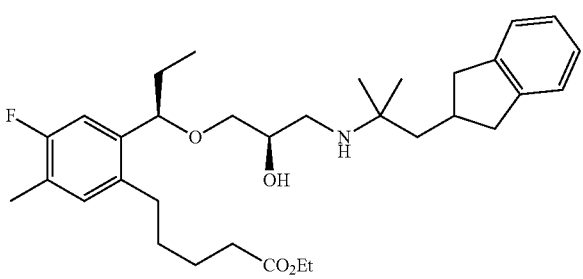 | ¹H-NMR (CDCl₃) δ: 0.95 (3H, t, J = 7.4 Hz), 1.10 (6H, s), 1.25 (3H, t, J = 7.1 Hz), 1.53-1.64 (3H, m), 1.65-1.77 (5H, m), 2.21 (3H, s), 2.33 (2H, t, J = 7.4 Hz), 2.49-2.63 (6H, m), 2.70 (1H, dd, J = 11.5, 4.0 Hz), 3.05 (2H, dd, J = 15.2, 7.2 Hz), 3.24-3.29 (2H, m), 3.72-3.77 (1H, m), 4.12 (2H, q, J = 7.1 Hz), 4.36-4.40 (1H, m), 6.91 (1H, d, J = 8.0 Hz), 7.01 (1H, d, J = 10.9 Hz), 7.09-7.17 (4H, m). |

TABLE 56

| 61(61c) | 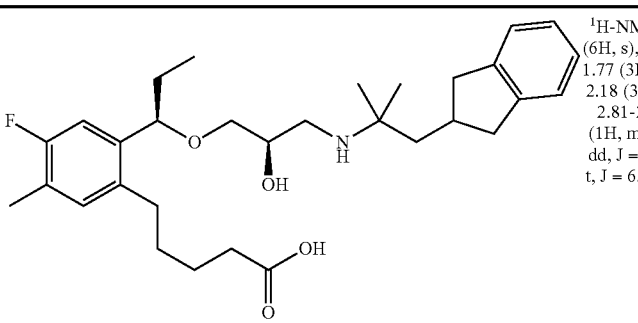 | ¹H-NMR (CDCl₃) δ: 0.94 (3H, t, J = 7.3 Hz), 1.35 (6H, s), 1.39-1.44 (1H, m), 1.44-1.55 (2H, m), 1.55-1.77 (3H, m), 1.86-1.95 (2H, m), 2.15-2.23 (1H, m), 2.18 (3H, s), 2.29-2.38 (2H, m), 2.43-2.64 (4H, m), 2.81-2.88 (1H, m), 2.99-3.09 (2H, m), 3.10-3.16 (1H, m), 3.30 (1H, dd, J = 11.2, 8.5 Hz), 3.50 (1H, dd, J = 11.0, 5.0 Hz), 4.26-4.34 (1H, m), 4.45 (1H, t, J = 6.2 Hz), 6.87 (1H, d, J = 7.8 Hz), 6.95 (1H, d, J = 11.0 Hz), 7.10-7.17 (4H, m). |
| --- | --- | --- |

TABLE 56-continued

62(62a) 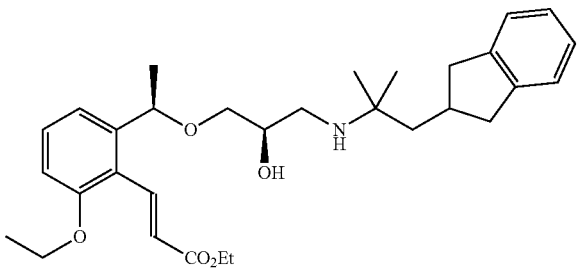 ¹H-NMR (CDCl₃) δ: 1.10 (6H, s), 1.34 (3H, t, J = 7.1 Hz), 1.45 (3H, d, J = 6.3 Hz), 1.46 (3H, t, J = 6.6 Hz), 1.67 (2H, d, J = 6.3 Hz), 2.49-2.64 (4H, m), 2.69 (1H, dd, J = 12.0, 4.0 Hz), 3.02-3.08 (2H, m), 3.28-3.35 (2H, m), 3.71-3.76 (1H, m), 4.05-4.11 (2H, m), 4.26 (2H, q, J = 7.1 Hz), 4.84 (1H, q, J = 6.3 Hz), 6.59 (1H, d, J = 16.3 Hz), 6.82 (1H, d, J = 8.0 Hz), 7.09-7.19 (5H, m), 7.29 (1H, t, J = 8.0 Hz), 7.92 (1H, d, J = 16.3 Hz).

62(62b) 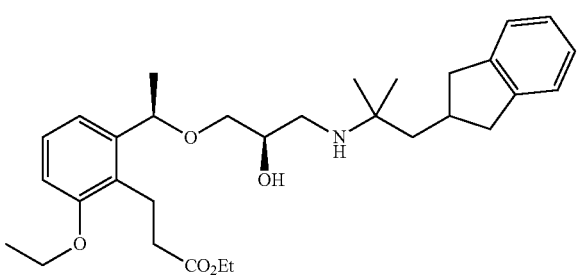 ¹H-NMR (CDCl₃) δ: 1.10 (3H, s), 1.10 (3H, s), 1.26 (3H, t, J = 7.1 Hz), 1.41 (3H, t, J = 6.9 Hz), 1.42 (3H, d, J = 6.9 Hz), 1.67 (2H, d, J = 5.7 Hz), 2.48-2.64 (6H, m), 2.68 (1H, dd, J = 11.5, 4.0 Hz), 2.89-2.96 (1H, m), 2.99-3.12 (3H, m), 3.27-3.34 (2H, m), 3.73-3.77 (1H, m), 4.01 (2H, q, J = 6.9 Hz), 4.15 (2H, q, J = 7.1 Hz), 4.76 (1H, q, J = 6.3 Hz), 6.73 (1H, d, J = 7.4 Hz), 7.03 (1H, d, J = 8.0 Hz), 7.10-7.20 (5H, m).

62(62c) 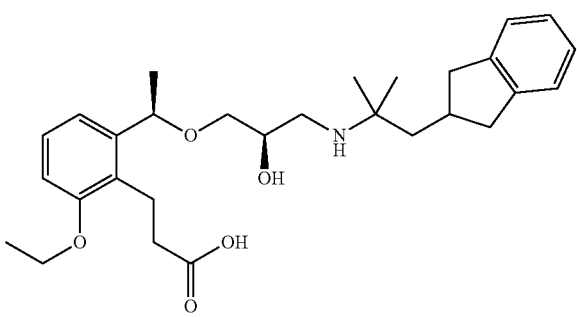 ¹H-NMR (CDCl₃) δ: 1.39 (3H, t, J = 7.1 Hz), 1.41 (3H, d, J = 7.4 Hz), 1.45 (3H, s), 1.46 (3H, s), 1.97-2.09 (2H, m), 2.44-2.68 (5H, m), 2.87-2.99 (2H, m), 3.05-3.14 (4H, m), 3.46-3.52 (1H, m), 3.57-3.62 (1H, m), 3.99 (2H, q, J = 7.1 Hz), 4.27-4.33 (1H, m), 5.03-5.09 (1H, m), 6.72 (1H, d, J = 8.0 Hz), 6.90 (1H, d, J = 7.4 Hz), 7.09-7.15 (5H, m).

63(63a) 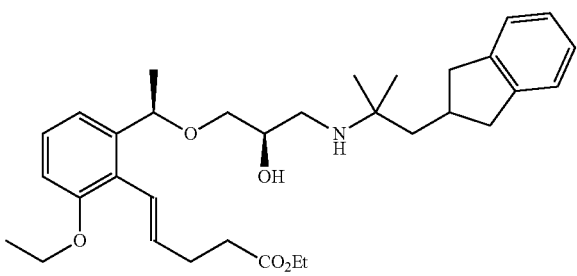 ¹H-NMR (CDCl₃) δ: 1.09 (6H, s), 1.27 (3H, t, J = 7.3 Hz), 1.38-1.42 (6H, m), 1.65-1.67 (2H, m), 2.48-2.69 (9H, m), 3.02-3.08 (2H, m), 3.20-3.31 (2H, m), 3.69-3.76 (1H, m), 4.00 (2H, q, J = 7.1 Hz), 4.15 (2H, q, J = 7.3 Hz), 4.79 (1H, q, J = 6.5 Hz), 5.95 (1H, dt, J = 16.1, 6.7 Hz), 6.43 (1H, d, J = 16.1 Hz), 6.74 (1H, d, J = 8.0 Hz), 7.07 (1H, d, J = 8.0 Hz), 7.09-7.20 (5H, m).

63(63b) 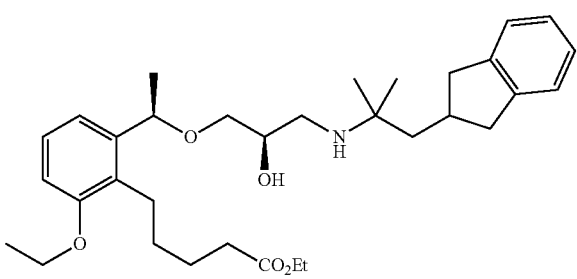 ¹H-NMR (CDCl₃) δ: 1.09 (3H, s), 1.10 (3H, s), 1.25 (3H, t, J = 7.1 Hz), 1.41 (3H, t, J = 6.9 Hz), 1.41 (3H, d, J = 6.7 Hz), 1.49-1.56 (2H, m), 1.66 (2H, d, J = 5.7 Hz), 1.68-1.76 (2H, m), 2.34 (2H, t, J = 7.4 Hz), 2.49-2.63 (5H, m), 2.65-2.75 (2H, m), 3.02-3.08 (2H, m), 3.24-3.30 (2H, m), 3.72-3.77 (1H, m), 3.99 (2H, q, J = 7.1 Hz), 4.12 (2H, q, J = 7.1 Hz), 4.71 (1H, q, J = 6.7 Hz), 6.71 (1H, d, J = 7.4 Hz), 7.02 (1H, d, J = 8.0 Hz), 7.10-7.17 (5H, m).

TABLE 56-continued

| 63(63c) | 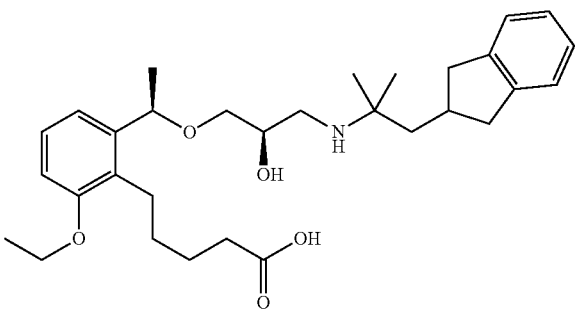 | ¹H-NMR (CDCl₃) δ: 1.37 (3H, d, J = 6.9 Hz), 1.38 (3H, t, J = 6.9 Hz), 1.41 (3H, s), 1.42 (3H, s), 1.45-1.48 (1H, m), 1.56-1.78 (3H, m), 1.97 (2H, d, J = 6.3 Hz), 2.18-2.25 (1H, m), 2.33-2.41 (2H, m), 2.46-2.55 (1H, m), 2.56-2.64 (2H, m), 2.80-2.92 (2H, m), 3.06 (2H, dd, J = 14.9, 7.4 Hz), 3.11-3.16 (1H, m), 3.31 (1H, dd, J = 10.9, 6.9 Hz), 3.45 (1H, dd, J = 11.2, 5.4 Hz), 3.95 (2H, q, J = 6.9 Hz), 4.30-4.36 (1H, m), 4.79 (1H, q, J = 6.3 Hz), 6.69 (1H, d, J = 8.6 Hz), 6.96 (1H, d, J = 8.0 Hz), 7.10-7.16 (5H, m). |
|---|---|---|

TABLE 57

| 64(64a) | 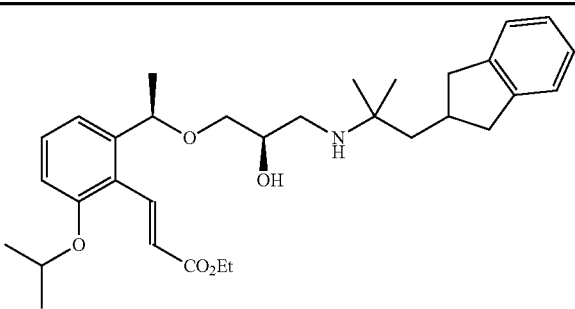 | ¹H-NMR (CDCl₃) δ: 1.10 (6H, s), 1.34 (3H, t, J = 7.2 Hz), 1.37 (3H, d, J = 5.7 Hz), 1.38 (3H, d, J = 5.7 Hz), 1.45 (3H, d, J = 6.9 Hz), 1.67 (2H, d, J = 5.7 Hz), 2.49-2.66 (4H, m), 2.69 (1H, dd, J = 11.7, 4.3 Hz), 3.03-3.12 (2H, m), 3.29-3.35 (2H, m), 3.71-3.76 (1H, m), 4.26 (2H, q, J = 7.2 Hz), 4.55-4.62 (1H, m), 4.82 (1H, q, J = 6.3 Hz), 6.57 (1H, d, J = 16.0 Hz), 6.83 (1H, d, J = 8.0 Hz), 7.08-7.19 (5H, m), 7.28 (1H, t, J = 8.0 Hz), 7.90 (1H, d, J = 16.0 Hz). |
|---|---|---|
| 64(64b) | 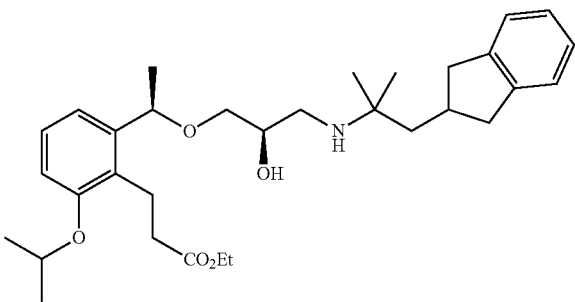 | ¹H-NMR (CDCl₃) δ: 1.10 (3H, s), 1.10 (3H, s), 1.26 (3H, t, J = 7.1 Hz), 1.34 (3H, d, J = 6.0 Hz), 1.34 (3H, d, J = 6.0 Hz), 1.42 (3H, d, J = 6.4 Hz), 1.67 (2H, d, J = 5.5 Hz), 2.48-2.71 (7H, m), 2.86-3.12 (4H, m), 3.26-3.34 (2H, m), 3.71-3.78 (1H, m), 4.15 (2H, q, J = 7.0 Hz), 4.50-4.59 (1H, m), 4.75 (1H, q, J = 6.4 Hz), 6.74 (1H, d, J = 7.8 Hz), 7.00 (1H, d, J = 6.9 Hz), 7.09-7.19 (5H, m). |
| 64(64c) | 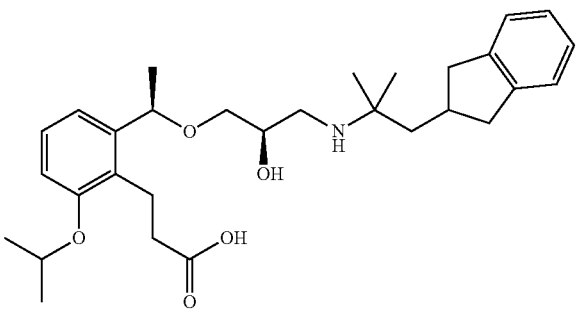 | ¹H-NMR (CDCl₃) δ: 1.31 (3H, d, J = 6.3 Hz), 1.32 (3H, d, J = 5.7 Hz), 1.40 (3H, d, J = 6.3 Hz), 1.45 (3H, s), 1.46 (3H, s), 1.99-2.09 (2H, m), 2.43-2.60 (3H, m), 2.61-2.68 (2H, m), 2.83-2.91 (1H, m), 2.92-2.98 (1H, m), 3.03-3.16 (4H, m), 3.43-3.52 (1H, m), 3.55-3.60 (1H, m), 4.28-4.34 (1H, m), 4.49-4.56 (1H, m), 5.00-5.09 (1H, m), 6.73 (1H, d, J = 8.0 Hz), 6.88 (1H, d, J = 8.0 Hz), 7.08-7.16 (5H, m). |
| 65(65a) | 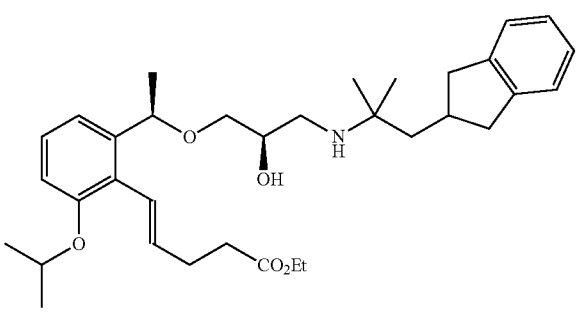 | ¹H-NMR (CDCl₃) δ: 1.10 (6H, s), 1.27 (3H, t, J = 7.2 Hz), 1.31 (6H, d, J = 5.7 Hz), 1.41 (3H, d, J = 5.2 Hz), 1.65-1.68 (2H, m), 2.47-2.70 (9H, m), 3.03-3.08 (2H, m), 3.21-3.31 (2H, m), 3.69-3.76 (1H, m), 4.15 (2H, q, J = 7.2 Hz), 4.43-4.50 (1H, m), 4.77 (1H, q, J = 6.5 Hz), 5.91 (1H, dt, J = 16.0, 6.6 Hz), 6.40 (1H, d, J = 16.0 Hz), 6.76 (1H, d, J = 6.9 Hz), 7.05 (1H, d, J = 7.4 Hz), 7.09-7.19 (5H, m). |

TABLE 57-continued

| | | |
|---|---|---|
| 65(65b) | 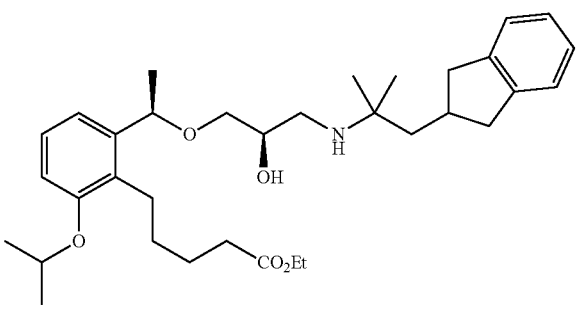 | ¹H-NMR (CDCl₃) δ: 1.10 (3H, s), 1.10 (3H, s), 1.25 (3H, t, J = 7.1 Hz), 1.33 (6H, d, J = 6.0 Hz), 1.41 (3H, d, J = 6.3 Hz), 1.47-1.55 (2H, m), 1.66 (2H, d, J = 6.0 Hz), 1.67-1.76 (2H, m), 2.34 (2H, t, J = 7.6 Hz), 2.51-2.73 (7H, m), 3.02-3.09 (2H, m), 3.26-3.29 (2H, m), 3.71-3.78 (1H, m), 4.12 (2H, q, J = 7.1 Hz), 4.48-4.57 (1H, m), 4.69 (1H, q, J = 6.3 Hz), 6.72 (1H, d, J = 8.3 Hz), 6.99 (1H, d, J = 7.8 Hz), 7.09-7.17 (5H, m). |
| 65(65c) | 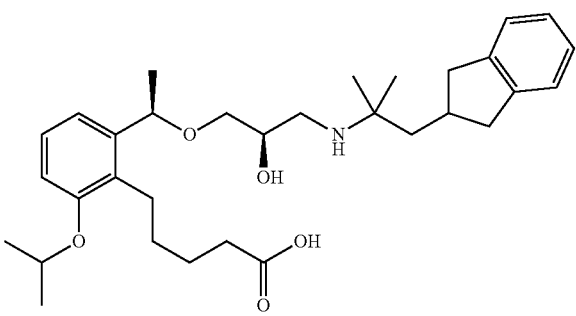 | ¹H-NMR (CDCl₃) δ: 1.30 (3H, d, J = 5.7 Hz), 1.30 (3H, d, J = 5.7 Hz), 1.37 (3H, d, J = 6.3 Hz), 1.40 (6H, s), 1.43-1.47 (1H, m), 1.54-1.78 (3H, m), 1.96 (2H, d, J = 6.3 Hz), 2.17-2.24 (1H, m), 2.31-2.39 (2H, m), 2.46-2.55 (1H, m), 2.56-2.64 (2H, m), 2.78-2.91 (2H, m), 3.06 (2H, dd, J = 15.5, 7.4 Hz), 3.11-3.15 (1H, m), 3.31 (1H, dd, J = 11.5, 7.4 Hz), 3.47 (1H, dd, J = 12.0, 6.3 Hz), 4.30-4.36 (1H, m), 4.43-4.51 (1H, m), 4.78 (1H, q, J = 6.3 Hz), 6.70 (1H, d, J = 8.0 Hz), 6.93 (1H, d, J = 8.0 Hz), 7.09-7.17 (5H, m). |

TABLE 58

| | | |
|---|---|---|
| 66(66a) | 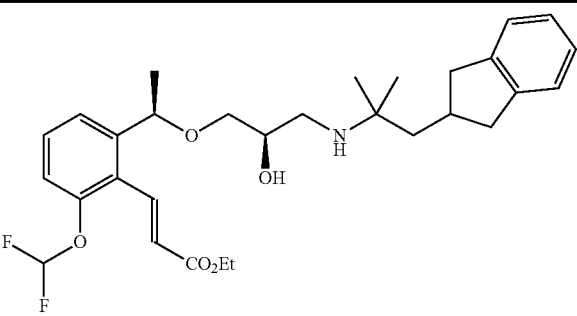 | ¹H-NMR (CDCl₃) δ: 1.11 (6H, s), 1.35 (3H, t, J = 7.1 Hz), 1.44 (3H, d, J = 6.4 Hz), 1.68 (2H, d, J = 5.5 Hz), 2.49-2.66 (4H, m), 2.70 (1H, dd, J = 11.7, 3.9 Hz), 3.02-3.09 (2H, m), 3.28-3.35 (2H, m), 3.70-3.76 (1H, m), 4.28 (2H, q, J = 7.2 Hz), 4.77 (1H, q, J = 6.4 Hz), 6.36 (1H, d, J = 16.3 Hz), 6.47 (1H, t, J = 73.4 Hz), 7.07-7.19 (5H, m), 7.35 (1H, t, J = 7.8 Hz), 7.40 (1H, dd, J = 7.8, 1.4 Hz), 7.79 (1H, d, J = 16.3 Hz). |
| 66(66b) | 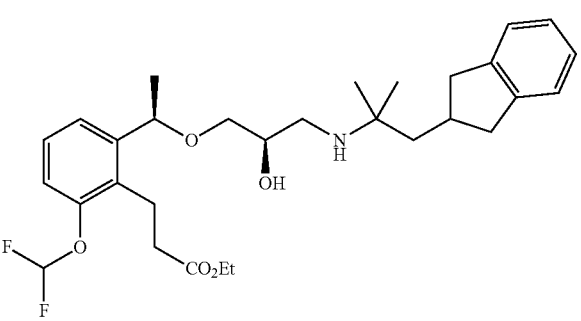 | ¹H-NMR (CDCl₃) δ: 1.11 (6H, s), 1.26 (3H, t, J = 7.2 Hz), 1.43 (3H, d, J = 6.4 Hz), 1.67 (2H, d, J = 6.3 Hz), 2.49-2.65 (6H, m), 2.70 (1H, dd, J = 12.0, 4.0 Hz), 2.92-2.99 (1H, m), 3.01-3.09 (3H, m), 3.29 (1H, dd, J = 9.2, 4.6 Hz), 3.34 (1H, dd, J = 9.5, 6.0 Hz), 3.71-3.77 (1H, m), 4.15 (2H, q, J = 7.2 Hz), 4.77 (1H, q, J = 6.4 Hz), 6.52 (1H, t, J = 73.9 Hz), 6.98 (1H, d, J = 8.0 Hz), 7.10-7.17 (4H, m), 7.24 (1H, t, J = 8.0 Hz), 7.31 (1H, dd, J = 8.0, 1.1 Hz). |
| 66(66c) | 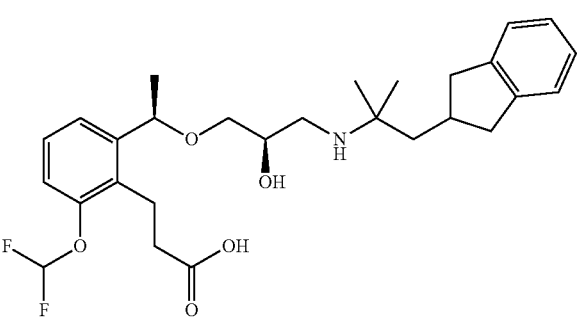 | ¹H-NMR (CDCl₃) δ: 1.44 (3H, d, J = 5.2 Hz), 1.45 (6H, s), 1.98-2.10 (2H, m), 2.34-2.45 (1H, m), 2.45-2.68 (4H, m), 2.92-3.05 (3H, m), 3.05-3.18 (3H, m), 3.51-3.60 (1H, m), 3.63-3.68 (1H, m), 4.19-4.25 (1H, m), 5.02-5.10 (1H, m), 6.48 (1H, t, J = 74.2 Hz), 7.00 (1H, d, J = 7.4 Hz), 7.08-7.15 (5H, m), 7.17 (1H, t, J = 8.0 Hz). |

TABLE 58-continued

| 67(67a) | 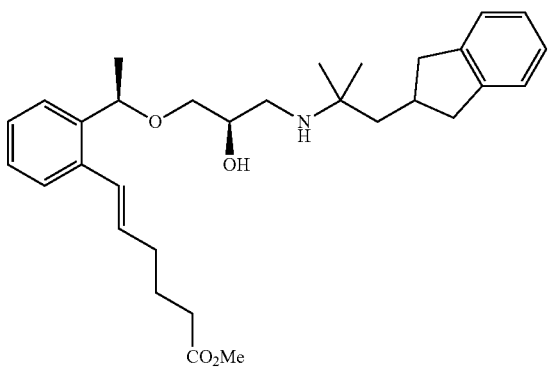 | ¹H-NMR (CDCl₃) δ: 1.07-1.12 (1H, m), 1.10 (6H, s), 1.43 (3H, d, J = 6.4 Hz), 1.66 (2H, d, J = 6.0 Hz), 1.77-1.87 (1H, m), 2.23-2.31 (1H, m), 2.31-2.40 (2H, m), 2.47-2.73 (6H, m), 3.05 (2H, dd, J = 14.7, 6.9 Hz), 3.24-3.38 (2H, m), 3.61-3.69 (1H, m), 3.67 (3H, s), 3.70-3.79 (1H, m), 4.68-4.79 (1H, m), 5.96-6.05 (1H, m), 6.70 (1H, d, J = 15.6 Hz), 7.08-7.28 (7H, m), 7.29 (0H, s), 7.38 (1H, d, J = 7.8 Hz). |
|---|---|---|
| 67(67b) | 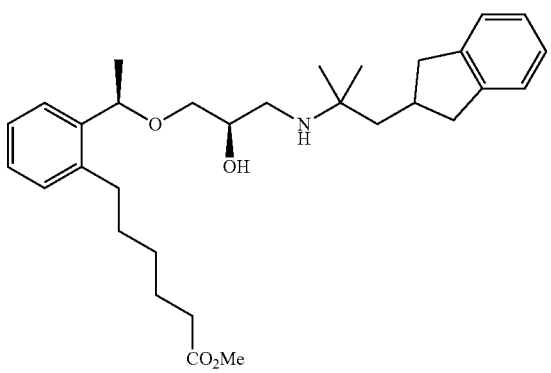 | ¹H-NMR (CDCl₃) δ: 1.10 (6H, s), 1.18-1.24 (1H, m), 1.36-1.46 (3H, m), 1.43 (2H, d, J = 6.4 Hz), 1.54-1.72 (6H, m), 2.32 (2H, t, J = 7.8 Hz), 2.47-2.66 (6H, m), 2.70 (1H, dd, J = 11.9, 3.7 Hz), 3.05 (2H, dd, J = 14.7, 6.9 Hz), 3.24-3.34 (2H, m), 3.67 (3H, s), 3.70-3.82 (1H, m), 4.72 (1H, q, J = 6.3 Hz), 7.08-7.24 (7H, m), 7.42 (1H, dd, J = 7.6, 1.6 Hz). |
| 67(67c) | 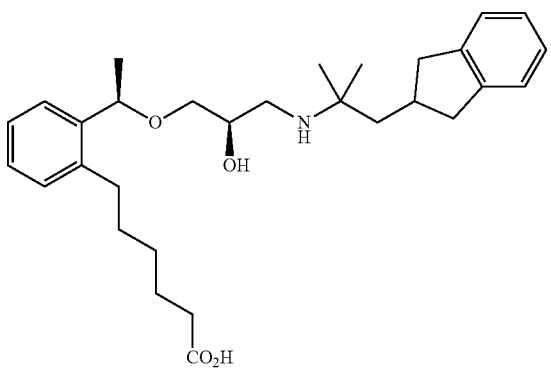 | ¹H-NMR (CDCl₃) δ: 1.32-1.45 (4H, m), 1.39 (6H, s), 1.48-1.70 (5H, m), 1.98 (2H, d, J = 6.0 Hz), 2.17 (2H, t, J = 5.7 Hz), 2.47-2.68 (5H, m), 2.73 (1H, dd, J = 10.8, 5.4 Hz), 2.97 (1H, d, J = 11.5 Hz), 3.08 (2H, dd, J = 14.9, 7.6 Hz), 3.34 (1H, dd, J = 11.0, 5.5 Hz), 3.41 (1H, dd, J = 10.8, 7.1 Hz), 4.22-4.31 (1H, m), 4.87 (1H, q, J = 6.0 Hz), 7.08-7.21 (7H, m), 7.28-7.34 (1H, m). |

TABLE 59

| 68(68a) | 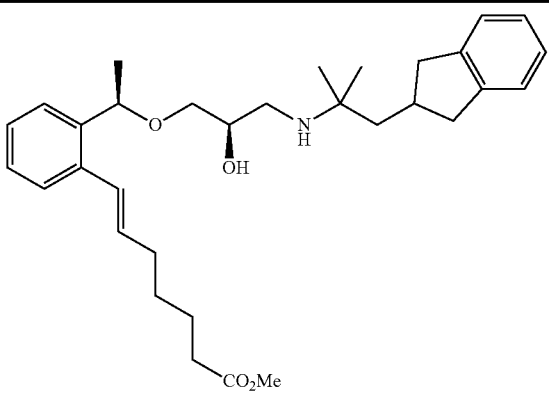 | ¹H-NMR (CDCl₃) δ: 1.07-1.12 (1H, m), 1.09 (6H, s), 1.42 (3H, d, J = 6.4 Hz), 1.46-1.55 (1H, m), 1.63-1.74 (2H, m), 1.66 (2H, d, J = 6.0 Hz), 2.20-2.39 (3H, m), 2.47-2.72 (5H, m), 3.05 (2H, dd, J = 14.7, 6.9 Hz), 3.23-3.37 (2H, m), 3.62-3.70 (1H, m), 3.67 (3H, s), 3.70-3.79 (1H, m), 4.68-4.80 (1H, m), 5.97-6.07 (1H, m), 6.68 (1H, d, J = 15.6 Hz), 7.08-7.29 (7H, m), 7.38 (1H, d, J = 7.8 Hz). |

TABLE 59-continued

| | | |
|---|---|---|
| 68(68b) | 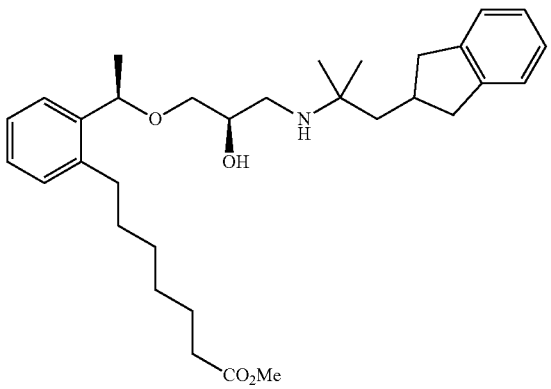 | $^1$H-NMR (CDCl$_3$) δ: 1.10 (6H, s), 1.35-1.40 (4H, m), 1.43 (3H, d, J = 6.4 Hz), 1.53-1.71 (5H, m), 1.66 (2H, d, J = 6.0 Hz), 2.31 (2H, t, J = 7.3 Hz), 2.43-2.67 (6H, m), 2.69 (1H, dd, J = 11.7, 3.9 Hz), 3.05 (2H, dd, J = 14.9, 7.1 Hz), 3.25-3.32 (2H, m), 3.67 (3H, s), 3.71-3.78 (1H, m), 4.73 (1H, q, J = 6.4 Hz), 7.10-7.23 (7H, m), 7.42 (1H, d, J = 7.3 Hz). |
| 68(68c) | 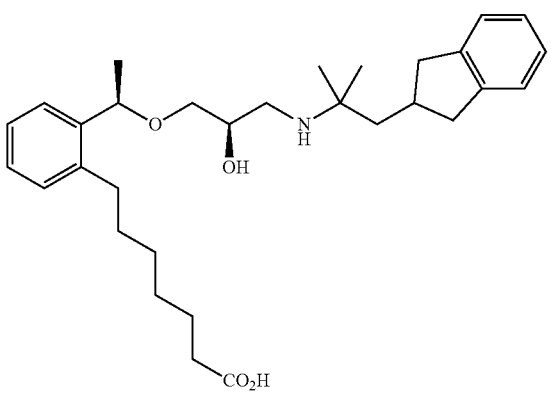 | $^1$H-NMR (CDCl$_3$) δ: 1.36 (6H, s), 1.38-1.44 (7H, m), 1.50-1.65 (4H, m), 1.92 (2H, d, J = 6.0 Hz), 2.20 (2H, t, J = 6.4 Hz), 2.43-2.68 (5H, m), 2.83 (1H, t, J = 10.8 Hz), 3.03-3.10 (3H, m), 3.35 (1H, dd, J = 10.8, 7.1 Hz), 3.48 (1H, dd, J = 10.5, 5.5 Hz), 4.19-4.30 (1H, m), 4.81 (1H, q, J = 6.3 Hz), 7.08-7.22 (7H, m), 7.32-7.39 (1H, m). |

The compounds of the Examples described below were produced with reference to the steps that are described in Examples 1 to 14 above. In Examples 1 to 68, for instance, the production steps are carried out in the order of (1) coupling reaction, (2) olefin hydrogenation, and (3) ester hydrolysis, like the production steps 1(a), 1(b), and 1(c) of Example 1. However, Examples 69 to 80 are distinguished in that the production steps are carried out in the order of (1) olefin hydrogenation, (2) coupling reaction, and (3) ester hydrolysis.

TABLE 60

| Example No. | Structure | Data |
|---|---|---|
| 69(69a) | ![structure] | $^1$H-NMR (CDCl$_3$) δ: 1.10 (6H, s), 1.25 (3H, td, J = 7.2, 2.9 Hz), 1.42 (3H, d, J = 6.9 Hz), 1.63-1.71 (2H, m), 2.49-2.64 (6H, m), 2.69 (1H, dd, J = 12.0, 4.0 Hz), 2.91-2.96 (2H, m), 3.06 (2H, dd, J = 14.3, 7.4 Hz), 3.26-3.33 (2H, m), 3.71-3.75 (1H, m), 4.14 (2H, q, J = 7.2 Hz), 4.71 (1H, q, J = 6.5 Hz), 7.09-7.17 (5H, m), 7.20 (1H, dd, J = 8.6, 2.3 Hz), 7.37 (1H, d, J = 8.6 Hz). |
| 69(69b) | ![structure] | $^1$H-NMR (CDCl$_3$) δ: 1.40 (3H, s), 1.42 (3H, s), 1.45 (3H, d, J = 6.3 Hz), 1.95-2.07 (2H, m), 2.38-2.50 (2H, m), 2.44 (2H, d, J = 5.2 Hz), 2.53-2.68 (3H, m), 2.95-3.14 (5H, m), 3.53-3.59 (1H, m), 3.64-3.68 (1H, m), 4.10-4.16 (1H, m), 4.93-5.01 (1H, m), 7.08-7.15 (5H, m), 7.16-7.21 (2H, m). |

TABLE 60-continued

| Example No. | Structure | Data |
|---|---|---|
| 70(70a) | 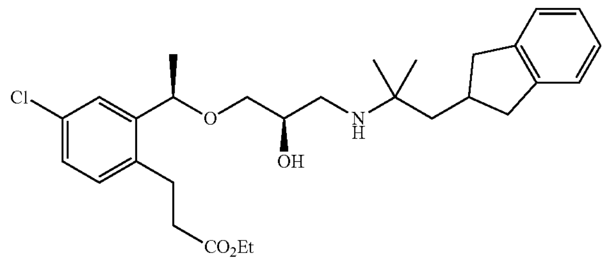 | ¹H-NMR (CDCl₃) δ: 1.11 (6H, s), 1.24 (3H, t, J = 7.2 Hz), 1.43 (3H, d, J = 6.3 Hz), 1.65-1.71 (2H, m), 2.51-2.64 (6H, m), 2.73 (1H, dd, J = 12.0, 4.0 Hz), 2.92 (2H, t, J = 7.7 Hz), 3.03-3.08 (2H, m), 3.28 (1H, dd, J = 9.5, 4.6 Hz), 3.35 (1H, dd, J = 9.5, 6.0 Hz), 3.73-3.78 (1H, m), 4.13 (2H, q, J = 7.2 Hz), 4.71 (1H, q, J = 6.3 Hz), 7.07-7.17 (6H, m), 7.41 (1H, d, J = 2.3 Hz). |
| 70(70b) | 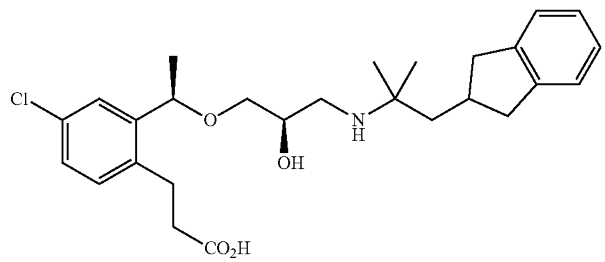 | ¹H-NMR (CDCl₃) δ: 1.40 (3H, s), 1.41 (3H, s), 1.45 (3H, d, J = 6.3 Hz), 1.98 (1H, dd, J = 13.7, 6.3 Hz), 2.04 (1H, dd, J = 13.7, 6.3 Hz), 2.37-2.49 (2H, m), 2.52-2.68 (4H, m), 2.95-3.14 (5H, m), 3.52-3.61 (1H, m), 3.66-3.70 (1H, m), 4.11-4.19 (1H, m), 4.92-5.00 (1H, m), 7.09-7.17 (7H, m), 7.23 (1H, br s). |
| 71(71a) | 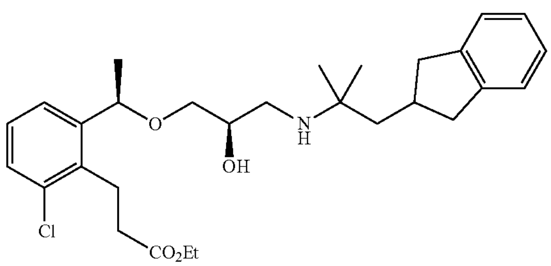 | ¹H-NMR (CDCl₃) δ: 1.10 (6H, s), 1.22-1.30 (3H, m), 1.40-1.47 (3H, m), 1.63-1.71 (2H, m), 2.45-2.75 (6H, m), 2.95-3.21 (4H, m), 3.25-3.36 (2H, m), 3.69-3.78 (1H, m), 4.11-4.22 (2H, m), 4.70-4.82 (1H, m), 5.26-5.32 (1H, m), 7.01-7.23 (6H, m), 7.32-7.42 (1H, m). |
| 71(71b) | 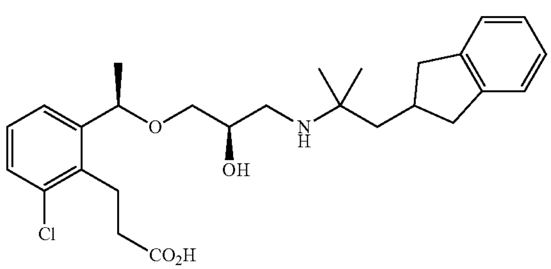 | ¹H-NMR (CDCl₃) δ: 1.42-1.49 (9H, m), 2.00-2.13 (2H, m), 2.37-2.68 (5H, m), 2.95-3.16 (5H, m), 3.24-3.31 (1H, m), 3.50-3.64 (1H, m), 3.65-3.73 (1H, m), 4.17-4.26 (1H, m), 4.93-5.15 (1H, m), 7.08-7.15 (6H, m), 7.27-7.29 (1H, m). |

TABLE 61

| Example No. | Structure | Data |
|---|---|---|
| 72(72a) | 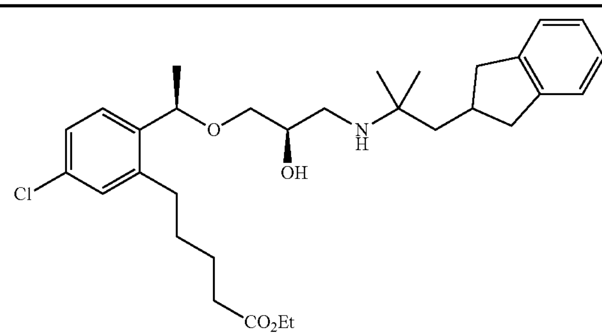 | ¹H-NMR (CDCl₃) δ: 1.10-1.12 (6H, m), 1.25-1.27 (3H, m), 1.40-1.41 (3H, m), 1.58-1.74 (6H, m), 2.32-2.37 (2H, m), 2.49-2.71 (7H, m), 3.02-3.09 (2H, m), 3.23-3.32 (2H, m), 3.70-3.76 (1H, m), 4.10-4.16 (2H, m), 4.65-4.71 (1H, m), 7.10-7.20 (6H, m), 7.36 (1H, dd, J = 8.5, 3.4 Hz). |

TABLE 61-continued
| | | |
|---|---|---|
| 72(72b) | 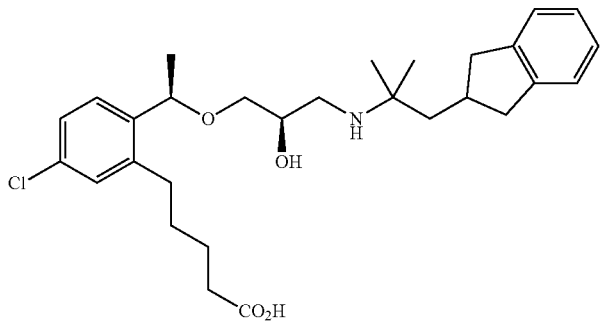 | ¹H-NMR (CDCl₃) δ: 1.32 (3H, s), 1.34 (3H, s), 1.37 (3H, d, J = 6.3 Hz), 1.44-1.56 (2H, m), 1.63-1.72 (2H, m), 1.85-1.92 (2H, m), 2.13-2.19 (1H, m), 2.29-2.34 (1H, m), 2.37-2.43 (1H, m), 2.45-2.52 (1H, m), 2.54-2.68 (3H, m), 2.82-2.87 (1H, m), 3.01-3.09 (3H, m), 3.25-3.32 (1H, m), 3.52 (1H, dd, J = 10.9, 5.7 Hz), 4.25-4.30 (1H, m), 4.72 (1H, q, J = 6.3 Hz), 7.08 (1H, d, J = 2.3 Hz), 7.11-7.17 (6H, m), 7.28 (1H, d, J = 7.7 Hz). |
| 73(73a) | 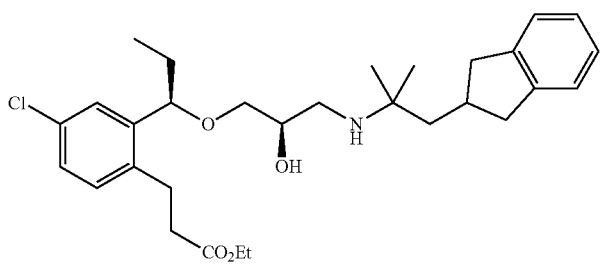 | ¹H-NMR (CDCl₃) δ: 0.97 (3H, t, J = 7.3 Hz), 1.11 (6H, s), 1.26 (3H, t, J = 7.3 Hz), 1.58-1.83 (4H, m), 2.48-2.67 (6H, m), 2.73 (1H, dd, J = 11.7, 3.9 Hz), 2.84-3.01 (2H, m), 3.06 (2H, dd, J = 14.9, 7.1 Hz), 3.26-3.36 (2H, m), 3.72-3.80 (1H, m), 4.13 (2H, q, J = 7.3 Hz), 4.43-4.49 (1H, m), 7.05-7.19 (6H, m), 7.37 (1H, s). |
| 73(73b) | 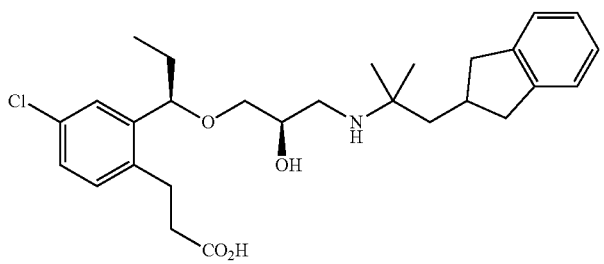 | ¹H-NMR (CDCl₃) δ: 0.88 (3H, t, J = 7.3 Hz), 1.41 (6H, s), 1.53-1.65 (1H, m), 1.74-1.84 (1H, m), 1.93-1.99 (2H, m), 2.43-2.67 (5H, m), 2.72-2.81 (1H, m), 2.82-2.90 (1H, m), 2.93-3.13 (3H, m), 3.16-3.23 (1H, m), 3.38-3.46 (1H, m), 3.48-3.55 (1H, m), 4.30-4.38 (1H, m), 4.73-4.80 (1H, m), 7.08-7.18 (6H, m), 7.27-7.29 (1H, m). |
| 74(74a) | 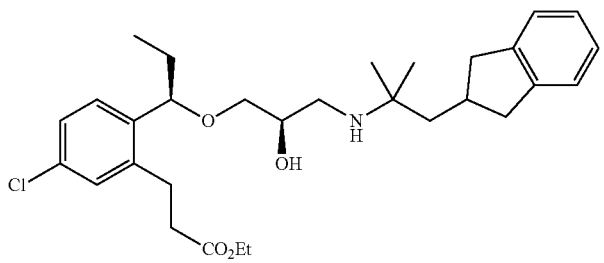 | ¹H-NMR (CDCl₃) δ: 0.92-1.00 (3H, m), 1.11 (6H, s), 1.22-1.30 (3H, m), 1.57-1.72 (3H, m), 1.72-1.85 (1H, m), 2.46-2.75 (7H, m), 2.86-3.13 (4H, m), 3.24-3.35 (2H, m), 3.69-3.79 (1H, m), 4.08-4.20 (2H, m), 4.42-4.51 (1H, m), 7.07-7.23 (6H, m), 7.28-7.36 (1H, m). |
| 74(74b) | 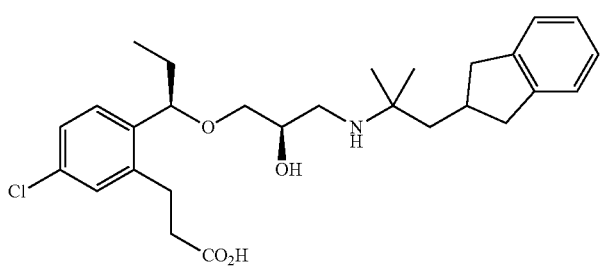 | ¹H-NMR (CDCl₃) δ: 0.84 (3H, t, J = 7.3 Hz), 1.40 (6H, s), 1.55-1.66 (1H, m), 1.76-1.88 (1H, m), 1.90-2.03 (2H, m), 2.44-2.69 (5H, m), 2.76-2.94 (2H, m), 2.97-3.17 (4H, m), 3.38-3.55 (2H, m), 4.24-4.33 (1H, m), 4.77 (1H, t, J = 6.6 Hz), 7.09-7.20 (6H, m), 7.22 (1H, d, J = 8.3 Hz). |

TABLE 61-continued

| | | |
|---|---|---|
| 75(75a) | 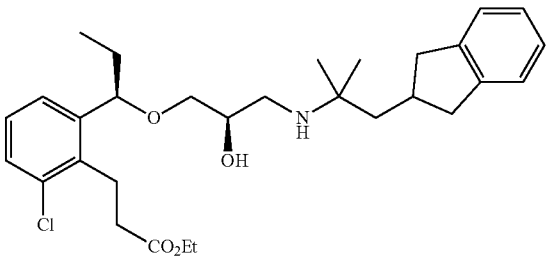 | ¹H-NMR (CDCl₃) δ: 0.98 (3H, t, J = 7.3 Hz), 1.11 (6H, s), 1.28 (3H, t, J = 7.1 Hz), 1.60-1.84 (4H, m), 2.47-2.67 (6H, m), 2.67-2.75 (1H, m), 2.99-3.21 (4H, m), 3.25-3.34 (2H, m), 3.70-3.79 (1H, m), 4.17 (2H, q, J = 7.1 Hz), 4.47-4.54 (1H, m), 7.09-7.20 (5H, m), 7.25-7.35 (2H, m). |

TABLE 62

| | | |
|---|---|---|
| 75(75b) | 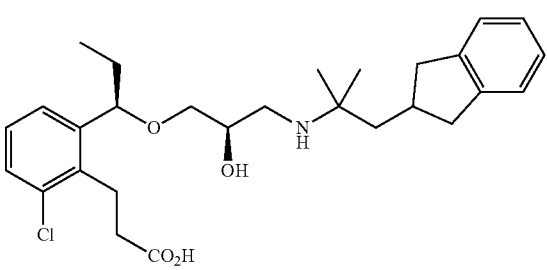 | ¹H-NMR (CDCl₃) δ: 0.83-0.91 (3H, m), 1.45 (6H, s), 1.57-1.67 (1H, m), 1.79-1.89 (1H, m), 1.95-2.04 (2H, m), 2.50-2.69 (5H, m), 2.86-2.95 (1H, m), 2.98-3.24 (5H, m), 3.44-3.59 (2H, m), 4.35-4.43 (1H, m), 4.85-4.95 (1H, m), 7.09-7.17 (6H, m), 7.20-7.28 (1H, m). |
| 76(76a) | 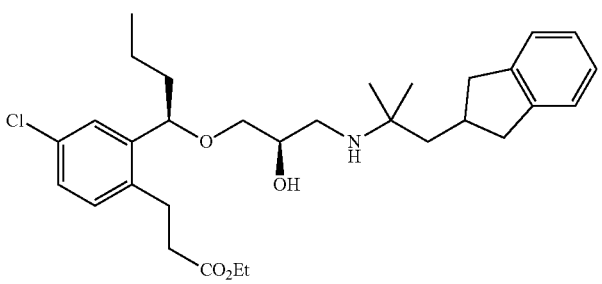 | ¹H-NMR (CDCl₃) δ: 0.93 (3H, t, J = 6.9 Hz), 1.11 (6H, s), 1.24 (3H, t, J = 7.3 Hz), 1.32-1.43 (1H, m), 1.48-1.58 (2H, m), 1.68 (2H, d, J = 6.0 Hz), 1.70-1.78 (1H, m), 2.50-2.68 (6H, m), 2.72 (1H, dd, J = 11.7, 3.9 Hz), 2.85-2.99 (2H, m), 3.06 (2H, dd, J = 14.4, 6.6 Hz), 3.28 (2H, d, J = 5.5 Hz), 3.72-3.78 (1H, m), 4.13 (2H, q, J = 7.3 Hz), 4.53 (1H, dd, J = 8.5, 3.9 Hz), 7.07 (1H, d, J = 8.3 Hz), 7.10-7.13 (2H, m), 7.14-7.19 (3H, m), 7.38 (1H, d, J = 2.3 Hz). |
| 76(76b) | 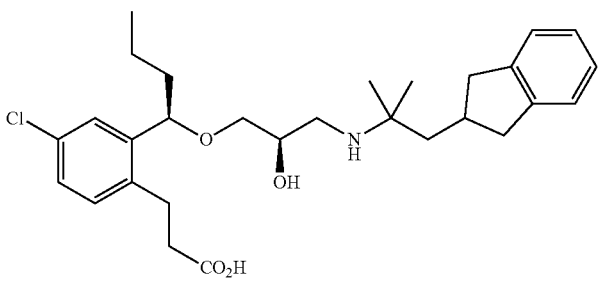 | ¹H-NMR (CDCl₃) δ: 0.88 (3H, t, J = 7.2 Hz), 1.42 (6H, s), 1.49-1.55 (1H, m), 1.73-1.79 (1H, m), 1.97-1.99 (2H, m), 2.46-2.57 (4H, m), 2.60-2.66 (3H, m), 2.75-2.81 (1H, m), 2.83-2.89 (1H, m), 2.96-3.03 (1H, m), 3.06-3.12 (3H, m), 3.19 (1H, d, J = 10.9 Hz), 3.41-3.45 (1H, m), 3.49-3.53 (1H, m), 4.31-4.36 (1H, m), 4.85-4.87 (1H, m), 7.09-7.17 (6H, m), 7.28 (1H, s). |
| 77(77a) | 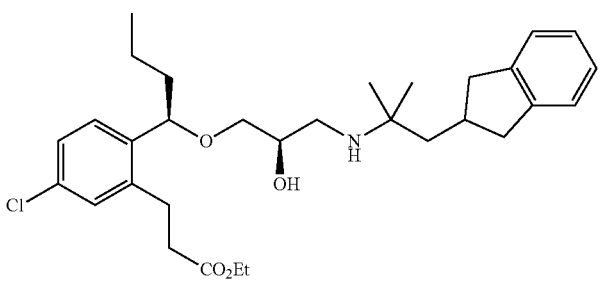 | ¹H-NMR (CDCl₃) δ: 0.92 (3H, t, J = 7.2 Hz), 1.10 (6H, s), 1.25 (3H, t, J = 7.2 Hz), 1.31-1.40 (1H, m), 1.48-1.56 (2H, m), 1.67 (2H, d, J = 6.3 Hz), 1.70-1.78 (1H, m), 2.52-2.64 (6H, m), 2.69 (1H, dd, J = 12.0, 4.0 Hz), 2.88-2.99 (2H, m), 3.06 (2H, dd, J = 14.6, 7.2 Hz), 3.24-3.30 (2H, m), 3.70-3.74 (1H, m), 4.14 (2H, q, J = 7.2 Hz), 4.53 (1H, dd, J = 8.6, 4.0 Hz), 7.11 (2H, dd, J = 5.7, 3.4 Hz), 7.13 (1H, d, J = 2.3 Hz), 7.15-7.17 (2H, m), 7.19 (1H, dd, J = 8.3, 2.3 Hz), 7.33 (1H, d, J = 8.6 Hz). |

TABLE 62-continued

| 77(77b) | 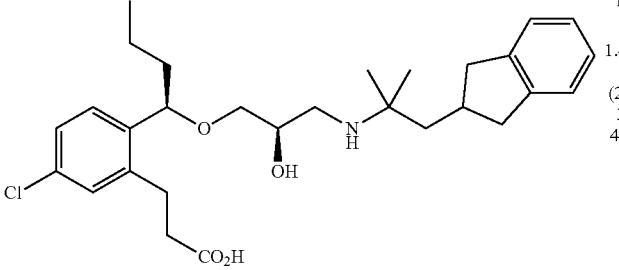 | ¹H-NMR (CDCl₃) δ: 0.87 (3H, t, J = 7.3 Hz), 1.37-1.45 (1H, m), 1.43 (6H, d, J = 4.1 Hz), 1.48-1.58 (1H, m), 1.73-1.81 (1H, m), 1.97 (2H, d, J = 6.0 Hz), 2.51-2.66 (6H, m), 2.77-2.90 (2H, m), 2.97-3.04 (1H, m), 3.06-3.13 (2H, m), 3.18 (1H, d, J = 11.5 Hz), 3.39-3.50 (2H, m), 4.31-4.37 (1H, br m), 4.83-4.86 (1H, m), 7.11-7.16 (6H, m), 7.23 (1H, d, J = 8.3 Hz). |
| --- | --- | --- |
| 78(78a) | 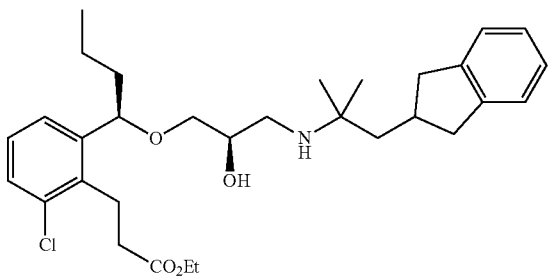 | ¹H-NMR (CDCl₃) δ: 0.93 (3H, t, J = 7.1 Hz), 1.11 (6H, s), 1.28 (3H, t, J = 6.6 Hz), 1.34-1.45 (1H, m), 1.49-1.58 (2H, m), 1.67 (2H, d, J = 6.0 Hz), 1.71-1.78 (1H, m), 2.52-2.66 (6H, m), 2.70 (1H, dd, J = 11.5, 4.1 Hz), 3.00-3.09 (3H, m), 3.12-3.20 (1H, m), 3.24-3.32 (2H, m), 3.71-3.76 (1H, m), 4.17 (2H, q, J = 6.6 Hz), 4.57 (1H, dd, J = 8.7, 3.7 Hz), 7.10-7.13 (2H, m), 7.14-7.18 (3H, m), 7.27 (1H, d, J = 7.8 Hz), 7.33 (1H, d, J = 7.8 Hz). |
| 78(78b) | 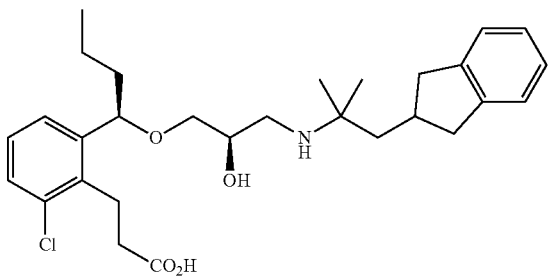 | ¹H-NMR (CDCl₃) δ: 0.89 (3H, t, J = 7.1 Hz), 1.32-1.38 (1H, m), 1.41-1.53 (2H, m), 1.49 (6H, s), 1.62-1.73 (1H, m), 2.02 (2H, d, J = 5.0 Hz), 2.51-2.59 (1H, m), 2.61-2.67 (4H, m), 2.91 (1H, dd, J = 11.9, 9.2 Hz), 2.96-3.04 (1H, m), 3.08-3.14 (3H, m), 3.29 (1H, d, J = 11.9 Hz), 3.39 (1H, dd, J = 11.5, 7.8 Hz), 3.45 (1H, dd, J = 11.5, 5.0 Hz), 4.43-4.48 (1H, m), 4.86 (1H, dd, J = 8.0, 3.9 Hz), 7.11-7.17 (6H, m), 7.25 (1H, t, J = 8.7 Hz). |

TABLE 63

| 79(79a) | 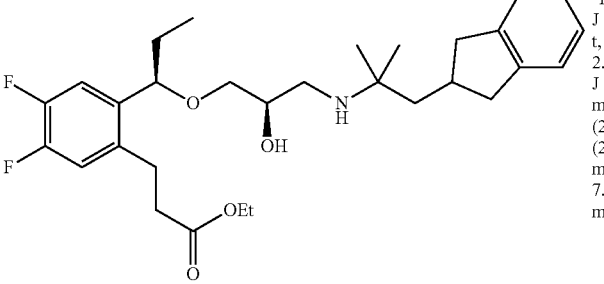 | ¹H-NMR (CDCl₃) δ: 0.96 (3H, t, J = 7.4 Hz), 1.11 (6H, s), 1.24 (3H, t, J = 7.4 Hz), 1.57-1.79 (4H, m), 2.49-2.66 (6H, m), 2.72 (1H, dd, J = 11.5, 4.0 Hz), 2.82-2.97 (2H, m), 3.02-3.10 (2H, m), 3.26-3.35 (2H, m), 3.70-3.77 (1H, m), 4.14 (2H, q, J = 7.4 Hz), 4.41-4.47 (1H, m), 6.95 (1H, dd, J = 11.5, 7.4 Hz), 7.09-7.13 (2H, m), 7.14-7.23 (3H, m). |
| --- | --- | --- |
| 79(79b) | 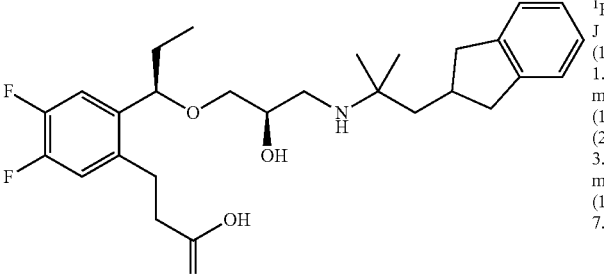 | ¹H-NMR (CDCl₃) δ: 0.87 (3H, t, J = 7.4 Hz), 1.43 (6H, s), 1.51-1.62 (1H, m), 1.72-1.82 (1H, m), 1.91-2.05 (2H, m), 2.40-2.67 (5H, m), 2.68-2.78 (1H, m), 2.83-2.90 (1H, m), 2.92-3.02 (1H, m), 3.10 (2H, dd, J = 15.2, 7.2 Hz), 3.14-3.22 (1H, m), 3.35-3.49 (2H, m), 4.30-4.38 (1H, m), 4.69-4.77 (1H, m), 6.93-6.99 (1H, m), 7.06-7.18 (5H, m). |

TABLE 63-continued

| | | |
|---|---|---|
| 80(80a) | [structure] | ¹H-NMR (CDCl₃) δ: 0.97 (3H, t, J = 7.4 Hz), 1.11 (6H, s), 1.25 (3H, t, J = 6.9 Hz), 1.58-1.66 (1H, m), 1.68 (2H, d, J = 5.7 Hz), 1.70-1.78 (1H, m), 2.48-2.66 (6H, m), 2.72 (1H, dd, J = 12.0, 4.0 Hz), 2.86-3.00 (2H, m), 3.06 (2H, dd, J = 14.9, 7.4 Hz), 3.30-3.33 (2H, m), 3.73-3.77 (1H, m), 4.14 (2H, q, J = 7.4 Hz), 4.48-4.53 (1H, m), 6.67-6.71 (1H, m), 6.92-6.98 (1H, m), 7.09-7.13 (2H, m), 7.14-7.18 (2H, m). |
| 80(80b) | [structure] | ¹H-NMR (CDCl₃) δ: 0.74-0.83 (3H, m), 1.41 (6H, s), 1.57-1.63 (1H, m), 1.83-2.06 (3H, m), 2.34-2.68 (5H, m), 2.81-3.14 (6H, m), 3.41-3.67 (2H, m), 4.17-4.33 (1H, m), 4.77-4.90 (1H, m), 6.63-6.69 (1H, m), 6.77-6.83 (1H, m), 7.07-7.17 (4H, m). |

Example 81

(2R)-1-[(2S)-2-(3-Fluoro-4-methylbenzyl)pyrrolidin-1-yl]-3-[(1R)-1-{2-[2-(2H-tetrazol-5-yl)ethyl]phenyl}ethoxy]propan-2-ol (81a) 5-Ethenyl-2-{[2-(trimethylsilyl)ethoxy]methyl-2H-tetrazole 5-Ethenyl-2H-tetrazole (5.85 g, 60.9 mmol) described in WO 2009/10530, [2-(chloromethoxy)ethyl](trimethyl)silane (12.9 mL, 73.1 mmol), and potassium carbonate (16.8 g, 122 mmol) were dissolved in N,N-dimethyl formamide (300 mL) and stirred for 22 hours at room temperature under a nitrogen atmosphere. The reaction solution was fractionated by adding ethyl acetate/hexane (1:1, V/V) and water thereto, and the aqueous layer was extracted with ethyl acetate/hexane (1:1, V/V). The organic layers were combined, washed with saturated brine, and dried over anhydrous sodium sulfate. The solvent was distilled off under reduced pressure. The residue was purified by silica gel column chromatography (hexane:ethyl acetate, 100:0-70:30, V/V) to give the title compound as a colorless oily substance (6.31 g, yield 46%).

(81b) 5-[(E)-2-(2-{(1R)-1-[(2R)-Oxiran-2-yl methoxy]ethyl}phenyl)ethenyl]-2-[[2-(trimethylsilyl)ethoxy]methyl]-2H-tetrazole By using 5-ethenyl-2-{[2-(trimethylsilyl)ethoxy]methyl-2H-tetrazole which had been obtained in Example 81(81a), the reaction was carried out in the same manner as the method described in Example 4(4c) to give the title compound as a yellow oily substance (yield 88%).

(81c) (2R)-1-{[2-(2,3-Dihydro-1H-inden-2-yl)-1,1-dimethylethyl]amino}-3-[(1R)-1-{2-[(E)-2-(2-{[2-(trimethylsilyl)ethoxy]methyl}-2H-tetrazol-5-yl)ethenyl]phenyl}ethoxy]propan-2-ol By using 5-[(E)-2-(2-{(1R)-1-[(2R)-oxiran-2-yl methoxy]ethyl}phenyl)ethenyl]-2-[[2-(trimethylsilyl)ethoxy]methyl]-2H-tetrazole which had been obtained in Example 81(81b), the reaction was carried out in the same manner as the method described in Example 1(1a) to give the title compound as a colorless oily substance (quantitative).

(81d) (2R)-1-{[2-(2,3-Dihydro-1H-inden-2-yl)-1,1-dimethylethyl]amino}-3-[(1R)-1-{2-[2-(2-{[2-(trimethylsilyl)ethoxy]methyl}-2H-tetrazol-5-yl)ethyl]phenyl}ethoxy]propan-2-ol By using (2R)-1-{[2-(2,3-dihydro-1H-inden-2-yl)-1,1-dimethylethyl]amino}-3-[(1R)-1-{2-[(E)-2-(2-{[2-(trimethylsilyl)ethoxy]methyl}-2H-tetrazol-5-yl)ethenyl]phenyl}ethoxy]propan-2-ol which had been obtained in Example 81(81c), the reaction was carried out in the same manner as the method described in Example 1(1b) to give the title compound as a colorless oily substance (yield 99%).

(81e) (2R)-1-{[2-(2,3-Dihydro-1H-inden-2-yl)-1,1-dimethylethyl]amino}-3-[(1R)-1-{2-[2-(2H-tetrazol-5-yl)ethyl]phenyl}ethoxy]propan-2-ol formate (2R)-1-{[2-(2,3-Dihydro-1H-inden-2-yl)-1,1-dimethylethyl]amino}-3-[(1R)-1-{2-[2-(2-{[2-(trimethylsilyl)ethoxy]methyl}-2H-tetrazol-5-yl)ethyl]phenyl}ethoxy]propan-2-ol (580 mg, 0.977 mmol), which had been obtained in Example 81(81d), was dissolved in tetrahydrofuran (4.0 mL), added with 1.0 M solution of tetrabutylammonium fluoride in tetrahydrofuran (3.22 mL, 3.22 mmol), and then stirred at 45° C. for 27 hours. The reaction solution was cooled to room temperature and the solvent was distilled off under reduced pressure. The resultant was added with ethyl acetate and 1 N aqueous hydrochloride solution for neutralization and extracted with ethyl acetate. The solvent was removed under reduced pressure. The residue was purified by reverse phase HPLC (column: Develosil (NOMURA CHEMICAL) 28 mm×10 cm; flow rate: 25 mL/min; mobile phase: 0.1% aqueous formic acid solution: 0.1% acetonitrile formate solution, 55:45, V/V) to give the title compound as a colorless amorphous substance (170 mg, yield 34%).

Example 82

3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}-2,2-dimethylpropanoic acid (82a) Methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}propanoate To a solution of methyl 3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}propanoate (557 mg, 1.23 mmol), which had been obtained in Example 1(1b), in tetrahydrofuran (12 mL), carbonyl diimidazole (398 mg, 2.46 mmol) and 4-dimethylaminopyridine (14.7 mg, 0.12 mmol) were added and stirred at 50° C. for 26 hours. Upon the completion of the reaction, the reaction solution was diluted with ethyl acetate, washed with 1 N aqueous hydrogen chloride solution and saturated brine, and then dried over anhydrous magnesium sulfate. After that, the solvent was distilled off under reduced pressure. The residue was purified by silica gel chromatography (n-hexane/ethyl acetate=65/35) to give the title compound as a colorless oily substance (493 mg, yield 84%).

(82b) Methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}-2-methylpropanoate To diisopropylamine (0.028 mL, 0.20 mmol), a 2.69 M solution of n-butyl lithium in hexane (0.74 mL, 0.20 mmol) was added at −78° C. followed by stirring for 15 minutes. After adding anhydrous tetrahydrofuran (0.2 mL), the mixture was further stirred for 5 minutes at −78° C. Subsequently, a solution of methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}propanoate (48 mg, 0.10 mmol), which had been obtained in Example 82(82a), in tetrahydrofuran (0.2 mL) was added thereto and stirred at −78° C. for 15 minutes. After adding methyl iodide (0.013 mL, 0.20 mmol), the mixture was stirred at −78° C. for 1.25 hours. Upon the completion of the reaction, the temperature was raised to room temperature. The mixture was added with a saturated aqueous ammonium chloride solution and extracted with dichloromethane. The solvent was distilled off under reduced pressure. The residue was purified by silica gel chromatography (n-hexane/ethyl acetate=7/3) to give the title compound as a colorless oily substance (29.6 mg, yield 60%).

(82c) Methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}-2,2-dimethylpropanoate To diisopropylamine (0.07 mL, 0.50 mmol), a 2.69 M solution of n-butyl lithium in hexane (0.19 mL, 0.50 mmol) was added at −78° C. followed by stirring for 20 minutes. After adding anhydrous tetrahydrofuran (0.5 mL), the mixture was further stirred for 15 minutes at −78° C. Subsequently, a solution of methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}-2-methylpropanoate (245 mg, 0.50 mmol), which had been obtained in Example 82(82b), in tetrahydrofuran (0.5 mL) was added thereto and stirred at −78° C. for 1 hour. After adding methyl iodide (0.14 mL, 2.28 mmol), the mixture was stirred at room temperature for 22 hours. Upon the completion of the reaction, the mixture was added with a saturated aqueous ammonium chloride solution and extracted with ethyl acetate. The solvent was distilled off under reduced pressure. The residue was purified by silica gel chromatography (n-hexane/ethyl acetate=75/25) to give the title compound as a pale yellow oily substance (207 mg, yield 82%).

(82d) 3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}-2,2-dimethylpropanoic acid To a solution of methyl 3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}-2,2-dimethylpropanoate (206 mg, 0.41 mmol), which had been obtained in Example 82(82c), in methanol (3 mL), 50% aqueous potassium hydroxide solution (1.5 mL) was added, and stirred at 100° C. for 26 hours. Upon the completion of the reaction, the reaction solution was neutralized by adding 6 N aqueous hydrogen chloride solution, diluted with water, and extracted with ethyl acetate. After that, the solvent was distilled off under reduced pressure. The residue was purified by silica gel chromatography (ethyl acetate/methanol=85/15) to give the title compound as a white solid (112 mg, yield 59%).

Example 83

(2-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}ethoxy)acetic acid (83a) (2R)-1-[(1R)-1-(2-Bromophenyl)ethoxy]-3-{[1-(2,3-dihydro-1H-inden-2-yl)-2-methylpropan-2-yl]amino}propan-2-ol By using (2R)-2-{[(1R)-1-(2-bromo phenyl)ethoxy]methyl}oxirane described in WO 2004/106280, the reaction was carried out in the same manner as the method described in Example 1(1a) to give the title compound as a colorless oily substance (yield 99%).

(83b)

(5R)-5-{[(1R)-1-(2-Bromophenyl)ethoxy]methyl}-3-[1-(2,3-dihydro-1H-inden-2-yl)-2-methylpropan-2-yl]-1,3-oxazolidin-2-one By using (2R)-1-[(1R)-1-(2-bromophenyl)ethoxy]-3-{[1-(2,3-dihydro-1H-inden-2-yl)-2-methylpropan-2-yl]amino}propan-2-ol which had been obtained in Example 83(83a), the reaction was carried out in the same manner as the method described in Example 82(82a) to give the title compound as an oily substance (yield 94%).

(83c) (5R)-3-[1-(2,3-Dihydro-1H-inden-2-yl)-2-methylpropan-2-yl]-5-{[(1R)-1-(2-ethenylphenyl)ethoxy]methyl}-1,3-oxazolidin-2-one (5R)-5-{[(1R)-1-(2-Bromophenyl)ethoxy]methyl}-3-[1-(2,3-dihydro-1H-inden-2-yl)-2-methylpropan-2-yl]-1,3-oxazolidin-2-one (1.12 g, 2.38 mmol), which had been obtained in Example 83(83b), was dissolved in 1,4-dioxane (25 mL), added with tributyl(vinyl) tin (1.04 mL, 3.57 mmol) and tetrakistriphenyl phosphine palladium (277 mg, 0.24 mmol), and stirred for 16 hours at 100° C. After cooling the reaction solution to room temperature, the solvent was distilled off under reduced pressure. The residue was purified by silica gel chromatography (n-hexane/ethyl acetate=4/1) to give the title compound as a colorless oily substance (970 mg, yield 97%).

(83d) (5R)-3-[1-(2,3-Dihydro-1H-inden-2-yl)-2-methylpropan-2-yl]-5-({(1R)-1-[2-(2-hydroxyethyl)phenyl]ethoxy}methyl)-1,3-oxazolidin-2-one (5R)-3-[1-(2,3-Dihydro-1H-inden-2-yl)-2-methylpropan-2-yl]-5-{[(1R)-1-(2-ethenylphenyl)ethoxy]methyl}-1,3-oxazolidin-2-one (970 mg, 2.32 mmol), which had been obtained in Example 83(83c), was dissolved in tetrahydrofuran (20 mL) and added at 0° C. with a 0.5 M solution of 9-borabicyclo[3,3,1]nonane (5.56 mL, 2.78 mmol) in tetrahydrofuran. After raising the temperature to room temperature, the mixture was stirred for 16 hours. The reaction solution was again cooled to 0° C., added with 1 N aqueous sodium hydroxide solution (10 mL) and 30% hydrogen peroxide solution (10 mL), and then stirred for 4 hours. The reaction solution was extracted with ethyl acetate. The organic layer was washed with saturated brine and dried over anhydrous magnesium sulfate. The solvent was distilled off under reduced pressure. The residue was purified by basic silica gel chromatography (n-hexane/ethyl acetate=2/3) to give the title compound as a colorless oily substance (800 g, yield 79%).

(83e) Ethyl (2-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}ethoxy)acetate (5R)-3-[1-(2,3-Dihydro-1H-inden-2-yl)-2-methylpropan-2-yl]-5-({(1R)-1-[2-(2-hydroxyethyl)phenyl]ethoxy}methyl)-1,3-oxazolidin-2-one (371 mg, 0.82 mmol), which had been obtained in Example 83(83d), was dissolved in methylene chloride (10 mL), added with rhodium diacetate dimer (36 mg, 0.082 mmol) and ethyl diazoacetate (128 µL, 1.23 mmol) at 0° C., and stirred for 1.5 hours. Ethanol was added to the reaction solution to terminate the reaction. The solvent was distilled off under reduced pressure. The residue was purified by basic silica gel chromatography (n-hexane/ethyl acetate=4/1) to give the title compound as a colorless oily substance (298 mg, yield 68%).

(83f) (2-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}ethoxy)acetic acid Ethyl (2-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}ethoxy)acetate (298 mg, 0.56 mmol) which had been obtained in Example 83(83e) was dissolved in a mixture solution of methanol-water (1:1, 8 mL), added with potassium hydroxide (3.33 g, 50.5 mmol), and then refluxed with heating for 16 hours. The reaction solution was cooled to 0° C., and neutralized by adding 10 N aqueous hydrogen chloride solution (50.5 mmol), and then extracted with ethyl acetate. The organic layer was washed with saturated brine and dried over anhydrous magnesium sulfate. The solvent was distilled off under reduced pressure. The residue was purified by diolsilica gel (SHOKO SCIENTIFIC CO., LTD.) column chromatography (dichloromethane/methanol=15/1) to give the title compound as a colorless amorphous substance (165 mg, yield 63%).

Example 84

{2-[(1R)-1-{[(2R)-3-{[1-(2,3-Dihydro-1H-inden-2-yl)-2-methylpropan-2-yl]amino}-2-hydroxypropyl]oxy}ethyl]phenyl}acetic acid (84a) {2-[(1R)-1-({(5R)-3-[1-(2,3-Dihydro-1H-inden-2-yl)-2-methylpropan-2-yl]-2-oxo-1,3-oxazolidin-5-yl}methoxy)ethyl]phenyl}acetic acid (5R)-3-[1-(2,3-Dihydro-1H-inden-2-yl)-2-methylpropan-2-yl]-5-({(1R)-1-[2-(2-hydroxyethyl)phenyl]ethoxy}methyl)-1,3-oxazolidin-2-one (200 mg, 0.46 mmol) which had been obtained in Example 83(83d) was dissolved in a mixture solution of acetonitrile-water (2:1, 4 mL), added with 2,2,6,6-tetramethylpiperidine 1-oxyl free radical (36 mg, 0.23 mmol) and iodobenzene diacetate (589 mg, 1.83 mmol), and stirred at room temperature for 16 hours. The reaction solution was added with 1 N aqueous hydrogen chloride solution, and then extracted with ethyl acetate. The organic layer was washed with saturated brine and dried over anhydrous magnesium sulfate. The solvent was distilled off under reduced pressure. The residue was purified by silica gel column chromatography (n-hexane/ethyl acetate=3/7) to give the title compound as a colorless oily substance (121 mg, yield 59%).

(84b) {2-[(1R)-1-{[(2R)-3-{[1-(2,3-Dihydro-1H-inden-2-yl)-2-methylpropan-2-yl]amino}-2-hydroxypropyl]oxy}ethyl]phenyl}acetic acid By using {2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}acetic acid which had been obtained in Example 84(84a), the reaction was carried out in the same manner as the method described in Example 83(83f) to give the title compound as a colorless amorphous substance (yield 31%).

Example 85

(3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}propoxy)acetic acid (85a) Ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}prop-2-enoate By using ethyl (2E)-3-(2-{(1R)-1-[(2R)-oxiran-2-yl methoxy]ethyl}phenyl)prop-2-enoate which had been obtained in Example 14(14a), the reaction was carried out in the same manner as the method described in Example 1(1a) to give the title compound as a colorless oily substance (yield 92%).

(85b) (5R)-3-[1-(2,3-Dihydro-1H-inden-2-yl)-2-methylpropan-2-yl]-5-({(1R)-1-[2-(3-hydroxypropyl)phenyl]ethoxy}methyl)-1,3-oxazolidin-2-one To a solution of ethyl (2E)-3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}prop-2-enoate (710 mg, 1.53 mmol), which had been obtained in Example 85(85a), in tetrahydrofuran (15 mL), carbonyl diimidazole (497 mg, 3.07 mmol) and 4-dimethylamino pyridine (18 mg, 0.15 mmol) were added and stirred at 50° C. for 5 hours. The reaction solution was cooled to room temperature. 1 N aqueous hydrogen chloride solution was added to the reaction solution, which was then extracted with ethyl acetate. After that, the organic layer was washed with saturated brine, and dried over anhydrous sodium sulfate. The solvent was distilled off under reduced pressure. The residue was dissolved in ethanol (20 mL), added with 10% palladium-carbon (wet, 50 wt %, 70 mg), and then vigorously stirred at room temperature for 9 hours under a hydrogen atmosphere. The reaction solution was filtered through Celite and washed with ethanol. The solvent was distilled off under reduced pressure. Subsequently, the residue was dissolved in tetrahydrofuran (15 mL), added with methanol (1 mL) and sodium borohydride (116 mg, 3.06 mmol), and then stirred at room temperature for 2 hours. The reaction solution was added with 1 N aqueous hydrogen chloride solution and extracted with ethyl acetate. The organic layer was washed with saturated brine, dried over anhydrous magnesium sulfate. The solvent was distilled off under reduced pressure. The residue was purified by silica gel column chromatography (n-hexane/ethyl acetate=2/3) to give the title compound as a colorless oily substance (548 mg, 3 step, yield 79%).

(85c) Ethyl (3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}propoxy)acetate By using (5R)-3-[1-(2,3-dihydro-1H-inden-2-yl)-2-methylpropan-2-yl]-5-({(1R)-1-[2-(3-hydroxypropyl)phenyl]ethoxy}methyl)-1,3-oxazolidin-2-one which had been obtained in Example 85(85b), the reaction was carried out in the same manner as the method described in Example 83(83e) to give the title compound as a colorless oily substance (yield 72%).

(85d) (3-{2-[(1R)-1-{[(2R)-3-{[1-(2,3-Dihydro-1H-inden-2-yl)-2-methylpropan-2-yl]amino}-2-hydroxypropyl]oxy}ethyl]phenyl}propoxy)acetic acid By using ethyl (3-{2-[(1R)-1-({(5R)-3-[1-(2,3-dihydro-1H-inden-2-yl)-2-methylpropan-2-yl]-2-oxo-1,3-oxazolidin-5-yl}methoxy)ethyl]phenyl}propoxy)acetate which had been obtained in Example 85(85c), the reaction was carried out in the same manner as the method described in Example 83(83f) to give the title compound as a colorless amorphous substance (yield 83%).

The structures and physicochemical data of the compounds that are described in Examples 81 to 85 are given below. Further, the compounds described with a number behind the hyphen indicate that the compounds are produced according to the same method as the corresponding compounds on which they are based. Specifically, Reference example 1(1a)-2 indicates that the production is carried out with the same method as Reference example 1(1a).

TABLE 64

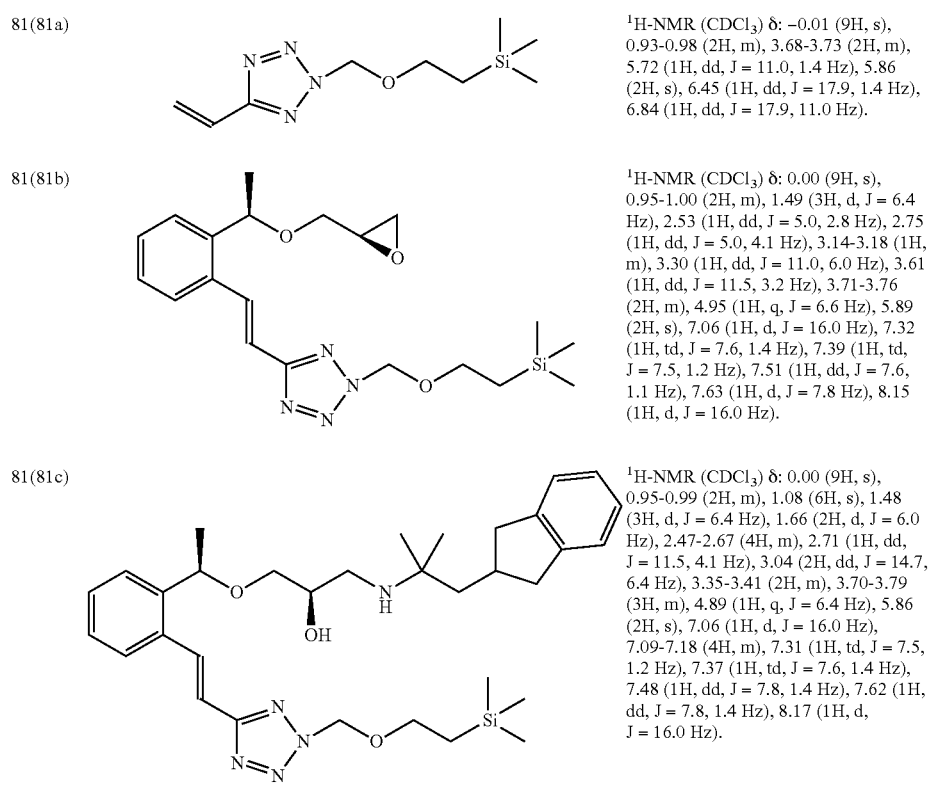

| 81(81a) | | $^1$H-NMR (CDCl$_3$) δ: −0.01 (9H, s), 0.93-0.98 (2H, m), 3.68-3.73 (2H, m), 5.72 (1H, dd, J = 11.0, 1.4 Hz), 5.86 (2H, s), 6.45 (1H, dd, J = 17.9, 1.4 Hz), 6.84 (1H, dd, J = 17.9, 11.0 Hz). |
| 81(81b) | | $^1$H-NMR (CDCl$_3$) δ: 0.00 (9H, s), 0.95-1.00 (2H, m), 1.49 (3H, d, J = 6.4 Hz), 2.53 (1H, dd, J = 5.0, 2.8 Hz), 2.75 (1H, dd, J = 5.0, 4.1 Hz), 3.14-3.18 (1H, m), 3.30 (1H, dd, J = 11.0, 6.0 Hz), 3.61 (1H, dd, J = 11.5, 3.2 Hz), 3.71-3.76 (2H, m), 4.95 (1H, q, J = 6.6 Hz), 5.89 (2H, s), 7.06 (1H, d, J = 16.0 Hz), 7.32 (1H, td, J = 7.6, 1.4 Hz), 7.39 (1H, td, J = 7.5, 1.2 Hz), 7.51 (1H, dd, J = 7.6, 1.1 Hz), 7.63 (1H, d, J = 7.8 Hz), 8.15 (1H, d, J = 16.0 Hz). |
| 81(81c) | | $^1$H-NMR (CDCl$_3$) δ: 0.00 (9H, s), 0.95-0.99 (2H, m), 1.08 (6H, s), 1.48 (3H, d, J = 6.4 Hz), 1.66 (2H, d, J = 6.0 Hz), 2.47-2.67 (4H, m), 2.71 (1H, dd, J = 11.5, 4.1 Hz), 3.04 (2H, dd, J = 14.7, 6.4 Hz), 3.35-3.41 (2H, m), 3.70-3.79 (3H, m), 4.89 (1H, q, J = 6.4 Hz), 5.86 (2H, s), 7.06 (1H, d, J = 16.0 Hz), 7.09-7.18 (4H, m), 7.31 (1H, td, J = 7.5, 1.2 Hz), 7.37 (1H, td, J = 7.6, 1.4 Hz), 7.48 (1H, dd, J = 7.8, 1.4 Hz), 7.62 (1H, dd, J = 7.8, 1.4 Hz), 8.17 (1H, d, J = 16.0 Hz). |

TABLE 65

| | | |
|---|---|---|
| 81(81d) | 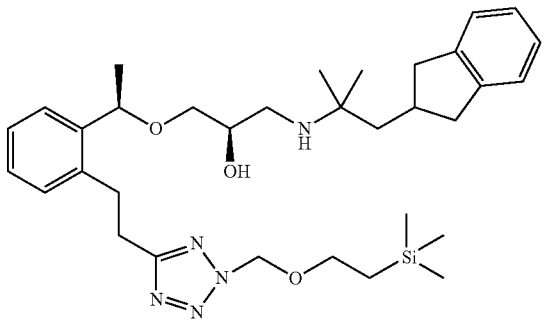 | ¹H-NMR (CDCl$_3$) δ: −0.01 (9H, s), 0.92-0.97 (2H, m), 1.10 (6H, s), 1.46 (3H, d, J = 6.4 Hz), 1.67 (2H, d, J = 6.0 Hz), 2.49-2.66 (4H, m), 2.69 (1H, dd, J = 11.9, 4.1 Hz), 3.02-3.09 (2H, m), 3.12-3.24 (4H, m), 3.28-3.36 (2H, m), 3.65-3.70 (2H, m), 3.72-3.79 (1H, m), 4.81 (1H, q, J = 6.4 Hz), 5.82 (2H, s), 7.09-7.20 (6H, m), 7.21-7.27 (1H, m), 7.44 (1H, d, J = 6.9 Hz). |
| 81(81e) | 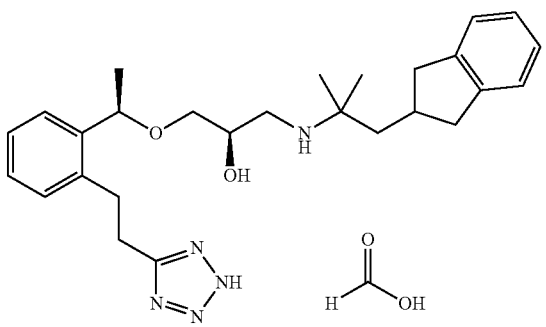 | ¹H-NMR (DMSO-D$_6$) δ: 1.32 (3H, s), 1.33 (3H, s), 1.34 (3H, d, J = 6.4 Hz), 1.91 (2H, d, J = 6.0 Hz), 2.50-2.61 (3H, m), 2.77 (1H, dd, J = 12.4, 8.7 Hz), 3.00-3.09 (4H, m), 3.01 (3H, s), 3.19-3.28 (2H, m), 3.88-3.96 (1H, m), 4.84 (1H, q, J = 6.4 Hz), 7.07-7.12 (2H, m), 7.15-7.21 (4H, m), 7.21-7.26 (1H, m), 7.30-7.35 (1H, m), 8.20 (1H, s). |
| 82(82a) | 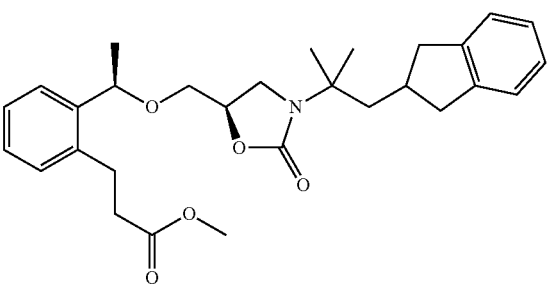 | ¹H-NMR (CDCl$_3$) δ: 1.38 (3H, s), 1.39 (3H, s), 1.42 (3H, d, J = 6.3 Hz), 2.12 (2H, d, J = 6.3 Hz), 2.42-2.51 (1H, m), 2.57-2.67 (4H, m), 2.94-3.04 (4H, m), 3.38 (1H, dd, J = 10.3, 5.7 Hz), 3.44-3.47 (2H, m), 3.66 (1H, t, J = 8.6 Hz), 3.67 (3H, s), 4.52 (1H, ddd, J = 12.3, 7.2, 4.0 Hz), 4.78 (1H, q, J = 6.5 Hz), 7.09-7.12 (4H, m), 7.14 (1H, t, J = 6.0 Hz), 7.17 (1H, td, J = 7.4, 1.7 Hz), 7.22 (1H, td, J = 7.4, 1.1 Hz), 7.42 (1H, dd, J = 7.7, 1.4 Hz). |
| 82(82b) | 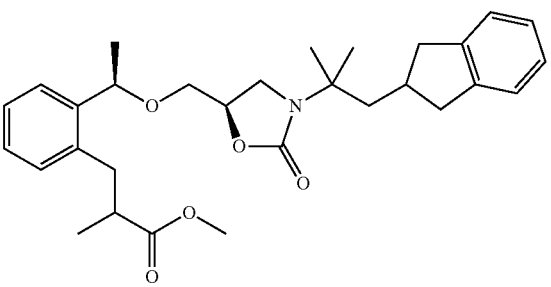 | ¹H-NMR (CDCl$_3$) δ: 1.16 (1.5H, d, J = 6.3 Hz), 1.19 (1.5H, d, J = 6.9 Hz), 1.37-1.42 (9.0H, m), 2.12 (2.0H, d, J = 6.3 Hz), 2.43-2.51 (1.0H, m), 2.61-2.73 (4.0H, m), 2.98-3.08 (3.0H, m), 3.35 (0.5H, dd, J = 9.7, 5.7 Hz), 3.37 (0.5H, dd, J = 10.0, 5.4 Hz), 3.43-3.48 (2.0H, m), 3.59 (1.5H, s), 3.62 (1.5H, s), 3.65 (0.5H, dd, J = 12.6, 10.9 Hz), 3.67 (0.5H, dd, J = 8.6, 1.1 Hz), 4.52 (1.0H, ddd, J = 12.5, 7.3, 3.9 Hz), 4.78 (0.5H, q, J = 6.5 Hz), 4.81 (0.5H, q, J = 6.5 Hz), 7.07 (1.0H, ddd, J = 7.4, 1.5, 0.8 Hz), 7.09-7.12 (3.0H, m), 7.13-7.17 (2.0H, m), 7.22 (1.0H, tdd, J = 7.5, 3.3, 1.2 Hz), 7.42 (1.0H, dd, J = 8.0, 1.1 Hz). |
| 82(82c) | 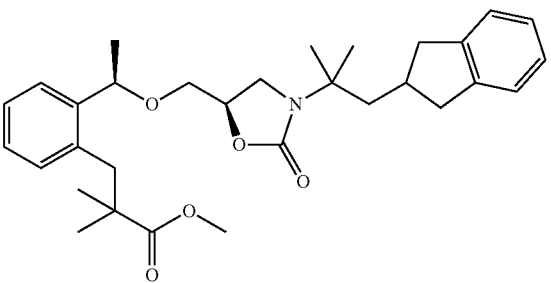 | ¹H-NMR (CDCl$_3$) δ: 1.19 (3H, s), 1.19 (3H, s), 1.36 (3H, s), 1.38 (3H, s), 1.38 (3H, d, J = 6.4 Hz), 2.11 (2H, dd, J = 6.2, 1.1 Hz), 2.40-2.51 (1H, m), 2.60-2.67 (2H, m), 2.87 (1H, d, J = 14.2 Hz), 2.96 (1H, d, J = 14.2 Hz), 2.97-3.05 (2H, m), 3.35 (1H, dd, J = 10.1, 6.0 Hz), 3.41 (1H, dd, J = 8.7, 6.0 Hz), 3.47 (1H, dd, J = 9.8, 4.8 Hz), 3.65 (1H, t, J = 8.7 Hz), 3.68 (3H, s), 4.50 (1H, ddd, J = 12.6, 6.6, 3.9 Hz), 4.83 (1H, q, J = 6.3 Hz), 6.98 (1H, dd, J = 7.8, 1.4 Hz), 7.09-7.16 (5H, m), 7.22 (1H, td, J = 7.6, 1.4 Hz), 7.44 (1H, dd, J = 7.8, 1.4 Hz). |

TABLE 65-continued

| | | |
|---|---|---|
| 82(82d) | 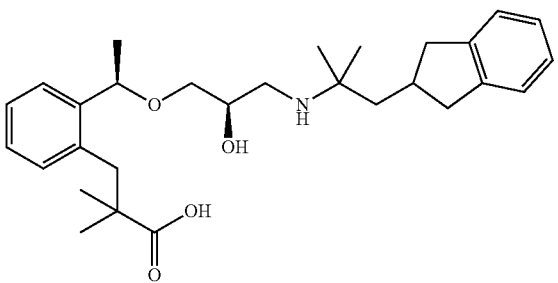 | $^1$H-NMR (CDCl$_3$) δ: 1.11 (3H, s), 1.18 (3H, s), 1.19 (3H, s), 1.31 (3H, s), 1.33 (3H, d, J = 6.4 Hz), 1.67 (1H, dd, J = 14.2, 6.4 Hz), 1.81 (1H, dd, J = 14.2, 6.4 Hz), 2.32 (1H, d, J = 13.3 Hz), 2.33-2.44 (1H, m), 2.54 (2H, dd, J = 15.1, 9.6 Hz), 2.89 (1H, dd, J = 12.1, 3.4 Hz), 2.99 (1H, dd, J = 7.6, 1.6 Hz), 3.02-3.07 (2H, m), 3.29 (1H, d, J = 13.7 Hz), 3.65 (1H, dd, J = 11.2, 5.3 Hz), 3.86 (1H, dd, J = 11.2, 5.7 Hz), 4.08-4.15 (1H, m), 5.22 (1H, q, J = 6.3 Hz), 7.08-7.18 (7H, m), 7.36 (1H, d, J = 6.9 Hz). |

TABLE 66

| | | |
|---|---|---|
| 83(83a) | 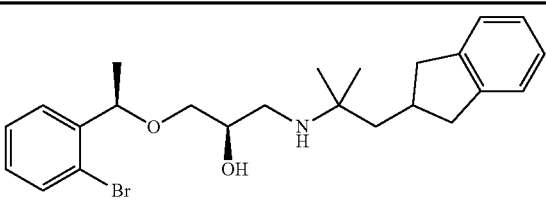 | $^1$H-NMR (CDCl$_3$) δ: 1.11 (6H, s), 1.43 (3H, d, J = 6.4 Hz), 1.68 (2H, d, J = 6.0 Hz), 2.51-2.65 (4H, m), 2.71 (1H, dd, J = 11.5, 4.1 Hz), 3.04-3.10 (2H, m), 3.36 (2H, d, J = 5.5 Hz), 3.73-3.78 (1H, m), 4.85 (1H, q, J = 6.4 Hz), 7.09-7.18 (5H, m), 7.32 (1H, t, J = 7.6 Hz), 7.47-7.52 (2H, m). |
| 83(83b) | 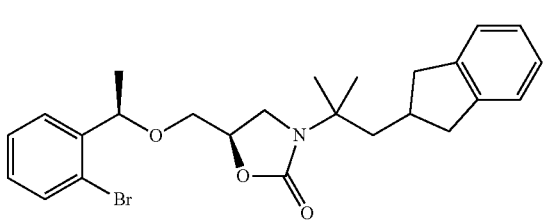 | $^1$H-NMR (CDCl$_3$) δ: 1.38-1.42 (9H, m), 2.10-2.19 (2H, m), 2.44-2.56 (1H, m), 2.62-2.70 (2H, m), 3.00-3.07 (2H, m), 3.44-3.56 (3H, m), 3.68 (1H, t, J = 8.7 Hz), 4.49-4.55 (1H, m), 4.86 (1H, q, J = 6.3 Hz), 7.07-7.17 (5H, m), 7.31 (1H, t, J = 7.6 Hz), 7.46-7.50 (2H, m). |
| 83(83c) | 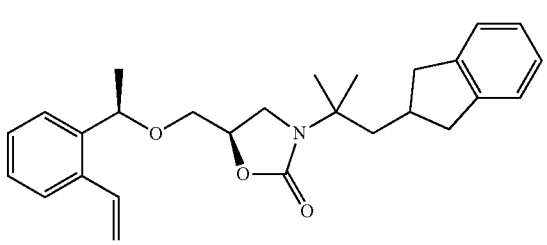 | $^1$H-NMR (CDCl$_3$) δ: 1.37-1.43 (9H, m), 2.10-2.14 (2H, m), 2.42-2.52 (1H, m), 2.60-2.68 (2H, m), 2.97-3.05 (2H, m), 3.39-3.48 (3H, m), 3.63-3.69 (1H, m), 4.49-4.56 (1H, m), 4.75-4.81 (1H, m), 5.29-5.33 (1H, m), 5.57-5.62 (1H, m), 7.01-7.17 (5H, m), 7.20-7.28 (2H, m), 7.38 (1H, d, J = 7.3 Hz), 7.44 (1H, d, J = 7.3 Hz). |
| 83(83d) | 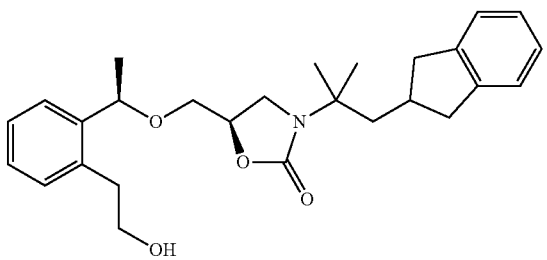 | $^1$H-NMR (CDCl$_3$) δ: 1.37 (3H, s), 1.39 (3H, s), 1.42 (3H, d, J = 6.9 Hz), 2.07-2.15 (3H, m), 2.42-2.52 (1H, m), 2.61-2.67 (2H, m), 2.87-3.04 (4H, m), 3.43-3.50 (3H, m), 3.67 (1H, t, J = 8.9 Hz), 3.77-3.88 (2H, m), 4.50-4.55 (1H, m), 4.80 (1H, q, J = 6.5 Hz), 7.09-7.23 (7H, m), 7.36-7.38 (1H, m). |
| 83(83e) | 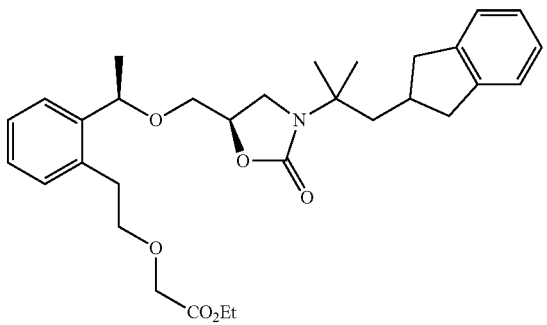 | $^1$H-NMR (CDCl$_3$) δ: 1.74 (3H, t, J = 7.2 Hz), 1.37 (3H, s), 1.39 (3H, s), 1.41 (3H, d, J = 6.4 Hz), 2.10-2.13 (2H, m), 2.40-2.52 (1H, m), 2.60-2.67 (2H, m), 2.90-3.04 (4H, m), 3.38 (1H, dd, J = 10.1, 6.0 Hz), 3.44-3.48 (2H, m), 3.64-3.76 (3H, m), 4.05 (2H, s), 4.20 (2H, q, J = 7.2 Hz), 4.48-4.55 (1H, m), 4.83 (1H, q, J = 6.4 Hz), 7.09-7.24 (7H, m), 7.42 (1H, d, J = 7.3 Hz). |

TABLE 66-continued

| 83(83f) | 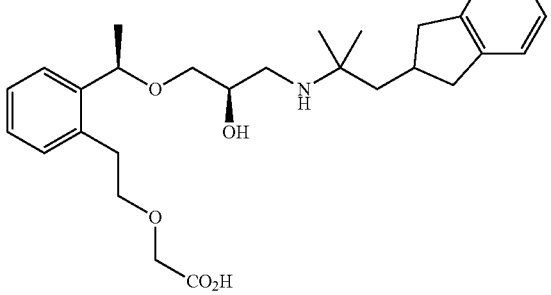 | ¹H-NMR (CDCl₃) δ: 1.89 (3H, d, J = 6.5 Hz), 1.45 (6H, s), 2.00 (2H, d, J = 6.3 Hz), 2.47-2.56 (1H, m), 2.58-2.65 (2H, m), 2.82-2.88 (1H, m), 2.92-2.98 (1H, m), 2.99-3.11 (3H, m), 3.22-3.26 (1H, m), 3.42 (1H, dd, J = 11.2, 6.3 Hz), 3.51 (1H, dd, J = 11.2, 4.9 Hz), 3.61-3.65 (2H, m), 3.86 (1H, d, J = 16.0 Hz), 4.04 (1H, d, J = 16.0 Hz), 4.33-4.40 (1H, m), 4.94 (1H, q, J = 6.5 Hz), 7.10-7.23 (7H, m), 7.35-7.37 (1H, m). |
|---|---|---|
| 84(84e) | 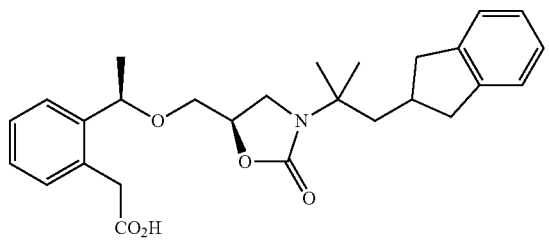 | ¹H-NMR (CDCl₃) δ: 1.36 (6H, s), 1.40 (3H, d, J = 6.0 Hz), 2.02 (1H, dd, J = 13.7, 6.2 Hz), 2.17 (1H, dd, J = 13.7, 6.4 Hz), 2.41-2.51 (1H, m), 2.59-2.67 (2H, m), 2.97-3.04 (2H, m), 3.31 (1H, dd, J = 8.7, 6.4 Hz), 3.39-3.47 (2H, m), 3.62-3.67 (2H, m), 3.75 (1H, d, J = 16.5 Hz), 4.55-4.61 (1H, m), 4.84 (1H, q, J = 6.4 Hz), 7.09-7.18 (5H, m), 7.20-7.24 (1H, m), 7.27-7.31 (1H, m), 7.42-7.44 (1H, m). |

TABLE 67

| 84(84f) | 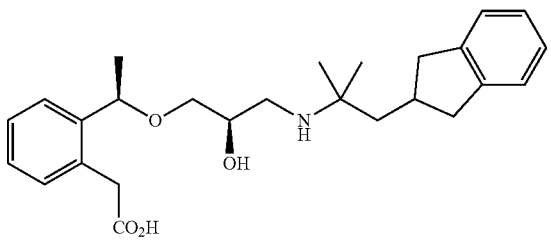 | ¹H-NMR (CDCl₃) δ: 1.71 (6H, s), 1.43 (3H, d, J = 6.3 Hz), 1.79-1.88 (2H, m), 2.39-2.49 (1H, m), 2.53-2.59 (2H, m), 2.82 (1H, dd, J = 12.6, 8.0 Hz), 3.00-3.05 (2H, m), 3.11-3.15 (1H, m), 3.39 (1H, dd, J = 10.9, 6.9 Hz), 3.53-3.61 (3H, m), 4.17-4.23 (1H, m), 4.87 (1H, q, J = 6.3 Hz), 7.11-7.19 (8H, m), 7.27-7.30 (1H, m). |
|---|---|---|
| 85(85a) | 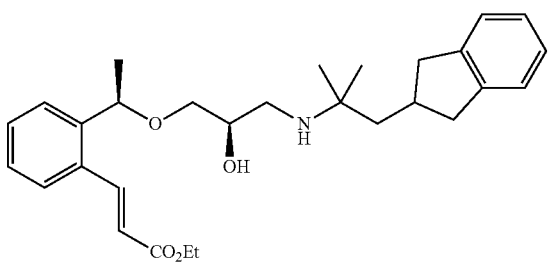 | ¹H-NMR (CDCl₃) δ: 1.10 (6H, s), 1.34 (3H, t, J = 7.1 Hz), 1.45 (3H, d, J = 6.5 Hz), 1.67 (2H, d, J = 7.2 Hz), 2.50-2.63 (4H, m), 2.71 (1H, dd, J = 11.5, 4.0 Hz), 3.05 (2H, dd, J = 14.6, 7.7 Hz), 3.32-3.39 (2H, m), 3.73-3.78 (1H, m), 4.27 (2H, q, J = 7.1 Hz), 4.83 (1H, q, J = 6.5 Hz), 6.33 (1H, d, J = 15.5 Hz), 7.10-7.13 (2H, m), 7.14-7.18 (2H, m), 7.29 (1H, d, J = 7.4 Hz), 7.39 (1H, t, J = 7.4 Hz), 7.47 (1H, d, J = 8.0 Hz), 7.54 (1H, d, J = 8.0 Hz), 8.10 (1H, d, J = 15.5 Hz). |
| 85(85b) | 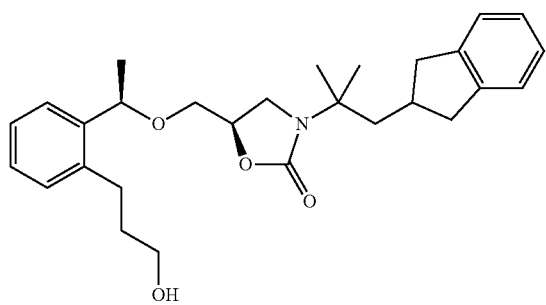 | ¹H-NMR (CDCl₃) δ: 1.35 (3H, s), 1.38 (3H, s), 1.42 (3H, d, J = 6.3 Hz), 1.77-1.86 (2H, m), 2.05-2.13 (2H, m), 2.19 (1H, t, J = 6.0 Hz), 2.39-2.49 (1H, m), 2.59-2.69 (3H, m), 2.73-2.79 (1H, m), 2.95-3.02 (2H, m), 3.40 (1H, dd, J = 8.6, 6.3 Hz), 3.45 (2H, d, J = 5.2 Hz), 3.65-3.69 (3H, m), 4.54-4.59 (1H, m), 4.91 (1H, q, J = 6.5 Hz), 7.09-7.21 (7H, m), 7.38-7.40 (1H, m). |

TABLE 67-continued

| 85(85c) | 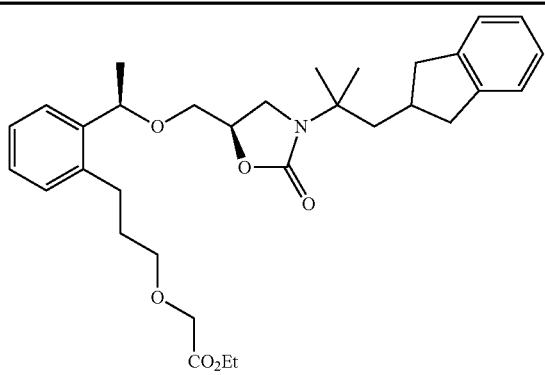 | ¹H-NMR (CDCl₃) δ: 1.29 (3H, t, J = 7.1 Hz), 1.36-1.42 (9H, m), 1.84-1.91 (2H, m), 2.11 (2H, d, J = 6.1 Hz), 2.42-2.52 (1H, m), 2.60-2.67 (2H, m), 2.70-2.75 (2H, m), 2.96-3.05 (2H, m), 3.37 (1H, dd, J = 10.0, 5.9 Hz), 3.42-3.46 (2H, m), 3.55-3.59 (2H, m), 3.66 (1H, t, J = 8.8 Hz), 4.07 (2H, s), 4.22 (2H, q, J = 7.1 Hz), 4.48-4.55 (1H, m), 4.78 (1H, q, J = 6.3 Hz), 7.09-7.22 (7H, m), 7.41 (1H, t, J = 4.4 Hz). |
|---|---|---|
| 85(85d) | 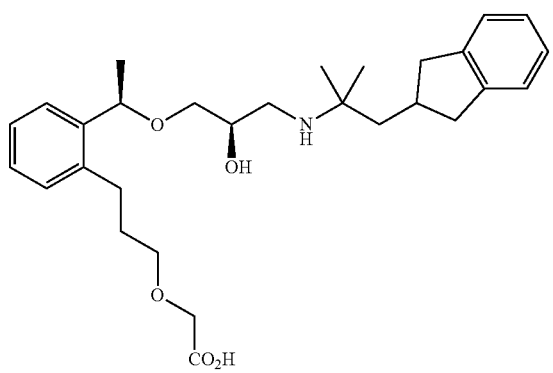 | ¹H-NMR (CDCl₃) δ: 1.40-1.44 (9H, m), 1.86-1.94 (2H, m), 1.96-2.07 (2H, m), 2.46-2.57 (1H, m), 2.59-2.69 (3H, m), 2.79-2.90 (2H, m), 3.03-3.15 (3H, m), 3.43 (1H, dd, J = 11.0, 6.0 Hz), 3.50-3.60 (3H, m), 3.85 (1H, d, J = 14.7 Hz), 3.92 (1H, d, J = 14.7 Hz), 4.28-4.35 (1H, m), 4.90 (1H, q, J = 6.3 Hz), 7.10-7.22 (7H, m), 7.26-7.29 (1H, m). |

REFERENCE EXAMPLE

Reference Example 1

1-(2-Bromo-3-ethoxyphenyl)ethanone (1a) 2-Bromo-N,3-dimethoxy-N-methylbenzamide

2-Bromo-3 methoxy benzoic acid (14.2 g, 61.5 mmol) was dissolved in acetonitrile (250 mL), added with 4-methylmorpholine (13.5 mL, 123 mmol), N-methoxy methanamine hydrochloride (7.19 g, 73.8 mmol), and 4-(4,6-dimethoxy-1,3,5-triazin-2-yl)-4-methylmorpholin-4-ium chloride (20.4 g, 73.8 mmol), and stirred for 17 hours at room temperature. 1 N aqueous hydrochloric acid solution was added to the reaction solution, which was then extracted with ethyl acetate. The organic layers were combined, washed with saturated brine, and dried over anhydrous sodium sulfate. The solvent was distilled off under reduced pressure. The residue was purified by silica gel column chromatography (hexane:ethyl acetate, 85:15 to 25:75, V/V) to give the title compound as a colorless oily substance (16.8 g, quantitative).

(1b) 1-(2-Bromo-3-methoxyphenyl)ethanone

Under a nitrogen atmosphere, 2-bromo-N,3-dimethoxy-N-methylbenzamide (16.8 g, 61.5 mmol) which had been obtained in Reference example 1(1a) was dissolved in tetrahydrofuran (300 mL), and added dropwise with a 1.0 M solution of methyl magnesium bromide in tetrahydrofuran (123 mL, 123 mmol) at 0° C. Upon the completion of the dropwise addition, the temperature of the reaction solution was raised to room temperature and stirred for 15 hours. The reaction solution was added with ethyl acetate and 1 N aqueous hydrochloric acid solution for fractionation, and the aqueous layer was extracted with ethyl acetate. The organic layers were combined, washed with saturated aqueous sodium hydrogen carbonate solution, and dried over anhydrous sodium sulfate. The solvent was distilled off under reduced pressure. The residue was purified by silica gel column chromatography (hexane:ethyl acetate, 100:0 to 60:40, V/V) to give the title compound as a colorless oily substance (12.7 g, yield 90%).

(1c) 1-(2-Bromo-3-hydroxy phenyl)ethanone

Under a nitrogen atmosphere, 1-(2-bromo-3-methoxy phenyl)ethanone (30.5 g, 229 mmol) which had been obtained in Reference example 1(1b) was dissolved in methylene chloride (500 mL), and added dropwise with a 1.0 M solution of tribromo phosphine in dichloromethane (293 mL, 293 mmol) at −80° C. over 5 hours. Upon the completion of the dropwise addition, the mixture was stirred for 17 hours at −40° C. Subsequently, the reaction solution was cooled to −80° C. and added dropwise with methanol (500 mL). Upon the completion of the dropwise addition, the temperature was raised to −40° C. followed by stirring for 3 hours. The temperature of the reaction solution was raised to room temperature. The solvent was distilled off under reduced pressure until the solution turned green. After adding ethanol, the mixture was extracted with ethyl acetate/hexane (1:1, V/V). After neutralization with a saturated aqueous solution of sodium hydrogen carbonate, the solvent was distilled off under reduced pressure. The residue was purified by silica gel chromatography (hexane:ethyl acetate, 100:0-55:45, V/V) to give the title compound as a colorless oily substance (13.5 g, yield 47%).

(1d) 1-(2-Bromo-3-ethoxy phenyl)ethanone

Under nitrogen atmosphere, 1-(2-bromo-3-hydroxy phenyl)ethanone (6.50 g, 30.2 mmol), which had been obtained in Reference example 1(1c), and potassium carbonate (8.36 g, 60.5 mmol) were dissolved in N,N-dimethyl formamide (60 mL), and stirred at room temperature for 10 minutes. Subsequently, ethyl iodide (3.14 mL, 39.3 mmol) was added to the mixture, which was then further stirred for 21 hours. Ethyl acetate/hexane (1:1, V/V) and water were added to the reaction solution for fractionation, and the aqueous layer was extracted with ethyl acetate/hexane (1:1, V/V). The organic layers were combined, washed with saturated brine, and dried over anhydrous magnesium sulfate. The solvent was distilled off under reduced pressure. The residue was purified by silica gel chromatography (hexane:ethyl acetate, 100:0-85:15, V/V) to give the title compound as a colorless oily substance (4.89 g, yield 67%).

Reference Example 2

1-[2-Bromo-3-(difluoromethoxy)phenyl]ethanone 1-(2-Bromo-3-hydroxy phenyl)ethanone (6.50 g, 30.2 mmol), which had been obtained in Reference example 1(1c), and copper (I) iodide (2.51 g, 13.2 mmol) were dissolved in acetonitrile (150 mL), followed by addition of a solution of difluoro(fluorosulfonyl)acetic acid (50.0 g, 281 mmol) dissolved in acetonitrile (50 mL) over 1 hour and 30 minutes under heating at 55° C. Upon the completion of the dropwise addition, the reaction solution was stirred at 55° C. for 3 hours, cooled to room temperature, added with water, and then extracted with ethyl acetate/hexane (2:1, V/V). The organic layer was washed with a saturated aqueous sodium hydrogen carbonate solution and dried over anhydrous sodium sulfate. The solvent was distilled off under reduced pressure. The residue was purified by silica gel chromatography (neutral silica gel, hexane:ethyl acetate, 100:0-75:25, V/V and basic silica gel, hexane:ethyl acetate, 100:0-50:50, V/V) to give the title compound as a colorless oily substance (1.53 g, yield 18%).

Reference Example 3

1-(2-Bromo-5-fluoro-3-methoxy phenyl)ethanone (3a) 2-Bromo-4-fluoro-6-methoxy aniline 4-Fluoro-2-methoxy aniline (8.25 g, 58.5 mmol) was dissolved in methylene chloride (200 mL) and added with N-bromosuccinic imide (11.4 g, 64.3 mmol) at −78° C. followed by stirring for 2 hours. The mixture was further stirred at 0° C. for 1.5 hours. The reaction solution was concentrated under reduced pressure. The residue was purified by silica gel chromatography (n-hexane/ethyl acetate=4/1) to give the title compound as a colorless oily substance (4.80 g, yield 37%).

(3b) 1-(2-Amino-5-fluoro-3-methoxy phenyl)ethanone

To a solution of 2-bromo-4-fluoro-6-methoxy aniline (4.80 g, 21.8 mmol), which had been obtained in Reference example 3(3a), in 1,4-dioxane (200 mL), tributyl (1-ethoxy vinyl) tin (11.1 mL, 32.7 mmol) and tetrakistriphenyl phosphine palladium (2.52 g, 2.18 mmol) were added, and the mixture was stirred for 16 hours at 100° C. After cooling the reaction solution to room temperature, 1 N aqueous hydrogen chloride solution (100 mL) was added and stirred further for 2 hours. The reaction solution was concentrated under reduced pressure, neutralized by adding 1 N aqueous sodium hydroxide solution, and then extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a yellow solid substance (2.80 g, yield 70%).

(3c) 1-(2-Bromo-5-fluoro-3-methoxy phenyl)ethanone 1-(2-Amino-5-fluoro-3-methoxy phenyl)ethanone (2.66 g, 14.2 mmol), which had been obtained in Reference example 3(3b), was suspended in 10% aqueous hydrogen bromide solution (22 mL). Then, a 9% aqueous sodium nitrite solution (11 mL, 14.4 mmol) was slowly added dropwise thereto at 0° C. After stirring the mixture solution for 1 hour at 0° C., a solution in which copper bromide (I) (2.24 g, 15.7 mmol) is dissolved in 47% aqueous hydrogen bromide solution (15 mL) was added thereto, and the mixture was refluxed with heating at 110° C. for 2 hours. The reaction solution was cooled to room temperature and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a pale yellow solid (2.15 g, yield 61%).

Reference Example 4

1-(2-Bromo-3-fluoro-4-methylphenyl)ethanone (4a) 6-Bromo-2-fluoro-3-methylaniline By using 2-fluoro-3-methylaniline, the reaction was carried out in the same manner as the method described in Reference example 3(3a) to give the title compound as a pale red solid (yield 60%).

(4b) 2-Fluoro-3-methylaniline

6-Bromo-2-fluoro-3-methylaniline (9.00 g, 44.1 mmol), which had been obtained in Reference example 4(4a), was dissolved in a 1:1 mixture (130 mL) of N,N-dimethyl formamide and methanol, and added with [1,1'-bis(diphenylphosphino)ferrocene]palladium (II) dichloride-dichloromethane complex (10.8 g, 13.2 mmol) and N,N-diisopropylethylamine (23 mL, 132.3 mmol). The mixture was vigorously stirred at 85° C. for 2 hours under a carbon monoxide atmosphere. The reaction solution was cooled to room temperature, added with ethyl acetate and water, filtered using Millicup (registered trademark)-LH, and washed with ethyl acetate. The filtered solution was extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a colorless solid (5.70 g, yield 71%).

(4c) 2-Bromo-3-fluoro-N-methoxy-N,4-dimethylbenzamide

2-Fluoro-3-methylaniline (5.70 g, 31.1 mmol), which had been obtained in Reference example 4(4b), was dissolved in acetonitrile (75 mL), added with t-butyl nitrite (4.85 mL) and copper bromide (II) (7.65 g, 34.3 mmol) at 0° C., and stirred at 65° C. for 2 hours. After cooling to room temperature, 1 N aqueous hydrochloride solution was added to the mixture, which was then extracted with ethyl acetate. The organic layer was washed with saturated brine and dried over anhydrous magnesium sulfate. The solvent was distilled off under reduced pressure. The residue was dissolved in a mixture solution of tetrahydrofuran-methanol-water (4:1:1, 200 mL), added with lithium hydroxide monohydrate (1.38 g, 33.0 mmol), and stirred at room temperature for 4 hours. The mixture was neutralized by adding 1 N aqueous hydrochloride solution, and then extracted with ethyl acetate. The organic layer was washed with saturated brine and dried over anhydrous magnesium sulfate. The solvent was distilled off under reduced pressure. The residue was dissolved in acetonitrile (200 mL), added with N,O-dimethylhydroxylamine hydrochloride (3.80 g, 39.0 mmol), N-methylmorpholine (6.6 mL, 60.0 mmol), and 4-(4,6-dimethoxy-1,3,5-triazin-2-yl)-4-methylmorpholium chloride (12.2 g, 39.0 mmol), and stirred at room temperature for 18 hours. The reaction solution was concentrated under reduced pressure. The resulting residue was added with 1 N aqueous hydrochloride solution and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=3/2) to give the title compound as a colorless oily substance (5.58 g, yield 65%).

(4d) 1-(2-Bromo-3-fluoro-4-methylphenyl)ethanone

By using 2-bromo-3-fluoro-N-methoxy-N, 4-dimethylbenzamide which had been obtained in Reference example 4(4c), the reaction was carried out in the same manner as the method described in Reference example 3(3b) to give the title compound as a colorless oily substance (yield 92%).

Reference Example 5

1-(2-Bromo-3-chloro phenyl)butan-1-one (5a) (2-Bromo-3-chloro phenyl)methanol

A solution of 2-bromo-4-chloro benzoic acid (5.0 g, 21.24 mmol) in tetrahydrofuran (100 mL) was added with 0.99 M solution of borane-tetrahydrofuran complex in tetrahydrofuran (32.2 mL, 21.24 mmol) and stirred at room temperature for 4 hours. The reaction solution was distilled under reduced pressure to remove the solvent, and then slowly added with water (50 mL) under ice cooling. The mixture obtained was extracted with dichloromethane (50 mL×2). After that, the organic layers were washed with saturated sodium hydrogen carbonate (50 mL). The organic layers were combined, washed with saturated brine, and dried over anhydrous sodium sulfate. The solvent was distilled off under reduced pressure to give the title compound as a white solid (4.73 g, quantitative).

(5b) 2-Bromo-3-chlorobenzaldehyde

A solution of (2-bromo-3-chloro phenyl)methanol (4.73 g, 21.24 mmol), which had been obtained in Reference example 5(5a), in methylene chloride (120 mL) was added with 1,1,1-tris(acetoxy)-1,1-dihydro-1,2-benziodoxol-3-(1H)-one (10.8 g, 25.49 mmol) under ice cooling, and stirred at room temperature for 2 hours. The reaction solution was added with a mixture of saturated aqueous sodium hydrogen carbonate solution (60 mL) and saturated aqueous sodium thiosulfate solution (30 mL), and then stirred at room temperature for 0.5 hours. The mixture obtained was extracted with dichloromethane (90 mL×2). After that, the organic layers were combined and dried over anhydrous sodium sulfate. The solvent was distilled off under reduced pressure. The residue was purified by silica gel chromatography (n-hexane/ethyl acetate=5/1) to give the title compound as a white solid (4.36 g, yield 94%).

(5c) 1-(2-Bromo-3-chloro phenyl)butan-1-ol

Under an argon atmosphere, zinc chloride (0.68 g, 4.97 mmol) was added to a 2.0 M solution of n-propyl magnesium chloride in diethyl ether (12.42 mL, 24.93 mmol), and the mixture was stirred at room temperature. After stirring for 0.5 hours, a solution of 2-bromo-3-chlorobenzaldehyde (4.36 g, 19.87 mmol), which had been obtained in Reference example 5(5b), in tetrahydrofuran (10 mL) was added dropwise thereto. After stirring for 2 hours under ice cooling, a saturated aqueous ammonium chloride solution (20 mL) was added thereto. The mixture obtained was extracted with ethyl acetate (20 mL×2). After that, the organic layers were washed with saturated brine and dried over anhydrous sodium sulfate. The solvent was distilled off under reduced pressure. The residue was purified by silica gel chromatography (n-hexane/ethyl acetate=5/1) to give the title compound as a white solid (3.23 g, yield 62%).

(5d) 1-(2-Bromo-3-chloro phenyl)butan-1-one

By using 1-(2-bromo-3-chlorophenyl)butan-1-ol which had been obtained in Reference example 5(5c), the reaction was carried out in the same manner as the method described in Reference example 5(5a) to give the title compound as a yellow oily substance (yield 94%).

Reference Example 6

(1R)-1-(2-Bromo-5-fluorophenyl)propan-1-ol

With reference to Chirality, 2005, 17, 476-480, 1.06 M solution of diethyl zinc in hexane (18.6 ml, 19.7 mmol) was added dropwise under ice cooling to a solution of 1-[(S)-(2-methoxy phenyl){[(1S)-1-phenylethyl]amino}methyl]-2-naphthol (0.38 g, 0.99 mmol) in toluene (5 ml). The mixture was stirred at room temperature for 1 hour. After stirring, the mixture was added with 2-bromo-5-fluorobenzaldehyde (2.0 g, 9.85 mmol) under ice cooling and stirred at room temperature for 16 hours. The reaction solution was added with 1 N aqueous hydrochloride solution and extracted with dichloromethane. The organic layer was washed with saturated brine and dried over anhydrous magnesium sulfate. The solvent was distilled off under reduced pressure. The residue was purified by silica gel chromatography (hexane/ethyl acetate=5/1) to give the title compound as a transparent oily substance (1.81 g, yield 79%).

Reference Example 7

1-Bromo-2-[(1R)-1-cyclopropylethyl]benzene and 1-bromo-2-[(1S)-1-cyclopropylethyl]benzene 2-Bromobenzaldehyde (3.00 g, 16.2 mmol) was dissolved in tetrahydrofuran (50 mL) and added with 1 M solution of cyclopropyl magnesium bromide in tetrahydrofuran (19 mL, 19.0 mmol) at room temperature, and stirred for 3 hours. The reaction solution was added with 1 N aqueous hydrochloride solution and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=7/3) to give the title compound as a colorless oily mixture of enantiomers (3.00 g). The mixture of enantiomers was subjected to optical resolution by supercritical liquid chromatography (column: CHIRALPAK AD-H, 2×25 cm; mobile phase: 10% MeOH in $CO_2$; flow rate: 20 mL/min) to give both the title compounds 1-bromo-2-[(1R)-1-cyclopropylethyl]benzene (1.22 g, RT: 8.5 min, yield 33%) and 1-bromo-2-[(1S)-1-cyclopropylethyl]benzene (1.20 g, RT: 12.5 min, yield 33%), each as a colorless oily substance.

Reference Example 8

Ethyl 3-(5-chloro-2-{(1R)-1-[(2R)-oxiran-2-yl methoxy]ethyl}phenyl)propanoate

Ethyl (2E)-3-(5-chloro-2-{(1R)-1-[(2R)-oxiran-2-yl methoxy]ethyl}phenyl)acrylate (822 mg, 2.65 mmol), which had been obtained in Example 4(4c)-15, was dissolved in ethanol (25 mL), added with rhodium/alumina (246 mg), and stirred for 5 hours at room temperature under a hydrogen atmosphere. The reaction solution was filtered using Celite. The solvent was distilled off under reduced pressure to give the title compound as a colorless oily substance (816 mg, yield 99%).

The structures and physicochemical data of the compounds that are produced in the reference examples are given below.

TABLE 68

| Reference Example No. | Structure | Data |
|---|---|---|
| 1(1a) | 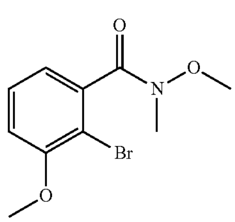 | $^1$H-NMR (CDCl$_3$) δ: 3.11 (0.8H, br s), 3.39 (2.2H, s), 3.48 (2.2H, s), 3.92 (3.8H, s), 6.90-6.94 (2H, m), 7.32 (1H, t, J = 8.0 Hz). |
| 1(1b) | 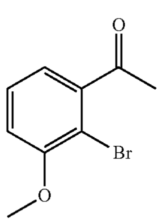 | $^1$H-NMR (CDCl$_3$) δ: 2.61 (3H, s), 3.93 (3H, s), 6.95-6.98 (2H, m), 7.33 (1H, t, J = 8.0 Hz). |
| 1(1c) | 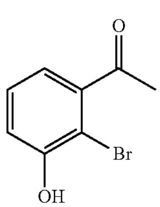 | $^1$H-NMR (CDCl$_3$) δ: 2.62 (3H, s), 5.94 (1H, s), 7.11 (1H, dd, J = 7.9, 1.6 Hz), 7.14 (1H, dd, J = 7.9, 1.6 Hz), 7.29 (1H, t, J = 7.9 Hz). |

TABLE 68-continued

| Reference Example No. | Structure | Data |
|---|---|---|
| 1(1d) | 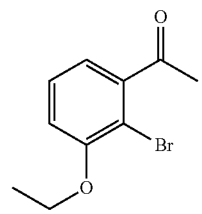 | $^1$H-NMR (CDCl$_3$) δ: 1.49 (3H, t, J = 7.2 Hz), 2.61 (3H, s), 4.13 (2H, q, J = 6.9 Hz), 6.92-6.95 (2H, m), 7.30 (1H, t, J = 7.7 Hz). |
| 1(1d)-2 | 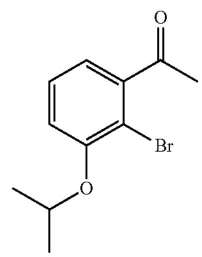 | $^1$H-NMR (CDCl$_3$) δ: 1.39 (6H, d, J = 5.7 Hz), 2.61 (3H, s), 4.55-4.62 (1H, m), 6.92 (1H, dd, J = 8.0, 1.4 Hz), 6.97 (1H, dd, J = 8.0, 1.4 Hz), 7.28 (1H, t, J = 8.0 Hz). |
| 2 | 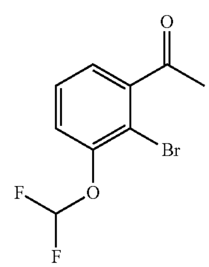 | $^1$H-NMR (CDCl$_3$) δ: 2.63 (3H, s), 6.55 (1H, t, J = 73.0 Hz), 7.26 (1H, dd, J = 7.7, 1.4 Hz), 7.29-7.32 (1H, m), 7.39 (1H, t, J = 7.7 Hz). |

TABLE 69

| Reference Example No. | Structure | Data |
|---|---|---|
| 1(1a)-2 | 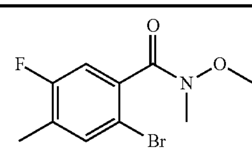 | $^1$H-NMR (CDCl$_3$) δ: 2.28 (3H, d, J = 1.7 Hz), 3.15 (0.3H, s), 3.37 (2.7H, s), 3.50 (2.7H, s), 3.88 (0.3H, s), 6.99 (1H, d, J = 8.6 Hz), 7.40 (1H, d, J = 6.9 Hz). |
| 1(1b)-2 | 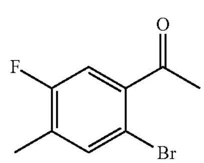 | $^1$H-NMR (CDCl$_3$) δ: 2.29 (3H, d, J = 1.7 Hz), 2.62 (3H, s), 7.20 (1H, d, J = 9.2 Hz), 7.45 (1H, d, J = 6.3 Hz). |
| 1(1a)-3 | 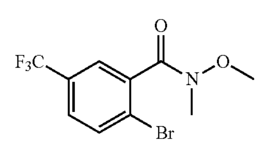 | $^1$H-NMR (CDCl$_3$) δ: 3.19 (0.5H, s), 3.35 (2.5H, s), 3.58 (2.5H, s), 3.93 (0.5H, s), 7.52 (1H, d, J = 8.3 Hz), 7.58 (1H, s), 7.73 (1H, d, J = 8.3 Hz). |
| 1(1b)-3 | 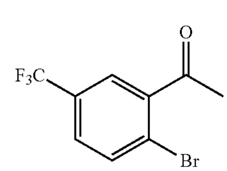 | $^1$H-NMR (CDCl$_3$) δ: 2.67 (3H, s), 7.55 (1H, dd, J = 8.3, 2.3 Hz), 7.70 (1H, s), 7.77 (1H, d, J = 8.3 Hz). |

TABLE 69-continued

| | | |
|---|---|---|
| 1(1a)-4 | [structure: N-methoxy-N-methylbenzamide with Br, F, Me substituents] | ¹H-NMR (CDCl₃) δ: 2.37 (3H, d, J = 2.4 Hz), 3.34 (3H, br s), 3.55 (3H, br s), 7.12 (1H, t, J = 7.4 Hz), 7.39 (1H, d, J = 8.3 Hz). |
| 1(1b)-4 | [structure: 1-(aryl)ethanol with Br, F, Me] | ¹H-NMR (CDCl₃) δ: 1.49 (3H, d, J = 6.9 Hz), 1.83 (1H, d, J = 4.6 Hz), 2.33 (3H, d, J = 2.3 Hz), 5.12-5.18 (1H, m), 7.21 (1H, t, J = 8.0 Hz), 7.34 (1H, d, J = 8.3 Hz). |
| 3(3a) | [structure: aniline with Br, F, OMe] | ¹H-NMR (CDCl₃) δ: 3.84 (3H, s), 4.00 (2H, br s), 6.54 (1H, dd, J = 10.3, 2.6 Hz), 6.81 (1H, dd, J = 8.3, 2.6 Hz). |
| 3(3b) | [structure: acetophenone with NH₂, OMe, F] | ¹H-NMR (CDCl₃) δ: 2.54 (3H, s), 3.87 (3H, s), 6.43 (2H, br s), 6.66 (1H, dd, J = 9.6, 2.3 Hz), 7.00 (1H, dd, J = 10.3, 2.3 Hz). |
| 3(3c) | [structure: acetophenone with F, Br, OMe] | ¹H-NMR (CDCl₃) δ: 2.60 (3H, s), 3.91 (3H, s), 6.68-6.73 (2H, m). |

TABLE 70

| | | |
|---|---|---|
| 4(4a) | [structure: aniline with Br, Me, F] | ¹H-NMR (CDCl₃) δ: 2.29 (3H, d, J = 2.9 Hz), 3.68 (2H, br s), 6.52 (1H, t, J = 8.6 Hz), 7.09 (1H, dd, J = 8.6, 1.7 Hz). |
| 4(4b) | [structure: methyl benzoate with NH₂, Me, F] | ¹H-NMR (CDCl₃) δ: 2.51 (3H, d, J = 2.6 Hz), 3.84 (3H, s), 4.00-4.10 (2H, br m), 6.58 (1H, t, J = 8.6 Hz), 7.62 (1H, d, J = 8.6 Hz). |
| 4(4c) | [structure: Weinreb amide with Me, Br, F] | ¹H-NMR (CDCl₃) δ: 2.28 (3H, s), 3.25-3.60 (6H, br m), 6.97 (1H, d, J = 8.0 Hz), 7.42 (1H, t, J = 7.2 Hz). |
| 4(4d) | [structure: acetophenone with Me, Br, F] | ¹H-NMR (CDCl₃) δ: 2.45 (3H, d, J = 2.3 Hz), 2.57 (3H, s), 7.33 (1H, d, J = 8.0 Hz), 7.44-7.49 (1H, m). |
| 5(5a) | [structure: benzyl alcohol with Br, Cl] | ¹H-NMR (CDCl₃) δ: 2.05 (1H, t, J = 6.4 Hz), 4.78 (2H, d, J = 6.4 Hz), 7.30 (1H, d, J = 7.3 Hz), 7.41 (2H, d, J = 7.8 Hz). |
| 5(5b) | [structure: benzaldehyde with Br, Cl] | ¹H-NMR (CDCl₃) δ: 7.40 (1H, t, J = 7.8 Hz), 7.71 (1H, d, J = 7.8 Hz), 7.82 (1H, d, J = 7.8 Hz), 10.40 (1H, s). |
| 5(5c) | [structure: 1-(aryl)butan-1-ol with Br, Cl] | ¹H-NMR (CDCl₃) δ: 0.97 (3H, t, J = 7.3 Hz), 1.40-1.68 (3H, m), 1.71-1.79 (1H, m), 1.99-2.01 (1H, m), 5.12-5.16 (1H, m), 7.29 (1H, d, J = 7.8 Hz), 7.38 (1H, d, J = 7.8 Hz), 7.47 (1H, d, J = 7.8 Hz). |
| 5(5d) | [structure: butyrophenone with Br, Cl] | ¹H-NMR (CDCl₃) δ: 1.00 (3H, t, J = 7.6 Hz), 1.75 (2H, td, J = 14.7, 7.3 Hz), 2.86 (2H, t, J = 7.1 Hz), 7.14 (1H, d, J = 7.3 Hz), 7.31 (1H, t, J = 7.8 Hz), 7.51 (1H, d, J = 7.8 Hz). |
| 5(5a)-2 | [structure: benzyl alcohol with Br, Me] | ¹H-NMR (CDCl3) δ: 2.43 (3H, s), 4.77 (2H, d, J = 6.4 Hz), 7.18-7.25 (2H, m), 7.30 (1H, d, J = 7.3 Hz). |

TABLE 71

| | | |
|---|---|---|
| 5(5b)-2 | [structure: benzaldehyde with Br, Me] | Tetrahedoron, 2008, 64, 11852-11859. |

TABLE 71-continued

| | | |
|---|---|---|
| 5(5c)-2 | 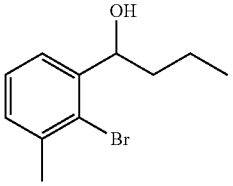 | ¹H-NMR (CDCl₃) δ: 0.97 (3H, t, J = 7.3 Hz), 1.39-1.59 (2H, m), 1.59-1.70 (1H, m), 1.72-1.80 (1H, m), 1.94 (1H, d, J = 3.7 Hz), 2.42 (3H, s), 5.14-5.18 (1H, m), 7.15 (1H, d, J = 7.3 Hz), 7.23 (1H, t, J = 7.6 Hz), 7.38 (1H, d, J = 7.3 Hz) |
| 5(5d)-2 | 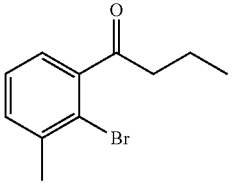 | ¹H-NMR (CDCl₃) δ: 1.00 (3H, t, J = 7.3 Hz), 1.70-1.79 (2H, m), 2.44 (3H, s), 2.86 (2H, t, J = 7.3 Hz), 7.07 (1H, dd, J = 7.3, 1.8 Hz), 7.24 (1H, t, J = 7.3 Hz), 7.28 (1H, dd, J = 7.3, 1.8 Hz). |
| 5(5a)-3 | 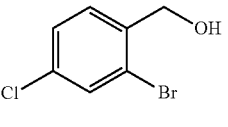 | ¹H-NMR (CDCl₃) δ: 1.99 (1H, t, J = 6.4 Hz), 4.72 (2H, d, J = 6.4 Hz), 7.32 (1H, d, J = 8.3 Hz), 7.43 (1H, d, J = 8.3 Hz), 7.56 (1H, s). |
| 5(5b)-3 | 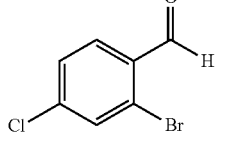 | Bioorg. Med. ChemLett., 2007, 17, 6463-6466. |
| 5(5c)-3 | 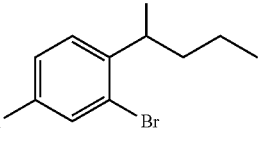 | ¹H-NMR (CDCl₃) δ: 0.96 (3H, t, J = 7.3 Hz), 1.36-1.60 (2H, m), 1.61-1.76 (2H, m), 1.93-1.96 (1H, m), 5.02-5.06 (1H, m), 7.31 (1H, dd, J = 8.3, 2.3 Hz), 7.49 (1H, d, J = 8.3 Hz), 7.52 (1H, d, J = 2.3 Hz). |
| 5(5d)-3 | 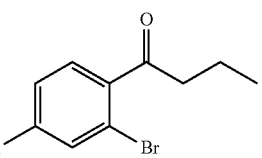 | ¹H-NMR (CDCl₃) δ: 0.99 (3H, t, J = 7.6 Hz), 1.74 (2H, td, J = 14.7, 7.3 Hz), 2.88 (2H, t, J = 7.3 Hz), 7.34 (1H, s), 7.34 (1H, d, J = 1.8 Hz), 7.63 (1H, d, J = 1.8 Hz). |
| 5(5a)-4 | 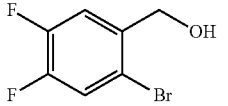 | ¹H-NMR (CDCl₃) δ: 4.69 (2H, s), 7.36-7.42 (2H, m). |
| 5(5b)-4 | 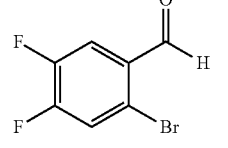 | ¹H-NMR (CDCl₃) δ: 7.51 (1H, dd, J = 9.2, 6.9 Hz), 7.77 (1H, dd, J = 10.0, 8.3 Hz), 10.23 (1H, d, J = 3.4 Hz). |
| 5(5c)-4 | 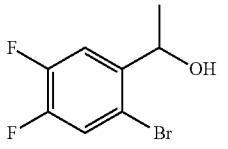 | ¹H-NMR (CDCl₃) δ: 1.45 (3H, d, J = 6.3 Hz), 1.98 (1H, d, J = 2.9 Hz), 5.12-5.18 (1H, m), 7.35 (1H, dd, J = 9.5, 7.2 Hz), 7.46 (1H, dd, J = 11.5, 8.6 Hz). |

TABLE 72

| | | |
|---|---|---|
| 5(5d)-4 | 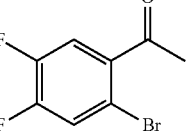 | ¹H-NMR (CDCl₃) δ: 2.64 (3H, s), 7.40 (1H, dd, J = 10.3, 8.0 Hz), 7.47 (1H, dd, J = 9.5, 7.2 Hz). |
| 5(5a)-5 | 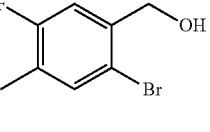 | ¹H-NMR (CDCl₃) δ: 1.95 (1H, t, J = 6.2 Hz), 2.25 (3H, s), 4.68 (2H, d, J = 6.2 Hz), 7.17 (1H, d, J = 10.1 Hz), 7.36 (1H, d, J = 6.9 Hz). |
| 5(5b)-5 | 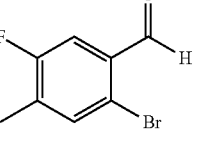 | ¹H-NMR (CDCl₃) δ: 2.34 (3H, s), 7.50 (1H, d, J = 6.4 Hz), 7.56 (1H, d, J = 9.2 Hz), 10.25 (1H, s). |
| 5(5b)-6 | 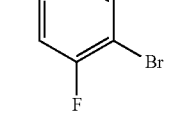 | ¹H-NMR (CDCl₃) δ: 7.14-7.18 (1H, m), 7.47-7.50 (1H, m), 10.34 (1H, d, J = 2.9 Hz). |
| 5(5c)-6 | 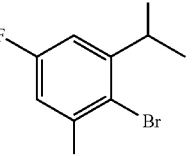 | ¹H-NMR (CDCl₃) δ: 1.47 (3H, d, J = 6.3 Hz), 1.98 (1H, d, J = 3.4 Hz), 5.21-5.27 (1H, m), 6.82 (1H, td, J = 8.2, 3.1 Hz), 7.19-7.23 (1H, m). |
| 5(5d)-6 | 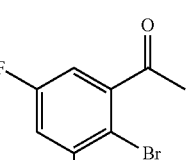 | ¹H-NMR (CDCl₃) δ: 2.63 (3H, s), 6.98-7.03 (2H, m). |
| 5(5c)-7 | 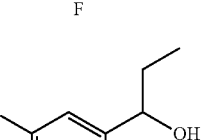 | ¹H-NMR (CDCl₃) δ: 1.02 (3H, t, J = 7.3 Hz), 1.61-1.72 (1H, m), 1.78-1.88 (1H, m), 2.00 (1H, d, J = 3.7 Hz), 5.01-5.05 (1H, m), 6.82 (1H, td, J = 8.2, 2.9 Hz), 7.16 (1H, dq, J = 9.5, 1.5 Hz). |
| 5(5d)-7 | 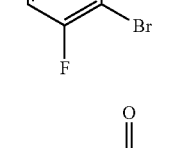 | ¹H-NMR (CDCl₃) δ: 1.22 (3H, t, J = 7.3 Hz), 2.91 (2H, q, J = 7.3 Hz), 6.90-6.93 (1H, m), 6.97 (1H, td, J = 8.0, 2.9 Hz). |
| 5(5b)-8 | 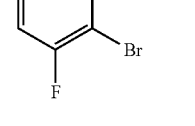 | ¹H-NMR (CDCl₃) δ: 1.43 (3H, t, J = 6.9 Hz), 4.07 (2H, q, J = 6.9 Hz), 7.02 (1H, dd, J = 8.8, 3.1 Hz), 7.40 (1H, d, J = 3.1 Hz), 7.52 (1H, d, J = 8.8 Hz), 10.31 (1H, s). |

TABLE 73

| | | |
|---|---|---|
| 5(5c)-8 | 5-ethoxy-2-bromo-α-methylbenzyl alcohol | ¹H-NMR (CDCl₃) δ: 1.41 (3H, t, J = 7.0 Hz), 1.47 (3H, d, J = 6.4 Hz), 1.95 (1H, d, J = 3.7 Hz), 4.03 (2H, q, J = 7.0 Hz), 5.18 (1H, qd, J = 6.4, 3.7 Hz), 6.68 (1H, dd, J = 8.7, 3.0 Hz), 7.15 (1H, d, J = 3.0 Hz), 7.38 (1H, d, J = 8.7 Hz). |
| 5(5d)-8 | | ¹H-NMR (CDCl₃) δ: 1.41 (3H, t, J = 7.1 Hz), 2.62 (3H, s), 4.02 (2H, q, J = 7.1 Hz), 6.84 (1H, dd, J = 8.9, 3.2 Hz), 6.97 (1H, d, J = 3.2 Hz), 7.47 (1H, d, J = 8.9 Hz). |
| 5(5c)-9 | | ¹H-NMR (CDCl₃) δ: 0.98 (3H, q, J = 7.5 Hz), 1.18-1.30 (1H, m), 1.42-1.59 (1H, m), 1.61-1.81 (2H, m), 1.98 (1H, br s), 5.10-5.15 (1H, m), 7.02-7.07 (1H, m), 7.30-7.38 (2H, m). |
| 5(5d)-9 | | ¹H-NMR (CDCl₃) δ: 1.00 (3H, t, J = 7.6 Hz), 1.75 (2H, td, J = 14.7, 7.6 Hz), 2.89 (2H, t, J = 7.3 Hz), 7.13-7.21 (2H, m), 7.32-7.37 (1H, m). |
| 5(5c)-10 | | ¹H-NMR (CDCl₃) δ: 0.96 (3H, t, J = 7.3 Hz), 1.35-1.54 (2H, m), 1.55-1.58 (1H, m), 1.63-1.77 (1H, m), 1.88-1.91 (1H, m), 2.31 (3H, s), 5.03-5.07 (1H, m), 7.14 (1H, d, J = 7.8 Hz), 7.34 (1H, s), 7.41 (1H, d, J = 7.8 Hz). |
| 5(5d)-10 | | ¹H-NMR (CDCl₃) δ: 0.98 (3H, t, J = 7.3 Hz), 1.73 (2H, td, J = 14.7, 7.3 Hz), 2.35 (3H, s), 2.88 (2H, t, J = 7.3 Hz), 7.15 (1H, d, J = 7.8 Hz), 7.30 (1H, d, J = 7.8 Hz), 7.43 (1H, s). |
| 5(5c)-11 | | ¹H-NMR (CDCl₃) δ: 0.96 (3H, t, J = 7.3 Hz), 1.37-1.59 (2H, m), 1.61-1.82 (2H, m), 1.92-1.97 (1H, m), 3.90 (3H, s), 5.14-5.18 (1H, m), 6.82 (1H, d, J = 7.8 Hz), 7.17 (1H, d, J = 7.8 Hz), 7.30 (1H, t, J = 8.0 Hz). |
| 5(5d)-11 | | ¹H-NMR (CDCl₃) δ: 1.00 (3H, t, J = 7.5 Hz), 1.75 (2H, td, J = 14.9, 7.5 Hz), 2.87 (2H, t, J = 7.5 Hz), 3.92 (3H, s), 6.87 (1H, d, J = 7.3 Hz), 6.95 (1H, d, J = 8.3 Hz), 7.32 (1H, t, J = 7.9 Hz). |
| 5(5c)-12 | | ¹H-NMR (CDCl₃) δ: 0.97 (3H, t, J = 7.3 Hz), 1.38-1.60 (2H, m), 1.61-1.67 (1H, m), 1.68-1.77 (1H, m), 1.99 (1H, d, J = 4.1 Hz), 5.01-5.05 (1H, m), 7.10 (1H, dd, J = 8.7, 2.8 Hz), 7.43 (1H, d, J = 8.7 Hz), 7.55 (1H, d, J = 2.8 Hz). |
| 5(5d)-12 | | ¹H-NMR (CDCl₃) δ: 1.00 (3H, t, J = 7.3 Hz), 1.74 (2H, td, J = 14.8, 7.5 Hz), 2.87 (2H, t, J = 7.5 Hz), 7.25 (1H, dd, J = 8.5, 2.5 Hz), 7.32 (1H, d, J = 1.8 Hz), 7.52 (1H, d, J = 9.2 Hz). |
| 5(5c)-13 | | ¹H-NMR (CDCl₃) δ: 1.33 (3H, d, J = 6.0 Hz), 1.33 (3H, d, J = 6.0 Hz), 1.47 (3H, d, J = 6.0 Hz), 1.94 (1H, d, J = 3.2 Hz), 4.50-4.59 (1H, m), 5.14-5.21 (1H, m), 6.67 (1H, dd, J = 8.7, 3.2 Hz), 7.14 (1H, d, J = 3.2 Hz), 7.37 (1H, d, J = 8.7 Hz). |
| 5(5d)-13 | | ¹H-NMR (CDCl₃) δ: 1.33 (6H, d, J = 6.3 Hz), 2.62 (3H, s), 4.49-4.57 (1H, m), 6.82 (1H, dd, J = 8.7, 3.0 Hz), 6.97 (1H, d, J = 3.0 Hz), 7.46 (1H, d, J = 8.7 Hz). |
| 5(5c)-14 | | ¹H-NMR (CDCl₃) δ: 0.97 (3H, t, J = 7.3 Hz), 1.36-1.80 (4H, m), 1.98 (1H, br s), 5.02-5.05 (1H, m), 6.85 (1H, dq, J = 9.9, 2.9 Hz), 7.30 (1H, dd, J = 9.9, 3.2 Hz), 7.46 (1H, dd, J = 8.7, 5.5 Hz). |
| 5(5d)-14 | | ¹H-NMR (CDCl₃) δ: 1.00 (3H, t, J = 7.3 Hz), 1.74 (2H, td, J = 14.7, 7.3 Hz), 2.88 (2H, t, J = 7.1 Hz), 7.01 (1H, td, J = 8.1, 3.2 Hz), 7.08 (1H, dd, J = 8.1, 3.2 Hz), 7.56 (1H, dd, J = 8.7, 4.6 Hz). |

TABLE 73-continued

| | | |
|---|---|---|
| 5(5c)-15 | 2-bromo-6-fluoro-α-methylbenzyl alcohol | $^1$H-NMR (CDCl$_3$) δ: 1.62 (3H, d, J = 6.7 Hz), 2.48 (1H, dd, J = 9.4, 5.5 Hz), 5.31-5.38 (1H, m), 7.01-7.13 (2H, m), 7.33-7.36 (1H, m). |
| 5(5c)-16 | 2-bromo-6-methyl-α-methylbenzyl alcohol | *Journal of Organic Chemistry*; English; 1993; 58, 3308-3316 |
| 5(5c)-17 | 2-bromo-6-chloro-α-methylbenzyl alcohol | $^1$H-NMR (CDCl$_3$) δ: 1.64 (3H, d, J = 6.9 Hz), 3.00 (1H, d, J = 10.3 Hz), 5.55-5.61 (1H, m), 7.05 (1H, t, J = 8.0 Hz), 7.33 (1H, d, J = 8.0 Hz), 7.49 (1H, d, J = 8.0 Hz). |

TABLE 74

| | | |
|---|---|---|
| 5(5c)-18 | | $^1$H-NMR (CDCl$_3$) δ: 1.62-1.65 (3H, m), 2.43 (1H, dd, J = 9.2, 4.0 Hz), 5.30-5.36 (1H, m), 6.99 (1H, dd, J = 17.5, 8.9 Hz), 7.28-7.31 (1H, m). |
| 6 | | $^1$H-NMR (CDCl$_3$) δ: 1.02 (3H, t, J = 8.3 Hz), 1.61-1.74 (1H, m), 1.77-1.89 (1H, m), 4.92-5.00 (1H, m), 6.81-6.90 (1H, m), 7.24-7.33 (1H, m), 7.43-7.51 (1H, m). Optical purity: 99.9% ee |
| 6-2 | | $^1$H-NMR (CDCl$_3$) δ: 1.01 (3H, t, J = 7.3 Hz), 1.64-1.77 (1H, m), 1.78-1.90 (1H, m), 2.01 (1H, d, J = 3.7 Hz), 5.00-5.08 (1H, m), 7.00-7.08 (1H, m), 7.25-7.38 (2H, m). Optical purity: 87.3% ee |
| 6-3 | | $^1$H-NMR (CDCl$_3$) δ: 0.99 (3H, t, J = 7.5 Hz), 1.65-1.87 (2H, m), 1.90-1.94 (1H, m), 2.31 (3H, s), 4.94-5.01 (1H, m), 7.13 (1H, d, J = 7.8 Hz), 7.35 (1H, s), 7.40 (1H, d, J = 7.8 Hz). Optical purity: 90.1% ee |
| 6-4 | | $^1$H-NMR (CDCl$_3$) δ: 1.01 (3H, t, J = 7.3 Hz), 1.64-1.77 (1H, m), 1.79-1.90 (1H, m), 1.99 (1H, d, J = 3.7 Hz), 3.90 (3H, s), 5.05-5.12 (1H, m), 6.83 (1H, d, J = 8.3 Hz), 7.16 (1H, d, J = 7.8 Hz), 7.25-7.33 (1H, m). Optical purity: 92.8% ee |

TABLE 74-continued

| | | |
|---|---|---|
| 6-5 | | $^1$H-NMR (CDCl$_3$) δ: 1.01 (3H, t, J = 7.3 Hz), 1.25 (1H, t, J = 8.3 Hz), 1.59-1.75 (1H, m), 1.78-1.90 (1H, m), 2.42 (3H, s), 5.05-5.11 (1H, m), 7.15 (1H, d, J = 7.3 Hz), 7.20-7.27 (1H, m), 7.36 (1H, d, J = 7.3 Hz). Optical purity: 99.8% ee |
| 6-6 | | $^1$H-NMR (CDCl$_3$) δ: 1.01 (3H, t, J = 7.3 Hz), 1.62-1.74 (2H, m), 1.76-1.88 (1H, m), 4.92-4.99 (1H, m), 7.10 (1H, dd, J = 8.7, 2.8 Hz), 7.43 (1H, d, J = 8.7 Hz), 7.54 (1H, s). Optical purity: 99.8% ee |
| 6-7 | | $^1$H-NMR (CDCl$_3$) δ: 0.99 (3H, t, J = 7.3 Hz), 1.61-1.74 (1H, m), 1.74-1.86 (1H, m), 2.01 (1H, d, J = 3.7 Hz), 4.94-5.00 (1H, m), 7.32 (1H, dd, J = 8.3, 1.8 Hz), 7.48 (1H, d, J = 8.3 Hz), 7.53 (1H, d, J = 1.8 Hz). Optical purity: 89.1% ee |

TABLE 75

| | | |
|---|---|---|
| 6-8 | | $^1$H-NMR (CDCl$_3$) δ: 0.97-1.07 (3H, m), 1.61-1.75 (1H, m), 1.78-1.92 (1H, m), 1.95-2.03 (1H, m), 5.02-5.12 (1H, m), 7.22-7.33 (1H, m), 7.34-7.51 (2H, m). Optical purity: 88.1% ee |
| 6-9 | | $^1$H-NMR (CDCl$_3$) δ: 1.00 (3H, t, J = 7.3 Hz), 1.59-1.71 (1H, m), 1.74-1.85 (1H, m), 1.97 (1H, d, J = 3.7 Hz), 4.90-4.95 (1H, m), 7.35 (1H, dd, J = 9.6, 7.3 Hz), 7.40 (1H, dd, J = 11.5, 8.3 Hz). Optical purity: 87.2% ee |
| 6-10 | | $^1$H-NMR (CDCl$_3$) δ: 1.00 (3H, t, J = 7.3 Hz), 1.62-1.73 (1H, m), 1.75-1.85 (1H, m), 1.93 (1H, d, J = 3.7 Hz), 2.24 (3H, s), 4.90-4.95 (1H, m), 7.20 (1H, d, J = 10.5 Hz), 7.33 (1H, d, J = 6.9 Hz). Optical purity: 86.6% ee |

TABLE 75-continued

| | | |
|---|---|---|
| 7 R-isomer | 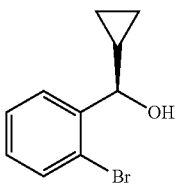 | ¹H-NMR (CDCl₃) δ: 0.44-0.57 (3H, m), 0.59-0.66 (1H, m), 1.24-1.35 (1H, m), 2.06 (1H, d, J = 3.2 Hz), 4.64 (1H, dd, J = 7.6, 3.4 Hz), 7.12-7.17 (1H, m), 7.33-7.37 (1H, m), 7.54 (1H, dd, J = 8.0, 1.1 Hz), 7.62 (1H, dd, J = 8.0, 1.8 Hz). Optical purity: 99.5% ee |
| 7 S-isomer | 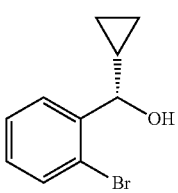 | ¹H-NMR (CDCl₃) δ: 0.44-0.57 (3H, m), 0.59-0.66 (1H, m), 1.24-1.35 (1H, m), 2.06 (1H, d, J = 3.2 Hz), 4.64 (1H, dd, J = 7.6, 3.4 Hz), 7.12-7.17 (1H, m), 7.33-7.37 (1H, m), 7.54 (1H, dd, J = 8.0, 1.1 Hz), 7.62 (1H, dd, J = 8.0, 1.8 Hz). Optical purity: 98.9% ee |
| 8 | 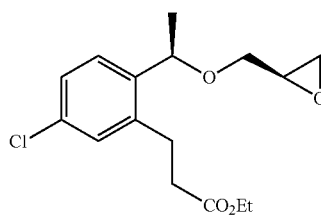 | ¹H-NMR (CDCl₃) δ: 1.25 (3H, t, J = 7.3 Hz), 1.44 (3H, d, J = 6.5 Hz), 2.50 (1H, dd, J = 4.9, 2.6 Hz), 2.57-2.61 (2H, m), 2.76 (1H, t, J = 4.3 Hz), 2.92-2.97 (2H, m), 3.12-3.21 (2H, m), 3.58 (1H, dd, J = 11.2, 2.6 Hz), 4.15 (2H, q, J = 7.1 Hz), 4.79 (1H, q, J = 6.5 Hz), 7.14 (1H, d, J = 2.3 Hz), 7.22 (1H, dd, J = 8.6, 2.3 Hz), 7.39 (1H, d, J = 8.0 Hz). |
| 8-2 | 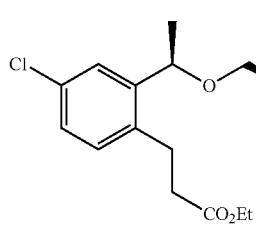 | ¹H-NMR (CDCl₃) δ: 1.24 (3H, t, J = 7.3 Hz), 1.44 (3H, d, J = 6.3 Hz), 2.50 (1H, dd, J = 4.6, 2.6 Hz), 2.55-2.59 (2H, m), 2.77 (1H, t, J = 4.6 Hz), 2.91-2.95 (2H, m), 3.15-3.22 (2H, m), 3.61 (1H, dd, J = 10.6, 2.0 Hz), 4.13 (2H, q, J = 7.3 Hz), 4.79 (1H, q, J = 6.5 Hz), 7.08 (1H, d, J = 8.3 Hz), 7.17 (1H, dd, J = 8.3, 2.3 Hz), 7.44 (1H, d, J = 2.3 Hz). |
| 8-3 | 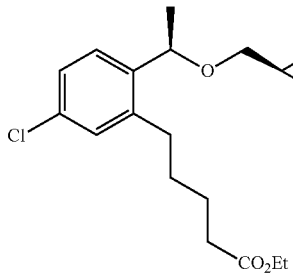 | ¹H-NMR (CDCl₃) δ: 1.26 (3H, t, J = 7.4 Hz), 1.42 (3H, d, J = 6.3 Hz), 1.58-1.64 (2H, m), 1.68-1.74 (2H, m), 2.35 (2H, t, J = 7.2 Hz), 2.48-2.50 (1H, m), 2.58-2.65 (2H, m), 2.74-2.77 (1H, m), 3.11-3.18 (2H, m), 3.55-3.58 (1H, m), 4.13 (2H, q, J = 7.4 Hz), 4.75 (1H, q, J = 6.3 Hz), 7.12 (1H, d, J = 2.3 Hz), 7.20 (1H, dd, J = 8.6, 2.3 Hz), 7.38 (1H, d, J = 8.0 Hz). |

TABLE 76

| | | |
|---|---|---|
| 8-4 | 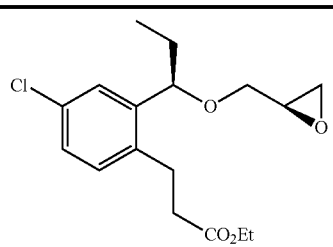 | ¹H-NMR (CDCl₃) δ: 0.99 (3H, t, J = 7.4 Hz), 1.24 (3H, t, J = 7.1 Hz), 1.56-1.70 (1H, m), 1.72-1.82 (1H, m), 2.47-2.51 (1H, m), 2.51-2.63 (2H, m), 2.73-2.78 (1H, m), 2.86-3.00 (2H, m), 3.13-3.19 (2H, m), 3.59-3.65 (1H, m), 4.09-4.17 (2H, m), 4.54-4.58 (1H, m), 7.08 (1H, d, J = 8.4 Hz), 7.17 (1H, dd, J = 8.4, 2.1 Hz), 7.40 (1H, d, J = 2.3 Hz). |
| 8-5 | 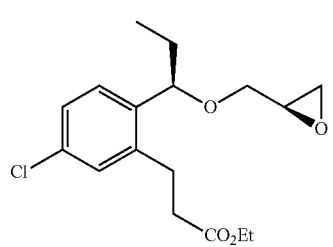 | ¹H-NMR (CDCl₃) δ: 0.97 (3H, t, J = 7.3 Hz), 1.25 (3H, t, J = 7.1 Hz), 1.58-1.71 (1H, m), 1.71-1.84 (1H, m), 2.47-2.51 (1H, m), 2.55-2.62 (2H, m), 2.73-2.77 (1H, m), 2.86-3.04 (2H, m), 3.09-3.19 (2H, m), 3.56-3.61 (1H, m), 4.15 (2H, q, J = 7.1 Hz), 4.55 (1H, dd, J = 7.8, 5.0 Hz), 7.13-7.16 (1H, m), 7.19-7.23 (1H, m), 7.33-7.37 (1H, m). |
| 8-6 | 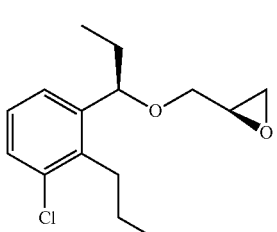 | ¹H-NMR (CDCl₃) δ: 1.00 (3H, t, J = 7.3 Hz), 1.28 (3H, t, J = 7.1 Hz), 1.62-1.83 (2H, m), 2.45-2.63 (3H, m), 2.70-2.81 (1H, m), 2.98-3.10 (1H, m), 3.10-3.22 (3H, m), 3.56-3.62 (1H, m), 4.18 (2H, q, J = 7.1 Hz), 4.59 (1H, q, J = 6.4 Hz), 7.18 (1H, t, J = 8.0 Hz), 7.25-7.31 (1H, m), 7.34 (1H, d, J = 7.8 Hz). |

TABLE 76-continued

| | | |
|---|---|---|
| 8-7 | 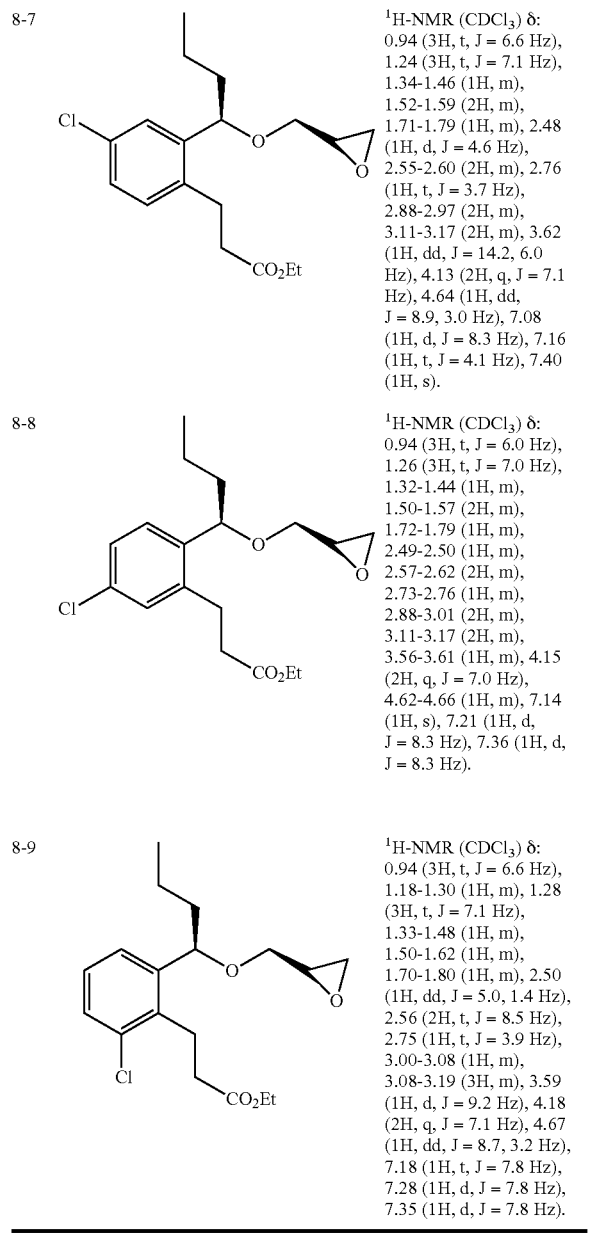 | $^1$H-NMR (CDCl$_3$) δ: 0.94 (3H, t, J = 6.6 Hz), 1.24 (3H, t, J = 7.1 Hz), 1.34-1.46 (1H, m), 1.52-1.59 (2H, m), 1.71-1.79 (1H, m), 2.48 (1H, d, J = 4.6 Hz), 2.55-2.60 (2H, m), 2.76 (1H, t, J = 3.7 Hz), 2.88-2.97 (2H, m), 3.11-3.17 (2H, m), 3.62 (1H, dd, J = 14.2, 6.0 Hz), 4.13 (2H, q, J = 7.1 Hz), 4.64 (1H, dd, J = 8.9, 3.0 Hz), 7.08 (1H, d, J = 8.3 Hz), 7.16 (1H, t, J = 4.1 Hz), 7.40 (1H, s). |
| 8-8 | | $^1$H-NMR (CDCl$_3$) δ: 0.94 (3H, t, J = 6.0 Hz), 1.26 (3H, t, J = 7.0 Hz), 1.32-1.44 (1H, m), 1.50-1.57 (2H, m), 1.72-1.79 (1H, m), 2.49-2.50 (1H, m), 2.57-2.62 (2H, m), 2.73-2.76 (1H, m), 2.88-3.01 (2H, m), 3.11-3.17 (2H, m), 3.56-3.61 (1H, m), 4.15 (2H, q, J = 7.0 Hz), 4.62-4.66 (1H, m), 7.14 (1H, s), 7.21 (1H, d, J = 8.3 Hz), 7.36 (1H, d, J = 8.3 Hz). |
| 8-9 | | $^1$H-NMR (CDCl$_3$) δ: 0.94 (3H, t, J = 6.6 Hz), 1.18-1.30 (1H, m), 1.28 (3H, t, J = 7.1 Hz), 1.33-1.48 (1H, m), 1.50-1.62 (1H, m), 1.70-1.80 (1H, m), 2.50 (1H, dd, J = 5.0, 1.4 Hz), 2.56 (2H, t, J = 8.5 Hz), 2.75 (1H, t, J = 3.9 Hz), 3.00-3.08 (1H, m), 3.08-3.19 (3H, m), 3.59 (1H, d, J = 9.2 Hz), 4.18 (2H, q, J = 7.1 Hz), 4.67 (1H, dd, J = 8.7, 3.2 Hz), 7.18 (1H, t, J = 7.8 Hz), 7.28 (1H, d, J = 7.8 Hz), 7.35 (1H, d, J = 7.8 Hz). |

TABLE 77

| | | |
|---|---|---|
| 8-10 | 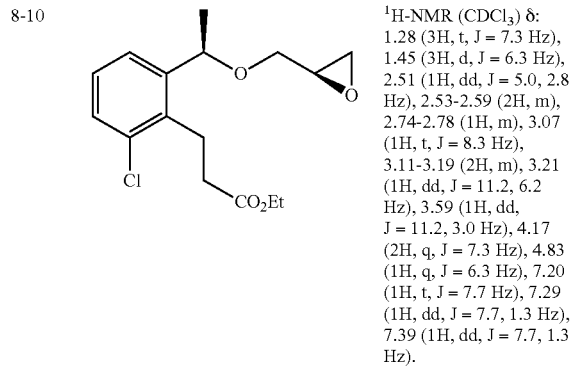 | $^1$H-NMR (CDCl$_3$) δ: 1.28 (3H, t, J = 7.3 Hz), 1.45 (3H, d, J = 6.3 Hz), 2.51 (1H, dd, J = 5.0, 2.8 Hz), 2.53-2.59 (2H, m), 2.74-2.78 (1H, m), 3.07 (1H, t, J = 8.3 Hz), 3.11-3.19 (2H, m), 3.21 (1H, dd, J = 11.2, 6.2 Hz), 3.59 (1H, dd, J = 11.2, 3.0 Hz), 4.17 (2H, q, J = 7.3 Hz), 4.83 (1H, q, J = 6.3 Hz), 7.20 (1H, t, J = 7.7 Hz), 7.29 (1H, dd, J = 7.7, 1.3 Hz), 7.39 (1H, dd, J = 7.7, 1.3 Hz). |

TABLE 77-continued

| | | |
|---|---|---|
| 8-11 | 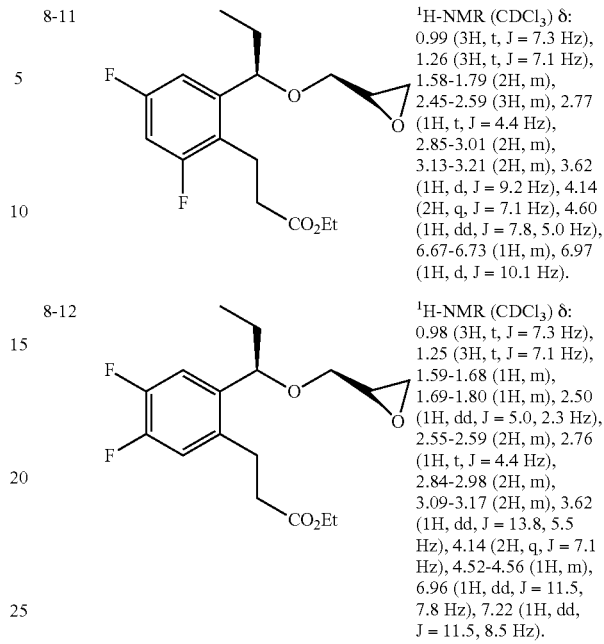 | $^1$H-NMR (CDCl$_3$) δ: 0.99 (3H, t, J = 7.3 Hz), 1.26 (3H, t, J = 7.1 Hz), 1.58-1.79 (2H, m), 2.45-2.59 (3H, m), 2.77 (1H, t, J = 4.4 Hz), 2.85-3.01 (2H, m), 3.13-3.21 (2H, m), 3.62 (1H, d, J = 9.2 Hz), 4.14 (2H, q, J = 7.1 Hz), 4.60 (1H, dd, J = 7.8, 5.0 Hz), 6.67-6.73 (1H, m), 6.97 (1H, d, J = 10.1 Hz). |
| 8-12 | 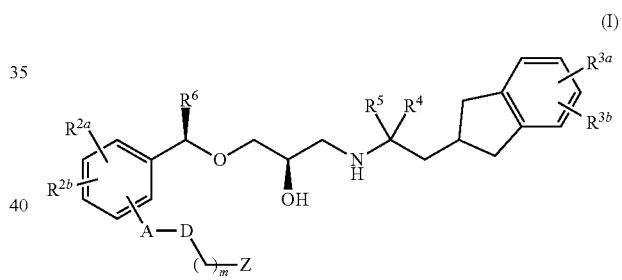 | $^1$H-NMR (CDCl$_3$) δ: 0.98 (3H, t, J = 7.3 Hz), 1.25 (3H, t, J = 7.1 Hz), 1.59-1.68 (1H, m), 1.69-1.80 (1H, m), 2.50 (1H, dd, J = 5.0, 2.3 Hz), 2.55-2.59 (2H, m), 2.76 (1H, t, J = 4.4 Hz), 2.84-2.98 (2H, m), 3.09-3.17 (2H, m), 3.62 (1H, dd, J = 13.8, 5.5 Hz), 4.14 (2H, q, J = 7.1 Hz), 4.52-4.56 (1H, m), 6.96 (1H, dd, J = 11.5, 7.8 Hz), 7.22 (1H, dd, J = 11.5, 8.5 Hz). |

The invention claimed is:

1. A compound having Formula (I) or a pharmaceutically acceptable salt thereof:

(I)

wherein

A: a single bond, a C1-C6 alkylene group, or a phenylene group which may be substituted by $R^1$, $R^1$: a hydrogen atom, a halogen atom, a cyano group, a C1-C6 alkyl group, a C1-C6 alkoxy group, a halogeno C1-C6 alkyl group, or a halogeno C1-C6 alkoxy group, D: a single bond, an oxygen atom, or a sulfur atom, $R^{2a}$ and $R^{2b}$: the same or different from each other, a hydrogen atom, a halogen atom, a cyano group, a C1-C6 alkyl group, a C1-C6 alkoxy group, a halogeno C1-C6 alkyl group, or a halogeno C1-C6 alkoxy group, $R^{3a}$ and $R^{3b}$: the same or different from each other, a hydrogen atom, a halogen atom, a cyano group, a C1-C6 alkyl group, a C1-C6 alkoxy group, a halogeno C1-C6 alkyl group, or a halogeno C1-C6 alkoxy group, $R^4$ and $R^5$: the same or different from each other, a hydrogen atom, a halogen atom, or a C1-C6 alkyl group, or $R^4$ and $R^5$ are bonded to each other to form a C2-C6 alkylene group, R⁶: a halogen atom, a cyano group, a C1-C6 alkyl group, a C1-C6 alkoxy group, a halogeno C1-C6 alkyl group, or a halogeno C1-C6 alkoxy group, m: an integer of 0 to 6, Z: a carboxy group, —SO$_2$NHR$^Z$, or a tetrazolyl group, and R$^z$: a hydrogen atom or a C1-C6 alkyl group.

2. The compound according to claim 1 or a pharmaceutically acceptable salt thereof wherein R$^1$ represents a hydrogen atom or a methyl group.

3. The compound according to claim 1 or a pharmaceutically acceptable salt thereof, wherein R$^{2a}$ and R$^{2b}$, which are identical or different from each other, represent a hydrogen atom, a fluorine atom, a chlorine atom, a cyano group, a methyl group, a methoxy group, an ethoxy group, a trifluoromethyl group, or a trifluoromethoxy group.

4. The compound according to claim 1 or a pharmaceutically acceptable salt thereof wherein R$^{3a}$ and R$^{3b}$, the same or different from each other, represent a hydrogen atom, a fluorine atom, a chlorine atom, a cyano group, a methyl group, a methoxy group, an ethoxy group, a trifluoromethyl group, or a trifluoromethoxy group.

5. The compound according to claim 1 or a pharmaceutically acceptable salt thereof wherein R$^4$ and R$^5$ represent methyl groups.

6. The compound according to claim 1 or a pharmaceutically acceptable salt thereof wherein R$^4$ and R$^5$ represent an ethylene group.

7. The compound according to claim 1 or a pharmaceutically acceptable salt thereof wherein m is 0 or 1.

8. The compound according to claim 1 or a pharmaceutically acceptable salt thereof wherein m is 2 to 4.

9. The compound according to claim 1 or a pharmaceutically acceptable salt thereof wherein A is a single bond.

10. The compound according to claim 1 or a pharmaceutically acceptable salt thereof wherein D is a single bond.

11. The compound according to claim 1 or a pharmaceutically acceptable salt thereof wherein Z is a carboxy group.

12. The compound according to claim 1 or a pharmaceutically acceptable salt thereof wherein R$^6$ represents a methyl group or an ethyl group.

13. A compound selected from the following group of compounds, or a pharmaceutically acceptable salt thereof:

3-{2-[(1R)-1-{[(2R)-3-{[1-(2,3-dihydro-1H-inden-2-yl)-2-methylpropan-2-yl]amino}-2-hydroxypropyl]oxy}ethyl]phenyl}propanoic acid, 4-{2-[(1R)-1-{[(2R)-3-{[1-(2,3-dihydro-1H-inden-2-yl)-2-methylpropan-2-yl]amino}-2-hydroxypropyl]oxy}ethyl]phenyl}butanoic acid, 2'-[(1R)-1-{[(2R)-3-{[1-(2,3-dihydro-1H-inden-2-yl)-2-methylpropan-2-yl]amino}-2-hydroxypropyl]oxy}ethyl]-3-methylbiphenyl-4-carboxylic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-5-methylphenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-4-methylphenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-4-fluorophenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-6-(trifluoromethyl)phenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-5-(trifluoromethyl)phenyl}propanoic acid, 2'-[(1R)-1-{[(2R)-3-{[1-(2,3-dihydro-1H-inden-2-ylmethyl)cyclopropyl]amino}-2-hydroxypropyl]oxy}ethyl]-3-methylbiphenyl-4-carboxylic acid, 5-{2-[(1R)-1-{[(2R)-3-{[1-(2,3-dihydro-1H-inden-2-yl)-2-methylpropan-2-yl]amino}-2-hydroxypropyl]oxy}ethyl]phenyl}pentanoic acid, 3-{2-[(1R)-1-{[(2R)-3-{[1-(2,3-dihydro-1H-inden-2-ylmethyl)cyclopropyl]amino}-2-hydroxypropyl]oxy}ethyl]phenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-6-methylphenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-5-fluorophenyl}propanoic acid, 3-{2-[(1R)-1-{[(2R)-3-{[1-(2,3-dihydro-1H-inden-2-yl)-2-methylpropan-2-yl]amino}-2-hydroxypropyl]oxy}ethyl]-6-fluorophenyl}propanoic acid, 3-{2-chloro-6-[(1R)-1-{[(2R)-3-{[1-(2,3-dihydro-1H-inden-2-yl)-2-methylpropan-2-yl]amino}-2-hydroxypropyl]oxy}ethyl]phenyl}propanoic acid, 3-{2-[(1R)-1-{[(2R)-3-{[2-(2,3-dihydro-1H-inden-2-yl)-1,1-dimethylethyl]amino}-2-hydroxypropyl]oxy}propyl]-6-methoxyphenyl}propanoic acid, 3-{2-[(1R)-1-{[(2R)-3-{[2-(2,3-dihydro-1H-inden-2-yl)-1,1-dimethylethyl]amino}-2-hydroxypropyl]oxy}ethyl]-6-ethoxyphenyl}propanoic acid, and 3-{2-[(1R)-1-{[(2R)-3-{[2-(2,3-dihydro-1H-inden-2-yl)-1,1-dimethylethyl]amino}-2-hydroxypropyl]oxy}ethyl]-4-fluoro-6-methoxyphenyl}propanoic acid.

14. A pharmaceutical composition which comprises the compound according to claim 1 or a pharmaceutically acceptable salt thereof.

15. A method of improving bone metabolism comprising administering an effective amount of the pharmaceutical composition of claim 14 to a subject in need thereof.

16. A method of treating osteoporosis comprising administering an effective amount of the pharmaceutical composition of claim 14 to a subject in need thereof.

17. A method for treating a disorder associated with abnormal bone or mineral homeostasis, comprising administering an effective amount of the pharmaceutical composition of claim 14 to a subject in need thereof.

18. The method of claim 17, wherein the disorder associated with abnormal bone or mineral homeostasis is hypoparathyroidism, osteosarcoma, periodontitis, bone fracture healing, deformative arthritis, rheumatoid arthritis, Paget's disease, humoral hypercalcemia syndrome associated with malignant tumor and bone fracture healing, or osteoporosis.

19. A method for antagonizing a calcium receptor, comprising administering an effective amount of the pharmaceutical composition of claim 14 to a subject in need thereof.

20. 3-{2-[(1R)-1-{[(2R)-3-{[1-(2,3-Dihydro-1H-inden-2-yl)-2-methylpropan-2-yl]amino}-2-hydroxypropyl]oxy}ethyl]-5-fluorophenyl} propanoic acid or a pharmaceutically acceptable salt thereof.

21. The compound according to claim 20, wherein the pharmaceutically acceptable salt thereof is a hydrogen chloride salt.

22. A pharmaceutical composition which comprises the compound according to claim 20 or a pharmaceutically acceptable salt thereof.

23. The pharmaceutical composition according to claim 22, wherein the pharmaceutically acceptable salt thereof is a hydrogen chloride salt.

24. A method of improving bone metabolism comprising administering an effective amount of the pharmaceutical composition of claim 22 to a subject in need thereof.

25. The method according to claim 24, wherein the pharmaceutically acceptable salt thereof is a hydrogen chloride salt.

26. A method of treating osteoporosis comprising administering an effective amount of the pharmaceutical composition of claim 22 to a subject in need thereof.

27. The method according to claim 26, wherein the pharmaceutically acceptable salt thereof is a hydrogen chloride salt.

28. A method for treating a disorder associated with abnormal bone or mineral homeostasis, comprising administering an effective amount of the pharmaceutical composition of claim 22 to a subject in need thereof.

29. The method according to claim 28, wherein the pharmaceutically acceptable salt thereof is a hydrogen chloride salt.

30. The method of claim 28, wherein the disorder associated with abnormal bone or mineral homeostasis is hypoparathyroidism, osteosarcoma, periodontitis, bone fracture healing, deformative arthritis, rheumatoid arthritis, Paget's disease, humoral hypercalcemia syndrome associated with malignant tumor and bone fracture healing, or osteoporosis.

31. A method for antagonizing a calcium receptor, comprising administering an effective amount of the pharmaceutical composition of claim 22 to a subject in need thereof.

32. The method according to claim 31, wherein the pharmaceutically acceptable salt thereof is a hydrogen chloride salt.

* * * * *

UNITED STATES PATENT AND TRADEMARK OFFICE
CERTIFICATE OF CORRECTION

Page 1 of 1

PATENT NO.       : 8,183,272 B2
APPLICATION NO.  : 13/167196
DATED            : May 22, 2012
INVENTOR(S)      : A. Nakao et al.

It is certified that error appears in the above-identified patent and that said Letters Patent is hereby corrected as shown below:

In the Claims

| COLUMN | LINE | ERROR |
|---|---|---|
| 220 | 66 | "oxy}ethyl]-5-fluorophenyl} propanoic" should read |
| (Claim 20, | line 4) | --oxy}ethyl]-4-fluorophenyl}propanoic-- |

Signed and Sealed this
Third Day of June, 2014

Michelle K. Lee
*Deputy Director of the United States Patent and Trademark Office*